US008293533B2

(12) United States Patent
Falco et al.

(10) Patent No.: US 8,293,533 B2
(45) Date of Patent: Oct. 23, 2012

(54) SITE-SPECIFIC INTEGRATION AND STACKING OF TRANSGENES IN SOYBEAN VIA DNA RECOMBINASE MEDIATED CASSETTE EXCHANGE

(75) Inventors: Saverio Carl Falco, Wilmington, DE (US); Zhongsen Li, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 250 days.

(21) Appl. No.: 12/634,775

(22) Filed: Dec. 10, 2009

(65) Prior Publication Data
US 2010/0162436 A1  Jun. 24, 2010

Related U.S. Application Data

(60) Provisional application No. 61/138,995, filed on Dec. 19, 2008.

(51) Int. Cl.
*C12N 15/82* (2006.01)
*A01H 5/00* (2006.01)
(52) U.S. Cl. ......... 435/468; 435/419; 800/278; 800/312
(58) Field of Classification Search ........................ None
See application file for complete search history.

(56) References Cited

U.S. PATENT DOCUMENTS

| 5,380,831 | A |   | 1/1995  | Adang et al.    |
|-----------|---|---|---------|-----------------|
| 5,436,391 | A |   | 7/1995  | Fujimoto et al. |
| 6,967,263 | B2| * | 11/2005 | Narvel ........................... 800/312 |

FOREIGN PATENT DOCUMENTS

| EP | 0359472     |   | 12/1995 |
|----|-------------|---|---------|
| EP | 0385962     |   | 7/2001  |
| WO | 91/16432    |   | 10/1991 |
| WO | 99/25821    |   | 5/1999  |
| WO | 99/25840    |   | 5/1999  |
| WO | 99/25854    |   | 5/1999  |
| WO | 99/25855    |   | 5/1999  |
| WO | WO 99/25821 | * | 5/1999  |
| WO | 01/11058    |   | 2/2001  |
| WO | 2007/011733 |   | 1/2007  |

OTHER PUBLICATIONS

Zhongsen Li et al., A *Cre/loxP*-mediated self-activating gene excision system to produce marker gene free transgenic soybean plants, Plant Mol. Biol., 2007, pp. 329-341, vol. 65.
L. Alexander Lyznik et al., Application of Site-Specific Recombination Systems for Targeted modification of Plant Genomes, Transgenic plant journal, 2007, pp. 1-9, vol. 1, No. 1.
Adam T. Watson et al., Gene tagging and gene replacement using recombinase-mediated cassette exchange in *Schizosaccharomyces pombe*, Gene Elsevier, 2006, pp. 63-74, vol. 407.
International Search Report.
Ken Abrembski et al., Bacteriophage P1 Site-specific Recombination, The Journal of Biological Chemistry, Feb. 10, 1984, vol. 259, No. 3, pp. 1509-1514.

Henrik Albert et al., Site-specific integration of DNA into wild-type and mutant lox sites placed in the plant genome. The Plant Journal, 1995, vol. 7, No. 4, pp. 649-659.
Alexandra Baer et al., Coping with kinetic and thermodynamic barriers: RMCE, an efficient strategy for the targeted integration of transgenes, Current Opinion in Biotechnology, 2001 vol. 12, pp. 473-480.
Rekha Chawla et al., Transgene expression produced by biolistic-mediated, site-specific gene integration is consistently inherited by the subsequent generations, Plant, Biotechnology Journal, 2006, vol. 4, pp. 208-218.
Liane Chen et al., Production and Characterization of Human 293 Cell Lines Expressing the Site-Specific Recombinase Cre, Somatic Cell and Molecular Genetics, 1996, vol. 22, No. 6, pp. 477-488.
Michael M Cox, The FLP protein of the yeast 2-μm plasmid: Expression of a eukaryotic genetic recombination system in *Esherichia coli*, Jul. 1983, Proc. Natl. Acad. Sci., vol. 80, pp. 4223-4227.
Christopher D. Day et al., Transgene integration into the same chromosome location can produce alleles that express at a predictable level, or alleles that are differentially silenced, Genes & Development, 2000, vol. 14, pp. 2869-2880.
Vesna Djukanovic et al., Gene conversion in transgenic maize plants expressing FLP/FRT and Cre/LoxP site-specific recombinations systems, Plant Biotechnology Journal, 2006, vol. 4, pp. 345-357.
Amy C. Groth et al., Phage Integrases: Biology and Applications J. Mol. Biol. 2004, vol. 335, pp. 667-678.
Feng Guo et al., Structure of Cre recombinase complexed with DNA in site-specific recombination synapse, Nature, Sep. 4, 1997, vol. 389, pp. 40-46.
Carsten Horn et al., Site-specific genorilie targeting in *Drosophila*, PNAS, Aug. 30, 2005, vol. 102, No. 35, pp. 12483-12488.
Shigeru Iida et al., Modification of endogenous natural genes by gene targeting in rice and other higher plants, Plant Molecular Biology, 2005, vol. 59, pp. 205-219.
Matthias Lauth et al., Stable and efficient cassette exchange under non-selectabie conditions by combines use of two site-specific recombinases, Nucleic Acids Research, 2002, vol. 30, No. 21 e115 pp. 1-7.
Zhongsen Li et al., Site-Specific Integration of Transgenes in Soybean via Recombinase-Mediated DNA Cassette Exchange [OA], Plant Physiology, Nov. 2009, vol. 151, pp. 1087-1095.

(Continued)

*Primary Examiner* — Cynthia Collins
(74) *Attorney, Agent, or Firm* — Alston & Bird LLP

(57) ABSTRACT

A targeting method is described that allows precise cassette replacement at a previously characterized genetic locus. A target DNA construct containing a pair of incompatible FRT sites flanking a target cassette was introduced into soybean by regular biolistic transformation. Transgenic events containing a single complete copy of the target site were then selected and retransformed with a donor DNA construct containing the identical pair of incompatible FRT sites flanking a donor cassette. Precise DNA cassette exchange happened between the target cassette and the donor cassette via recombinase mediated cassette exchange (RMCE) so that the donor cassette was introduced at the exact genomic site previously occupied by the target cassette. Through repeated RMCE using additional incompatible FRT sites, multiple groups of transgenes can be stacked at the same genomic locus.

19 Claims, 27 Drawing Sheets

OTHER PUBLICATIONS

Jeanne D. Louwerse et al., Stable Recombinase-Mediated Cassette Exchange in *Arabidopsis* Using *Agrobacterium tumefaciens*, Plant Physiology, Dec. 2007, vol. 145, pp. 1282-1293.

Leszek A. Lyznik et al., Activity oss yeast FLP recombinase in maize and rice protoplasts, Nucleic Acids Research, 1993, vol. 21, No. 4, pp. 969-975.

Elizabeth E. Murray et al., Codon usage in plant genes, Nucleic Acids Research, 1989, vol. 17, No. 2, pp. 477-498.

Kazuya Nanto et al., Agrobacterium-mediated RMCE approach for gene replacement, Plant Biotechnology Journal, 2005, vol. 3, pp. 203-214.

David W. Ow, Recombinase-directed plant transformation for the post-genomic era. Plant Molecular Biology, 2002, vol. 48, pp. 183-200.

Frederick, J. Perlak et al., Modification of the coding sequence enhances plant expression of insect control protein genes, Proc. Natl., Acad. Sci., Apr. 1991, vol. 88, pp. 3324-3328.

Thomas Schlake et al., Use of Mutated FLP Recognition Target (FRT) Sites for the Exchange of Expression Cassettes at Defined Chromosomal Loci, Biochemistry, 1994, Vol. 33, pp. 12746-12751.

A. C. Shaikh et al., The Cre Recombinase Cleaves the lox Site in trans, The Journal of Biological Chemistry, Feb. 28, 1997, vol. 272, No. 9, pp. 5695-5702.

Vibha Srivastava et al., Cre-mediated site-specific gene integration for consistent transgene expression in rice, Plant Biotechnology Journal, 2004, vol. 2, pp. 169-179.

Vibha Srivastava et al., Biolistic medited site-specific integration in rice, Molecular Breeding, 2001, vol. 8, pp. 345-350.

Vigha Srivastava et al., Marker-free site-specific gene integration in plants, TRENDS in Biotechnology, 2004, vol. 22, No. 12, pp. 627-629.

K. Ryan Trinh et al., Site-specific and directional gene replacement mediated by Cre recombinase, Journal of Immunological Methods, 2000, vol. 244, pp. 185-193.

Annette C. Vergunst et al., Site-specific integration of Agrobacterium T-DNA in *Arabidopsis thaliana* mediated by Cre recombinase, Nucleic Acids Research, 1998, vol. 26, No. 11, pp. 2729-2734.

David A. Wright et al., High-frequency homologous recombination in plants mediated by zinc-finger nucleases, The Plant Journal, 2006, vol. 44, 693-705, pp. 693-705.

* cited by examiner

FIG 1A - Target DNA fragment QC288A (4544 bp)
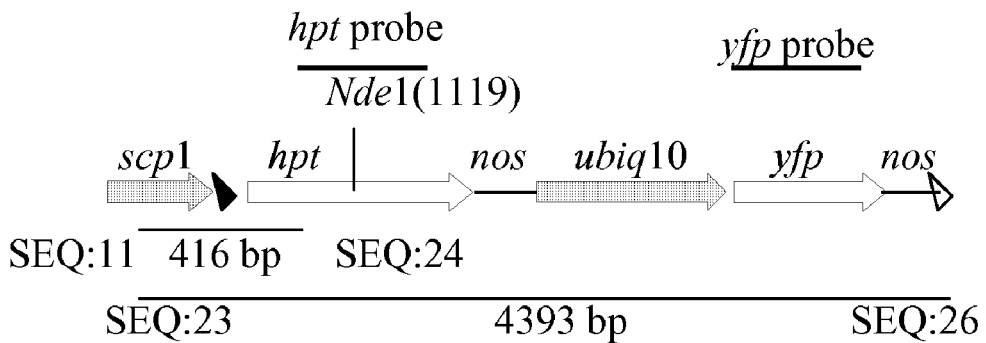
FIG. 1B - Donor construct QC329 (8533 bp)
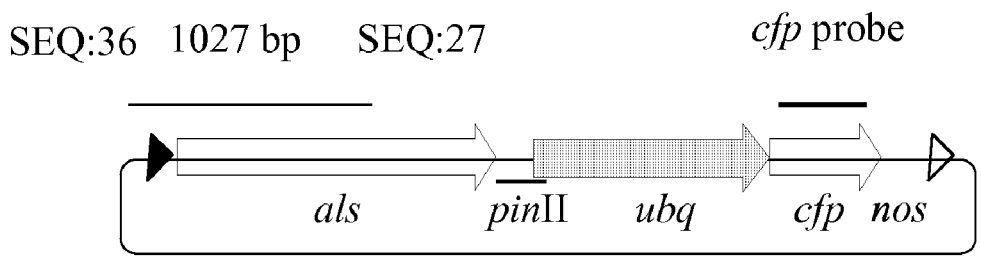
FIG. 1C - RMCE DNA QC288A329 (6133 bp)
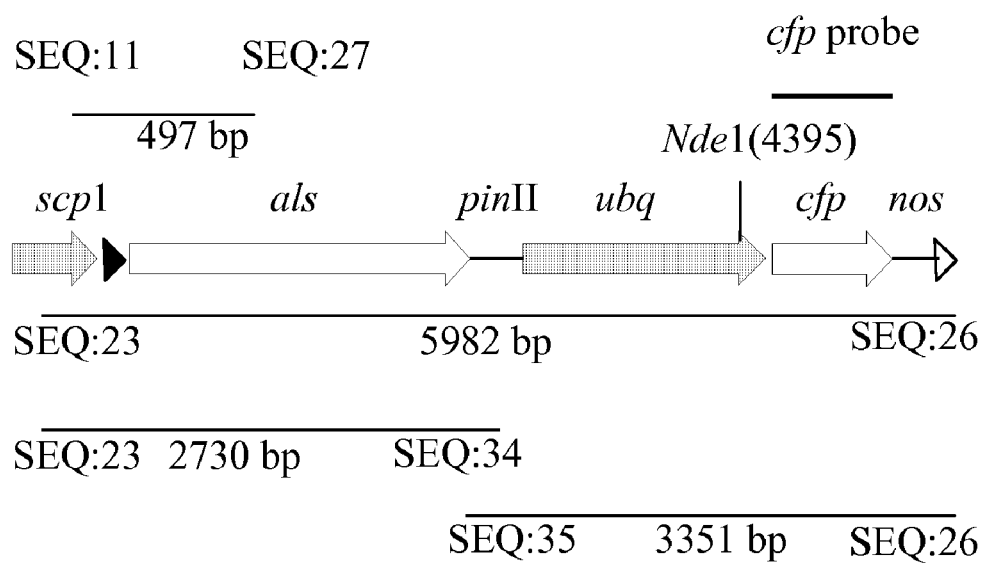

FLP Construct QC292 (4861 bp)

SEQ:11     368 bp     SEQ:37

RMCE PCR Positive Control DNA QC165 (5794 bp)

SEQ:11     426 bp     SEQ:27

SEQ:36     982 bp     SEQ:27

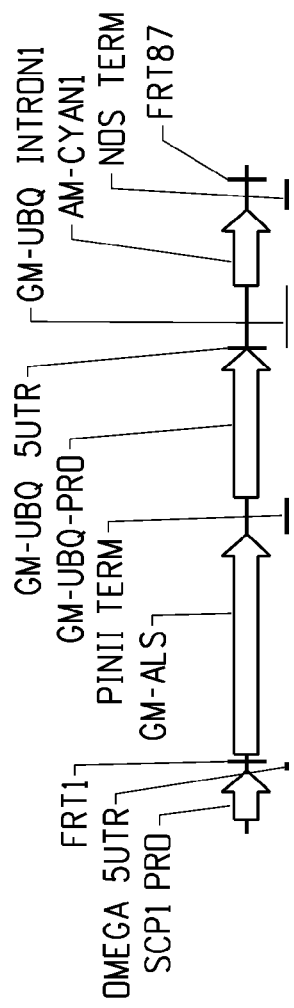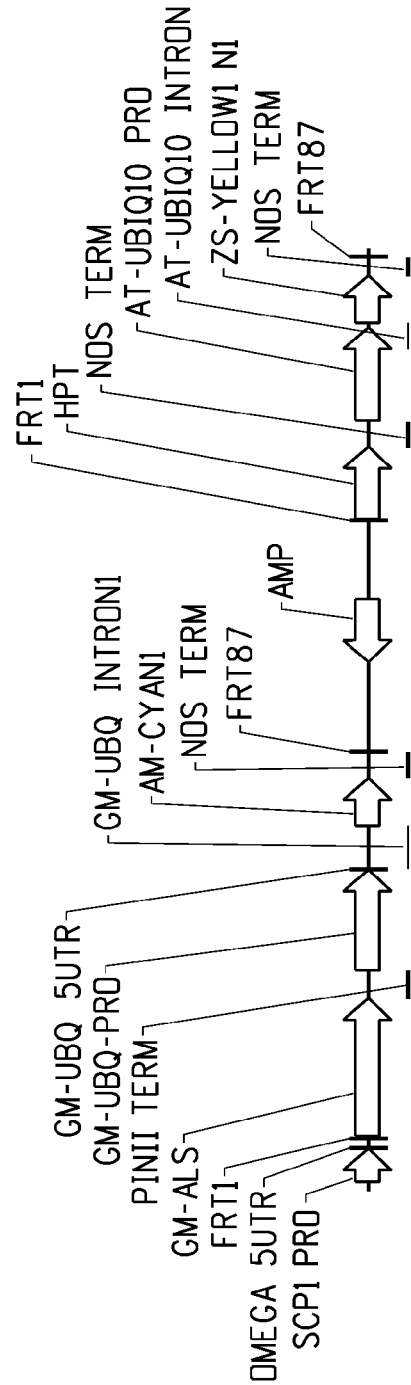

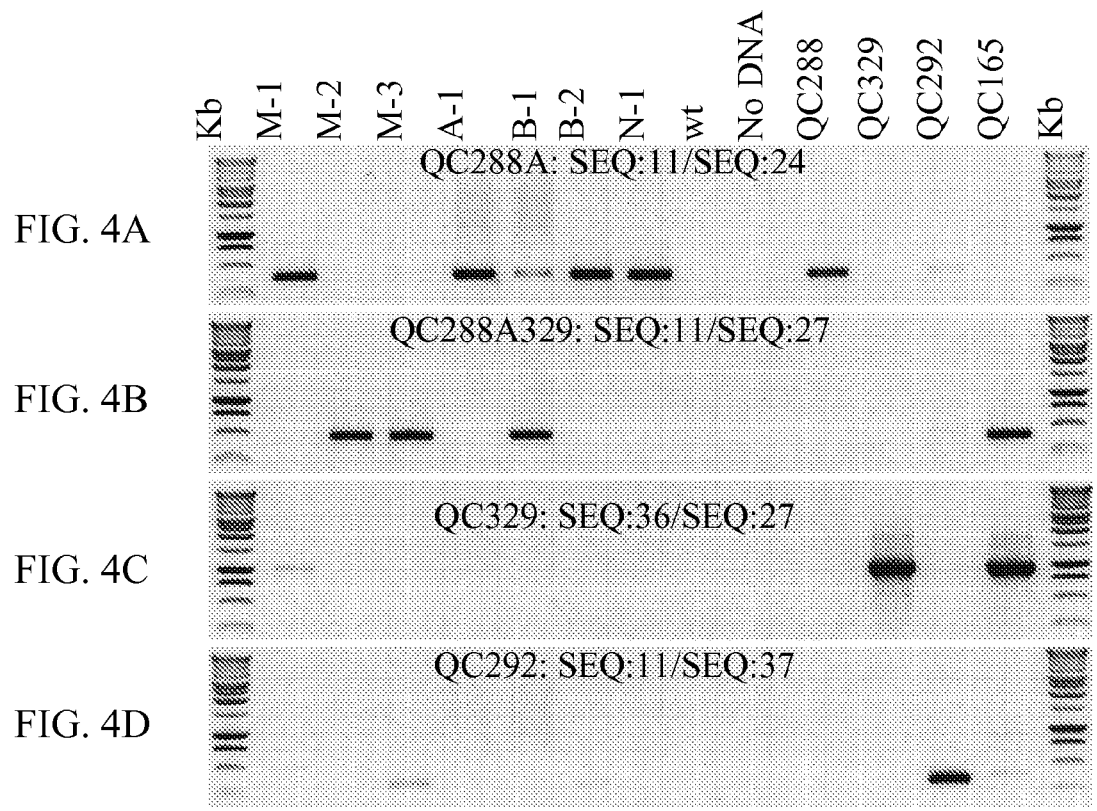

*yfp*

*cfp*

| Event | CFP | FRT1 PCR | qPCR | | | | RMCE PCR | | Target PCR | | Full length PCR | | |
| --- | --- | --- | --- | --- | --- | --- | --- | --- | --- | --- | --- | --- | --- |
| | | | RMCE | Donor | Target | Flp | 5' end | 3' end | 5' end | 3' end | Excision | Target | RMCE |
| A1 | + | + | 1.1 | 1.6 | | | + | + | - | - | + | - | - |
| A2 | + | + | 1.3 | 0.9 | | 1.0 | + | + | - | - | + | - | - |
| A3 | - | - | | 5.1 | 1.4 | | - | - | + | + | - | + | - |
| B1 | + | + | 1.1 | | | | + | + | - | - | + | - | - |
| B2 | + | + | 1.2 | 0.7 | | | + | + | - | - | + | - | - |
| B3 | + | + | 1.1 | | | | + | + | - | - | + | - | - |
| B4 | + | + | 1.3 | | | | + | + | - | - | + | - | - |
| C1 | + | + | 1.0 | 1.0 | 0.01 | | + | + | + | + | + | - | - |
| C2 | + | + | 1.9 | | | | + | + | - | - | - | - | + |
| C3 | + | + | 2.0 | 0.9 | | | + | + | - | - | - | - | + |

FIG. 6

| Event | CFP | FRT1 PCR | qPCR | | | | RMCE PCR | | Target PCR | | Full length PCR | | |
|---|---|---|---|---|---|---|---|---|---|---|---|---|---|
| | | | RMCE | Donor | Target | Flp | 5' end | 3' end | 5' end | 3' end | Excision | Target | RMCE |
| A1 | + | + | 1.1 | 1.6 | | | + | + | - | - | + | - | - |
| A2 | + | + | 1.3 | 0.9 | | 1.0 | + | + | - | - | + | - | - |
| A3 | - | - | | 5.1 | 1.4 | | - | - | + | + | - | + | - |
| B1 | + | + | 1.1 | | | | + | + | - | - | + | - | - |
| B2 | + | + | 1.2 | 0.7 | | | + | + | - | - | + | - | - |
| B3 | + | + | 1.1 | | | | + | + | - | - | + | - | - |
| B4 | + | + | 1.3 | | | | + | + | - | - | + | - | - |
| C1 | + | + | 1.0 | | 0.01 | | + | + | + | + | - | - | - |
| C2 | + | + | 1.9 | 1.0 | | | + | + | - | - | - | - | + |
| C3 | + | + | 2.0 | 0.9 | | | + | + | - | - | - | - | + |

```
Target     aacattacaattactattttacaattacagtcgacccaacaFRT1 cactagtccatgaaaaagcctgaactcaccgcgacgtctg
                      scp1 promoter                                    hpt coding sequence
RMCE       aacattacaattactattttacaattacagtcgacccaacaFRT1 CACTAGTGAGGATCTGATCATGCCACACAACACAATGGCG
                      scp1 promtoer                                    als coding sequence
Excision   aacattacaattactattttacaattacagtcgacccaacaFRT1 actagagcttgcggccgccccctggccggccactagtga
                      scp1 promoter                                    QC288A 3' end
Excision   aacattacaattactattttacaattacagtcgacccaacaFRT87 actagagcttgcggccgccccctggccggccactagtga
                      scp1 promoter                                    QC288A 3' end
```

FIG. 10B

```
Target     cgccttcccagcgccctggcctgagagct-nos term-FRT87 actagagcttgcggccgccccctggccggccactagtga
                      yfp coding sequence                        QC288A 3' end
RMCE       CATCACCTCCGTGGTGCCCTTCTGAGAGCT-NOS TERM-FRT87 actagagcttgcggccgccccctggccggccactagtga
                      cfp coding sequence                        QC288A 3' end
```

First round RMCE DNA QC288A422

Second round RMCE DNA QC288A422-429

Second round RMCE DNA QC288A422-459

Third round RMCE DNA QC288A422-459-460

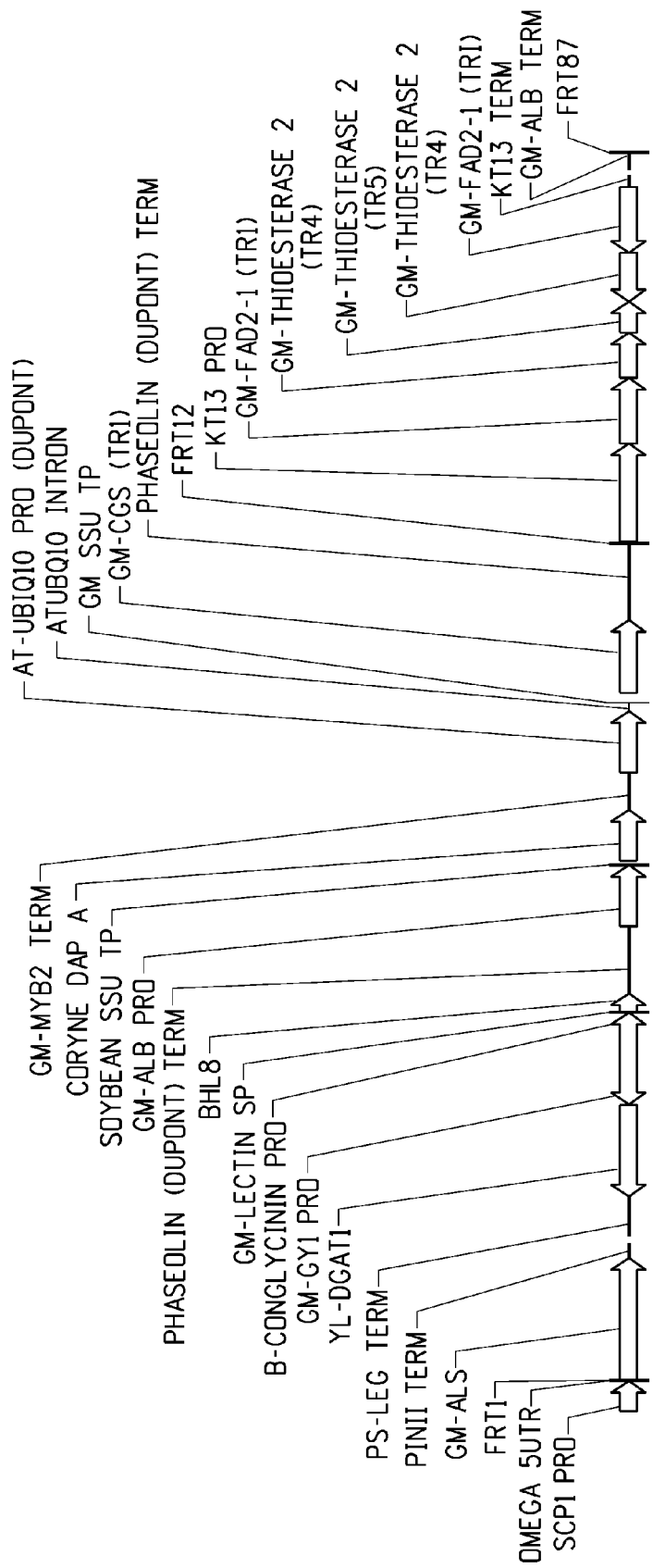

SEQUENCE LISTING

<160> NUMBER OF SEQ ID NOS: 94

<210> SEQ ID NO 1
<211> LENGTH: 4544
<212> TYPE: DNA
<213> ORGANISM: Artificial Sequence
<220> FEATURE:
<223> OTHER INFORMATION: Target DNA fragment QC288A

<400> SEQUENCE: 1

```
cgcgccggta ccgggccccc cctcgagcgg ccgcagattt aggtgacact atagaatatg      60
catcactagt aagcttgcat gcctgcaggt ttaaacagtc gactctagag atccgtcaac     120
atggtggagc acgacactct cgtctactcc aagaatatca aagatacagt ctcagaagac     180
caaagggcta ttgagacttt tcaacaaagg gtaatatcgg gaaacctcct cggattccat     240
tgcccagcta tctgtcactt catcaaaagg acagtagaaa aggaaggtgg cacctacaaa     300
tgccatcatt gcgataaagg aaaggctatc gttcaagatg cctctgccga cagtggtccc     360
aaagatggac ccccacccac gaggagcatc gtggaaaaag aagacgttcc aaccacgtct     420
tcaaagcaag tggattgatg tgatgatcct atgcgtatgg tatgacgtgt gttcaagatg     480
atgacttcaa acctacctat gacgtatggt atgacgtgtg tcgactgatg acttagatcc     540
```

```
actcgagcgg ctataaatac gtacctacgc accctgcgct accatcccta gagctgcagc      600 ttattttttac aacaattacc aacaacaaca aacaacaaac aacattacaa ttactattta     660
caattacagt cgacccaaca gaagttccta ttccgaagtt cctattctct agaaagtata      720
ggaacttcca ctagtccatg aaaaagcctg aactcaccgc gacgtctgtc gagaagtttc      780
tgatcgaaaa gttcgacagc gtctccgacc tgatgcagct ctcggagggc gaagaatctc      840
gtgctttcag cttcgatgta ggagggcgtg atatgtcct gcgggtaaat agctgcgccg       900
atggtttcta caaagatcgt tatgtttatc ggcactttgc atcggccgcg ctcccgattc      960
cggaagtgct tgacattggg gaattcagcg agagcctgac ctattgcatc tcccgccgtg     1020
cacagggtgt cacgttgcaa gacctgcctg aaaccgaact gcccgctgtt ctgcagccgg     1080
tcgcggaggc catggatgcg atcgctgcgg ccgatcttag ccagacgagc gggttcggcc     1140
cattcggacc gcaaggaatc ggtcaataca ctacatggcg tgatttcata tgcgcgattg     1200
ctgatcccca tgtgtatcac tggcaaactg tgatggacga caccgtcagt gcgtccgtcg     1260
cgcaggctct cgatgagctg atgctttggg ccgaggactg ccccgaagtc cggcacctcg     1320
tgcacgcgga tttcggctcc aacaatgtcc tgacggacaa tggccgcata acagcggtca     1380
ttgactggag cgaggcgatg ttcggggatt cccaatacga ggtcgccaac atcttcttct     1440
ggaggccgtg gttggcttgt atggagcagc agacgcgcta cttcgagcgg aggcatccgg     1500
agcttgcagg atcgccgcgg ctcccgggcgt atatgctccg cattggtctt gaccaactct     1560
atcagagctt ggttgacggc aatttcgatg atgcagcttg ggcgcagggt cgatgcgacg     1620
caatcgtccg atccggagcc gggactgtcg ggcgtacaca aatcgcccgc agaagcgcgg     1680
ccgtctggac cgatggctgt gtagaagtac tcgccgatag tggaaaccga cgccccagca     1740
ctcgtccgag ggcaaaggaa tagtgaggta cctaaagaag gagtgcgtcg aagcagatcg     1800
ttcaaacatt tggcaataaa gtttcttaag attgaatcct gttgccggtc ttgcgatgat     1860
tatcatataa tttctgttga attacgttaa gcatgtaata attaacatgt aatgcatgac     1920
gttatttatg agatgggttt ttatgattag agtcccgcaa ttatacattt aatacgcgat     1980
agaaaacaaa atatagcgcg caaactagga taaattatcg cgcgcggtgt catctatgtt     2040
actagatcga tgtcgacccg ggctgcagga attcgatatc aagcttatcg tcgacctgca     2100
ggtcaacgga tcaggatatt cttgtttaag atgttgaact ctatggaggt ttgtatgaac     2160
tgatgatcta ggaccggata agttcccttc ttcatagcga acttattcaa agaatgtttt     2220
gtgtatcatt cttgttacat tgttattaat gaaaaaatat tattggtcat tggactgaac     2280
acgagtgtta aatatggacc aggccccaaa taagatccat tgatatatga attaaataac     2340
aagaataaat cgagtcacca aaccacttgc cttttttaac gagacttgtt caccaacttg     2400
atacaaaagt cattatccta tgcaaatcaa taatcataca aaatatccaa ataacactaa     2460
aaaattaaaa gaaatggata atttcacaat atgttatacg ataaagaagt tacttttcca     2520
agaaattcac tgattttata agcccacttg cattagataa atggcaaaaa aaaacaaaaa     2580
ggaaaagaaa taaagcacga agaattctag aaaatacgaa atacgcttca atgcagtggg     2640
acccacggtt caattattgc caattttcag ctccaccgta tatttaaaaa ataaaacgat     2700
aatgctaaaa aaatataaat cgtaacgatc gttaaatctc aacggctgga tcttatgacg     2760
accgttagaa attgtggttg tcgacgagtc agtaataaac ggcgtcaaag tggttgcagc     2820
cggcacacac gagtcgtgtt tatcaactca aagcacaaat actttcctc aacctaaaaa      2880 taaggcaatt agccaaaaac aactttgcgt gtaaacaacg ctcaatacac gtgtcatttt     2940
```

```
attattagct attgcttcac cgccttagct ttctcgtgac ctagtcgtcc tcgtctttc    3000 ttcttcttct tctataaaac aatacccaaa gagctcttct tcttcacaat tcagatttca    3060
atttctcaaa atcttaaaaa ctttctctca attctctcta ccgtgatcaa ggtaaatttc    3120
tgtgttcctt attctctcaa aatcttcgat tttgttttcg ttcgatccca atttcgtata    3180
tgttctttgg tttagattct gttaatctta gatcgaagac gattttctgg gtttgatcgt    3240
tagatatcat cttaattctc gattagggtt tcataaatat catccgattt gttcaaataa    3300
tttgagtttt gtcgaataat tactcttcga tttgtgattt ctatctagat ctggtgttag    3360
tttctagttt gtgcgatcga atttgtcgat taatctgagt ttttctgatt aacagatgca    3420 gatccccgg atccatggcc cacagcaagc acggcctgaa ggaggagatg accatgaagt    3480
accacatgga gggctgcgtg aacgccaca agttcgtgat caccggcgag gcatcggct    3540 accccttcaa gggcaagcag accatcaacc tgtgcgtgat cgagggcggc cccctgccct    3600
tcagcgagga catcctgagc gccggcttca gtacggcga ccggatcttc accgagtacc    3660
cccaggacat cgtggactac ttcaagaaca gctgccccgc cggctacacc tggggccgga    3720
gcttcctgtt cgaggacggc gccgtgtgca tctgtaacgt ggacatcacc gtgagcgtga    3780
aggagaactg catctaccac aagagcatct tcaacggcgt gaacttcccc gccgacggcc    3840
ccgtgatgaa gaagatgacc accaactggg aggccagctg cgagaagatc atgcccgtgc    3900
ctaagcaggg catcctgaag ggcgacgtga gcatgtacct gctgctgaag gacggcggcc    3960
ggtaccggtg ccagttcgac accgtgtaca aggccaagag cgtgcccagc aagatgcccg    4020
agtggcactt catccagcac aagctgctgc gggaggaccg gagcgacgcc aagaaccaga    4080
agtggcagct gaccgagcac gccatcgcct tccccagcgc cctggcctga gagctcgaat    4140
ttccccgatc gttcaaacat ttggcaataa agtttcttaa gattgaatcc tgttgccggt    4200
cttgcgatga ttatcatata atttctgttg aattacgtta agcatgtaat aattaacatg    4260
taatgcatga cgttatttat gagatgggtt tttatgatta gagtcccgca attatacatt    4320
taatacgcga tagaaaacaa aatatagcgc gcaaactagg ataaattatc gcgcgcggtg    4380
tcatctatgt tactagatcg ggaattctag tggccggccc agctgatgat cccggtgaag    4440
ttcctattcc gaagttccta ttctccagaa agtataggaa cttcactaga gcttgcggcc    4500 gcccctggg ccggccacta gtgagctcgg tacccggta ccgg                    4544
```

<210> SEQ ID NO 2
<211> LENGTH: 7058
<212> TYPE: DNA
<213> ORGANISM: Artificial Sequence
<220> FEATURE:
<223> OTHER INFORMATION: Target construct QC288

<400> SEQUENCE: 2

```
cgcgccggta ccgggccccc cctcgagcgg ccgcagattt aggtgacact atagaatatg      60
catcactagt aagcttgcat gcctgcaggt ttaaacagtc gactctagag atccgtcaac     120
atggtggagc acgacactct cgtctactcc aagaatatca agatacagt ctcagaagac     180 caaagggcta ttgagacttt tcaacaaagg gtaatatcgg gaaacctcct cggattccat     240
tgcccagcta tctgtcactt catcaaaagg acagtagaaa aggaaggtgg cacctacaaa     300
tgccatcatt gcgataaagg aaaggctatc gttcaagatg cctctgccga cagtggtccc     360
aaagatggac ccccacccac gaggagcatc gtggaaaaag aagacgttcc aaccacgtct     420
tcaaagcaag tggattgatg tgatgatcct atgcgtatgg tatgacgtgt gttcaagatg     480
```

```
atgacttcaa acctacctat gacgtatggt atgacgtgtg tcgactgatg acttagatcc      540
actcgagcgg ctataaatac gtacctacgc accctgcgct accatcccta gagctgcagc      600
ttatttttac aacaattacc aacaacaaca aacaacaaac aacattacaa ttactattta      660
caattacagt cgacccaaca gaagttccta ttccgaagtt cctattctct agaaagtata      720
ggaacttcca ctagtccatg aaaaagcctg aactcaccgc gacgtctgtc gagaagtttc      780
tgatcgaaaa gttcgacagc gtctccgacc tgatgcagct ctcggagggc gaagaatctc      840
gtgctttcag cttcgatgta ggagggcgtg gatatgtcct gcgggtaaat agctgcgccg      900
atggtttcta caaagatcgt tatgtttatc ggcactttgc atcggccgcg ctcccgattc      960
cggaagtgct tgacattggg gaattcagcg agagcctgac ctattgcatc tcccgccgtg     1020
cacagggtgt cacgttgcaa gacctgcctg aaaccgaact gcccgctgtt ctgcagccgg     1080
tcgcggaggc catggatgcg atcgctgcgg ccgatcttag ccagacgagc gggttcggcc     1140
cattcggacc gcaaggaatc ggtcaataca ctacatggcg tgatttcata tgcgcgattg     1200
ctgatcccca tgtgtatcac tggcaaactg tgatggacga caccgtcagt gcgtccgtcg     1260
cgcaggctct cgatgagctg atgctttggg ccgaggactg ccccgaagtc cggcacctcg     1320
tgcacgcgga tttcggctcc aacaatgtcc tgacggacaa tggccgcata acagcggtca     1380
ttgactggag cgaggcgatg ttcgggatt cccaatacga ggtcgccaac atcttcttct     1440
ggaggccgtg gttggcttgt atggagcagc agacgcgcta cttcgagcgg aggcatccgg     1500
agcttgcagg atcgccgcgg ctccgggcgt atatgctccg cattggtctt gaccaactct     1560
atcagagctt ggttgacggc aatttcgatg atgcagcttg ggcgcagggt cgatgcgacg     1620
caatcgtccg atccggagcc gggactgtcg ggcgtacaca atcgcccgc agaagcgcgg     1680 ccgtctggac cgatggctgt gtagaagtac tcgccgatag tggaaaccga cgccccagca     1740
ctcgtccgag ggcaaaggaa tagtgaggta cctaaagaag gagtgcgtcg aagcagatcg     1800
ttcaaacatt tggcaataaa gtttcttaag attgaatcct gttgccggtc ttgcgatgat     1860
tatcatataa tttctgttga attacgttaa gcatgtaata attaacatgt aatgcatgac     1920
gttatttatg agatgggttt ttatgattag agtcccgcaa ttatacattt aatacgcgat     1980
agaaaacaaa atatagcgcg caaactagga taaattatcg cgcgcggtgt catctatgtt     2040
actagatcga tgtcgacccg ggctgcagga attcgatatc aagcttatcg tcgacctgca     2100
ggtcaacgga tcaggatatt cttgtttaag atgttgaact ctatggaggt ttgtatgaac     2160
tgatgatcta ggaccggata agttcccttc ttcatagcga acttattcaa agaatgtttt     2220
gtgtatcatt cttgttacat tgttattaat gaaaaatat tattggtcat tggactgaac     2280
acgagtgtta aatatggacc aggccccaaa taagatccat tgatatatga attaaataac     2340
aagaataaat cgagtcacca aaccacttgc cttttttaac gagacttgtt caccaacttg     2400
atacaaaagt cattatccta tgcaaatcaa taatcataca aaaatatcca ataacactaa     2460
aaaattaaaa gaaatggata atttcacaat atgttatacg ataagaagt tacttttcca      2520 agaaattcac tgattttata agcccacttg cattagataa atggcaaaaa aaaacaaaaa     2580
ggaaaagaaa taaagcacga agaattctag aaaatacgaa atacgcttca atgcagtggg     2640
acccacggtt caattattgc caattttcag ctccaccgta tatttaaaaa ataaaacgat     2700
aatgctaaaa aaatataaat cgtaacgatc gttaaatctc aacggctgga tcttatgacg     2760
accgttagaa attgtggttg tcgacgagtc agtaataaac ggcgtcaaag tggttgcagc     2820
cggcacacac gagtcgtgtt tatcaactca aagcacaaat acttttcctc aacctaaaaa     2880
```

```
taaggcaatt agccaaaaac aactttgcgt gtaaacaacg ctcaatacac gtgtcatttt    2940
attattagct attgcttcac cgccttagct ttctcgtgac ctagtcgtcc tcgtcttttc    3000
ttcttcttct tctataaaac aatacccaaa gagctcttct tcttcacaat tcagatttca    3060
atttctcaaa atcttaaaaa ctttctctca attctctcta ccgtgatcaa ggtaaatttc    3120
tgtgttcctt attctctcaa aatcttcgat tttgttttcg ttcgatccca atttcgtata    3180
tgttctttgg tttagattct gttaatctta gatcgaagac gattttctgg gtttgatcgt    3240
tagatatcat cttaattctc gattagggtt tcataaatat catccgattt gttcaaataa    3300
tttgagtttt gtcgaataat tactcttcga tttgtgatt t ctatctagat ctggtgttag    3360
tttctagttt gtgcgatcga atttgtcgat taatctgagt ttttctgatt aacagatgca    3420
gatcccccgg atccatggcc cacagcaagc acggcctgaa ggaggagatg accatgaagt    3480
accacatgga gggctgcgtg aacggccaca agttcgtgat caccggcgag ggcatcggct    3540 acccccttcaa gggcaagcag accatcaacc tgtgcgtgat cgagggcggc cccctgccct    3600
tcagcgagga catcctgagc gccggcttca gtacggcga ccggatcttc accgagtacc    3660
cccaggacat cgtggactac ttcaagaaca gctgccccgc cggctacacc tggggccgga    3720
gcttcctgtt cgaggacggc gccgtgtgca tctgtaacgt ggacatcacc gtgagcgtga    3780
aggagaactg catctaccac aagagcatct caacggcgt gaacttcccc gccgacggcc    3840
ccgtgatgaa gaagatgacc accaactggg aggccagctg cgagaagatc atgcccgtgc    3900
ctaagcaggg catcctgaag ggcgacgtga gcatgtacct gctgctgaag gacggcggcc    3960
ggtaccggtg ccagttcgac accgtgtaca aggccaagag cgtgcccagc aagatgcccg    4020
agtggcactt catccagcac aagctgctgc gggaggaccg gagcgacgcc aagaaccaga    4080
agtggcagct gaccgagcac gccatcgcct tccccagcgc cctggcctga gagctcgaat    4140
ttccccgatc gttcaaacat ttggcaataa agtttcttaa gattgaatcc tgttgccggt    4200
cttgcgatga ttatcatata atttctgttg aattacgtta agcatgtaat aattaacatg    4260
taatgcatga cgttattat gagatggggtt tttatgatta gagtcccgca attatacatt    4320
taatacgcga tagaaaacaa aatatagcgc gcaaactagg ataaattatc gcgcgcggtg    4380
tcatctatgt tactagatcg ggaattctag tggccggccc agctgatgat cccggtgaag    4440
ttcctattcc gaagttccta ttctccagaa agtataggaa cttcactaga gcttgcggcc    4500 gcccccctggg ccggccacta gtgagctcgg tacccgggta ccggcgcgcc cgatcatccg    4560
gatatagttc ctcctttcag caaaaaaccc ctcaagaccc gtttagaggc cccaaggggt    4620
tatgctagtt attgctcagc ggtggcagca gccaactcag cttcctttcg ggctttgtta    4680
gcagccggat cgatccaagc tgtacctcac tattcctttg ccctcggacg agtgctgggg    4740
cgtcggtttc cactatcggc gagtacttct acacagccat cggtccagac ggccgcgctt    4800
ctgcgggcga tttgtgtacg cccgacagtc ccggctccgg atcggacgat tgcgtcgcat    4860
cgaccctgcg cccaagctgc atcatcgaaa ttgccgtcaa ccaagctctg atagagttgg    4920
tcaagaccaa tgcggagcat atacgcccgg agccgcggcg atcctgcaag ctccggatgc    4980
ctccgctcga agtagcgcgt ctgctgctcc atacaagcca accacggcct ccagaagaag    5040
atgttggcga cctcgtattg ggaatccccg aacatcgcct cgctccagtc aatgaccgct    5100
gttatgcggc cattgtccgt caggacattg ttggagccga atccgcgtg cacgaggtgc    5160 cggacttcgg ggcagtcctc ggcccaaagc atcagctcat cgagagcctg cgcgacggac    5220
gcactgacgg tgtcgtccat cacagtttgc cagtgataca catgggatc agcaatcgcg    5280
```

| | |
|---|---|
| catatgaaat cacgccatgt agtgtattga ccgattcctt gcggtccgaa tgggccgaac | 5340 |
| ccgctcgtct ggctaagatc ggccgcagcg atcgcatcca tagcctccgc gaccggctgc | 5400 |
| agaacagcgg gcagttcggt ttcaggcagg tcttgcaacg tgacaccctg tgcacggcgg | 5460 |
| gagatgcaat aggtcaggct ctcgctgaat tccccaatgt caagcacttc cggaatcggg | 5520 |
| agcgcggccg atgcaaagtg ccgataaaca taacgatctt tgtagaaacc atcggcgcag | 5580 |
| ctatttaccc gcaggacata tccacgccct cctacatcga agctgaaagc acgagattct | 5640 |
| tcgccctccg agagctgcat caggtcggag acgctgtcga acttttcgat cagaaacttc | 5700 |
| tcgacagacg tcgcggtgag ttcaggcttt tccatgggta tatctccttc ttaaagttaa | 5760 |
| acaaaattat ttctagaggg aaaccgttgt ggtctcccta tagtgagtcg tattaatttc | 5820 |
| gcgggatcga gatctgatca acctgcatta atgaatcggc caacgcgcgg ggagaggcgg | 5880 |
| tttgcgtatt gggcgctctt ccgcttcctc gctcactgac tcgctgcgct cggtcgttcg | 5940 |
| gctgcggcga gcggtatcag ctcactcaaa ggcggtaata cggttatcca cagaatcagg | 6000 |
| ggataacgca ggaaagaaca tgtgagcaaa aggccagcaa aaggccagga accgtaaaaa | 6060 |
| ggccgcgttg ctggcgtttt tccataggct ccgcccccct gacgagcatc acaaaaatcg | 6120 |
| acgctcaagt cagaggtggc gaaacccgac aggactataa agataccagg cgtttccccc | 6180 |
| tggaagctcc ctcgtgcgct ctcctgttcc gaccctgccg cttaccggat acctgtccgc | 6240 |
| ctttctccct tcgggaagcg tggcgctttc tcaatgctca cgctgtaggt atctcagttc | 6300 |
| ggtgtaggtc gttcgctcca agctgggctg tgtgcacgaa ccccccgttc agcccgaccg | 6360 |
| ctgcgcctta tccggtaact atcgtcttga gtccaacccg gtaagacacg acttatcgcc | 6420 |
| actggcagca gccactggta acaggattag cagagcgagg tatgtaggcg gtgctacaga | 6480 |
| gttcttgaag tggtggccta actacggcta cactagaagg acagtatttg gtatctgcgc | 6540 |
| tctgctgaag ccagttacct tcggaaaaag agttggtagc tcttgatccg gcaaacaaac | 6600 |
| caccgctggt agcggtggtt tttttgtttg caagcagcag attacgcgca gaaaaaaagg | 6660 |
| atctcaagaa gatcctttga tcttttctac ggggtctgac gctcagtgga acgaaaactc | 6720 |
| acgttaaggg attttggtca tgacattaac ctataaaaat aggcgtatca cgaggccctt | 6780 |
| tcgtctcgcg cgtttcggtg atgacggtga aaacctctga cacatgcagc tcccggagac | 6840 |
| ggtcacagct tgtctgtaag cggatgccgg gagcagacaa gcccgtcagg gcgcgtcagc | 6900 |
| gggtgttggc gggtgtcggg gctggcttaa ctatgcggca tcagagcaga ttgtactgag | 6960 |
| agtgcaccat atggacatat tgtcgttaga acgcggctac aattaataca taaccttatg | 7020 |
| tatcatacac atacgattta ggtgacacta tagaacgg | 7058 |

<210> SEQ ID NO 3
<211> LENGTH: 8553
<212> TYPE: DNA
<213> ORGANISM: Artificial Sequence
<220> FEATURE:
<223> OTHER INFORMATION: Donor construct QC329

<400> SEQUENCE: 3

| | |
|---|---|
| gaagttccta ttccgaagtt cctattctct agaaagtata ggaacttcca ctagtgagga | 60 |
| tctgatcatg ccacacaaca caatggcggc caccgcttcc agaaccaccc gattctcttc | 120 |
| ttcctcttca caccccacct tccccaaacg cattactaga tccaccctcc ctctctctca | 180 |
| tcaaaccctc accaaaccca accacgctct caaaatcaaa tgttccatct ccaaccccc | 240 |
| cacggcggcg cccttcacca aggaagcgcc gaccacggag cccttcgtgt cacggttcgc | 300 |

-continued

```
ctccggcgaa cctcgcaagg gcgcggacat ccttgtggag gcgctggaga ggcagggcgt      360
gacgacggtg ttcgcgtacc ccggcggtgc gtcgatggag atccaccagg cgctcacgcg      420
ctccgccgcc atccgcaacg tgctcccgcg ccacgagcag ggcggcgtct tcgccgccga      480
aggctacgcg cgttcctccg gcctcccgg  cgtctgcatt gccacctccg gccccggcgc      540
caccaacctc gtgagcggcc tcgccgacgc tttaatggac agcgtcccag tcgtcgccat      600
caccggccag gtcgcccgcc ggatgatcgg caccgacgcc ttccaagaaa ccccgatcgt      660
ggaggtgagc agatccatca cgaagcacaa ctacctcatc ctcgacgtcg acgacatccc      720
ccgcgtcgtc gccgaggctt tcttcgtcgc cacctccggc cgccccggtc cggtcctcat      780
cgacattccc aaagacgttc agcagcaact cgccgtgcct aattgggacg agcccgttaa      840
cctccccggt tacctcgcca ggctgccag  gccccccgcc gaggcccaat ggaacacat       900 tgtcagactc atcatggagg cccaaaagcc cgttctctac gtcggcggtg gcagtttgaa      960
ttccagtgct gaattgaggc gctttgttga actcactggt attcccgttg ctagcacttt     1020
aatgggtctt ggaacttttc ctattggtga tgaatattcc cttcagatgc tgggtatgca     1080
tggtactgtt tatgctaact atgctgttga caatagtgat ttgttgcttg cctttggggt     1140
aaggtttgat gaccgtgtta ctgggaagct tgaggctttt gctagtaggg ctaagattgt     1200
tcacattgat attgattctg ccgagattgg gaagaacaag caggcgcacg tgtcggtttg     1260
cgcggatttg aagttggcct tgaagggaat taatatgatt ttggaggaga aggagtgga      1320 gggtaagttt gatcttggag gttggagaga agagattaat gtgcagaaac acaagtttcc     1380
attgggttac aagacattcc aggacgcgat ttctccgcag catgctatcg aggttcttga     1440
tgagttgact aatggagatg ctattgttag tactgggggtt gggcagcatc aaatgtgggc     1500
tgcgcagttt tacaagtaca agagaccgag gcagtggttg acctcagggg gtcttggagc     1560
catgggtttt ggattgcctg cggctattgg tgctgctgtt gctaaccctg gggctgttgt     1620
ggttgacatt gatggggatg gtagtttcat catgaatgtt caggagttgg ccactataag     1680
agtggagaat ctcccagtta agatattgtt gttgaacaat cagcatttgg gtatggtggt     1740
tcagttggag gataggttct acaagtccaa tagagctcac acctatcttg agatccgtc      1800 tagcgagagc gagatattcc caaacatgct caagtttgct gatgcttgtg ggataccggc     1860
agcgcgagtg acgaagaagg aagagcttag agcggcaatt cagagaatgt ggacaccccc     1920 tggccctac  cttcttgatg tcattgtgcc ccatcaggag catgtgttgc cgatgattcc     1980
cagtaatgga tccttcaagg atgtgataac tgagggtgat ggtagaacga ggtactgact     2040
agctagtcag ttaacctaga cttgtccatc ttctggattg ccaacttaa  ttaatgtatg     2100 aaataaaagg atgcacacat agtgacatgc taatcactat aatgtgggca tcaaagttgt     2160
gtgttatgtg taattactag ttatctgaat aaaagagaaa gagatcatcc atatttctta     2220
tcctaaatga atgtcacgtg tcttttataat tctttgatga accagatgca tttcattaac     2280
caaatccata tacatataaa tattaatcat atataattaa tatcaattgg gttagcaaaa     2340
caaatctagt ctaggtgtgt tttgccccca agcttatcga taccgtcggc gcggggtacc     2400
cgggtgattg cggttacatc atgtacggaa aaataattct aatccttgat ttaaatttga     2460
acttgactat ttatttattc tttatttcat tttgtaaatc attttatgta tctcctggca     2520
agcaatttta tccaccttgc accaacaccct tcgggttcca taatcaaacc accttaactt     2580
cacaccatgc tgtaactcac accgcccagc atctccaatg tgaaagaagc taaaatttaa     2640
taaacaatca tacgaagcag tgacaaaata ccagatggta ttaatgcttc gataaaatta     2700
```

```
attggaaagt ataaaatggt agaaaataat aaattataat taatttaagt aagataaaaa    2760
ataattaaaa actaaaatgt taaaatttta aaaaaattat tttaaataat atttaaaaac    2820
attaaaaatc attttaaaaa atttatttat agaacaatta aataaatatt tcagctaata    2880
aaaaacaaaa gcttacctag ccttagaaga caacttgtcc aacaattaga tgatacccat    2940
tgcccttacg ttttctttaa catcaattat tgttttgtc aacaagctat cttttagttt    3000
tattttattg gtaaaaata tgtcgccttc aagttgcatc atttaacaca tctcgtcatt    3060
agaaaaataa aactcttccc taaacgatta gtagaaaaaa tcattcgata taaataaga    3120 aagaaaaatt agaaaaaaat aacttcattt taaaaaaatc attaaggcta tattttttaa    3180
atgactaatt ttatatagac tgtaactaaa agtatacaat ttattatgct atgtatctta    3240
aagaattact tataaaaatc tacgaagaa tatcttacaa agtgaaaaac aaatgagaaa    3300
gaatttagtg ggatgattat gattttattt gaaaattgaa aaaataatta ttaaagactt    3360
tagtggagta agaaagcttt cctattagtc ttttcttatc cataaaaaaa aaaaaaaaaa    3420
tctagcgtga cagcttttcc atagatttta ataatgtaaa atactggtag cagccgaccg    3480
ttcaggtaat ggacactgtg gtcctaactt gcaacgggtg cgggcccaat ttaataacgc    3540
cgtggtaacg gataaagcca agcgtgaagc ggtgaaggta catctctgac tccgtcaaga    3600
ttacgaaacc gtcaactacg aaggactccc cgaaatatca tctgtgtcat aaacaccaag    3660
tcacaccata catgggcacg cgtcacaata tgattggaga acggttccac cgcatatgct    3720
ataaaatgcc cccacacccc tcgacccctaa tcgcacttca attgcaatca aattagttca    3780
ttctctttgc gcagttccct acctctcctt tcaaggttcg tagatttctt ccgttttttt    3840
ttcttcttct ttattgtttg ttctacatca gcatgatgtt gatttgattg tgttttctat    3900
cgtttcatcg attataaatt ttcataatca gaagattcag cttttattaa tgcaagaacg    3960
tccttaattg atgattttat aaccgtaaat taggtctaat tagagttttt ttcataaaga    4020
ttttcagatc cgtttacaac aagccttaat tgttgattct gtagtcgtag attaaggttt    4080
ttttcatgaa ctacttcaga tccgttaaac aacagcctta tttgttgata cttcagtcgt    4140
ttttcaagaa attgttcaga tccgttgata aaagccttat tcgttgattc tgtatggtat    4200
ttcaagagat attgctcagg tccttttagca actaccttat ttgttgattc tgtggccata    4260
gattaggatt ttttttcacg aaattgcttc ttgaaattac gtgatggatt ttgattctga    4320
tttatcttgt gattgttgac tctacagcca tggccctgtc caacaagttc atcggcgacg    4380
acatgaagat gacctaccac atggacggct gcgtgaacgg ccactacttc accgtgaagg    4440
gcgagggcag cggcaagccc tacgagggca cccagacctc caccttcaag gtgaccatgg    4500
ccaacgggcg ccccctggcc ttctcccttcg acatcctgtc caccgtgttc atgtacggca    4560
accgctgctt caccgcctac cccaccagca tgcccgacta cttcaagcag gccttccccg    4620
acggcatgtc ctacgagaga accttcaccct acgaggacgg cggcgtggcc accgccagct    4680
gggagatcag cctgaagggc aactgcttcg agcacaagtc caccttccac ggcgtgaact    4740
tccccgccga cggccccgtg atggccaaga agaccaccgg ctgggacccc tccttcgaga    4800
agatgaccgt gtgcgacggc atcttgaagg gcgacgtgac cgccttcctg atgctgcagg    4860
gcggcggcaa ctacagatgc cagttccaca cctcctacaa gaccaagaag cccgtgacca    4920
tgccccccaa ccacgtggtg gagcaccgca tcgccagaac cgacctggac aagggcggca    4980
acagcgtgca gctgaccgag cacgccgtgg cccacatcac ctccgtggtg cccttctgag    5040
agctcgaatt tccccgatcg ttcaaacatt tggcaataaa gtttcttaag attgaatcct    5100
```

```
gttgccggtc ttgcgatgat tatcatataa tttctgttga attacgttaa gcatgtaata   5160
attaacatgt aatgcatgac gttatttatg agatgggttt ttatgattag agtcccgcaa   5220
ttatacattt aatacgcgat agaaaacaaa atatagcgcg caaactagga taaattatcg   5280
cgcgcggtgt catctatgtt actagatcgg gaattctagt ggccggccca gctgatgatc   5340
ccggtgaagt tcctattccg aagttcctat tctccagaaa gtataggaac ttcactagag   5400
cttgcggccg cccctgggc cggccactag aattcgtaat catggtcata gctgtttcct   5460
gtgtgaaatt gttatccgct cacaattcca cacaacatac gagccggaag cataaagtgt   5520
aaagcctggg gtgcctaatg agtgagctaa ctcacattaa ttgcgttgcg ctcactgccc   5580
gctttccagt cgggaaacct gtcgtgccag ctgcattaat gaatcggcca acgcgcgggg   5640
agaggcggtt tgcgtattgg gcgctcttcc gcttcctcgc tcactgactc gctgcgctcg   5700
gtcgttcggc tgcggcgagc ggtatcagct cactcaaagg cggtaatacg gttatccaca   5760
gaatcagggg ataacgcagg aaagaacatg tgagcaaaag gccagcaaaa ggccaggaac   5820
cgtaaaaagg ccgcgttgct ggcgtttttc cataggctcc gcccccctga cgagcatcac   5880
aaaaatcgac gctcaagtca gaggtggcga aacccgacag gactataaag ataccaggcg   5940
tttccccctg gaagctccct cgtgcgctct cctgttccga ccctgccgct taccggatac   6000
ctgtccgcct ttctcccttc gggaagcgtg gcgctttctc atagctcacg ctgtaggtat   6060
ctcagttcgg tgtaggtcgt tcgctccaag ctgggctgtg tgcacgaacc ccccgttcag   6120
cccgaccgct gcgccttatc cggtaactat cgtcttgagt ccaacccggt aagacacgac   6180
ttatcgccac tggcagcagc cactggtaac aggattagca gagcgaggta tgtaggcggt   6240
gctacagagt tcttgaagtg gtggcctaac tacggctaca ctagaaggac agtatttggt   6300
atctgcgctc tgctgaagcc agttaccttc ggaaaaagag ttggtagctc ttgatccggc   6360
aaacaaacca ccgctggtag cggtggtttt tttgtttgca agcagcagat tacgcgcaga   6420
aaaaaaggat ctcaagaaga tcctttgatc ttttctacgg ggtctgacgc tcagtggaac   6480
gaaaactcac gttaagggat tttggtcatg agattatcaa aaaggatctt cacctagatc   6540
cttttaaatt aaaaatgaag ttttaaatca atctaaagta tatatgagta aacttggtct   6600
gacagttacc aatgcttaat cagtgaggca cctatctcag cgatctgtct atttcgttca   6660
tccatagttg cctgactccc cgtcgtgtag ataactacga tacgggaggg cttaccatct   6720
ggccccagtg ctgcaatgat accgcgagac ccacgctcac cggctccaga tttatcagca   6780 ataaccagc cagccggaag ggccgagcgc agaagtggtc ctgcaacttt atccgcctcc   6840
atccagtcta ttaattgttg ccgggaagct agagtaagta gttcgccagt taatagtttg   6900
cgcaacgttg ttgccattgc tacaggcatc gtggtgtcac gctcgtcgtt tggtatggct   6960
tcattcagct ccggttccca acgatcaagg cgagttacat gatccccat gttgtgcaaa   7020 aaagcggtta gctccttcgg tcctccgatc gttgtcagaa gtaagttggc cgcagtgtta   7080
tcactcatgg ttatggcagc actgcataat tctcttactg tcatgccatc cgtaagatgc   7140
ttttctgtga ctggtgagta ctcaaccaag tcattctgag aatagtgtat gcggcgaccg   7200
agttgctctt gcccggcgtc aatacgggat aataccgcgc cacatagcag aactttaaaa   7260
gtgctcatca ttggaaaacg ttcttcgggg cgaaaactct caaggatctt accgctgttg   7320
agatccagtt cgatgtaacc cactcgtgca cccaactgat cttcagcatc ttttactttc   7380
accagcgttt ctgggtgagc aaaaacagga aggcaaaatg ccgcaaaaaa gggaataagg   7440
gcgacacgga aatgttgaat actcatactc ttcctttttc aatattattg aagcatttat   7500
```

-continued

| | |
|---|---|
| cagggttatt gtctcatgag cggatacata tttgaatgta tttagaaaaa taaacaaata | 7560 |
| ggggttccgc gcacatttcc ccgaaaagtg ccacctgacg tctaagaaac cattattatc | 7620 |
| atgacattaa cctataaaaa taggcgtatc acgaggccct ttcgtctcgc gcgtttcggt | 7680 |
| gatgacggtg aaaacctctg acacatgcag ctcccggaga cggtcacagc ttgtctgtaa | 7740 |
| gcggatgccg ggagcagaca gcccgtcag ggcgcgtcag cgggtgttgg cgggtgtcgg | 7800 |
| ggctggctta actatgcggc atcagagcag attgtactga gagtgcacca taaaattgta | 7860 |
| aacgttaata ttttgttaaa attcgcgtta aattttgtt aaatcagctc attttttaac | 7920 |
| caataggccg aaatcggcaa aatcccttat aaatcaaaag aatagcccga tagggttg | 7980 |
| agtgttgttc cagtttggaa caagagtcca ctattaaaga acgtggactc caacgtcaaa | 8040 |
| gggcgaaaaa ccgtctatca gggcgatggc ccactacgtg aaccatcacc caaatcaagt | 8100 |
| tttttgggt cgaggtgccg taaagcacta atcggaacc ctaaagggag cccccgattt | 8160 |
| agagcttgac ggggaaagcc ggcgaacgtg gcgagaaagg aagggaagaa agcgaaagga | 8220 |
| gcgggcgcta gggcgctggc aagtgtagcg gtcacgctgc gcgtaaccac cacacccgcc | 8280 |
| gcgcttaatg cgccgctaca gggcgcgtac tatggttgct ttgacgtatg cggtgtgaaa | 8340 |
| taccgcacag atgcgtaagg agaaaatacc gcatcaggcg ccattcgcca ttcaggctgc | 8400 |
| gcaactgttg ggaagggcga tcggtgcggg cctcttcgct attacgccag ctggcgaaag | 8460 |
| ggggatgtgc tgcaaggcga ttaagttggg taacgccagg ttttcccag tcacgacgtt | 8520 |
| gtaaaacgac ggccagtgcc aagcttgtta aca | 8553 |

<210> SEQ ID NO 4
<211> LENGTH: 6133
<212> TYPE: DNA
<213> ORGANISM: Artificial Sequence
<220> FEATURE:
<223> OTHER INFORMATION: Predicted product QC288A329 of RMCE between
      QC288A and QC329

<400> SEQUENCE: 4

| | |
|---|---|
| cgcgccggta ccgggccccc cctcgagcgg ccgcagattt aggtgacact atagaatatg | 60 |
| catcactagt aagcttgcat gcctgcaggt ttaaacagtc gactctagag atccgtcaac | 120 |
| atggtggagc acgacactct cgtctactcc aagaatatca agatacagt ctcagaagac | 180 |
| caaagggcta ttgagacttt tcaacaaagg gtaatatcgg gaaacctcct cggattccat | 240 |
| tgcccagcta tctgtcactt catcaaaagg acagtagaaa aggaaggtgg cacctacaaa | 300 |
| tgccatcatt gcgataaagg aaaggctatc gttcaagatg cctctgccga cagtggtccc | 360 |
| aaagatggac cccccaccac gaggagcatc gtggaaaaag aagacgttcc aaccacgtct | 420 |
| tcaaagcaag tggattgatg tgatgatcct atgcgtatgg tatgacgtgt gttcaagatg | 480 |
| atgacttcaa acctacctat gacgtatggt atgacgtgtg tcgactgatg acttagatcc | 540 |
| actcgagcgg ctataaatac gtacctacgc accctgcgct accatcccta gagctgcagc | 600 |
| ttattttac aacaattacc aacaacaaca acaacaaac acattacaa ttactattta | 660 |
| caattacagt cgacccaaca gaagttccta ttccgaagtt cctattctct agaaagtata | 720 |
| ggaacttcca ctagtgagga tctgatcatg ccacacaaca caatggcggc caccgcttcc | 780 |
| agaaccaccc gattctcttc ttcctcttca cccccacct tccccaaacg cattactaga | 840 |
| tccacccctcc ctctctctca tcaaaccctc accaaaccca accacgctct caaaatcaaa | 900 |
| tgttccatct ccaaaccccc cacggcgcg cccttcacca aggaagcgcc gaccacggag | 960 |
| cccttcgtgt cacggttcgc ctccggcgaa cctcgcaagg gcgcggacat ccttgtggag | 1020 |

```
gcgctggaga ggcagggcgt gacgacggtg ttcgcgtacc ccggcggtgc gtcgatggag   1080
atccaccagg cgctcacgcg ctccgccgcc atccgcaacg tgctcccgcg ccacgagcag   1140
ggcggcgtct tcgccgccga aggctacgcg cgttcctccg gcctcccggg cgtctgcatt   1200
gccacctccg gccccggcgc caccaacctc gtgagcggcc tcgccgacgc tttaatggac   1260
agcgtcccag tcgtcgccat caccggccag gtcgcccgcc ggatgatcgg caccgacgcc   1320
ttccaagaaa ccccgatcgt ggaggtgagc agatccatca cgaagcacaa ctacctcatc   1380
ctcgacgtcg acgacatccc ccgcgtcgtc gccgaggctt tcttcgtcgc cacctccggc   1440
cgccccggtc cggtcctcat cgacattccc aaagacgttc agcagcaact cgccgtgcct   1500
aattgggacg agcccgttaa cctccccggt tacctcgcca ggctgcccag gccccccgcc   1560
gaggcccaat tggaacacat tgtcagactc atcatggagg cccaaaagcc cgttctctac   1620
gtcggcggtg gcagtttgaa ttccagtgct gaattgaggc gctttgttga actcactggt   1680
attcccgttg ctagcacttt aatgggtctt ggaacttttc ctattggtga tgaatattcc   1740
cttcagatgc tgggtatgca tggtactgtt tatgctaact atgctgttga caatagtgat   1800
ttgttgcttg cctttggggt aaggtttgat gaccgtgtta ctgggaagct tgaggctttt   1860
gctagtaggg ctaagattgt tcacattgat attgattctg ccgagattgg gaagaacaag   1920
caggcgcacg tgtcggtttg cgcggatttg aagttggcct tgaagggaat taatatgatt   1980
ttggaggaga aaggagtgga gggtaagttt gatcttggag gttggagaga agagattaat   2040
gtgcagaaac acaagtttcc attgggttac aagacattcc aggacgcgat ttctccgcag   2100
catgctatcg aggttcttga tgagttgact aatggagatg ctattgttag tactggggtt   2160
gggcagcatc aaatgtgggc tgcgcagttt tacaagtaca agagaccgag gcagtggttg   2220
acctcagggg gtcttggagc catgggtttt ggattgcctg cggctattgg tgctgctgtt   2280
gctaaccctg gggctgttgt ggttgacatt gatgggatg gtagtttcat catgaatgtt   2340
caggagttgg ccactataag agtggagaat ctcccagtta agatattgtt gttgaacaat   2400
cagcatttgg gtatggtggt tcagttggag gataggttct acaagtccaa tagagctcac   2460
acctatcttg gagatccgtc tagcgagagc gagatattcc caaacatgct caagtttgct   2520
gatgcttgtg ggataccggc agcgcgagtg acgaagaagg aagagcttag agcggcaatt   2580
cagagaatgt tggacacccc tggcccctac cttcttgatg tcattgtgcc ccatcaggag   2640
catgtgttgc cgatgattcc cagtaatgga tccttcaagg atgtgataac tgagggtgat   2700
ggtagaacga ggtactgact agctagtcag ttaacctaga cttgtccatc ttctggattg   2760
gccaacttaa ttaatgtatg aaataaaagg atgcacacat agtgacatgc taatcactat   2820
aatgtgggca tcaaagttgt gtgttatgtg taattactag ttatctgaat aaaagagaaa   2880
gagatcatcc atatttctta tcctaaatga atgtcacgtg tctttataat tctttgatga   2940
accagatgca tttcattaac caaatccata tacatataaa tattaatcat atataattaa   3000
tatcaattgg gttagcaaaa caaatctagt ctaggtgtgt tttgccccca agcttatcga   3060
taccgtcggc gcggggtacc cgggtgattg cggttacatc atgtacggaa aaataattct   3120
aatccttgat ttaaatttga acttgactat ttatttattc tttatttcat tttgtaaatc   3180 atttatgta tctcctggca agcaatttta tccaccttgc accaacacct tcgggttcca   3240
taatcaaacc accttaactt cacaccatgc tgtaactcac accgcccagc atctccaatg   3300
tgaaagaagc taaatttaa taaacaatca tacgaagcag tgacaaaata ccagatggta   3360
ttaatgcttc gataaaatta attggaaagt ataaaatggt agaaaataat aaattataat   3420
```

```
taatttaagt aagataaaaa ataattaaaa actaaaatgt taaaatttta aaaaaattat    3480
tttaaataat atttaaaaac attaaaaatc attttaaaaa atttatttat agaacaatta    3540
aataaatatt tcagctaata aaaaacaaaa gcttacctag ccttagaaga caacttgtcc    3600
aacaattaga tgatacccat tgcccttacg ttttctttaa catcaattat tgtttttgtc    3660
aacaagctat cttttagttt tattttattg gtaaaaaata tgtcgccttc aagttgcatc    3720
atttaacaca tctcgtcatt agaaaaataa aactcttccc taaacgatta gtagaaaaaa    3780
tcattcgata ataataaga aagaaaaatt agaaaaaaat aacttcattt taaaaaaatc    3840
attaaggcta tattttttaa atgactaatt ttatatagac tgtaactaaa agtatacaat    3900
ttattatgct atgtatctta aagaattact tataaaaatc tacggaagaa tatcttacaa    3960
agtgaaaaac aaatgagaaa gaatttagtg ggatgattat gatttttattt gaaaattgaa    4020 aaaataatta ttaaagactt tagtggagta agaaagcttt cctattagtc ttttcttatc    4080
cataaaaaaa aaaaaaaaaa tctagcgtga cagcttttcc atagatttta ataatgtaaa    4140
atactggtag cagccgaccg ttcaggtaat ggacactgtg gtcctaactt gcaacgggtg    4200
cgggcccaat ttaataacgc cgtggtaacg gataaagcca agcgtgaagc ggtgaaggta    4260
catctctgac tccgtcaaga ttacgaaacc gtcaactacg aaggactccc cgaaatatca    4320
tctgtgtcat aaacaccaag tcacaccata catgggcacg cgtcacaata tgattggaga    4380
acggttccac cgcatatgct ataaaatgcc cccacacccc tcgaccctaa tcgcacttca    4440
attgcaatca aattagttca ttctctttgc gcagttccct acctctcctt tcaaggttcg    4500
tagatttctt ccgttttttt ttcttcttct ttattgtttg ttctacatca gcatgatgtt    4560
gatttgattg tgttttctat cgtttcatcg attataaatt ttcataatca gaagattcag    4620
cttttattaa tgcaagaacg tccttaattg atgatttat aaccgtaaat taggtctaat    4680
tagagttttt tcataaaga ttttcagatc cgtttacaac aagccttaat tgttgattct    4740
gtagtcgtag attaaggttt ttttcatgaa ctacttcaga tccgttaaac aacagcctta    4800
tttgttgata cttcagtcgt ttttcaagaa attgttcaga tccgttgata aaagccttat    4860
tcgttgattc tgtatggtat ttcaagagat attgctcagg tcctttagca actaccttat    4920
ttgttgattc tgtggccata gattaggatt tttttcacg aaattgcttc ttgaaattac    4980
gtgatggatt ttgattctga tttatcttgt gattgttgac tctacagcca tggccctgtc    5040
caacaagttc atcggcgacg acatgaagat gacctaccac atggacggct gcgtgaacgg    5100
ccactacttc accgtgaagg gcgagggcag cggcaagccc tacgagggca cccagaccctc   5160 caccttcaag gtgaccatgg ccaacggcgg ccccctggcc ttctccttcg acatcctgtc    5220
caccgtgttc atgtacggca accgctgctt caccgcctac cccaccagca tgcccgacta    5280
cttcaagcag gccttccccg acggcatgtc ctacgagaga accttcacct acgaggacgg    5340
cggcgtggcc accgccagct gggagatcag cctgaagggc aactgcttcg agcacaagtc    5400 cacccttccac ggcgtgaact tccccgccga cggccccgtg atggccaaga agaccaccgg    5460
ctgggacccc tccttcgaga agatgaccgt gtgcgacggc atcttgaagg cgacgtgac     5520 cgccttcctg atgctgcagg gcggcggcaa ctacagatgc cagttccaca cctcctacaa    5580
gaccaagaag cccgtgacca tgcccccaa ccacgtggtg gagcaccgca tcgccagaac     5640
cgacctggac aagggcggca acagcgtgca gctgaccgag cacgccgtgg cccacatcac    5700
ctccgtggtg cccttctgag agctcgaatt tccccgatcg ttcaaacatt tggcaataaa    5760
gtttcttaag attgaatcct gttgccggtc ttgcgatgat tatcatataa tttctgttga    5820
```

-continued

| | |
|---|---|
| attacgttaa gcatgtaata attaacatgt aatgcatgac gttatttatg agatgggttt | 5880 |
| ttatgattag agtcccgcaa ttatacattt aatacgcgat agaaaacaaa atatagcgcg | 5940 |
| caaactagga taaattatcg cgcgcggtgt catctatgtt actagatcgg gaattctagt | 6000 |
| ggccggccca gctgatgatc ccggtgaagt tcctattccg aagttcctat tctccagaaa | 6060 |
| gtataggaac ttcactagag cttgcggccg cccctgggc cggccactag tgagctcggt | 6120 |
| acccgggtac cgg | 6133 |

<210> SEQ ID NO 5
<211> LENGTH: 4860
<212> TYPE: DNA
<213> ORGANISM: Artificial Sequence
<220> FEATURE:
<223> OTHER INFORMATION: FLP recombinase expression construct QC292

<400> SEQUENCE: 5

| | |
|---|---|
| agcttgcatg cctgcaggtt taaacagtcg actctagaga tccgtcaaca tggtggagca | 60 |
| cgacactctc gtctactcca agaatatcaa agatacagtc tcagaagacc aaagggctat | 120 |
| tgagactttt caacaaaggg taatatcggg aaacctcctc ggattccatt gcccagctat | 180 |
| ctgtcacttc atcaaaagga cagtagaaaa ggaaggtggc acctacaaat gccatcattg | 240 |
| cgataaagga aaggctatcg ttcaagatgc ctctgccgac agtggtccca agatggaccc | 300 |
| cccacccacg aggagcatcg tggaaaaaga agacgttcca accacgtctt caaagcaagt | 360 |
| ggattgatgt gatgatccta tgcgtatggt atgacgtgtg ttcaagatga tgacttcaaa | 420 |
| cctacctatg acgtatggta tgacgtgtgt cgactgatga cttagatcca ctcgagcggc | 480 |
| tataaatacg tacctacgca ccctgcgcta ccatccctag agctgcagct tattttaca | 540 |
| acaattacca caacaacaa acaacaaaca acattacaat tactatttac aattacagtc | 600 |
| gacccgggat ccaacaatgc cccagttcga catcctctgc aagacccccc caaggtgct | 660 |
| cgtgaggcag ttcgtggaga ggttcgagag gccctccggc gagaagatcg ccctctgcgc | 720 |
| cgccgagctc acctacctct gctggatgat caccacaac ggcaccgcca ttaagagggc | 780 |
| caccttcatg tcatacaaca ccatcatctc caactccctc ccttcgaca tcgtgaacaa | 840 |
| gtccctccag ttcaaataca gacccgaaa ggcaccatc ctcgaggcct ccctcaagaa | 900 |
| gctcatccc gcctgggagt tcaccatcat ccctactac ggccagaagc accagtccga | 960 |
| catcaccgac atcgtgtcat ccctccagct tcagttcgag tcctccgagg aggctgacaa | 1020 |
| gggcaactcc cactccaaga agatgctgaa ggccctcctc tccgagggcg agtccatctg | 1080 |
| ggagatcacc gagaagatcc tcaactcctt cgagtacacc tccaggttca ctaagaccaa | 1140 |
| gaccctctac cagttcctct cctcgccac cttcatcaac tgcggcaggt tctcagacat | 1200 |
| caagaacgtg gaccccaagt ccttcaagct cgtgcagaac aagtacctcg gcgtgatcat | 1260 |
| ccagtgcctc gtgaccgaga ccaagaccct cgtgtccagg cacatctact tcttctccgc | 1320 |
| tcgcggcagg atcgacccc tcgtgtacct cgacgagttc ctcaggaact cagagcccgt | 1380 |
| gctcaagagg gtgaacagga ccggcaactc ctcctccaac aagcaggagt accagctcct | 1440 |
| caaggacaac ctcgtgaggt cctacaacaa ggccctcaag aagaacgccc cctactccat | 1500 |
| cttcgccatc aagaacggcc ccaagtccca catcggtagg cacctcatga cctccttcct | 1560 |
| ctcaatgaag ggcctcaccg agctcaccaa cgtggtgggc aactggtccg acaagagggc | 1620 |
| ctccgccgtg gccaggacca cctacaccca ccagatcacc gccatccccg accactactt | 1680 |
| cgccctcgtg tcaaggtact acgcctacga ccccatctcc aaggagatga tcgccctcaa | 1740 |

```
ggacgagact aacccatcg aggagtggca gcacatcgag cagctcaagg gctccgccga    1800
gggctccatc aggtaccccg cctggaacgg catcatctcc caggaggtgc tcgactacct    1860
ctcctcctac atcaacagga ggatctgagt taacctagac ttgtccatct tctggattgg    1920
ccaacttaat taatgtatga ataaaaagga tgcacacata gtgacatgct aatcactata    1980
atgtgggcat caaagttgtg tgttatgtgt aattactagt tatctgaata aaagagaaag    2040
agatcatcca tatttcttat cctaaatgaa tgtcacgtgt ctttataatt ctttgatgaa    2100
ccagatgcat ttcattaacc aaatccatat acatataaat attaatcata tataattaat    2160
atcaattggg ttagcaaaac aaatctagtc taggtgtgtt ttgcgaatgc ggccgcgatc    2220 tgggaattc gtaatcatgg tcatagctgt ttcctgtgtg aaattgttat ccgctcacaa    2280
ttccacacaa catacgagcc ggaagcataa agtgtaaagc ctggggtgcc taatgagtga    2340
gctaactcac attaattgcg ttgcgctcac tgcccgcttt ccagtcggga aacctgtcgt    2400
gccagctgca ttaatgaatc ggccaacgcg cggggagagg cggtttgcgt attgggcgct    2460
cttccgcttc ctcgctcact gactcgctgc gctcggtcgt tcggctgcgg cgagcggtat    2520
cagctcactc aaaggcggta atacggttat ccacagaatc aggggataac gcaggaaaga    2580
acatgtgagc aaaaggccag caaaaggcca ggaaccgtaa aaaggccgcg ttgctggcgt    2640
ttttccatag gctccgcccc cctgacgagc atcacaaaaa tcgacgctca agtcagaggt    2700
ggcgaaaccc gacaggacta taaagatacc aggcgtttcc ccctggaagc tccctcgtgc    2760
gctctcctgt tccgaccctg ccgcttaccg gatacctgtc cgcctttctc ccttcgggaa    2820
gcgtggcgct ttctcatagc tcacgctgta ggtatctcag ttcggtgtag gtcgttcgct    2880
ccaagctggg ctgtgtgcac gaaccccccg ttcagcccga ccgctgcgcc ttatccggta    2940
actatcgtct tgagtccaac ccggtaagac acgacttatc gccactggca gcagccactg    3000
gtaacaggat tagcagagcg aggtatgtag gcggtgctac agagttcttg aagtggtggc    3060
ctaactacgg ctacactaga aggacagtat ttggtatctg cgctctgctg aagccagtta    3120
ccttcggaaa aagagttggt agctcttgat ccggcaaaca aaccaccgct ggtagcggtg    3180
gtttttttgt ttgcaagcag cagattacgc gcagaaaaaa aggatctcaa gaagatcctt    3240
tgatcttttc tacggggtct gacgctcagt ggaacgaaaa ctcacgttaa gggattttgg    3300
tcatgagatt atcaaaaagg atcttcacct agatcctttt aaattaaaaa tgaagtttta    3360
aatcaatcta agtatatat gagtaaactt ggtctgacag ttaccaatgc ttaatcagtg    3420
aggcacctat ctcagcgatc tgtctatttc gttcatccat agttgcctga ctccccgtcg    3480
tgtagataac tacgatacgg gagggcttac catctggccc cagtgctgca atgataccgc    3540
gagacccacg ctcaccggct ccagatttat cagcaataaa ccagccagcc ggaagggccg    3600
agcgcagaag tggtcctgca actttatccg cctccatcca gtctattaat tgttgccggg    3660
aagctagagt aagtagttcg ccagttaata gtttgcgcaa cgttgttgcc attgctacag    3720
gcatcgtggt gtcacgctcg tcgtttggta tggcttcatt cagctccggt tcccaacgat    3780
caaggcgagt tacatgatcc cccatgttgt gcaaaaaagc ggttagctcc ttcggtcctc    3840
cgatcgttgt cagaagtaag ttggccgcag tgttatcact catggttatg gcagcactgc    3900
ataattctct tactgtcatg ccatccgtaa gatgcttttc tgtgactggt gagtactcaa    3960
ccaagtcatt ctgagaatag tgtatgcggc gaccgagttg ctcttgcccg gcgtcaatac    4020
gggataatac cgcgccacat agcagaactt taaaagtgct catcattgga aaacgttctt    4080
cggggcgaaa actctcaagg atcttaccgc tgttgagatc cagttcgatg taacccactc    4140
```

-continued

```
gtgcacccaa ctgatcttca gcatctttta ctttcaccag cgtttctggg tgagcaaaaa    4200
caggaaggca aaatgccgca aaaagggaa taagggcgac acggaaatgt tgaatactca     4260
tactcttcct ttttcaatat tattgaagca tttatcaggg ttattgtctc atgagcggat    4320
acatatttga atgtatttag aaaaataaac aaatagggt tccgcgcaca tttccccgaa     4380
aagtgccacc tgacgtctaa gaaaccatta ttatcatgac attaacctat aaaaataggc    4440
gtatcacgag gccctttcgt ctcgcgcgtt tcggtgatga cggtgaaaac ctctgacaca    4500
tgcagctccc ggagacggtc acagcttgtc tgtaagcgga tgccgggagc agacaagccc    4560
gtcagggcgc gtcagcgggt gttggcgggt gtcggggctg gcttaactat gcggcatcag    4620
agcagattgt actgagagtg caccatatgc ggtgtgaaat accgcacaga tgcgtaagga    4680
gaaaataccg catcaggcgc cattcgccat tcaggctgcg caactgttgg gaagggcgat    4740
cggtgcgggc ctcttcgcta ttacgccagc tggcgaaagg gggatgtgct gcaaggcgat    4800
taagttgggt aacgccaggg ttttcccagt cacgacgttg taaaacgacg ccagtgcca    4860
```

<210> SEQ ID NO 6
<211> LENGTH: 92
<212> TYPE: DNA
<213> ORGANISM: Artificial Sequence
<220> FEATURE:
<223> OTHER INFORMATION: oligonucleotide to make FRT1 DNA duplex
<400> SEQUENCE: 6

```
ggatcaagct tgttaacaga agttcctatt ccgaagttcc tattctctag aaagtatagg    60
aacttccact agtacccggg aggatccacg tg                                   92
```

<210> SEQ ID NO 7
<211> LENGTH: 92
<212> TYPE: DNA
<213> ORGANISM: Artificial Sequence
<220> FEATURE:
<223> OTHER INFORMATION: oligonucleotide to make FRT1 DNA duplex
<400> SEQUENCE: 7

```
cacgtggatc ctcccgggta ctagtggaag ttcctatact ttctagagaa taggaacttc    60 ggataggaa cttctgttaa caagcttgat cc                                    92
```

<210> SEQ ID NO 8
<211> LENGTH: 24
<212> TYPE: DNA
<213> ORGANISM: Artificial Sequence
<220> FEATURE:
<223> OTHER INFORMATION: primer HSP-F1

<400> SEQUENCE: 8

```
caaacttgac aaagccacaa ctct                                            24
```

<210> SEQ ID NO 9
<211> LENGTH: 21
<212> TYPE: DNA
<213> ORGANISM: Artificial Sequence
<220> FEATURE:
<223> OTHER INFORMATION: primer HSP-R1

<400> SEQUENCE: 9

```
ggagaaattg gtgtcgtgga a                                               21
```

<210> SEQ ID NO 10
<211> LENGTH: 20

```
<212> TYPE: DNA
<213> ORGANISM: Artificial Sequence
<220> FEATURE:
<223> OTHER INFORMATION: probe VIC-MGB

<400> SEQUENCE: 10
ctctcatctc atataaatac                                          20

<210> SEQ ID NO 11
<211> LENGTH: 21
<212> TYPE: DNA
<213> ORGANISM: Artificial Sequence
<220> FEATURE:
<223> OTHER INFORMATION: primer 35S-277F

<400> SEQUENCE: 11
gacagtggtc ccaaagatgg a                                        21

<210> SEQ ID NO 12
<211> LENGTH: 22
<212> TYPE: DNA
<213> ORGANISM: Artificial Sequence
<220> FEATURE:
<223> OTHER INFORMATION: primer 35S-345R

<400> SEQUENCE: 12
cgtggttgga acgtcttctt tt                                       22

<210> SEQ ID NO 13
<211> LENGTH: 21
<212> TYPE: DNA
<213> ORGANISM: Artificial Sequence
<220> FEATURE:
<223> OTHER INFORMATION: probe 35S-399T

<400> SEQUENCE: 13
ccccacccac gaggagcatc g                                        21

<210> SEQ ID NO 14
<211> LENGTH: 20
<212> TYPE: DNA
<213> ORGANISM: Artificial Sequence
<220> FEATURE:
<223> OTHER INFORMATION: primer Hygro-591F

<400> SEQUENCE: 14
ggatttcggc tccaacaatg                                          20

<210> SEQ ID NO 15
<211> LENGTH: 19
<212> TYPE: DNA
<213> ORGANISM: Artificial Sequence
<220> FEATURE:
<223> OTHER INFORMATION: primer Hygro-659R

<400> SEQUENCE: 15
gcctcgctcc agtcaatga                                           19

<210> SEQ ID NO 16
<211> LENGTH: 24
<212> TYPE: DNA
<213> ORGANISM: Artificial Sequence
<220> FEATURE:
<223> OTHER INFORMATION: probe Hygro-612T

<400> SEQUENCE: 16
cctgacggac aatggccgca taac                                     24
```

```
<210> SEQ ID NO 17
<211> LENGTH: 20
<212> TYPE: DNA
<213> ORGANISM: Artificial Sequence
<220> FEATURE:
<223> OTHER INFORMATION: primer Yfp-67F

<400> SEQUENCE: 17
aacggccaca agttcgtgat                                              20

<210> SEQ ID NO 18
<211> LENGTH: 20
<212> TYPE: DNA
<213> ORGANISM: Artificial Sequence
<220> FEATURE:
<223> OTHER INFORMATION: primer Yfp-130R

<400> SEQUENCE: 18
tggtctgctt gcccttgaag                                              20

<210> SEQ ID NO 19
<211> LENGTH: 20
<212> TYPE: DNA
<213> ORGANISM: Artificial Sequence
<220> FEATURE:
<223> OTHER INFORMATION: probe Yfp-88T

<400> SEQUENCE: 19
accggcgagg gcatcggcta                                              20

<210> SEQ ID NO 20
<211> LENGTH: 17
<212> TYPE: DNA
<213> ORGANISM: Artificial Sequence
<220> FEATURE:
<223> OTHER INFORMATION: primer Cfp-F

<400> SEQUENCE: 20
ctgccctcgc ccttcac                                                 17

<210> SEQ ID NO 21
<211> LENGTH: 24
<212> TYPE: DNA
<213> ORGANISM: Artificial Sequence
<220> FEATURE:
<223> OTHER INFORMATION: primer Cfp-R

<400> SEQUENCE: 21
catgaagatg acctaccaca tgga                                         24

<210> SEQ ID NO 22
<211> LENGTH: 17
<212> TYPE: DNA
<213> ORGANISM: Artificial Sequence
<220> FEATURE:
<223> OTHER INFORMATION: probe Cfp-T

<400> SEQUENCE: 22
aagtagtggc cgttcac                                                 17

<210> SEQ ID NO 23
<211> LENGTH: 23
<212> TYPE: DNA
<213> ORGANISM: Artificial Sequence
<220> FEATURE:
<223> OTHER INFORMATION: primer Scp1-S
```

-continued

```
<400> SEQUENCE: 23
gagatccgtc aacatggtgg agc                                              23

<210> SEQ ID NO 24
<211> LENGTH: 21
<212> TYPE: DNA
<213> ORGANISM: Artificial Sequence
<220> FEATURE:
<223> OTHER INFORMATION: primer Hygro-A

<400> SEQUENCE: 24
cgtcgcggtg agttcaggct t                                                21

<210> SEQ ID NO 25
<211> LENGTH: 22
<212> TYPE: DNA
<213> ORGANISM: Artificial Sequence
<220> FEATURE:
<223> OTHER INFORMATION: primer Yfp-3

<400> SEQUENCE: 25
ggagcgacgc caagaaccag aa                                               22

<210> SEQ ID NO 26
<211> LENGTH: 23
<212> TYPE: DNA
<213> ORGANISM: Artificial Sequence
<220> FEATURE:
<223> OTHER INFORMATION: primer Frt87-A

<400> SEQUENCE: 26
ggccgcaagc tctagtgaag ttc                                              23

<210> SEQ ID NO 27
<211> LENGTH: 23
<212> TYPE: DNA
<213> ORGANISM: Artificial Sequence
<220> FEATURE:
<223> OTHER INFORMATION: primer Als-3

<400> SEQUENCE: 27
gtggatctag taatgcgttt ggg                                              23

<210> SEQ ID NO 28
<211> LENGTH: 23
<212> TYPE: DNA
<213> ORGANISM: Artificial Sequence
<220> FEATURE:
<223> OTHER INFORMATION: primer Hpt-1

<400> SEQUENCE: 28
ttcagcttcg atgtaggagg gcg                                              23

<210> SEQ ID NO 29
<211> LENGTH: 20
<212> TYPE: DNA
<213> ORGANISM: Artificial Sequence
<220> FEATURE:
<223> OTHER INFORMATION: primer Hygro-2

<400> SEQUENCE: 29
gctccggatc ggacgattgc                                                  20

<210> SEQ ID NO 30
<211> LENGTH: 23
```

```
<212> TYPE: DNA
<213> ORGANISM: Artificial Sequence
<220> FEATURE:
<223> OTHER INFORMATION: primer Yfp-1

<400> SEQUENCE: 30
tggcccacag caagcacggc ctg                                              23

<210> SEQ ID NO 31
<211> LENGTH: 23
<212> TYPE: DNA
<213> ORGANISM: Artificial Sequence
<220> FEATURE:
<223> OTHER INFORMATION: primer Yfp-2

<400> SEQUENCE: 31
aggccagggc gctggggaag gcg                                              23

<210> SEQ ID NO 32
<211> LENGTH: 24
<212> TYPE: DNA
<213> ORGANISM: Artificial Sequence
<220> FEATURE:
<223> OTHER INFORMATION: primer Cyan-1

<400> SEQUENCE: 32
atggccctgt ccaacaagtt catc                                             24

<210> SEQ ID NO 33
<211> LENGTH: 25
<212> TYPE: DNA
<213> ORGANISM: Artificial Sequence
<220> FEATURE:
<223> OTHER INFORMATION: primer Cyan-2

<400> SEQUENCE: 33
ggaggtgtgg aactggcatc tgtag                                            25

<210> SEQ ID NO 34
<211> LENGTH: 26
<212> TYPE: DNA
<213> ORGANISM: Artificial Sequence
<220> FEATURE:
<223> OTHER INFORMATION: primer PinII-100R

<400> SEQUENCE: 34
actttgatgc ccacattata gtgatt                                           26

<210> SEQ ID NO 35
<211> LENGTH: 23
<212> TYPE: DNA
<213> ORGANISM: Artificial Sequence
<220> FEATURE:
<223> OTHER INFORMATION: primer PinII-2F

<400> SEQUENCE: 35
gacttgtcca tcttctggat tgg                                              23

<210> SEQ ID NO 36
<211> LENGTH: 24
<212> TYPE: DNA
<213> ORGANISM: Artificial Sequence
<220> FEATURE:
<223> OTHER INFORMATION: primer Vec81

<400> SEQUENCE: 36
aaacctctga cacatgcagc tccc                                             24
```

<210> SEQ ID NO 37
<211> LENGTH: 24
<212> TYPE: DNA
<213> ORGANISM: Artificial Sequence
<220> FEATURE:
<223> OTHER INFORMATION: primer Flp-A

<400> SEQUENCE: 37
gtcttgcaga ggatgtcgaa ctgg					24

<210> SEQ ID NO 38
<211> LENGTH: 106
<212> TYPE: DNA
<213> ORGANISM: Artificial Sequence
<220> FEATURE:
<223> OTHER INFORMATION: FLP oligonucleotide to make FRT12 DNA duplex

<400> SEQUENCE: 38
actgatcccg ggcagatcta ggcgcgcccg aagttcctat tccgaagttc ctattctaca			60 tagagtatag gaacttccga tatcactgca gtggccggcc cagtgt					106

<210> SEQ ID NO 39
<211> LENGTH: 106
<212> TYPE: DNA
<213> ORGANISM: Artificial Sequence
<220> FEATURE:
<223> OTHER INFORMATION: FLP oligonucleotide to make FRT12 DNA duplex

<400> SEQUENCE: 39
acactgggcc ggccactgca gtgatatcgg aagttcctat actctatgta gaataggaac			60 ttcggaatag gaacttcggg cgcgcctaga tctgcccggg atcagt					106

<210> SEQ ID NO 40
<211> LENGTH: 106
<212> TYPE: DNA
<213> ORGANISM: Artificial Sequence
<220> FEATURE:
<223> OTHER INFORMATION: FLP oligonucleotide to make FRT6 DNA duplex

<400> SEQUENCE: 40
actgatcccg ggcccctagga ggccggcccg aagttcctat tccgaagttc ctattcttca			60 aaaagtatag gaacttccga tatcacttaa gtggcgcgcc cagtgt					106

<210> SEQ ID NO 41
<211> LENGTH: 106
<212> TYPE: DNA
<213> ORGANISM: Artificial Sequence
<220> FEATURE:
<223> OTHER INFORMATION: FLP oligonucleotide to make FRT6 DNA duplex

<400> SEQUENCE: 41
acactgggcg cgccacttaa gtgatatcgg aagttcctat acttttgaa gaataggaac			60 ttcggaatag gaacttcggg ccggcctcct agggcccggg atcagt					106

<210> SEQ ID NO 42
<211> LENGTH: 5490
<212> TYPE: DNA
<213> ORGANISM: Artificial Sequence
<220> FEATURE:
<223> OTHER INFORMATION: donor construct QC422

<400> SEQUENCE: 42
gaagttccta ttccgaagtt cctattctct agaaagtata ggaacttcca ctagtgagga			60

```
tctgatcatg ccacacaaca caatggcggc caccgcttcc agaaccaccc gattctcttc    120
ttcctcttca cacccacct tccccaaacg cattactaga tccaccctcc ctctctctca     180
tcaaaccctc accaaaccca accacgctct caaaatcaaa tgttccatct ccaaaccccc    240
cacggcggcg cccttcacca aggaagcgcc gaccacggag cccttcgtgt cacggttcgc    300
ctccggcgaa cctcgcaagg gcgcggacat ccttgtggag gcgctggaga ggcagggcgt    360
gacgacggtg ttcgcgtacc ccggcggtgc gtcgatggag atccaccagg cgctcacgcg    420
ctccgccgcc atccgcaacg tgctcccgcg ccacgagcag ggcggcgtct cgccgccga    480 aggctacgcg cgttcctccg gcctcccggg cgtctgcatt gccacctccg gccccggcgc    540
caccaacctc gtgagcggcc tcgccgacgc tttaatggac agcgtcccag tcgtcgccat    600
caccggccag gtcgcccgcc ggatgatcgg caccgacgcc ttccaagaaa ccccgatcgt    660
ggaggtgagc agatccatca cgaagcacaa ctacctcatc ctcgacgtcg acgacatccc    720
ccgcgtcgtc gccgaggctt tcttcgtcgc cacctccggc cgccccggtc cggtcctcat    780
cgacattccc aaagacgttc agcagcaact cgccgtgcct aattgggacg agcccgttaa    840
cctccccggt tacctcgcca ggctgcccag gcccccgcc gaggcccaat ggaacacat     900 tgtcagactc atcatggagg cccaaaagcc cgttctctac gtcggcggtg gcagtttgaa    960
ttccagtgct gaattgaggc gctttgttga actcactggt attcccgttg ctagcacttt    1020
aatgggtctt ggaactttc ctattggtga tgaatattcc cttcagatgc tgggtatgca    1080
tggtactgtt tatgctaact atgctgttga caatagtgat tgttgcttg cctttgggt     1140 aaggtttgat gaccgtgtta ctgggaagct tgaggctttt gctagtaggg ctaagattgt    1200
tcacattgat attgattctg ccgagattgg gaagaacaag caggcgcacg tgtcggtttg    1260
cgcggatttg aagttggcct tgaagggaat taatatgatt ttggaggaga aggagtgga    1320 gggtaagttt gatcttggag gttggagaga agagattaat gtgcagaaac acaagtttcc    1380
attgggttac aagacattcc aggacgcgat ttctccgcag catgctatcg aggttcttga    1440
tgagttgact aatggagatg ctattgttag tactgggggtt gggcagcatc aaatgtgggc    1500
tgcgcagttt tacaagtaca agagaccgag gcagtggttg acctcagggg gtcttggagc    1560
catgggtttt ggattgcctg cggctattgg tgctgctgtt gctaaccctg gggctgttgt    1620
ggttgacatt gatggggatg gtagtttcat catgaatgtt caggagttgg ccactataag    1680
agtggagaat ctcccagtta agatattgtt gttgaacaat cagcatttgg gtatggtggt    1740
tcagttggag gataggttct acaagtccaa tagagctcac acctatcttg gagatccgtc    1800
tagcgagagc gagatattcc caaacatgct caagtttgct gatgcttgtg ggataccggc    1860
agcgcgagtg acgaagaagg aagagcttag agcggcaatt cagagaatgt ggacaccc    1920 tggccctac cttcttgatg tcattgtgcc ccatcaggag catgtgttgc cgatgattcc      1980
cagtaatgga tccttcaagg atgtgataac tgagggtgat ggtagaacga ggtactgact    2040
agctagtcag ttaacctaga cttgtccatc ttctggattg ccaacttaa ttaatgtatg     2100 aaataaaagg atgcacacat agtgacatgc taatcactat aatgtgggca tcaaagttgt    2160
gtgttatgtg taattactag ttatctgaat aaaagagaaa gagatcatcc atatttctta    2220
tcctaaatga atgtcacgtg tctttataat tctttgatga accagatgca tttcattaac    2280
caaatccata tacatataaa tattaatcat atataattaa tatcaattgg gttagcaaaa    2340
caaatctagt ctaggtgtgt tttgccccca agcttatcga taccgtcggc gcggggtacc    2400
cgggcagatc taggcgcgcc cgaagttcct attccgaagt tcctattcta catagagtat    2460
```

```
aggaacttcc gatatcactg cagtggccgg cccagctgat gatcccggtg aagttcctat    2520
tccgaagttc ctattctcca gaaagtatag gaacttcact agagcttgcg gccgccaccg    2580
cggtggagct ccaattcgcc ctatagtgag tcgtattaca attcactggc cgtcgtttta    2640
caacgtcgtg actgggaaaa ccctggcgtt acccaactta atcgccttgc agcacatccc    2700
cctttcgcca gctggcgtaa tagcgaagag gcccgcaccg atcgcccttc ccaacagttg    2760
cgcagcctga atggcgaatg gaaattgtaa gcgttaatat tttgttaaaa ttcgcgttaa    2820
atttttgtta aatcagctca ttttttaacc aataggccga atcggcaaaa tcccttata    2880
aatcaaaaga atagaccgag atagggttga gtgttgttcc agtttggaac aagagtccac    2940
tattaaagaa cgtggactcc aacgtcaaag ggcgaaaaac cgtctatcag ggcgatggcc    3000
cactacgtga accatcaccc taatcaagtt ttttggggtc gaggtgccgt aaagcactaa    3060
atcggaaccc taaagggagc ccccgattta gagcttgacg ggaaagccg gcgaacgtgg    3120
cgagaaagga agggaagaaa gcgaaaggag cgggcgctag ggcgctggca agtgtagcgg    3180
tcacgctgcg cgtaaccacc acacccgccg cgcttaatgc gccgctacag ggcgcgtcag    3240
gtggcacttt tcggggaaat gtgcgcggaa cccctatttg tttatttttc taaatacatt    3300
caaatatgta tccgctcatg agacaataac cctgataaat gcttcaataa tattgaaaaa    3360
ggaagagtat gagtattcaa catttccgtg tcgcccttat ccctttttt gcggcatttt    3420
gccttcctgt ttttgctcac cagaaacgc tggtgaaagt aaaagatgct gaagatcagt    3480
tgggtgcacg agtgggttac atcgaactgg atctcaacag cggtaagatc cttgagagtt    3540
ttcgccccga agaacgtttt ccaatgatga gcacttttaa agttctgcta tgtggcgcgg    3600
tattatcccg tattgacgcc gggcaagagc aactcggtcg ccgcatacac tattctcaga    3660
atgacttggt tgagtactca ccagtcacag aaaagcatct tacggatggc atgacagtaa    3720
gagaattatg cagtgctgcc ataaccatga gtgataacac tgcggccaac ttacttctga    3780
caacgatcgg aggaccgaag gagctaaccg cttttttgca acatggggg gatcatgtaa    3840
ctcgccttga tcgttgggaa ccggagctga atgaagccat accaaacgac gagcgtgaca    3900
ccacgatgcc tgtagcaatg gcaacaacgt tgcgcaaact attaactggc gaactactta    3960
ctctagcttc ccggcaacaa ttaatagact ggatggaggc ggataaagtt gcaggaccac    4020
ttctgcgctc ggcccttccg gctggctggt ttattgctga taaatctgga gccggtgagc    4080
gtgggtctcg cggtatcatt gcagcactgg ggccagatgg taagccctcc cgtatcgtag    4140
ttatctacac gacggggagt caggcaacta tggatgaacg aaatagacag atcgctgaga    4200
taggtgcctc actgattaag cattggtaac tgtcagacca agtttactca tatatacttt    4260
agattgattt aaaacttcat ttttaattta aaaggatcta ggtgaagatc ctttttgata    4320
atctcatgac caaaatccct taacgtgagt tttcgttcca ctgagcgtca gaccccgtag    4380
aaaagatcaa aggatcttct tgagatcctt ttttctgcg cgtaatctgc tgcttgcaaa    4440
caaaaaaacc accgctacca gcggtggttt gtttgccgga tcaagagcta ccaactcttt    4500
ttccgaaggt aactggcttc agcagagcgc agataccaaa tactgtcctt ctagtgtagc    4560
cgtagttagg ccaccacttc aagaactctg tagcaccgcc tacatacctc gctctgctaa    4620
tcctgttacc agtggctgct gccagtggcg ataagtcgtg tcttaccggg ttggactcaa    4680
gacgatagtt accggataag gcgcagcggt cgggctgaac ggggggttcg tgcacacagc    4740
ccagcttgga gcgaacgacc tacaccgaac tgagatacct acagcgtgag ctatgagaaa    4800
gcgccacgct tcccgaaggg agaaaggcgg acaggtatcc ggtaagcggc agggtcggaa    4860
```

| | |
|---|---|
| caggagagcg cacgagggag cttccagggg gaaacgcctg gtatctttat agtcctgtcg | 4920 |
| ggtttcgcca cctctgactt gagcgtcgat ttttgtgatg ctcgtcaggg gggcggagcc | 4980 |
| tatggaaaaa cgccagcaac gcggccttt tacggttcct ggccttttgc tggccttttg | 5040 |
| ctcacatgtt ctttcctgcg ttatccctg attctgtgga taaccgtatt accgcctttg | 5100 |
| agtgagctga taccgctcgc cgcagccgaa cgaccgagcg cagcgagtca gtgagcgagg | 5160 |
| aagcggaaga gcgcccaata cgcaaaccgc ctctccccgc gcgttggccg attcattaat | 5220 |
| gcagctggca cgacaggttt cccgactgga aagcgggcag tgagcgcaac gcaattaatg | 5280 |
| tgagttagct cactcattag gcaccccagg ctttacactt tatgcttccg gctcgtatgt | 5340 |
| tgtgtggaat tgtgagcgga taacaatttc acacaggaaa cagctatgac catgattacg | 5400 |
| ccaagctcga aattaaccct cactaaaggg aacaaaagct gggtaccggg ccccccctcg | 5460 |
| aggtcgacgg tatcgataag cttgttaaca | 5490 |

<210> SEQ ID NO 43
<211> LENGTH: 4372
<212> TYPE: DNA
<213> ORGANISM: Artificial Sequence
<220> FEATURE:
<223> OTHER INFORMATION: donor construct QC429

<400> SEQUENCE: 43

| | |
|---|---|
| gaagttccta ttccgaagtt cctattctct agaaagtata ggaacttcca ctagtccatg | 60 |
| aaaaagcctg aactcaccgc gacgtctgtc gagaagtttc tgatcgaaaa gttcgacagc | 120 |
| gtctccgacc tgatgcagct ctcggagggc gaagaatctc gtgctttcag cttcgatgta | 180 |
| ggagggcgtg gatatgtcct gcgggtaaat agctgcgccg atggtttcta caaagatcgt | 240 |
| tatgtttatc ggcactttgc atcggccgcg ctcccgattc cggaagtgct tgacattggg | 300 |
| gaattcagcg agagcctgac ctattgcatc tcccgccgtg cacagggtgt cacgttgcaa | 360 |
| gacctgcctg aaaccgaact gcccgctgtt ctgcagccgg tcgcggaggc catggatgcg | 420 |
| atcgctgcgg ccgatcttag ccagacgagc gggttcggcc cattcggacc gcaaggaatc | 480 |
| ggtcaataca ctacatggcg tgatttcata tgcgcgattg ctgatcccca tgtgtatcac | 540 |
| tggcaaactg tgatggacga caccgtcagt gcgtccgtcg cgcaggctct cgatgagctg | 600 |
| atgctttggg ccgaggactg ccccgaagtc cggcacctcg tgcacgcgga tttcggctcc | 660 |
| aacaatgtcc tgacggacaa tggccgcata acagcggtca ttgactggag cgaggcgatg | 720 |
| ttcggggatt cccaatacga ggtcgccaac atcttcttct ggaggccgtg gttggcttgt | 780 |
| atggagcagc agacgcgcta cttcgagcgg aggcatccgg agcttgcagg atcgccgcgg | 840 |
| ctccgggcgt atatgctccg cattggtctt gaccaactct atcagagctt ggttgacggc | 900 |
| aatttcgatg atgcagcttg ggcgcagggt cgatgcgacg caatcgtccg atccggagcc | 960 |
| gggactgtcg gcgtacaca atcgcccgc agaagcgcgg ccgtctggac cgatggctgt | 1020 |
| gtagaagtac tcgccgatag tggaaaccga cgccccagca ctcgtccgag gcaaaggaa | 1080 |
| tagtgaggta cctaaagaag gagtgcgtcg aagcagatcg ttcaaacatt tggcaataaa | 1140 |
| gtttcttaag attgaatcct gttgccggtc ttgcgatgat tatcatataa tttctgttga | 1200 |
| attacgttaa gcatgtaata attaacatgt aatgcatgac gttatttatg agatgggttt | 1260 |
| ttatgattag agtcccgcaa ttatacattt aatacgcgat agaaaacaaa atatagcgcg | 1320 |
| caaactagga taaattatcg cgcgcggtgt catctatgtt actagatcga tgtcgacccg | 1380 |
| ggcagatcta ggcgcgcccg aagttcctat tccgaagttc ctattctaca tagagtatag | 1440 |

```
gaacttccga tggccgccac cgcggtggag ctccaattcg ccctatagtg agtcgtatta    1500
caattcactg gccgtcgttt tacaacgtcg tgactgggaa aaccctggcg ttacccaact    1560
taatcgcctt gcagcacatc ccccttccgc cagctggcgt aatagcgaag aggcccgcac    1620
cgatcgccct tcccaacagt tgcgcagcct gaatggcgaa tggaaattgt aagcgttaat    1680
attttgttaa aattcgcgtt aaattttgt taaatcagct cattttttaa ccaataggcc    1740
gaaatcggca aaatcccta taaatcaaaa gaatagaccg atagggttt gagtgttgtt    1800 ccagtttgga acaagagtcc actattaaag aacgtggact ccaacgtcaa agggcgaaaa    1860
accgtctatc agggcgatgg cccactacgt gaaccatcac cctaatcaag tttttgggg    1920 tcgaggtgcc gtaaagcact aaatcggaac cctaaaggga gccccgatt tagagcttga    1980 cggggaaagc cggcgaacgt ggcgagaaag gaagggaaga agcgaaagg agcgggcgct    2040 agggcgctgg caagtgtagc ggtcacgctg cgcgtaacca ccacccgc cgcgcttaat    2100 gcgccgctac agggcgcgtc aggtggcact tttcggggaa atgtgcgcgg aaccctatt    2160 tgtttatttt tctaaataca ttcaaatatg tatccgctca tgagacaata accctgataa    2220
atgcttcaat aatattgaaa aaggaagagt atgagtattc aacatttccg tgtcgccctt    2280 attcccttt ttgcggcatt ttgccttcct gttttgctc acccagaaac gctggtgaaa    2340
gtaaaagatg ctgaagatca gttgggtgca cgagtgggtt acatcgaact ggatctcaac    2400
agcggtaaga tccttgagag ttttcgcccc gaagaacgtt ttccaatgat gagcactttt    2460
aaagttctgc tatgtggcgc ggtattatcc cgtattgacg ccgggcaaga gcaactcggt    2520
cgccgcatac actattctca gaatgacttg gttgagtact caccagtcac agaaaagcat    2580 cttacgatg gcatgacagt aagagaatta tgcagtgctg ccataaccat gagtgataac    2640
actgcggcca acttacttct gacaacgatc ggaggaccga aggagctaac cgcttttttg    2700
cacaacatgg gggatcatgt aactcgcctt gatcgttggg aaccggagct gaatgaagcc    2760
ataccaaacg acgagcgtga caccacgatg cctgtagcaa tggcaacaac gttgcgcaaa    2820
ctattaactg gcgaactact tactctagct tcccggcaac aattaataga ctggatggag    2880
gcggataaag ttgcaggacc acttctgcgc tcggcccttc cggctggctg gtttattgct    2940
gataaatctg gagccggtga gcgtgggtct cgcggtatca ttgcagcact ggggccagat    3000
ggtaagccct cccgtatcgt agttatctac acgacgggga gtcaggcaac tatggatgaa    3060
cgaaatagac agatcgctga gataggtgcc tcactgatta agcattggta actgtcagac    3120
caagtttact catatatact ttagattgat ttaaaacttc attttaatt taaaaggatc    3180 taggtgaaga tcctttttga taatctcatg accaaaatcc cttaacgtga gttttcgttc    3240
cactgagcgt cagaccccgt agaaaagatc aaaggatctt cttgagatcc ttttttctg    3300 cgcgtaatct gctgcttgca acaaaaaaa ccaccgctac cagcggtggt ttgtttgccg    3360
gatcaagagc taccaactct tttccgaag gtaactggct tcagcagagc gcagatacca    3420
aatactgtcc ttctagtgta gccgtagtta ggccaccact tcaagaactc tgtagcaccg    3480
cctacatacc tcgctctgct aatcctgtta ccagtggctg ctgccagtgg cgataagtcg    3540
tgtcttaccg ggttggactc aagacgatag ttaccggata aggcgcagcg gtcgggctga    3600
acggggggtt cgtgcacaca gcccagcttg gagcgaacga cctacaccga actgagatac    3660
ctacagcgtg agctatgaga aagcgccacg cttcccgaag ggagaaaggc ggacaggtat    3720
ccggtaagcg gcagggtcgg aacaggagag cgcacgaggg agcttccagg gggaaacgcc    3780
tggtatcttt atagtcctgt cgggtttcgc cacctctgac ttgagcgtcg attttgtga    3840
```

```
tgctcgtcag gggggcggag cctatggaaa aacgccagca acgcggcctt tttacggttc    3900 ctggccttt  gctggccttt tgctcacatg ttctttcctg cgttatcccc tgattctgtg    3960
gataaccgta ttaccgcctt tgagtgagct gataccgctc gccgcagccg aacgaccgag    4020
cgcagcgagt cagtgagcga ggaagcggaa gagcgcccaa tacgcaaacc gcctctcccc    4080
gcgcgttggc cgattcatta atgcagctgg cacgacaggt ttcccgactg gaaagcgggc    4140
agtgagcgca acgcaattaa tgtgagttag ctcactcatt aggcacccca ggctttacac    4200
tttatgcttc cggctcgtat gttgtgtgga attgtgagcg gataacaatt tcacacagga    4260
aacagctatg accatgatta cgccaagctc gaaattaacc ctcactaaag ggaacaaaag    4320
ctgggtaccg ggccccccct cgaggtcgac ggtatcgata agcttgttaa ca            4372
```

<210> SEQ ID NO 44
<211> LENGTH: 4444
<212> TYPE: DNA
<213> ORGANISM: Artificial Sequence
<220> FEATURE:
<223> OTHER INFORMATION: donor construct QC459

<400> SEQUENCE: 44

```
gaagttccta ttccgaagtt cctattctct agaaagtata ggaacttcca ctagtccatg      60
aaaaagcctg aactcaccgc gacgtctgtc gagaagtttc tgatcgaaaa gttcgacagc     120
gtctccgacc tgatgcagct ctcggagggc gaagaatctc gtgctttcag cttcgatgta     180
ggagggcgtg gatatgtcct gcgggtaaat agctgcgccg atggtttcta caaagatcgt     240
tatgtttatc ggcactttgc atcggccgcg ctcccgattc cggaagtgct tgacattggg     300
gaattcagcg agagcctgac ctattgcatc tcccgccgtg cacagggtgt cacgttgcaa     360
gacctgcctg aaaccgaact gcccgctgtt ctgcagccgg tcgcggaggc catggatgcg     420
atcgctgcgg ccgatcttag ccagacgagc gggttcggcc cattcggacc gcaaggaatc     480
ggtcaataca ctacatggcg tgatttcata tgcgcgattg ctgatcccca tgtgtatcac     540
tggcaaactg tgatggacga caccgtcagt gcgtccgtcg cgcaggctct cgatgagctg     600
atgctttggg ccgaggactg ccccgaagtc cggcacctcg tgcacgcgga tttcggctcc     660
aacaatgtcc tgacggacaa tggccgcata acagcggtca ttgactggag cgaggcgatg     720
ttcggggatt cccaatacga ggtcgccaac atcttcttct ggaggccgtg gttggcttgt     780
atggagcagc agacgcgcta cttcgagcgg aggcatccgg agcttgcagg atcgccgcgg     840
ctccgggcgt atatgctccg cattggtctt gaccaactct atcagagctt ggttgacggc     900
aatttcgatg atgcagcttg gcgcagggt  cgatgcgacg caatcgtccg atccggagcc     960
gggactgtcg ggcgtacaca atcgcccgc  agaagcgcgg ccgtctggac cgatggctgt    1020
gtagaagtac tcgccgatag tggaaaccga cgccccagca ctcgtccgag ggcaaaggaa    1080
tagtgaggta cctaaagaag gagtgcgtcg aagcagatcg ttcaaacatt tggcaataaa    1140
gtttcttaag attgaatcct gttgccggtc ttgcgatgat tatcatataa tttctgttga    1200
attacgttaa gcatgtaata attaacatgt aatgcatgac gttatttatg agatgggttt    1260
ttatgattag agtcccgcaa ttatacattt aatacgcgat agaaaacaaa atatagcgcg    1320
caaactagga taaattatcg cgcgcggtgt catctatgtt actagatcga tgtcgacccg    1380 ggcccctagga ggccggcccg aagttcctat tccgaagttc ctattcttca aaagtatag    1440 gaacttccga tatcacttaa gtggcgcgcc cgaagttcct attccgaagt tcctattcta    1500
catagagtat aggaacttcc gatggccgcc accgcggtgg agctccaatt cgccctatag    1560
```

```
tgagtcgtat tacaattcac tggccgtcgt tttacaacgt cgtgactggg aaaaccctgg    1620
cgttacccaa cttaatcgcc ttgcagcaca tcccccttc gccagctggc gtaatagcga    1680
agaggcccgc accgatcgcc cttcccaaca gttgcgcagc ctgaatggcg aatggaaatt    1740
gtaagcgtta atattttgtt aaaattcgcg ttaaattttt gttaaatcag ctcattttt    1800 aaccaatagg ccgaaatcgg caaaatccct tataaatcaa agaatagac cgagataggg    1860 ttgagtgttg ttccagtttg gaacaagagt ccactattaa agaacgtgga ctccaacgtc    1920
aaagggcgaa aaaccgtcta tcagggcgat ggcccactac gtgaaccatc accctaatca    1980
agttttttgg ggtcgaggtg ccgtaaagca ctaaatcgga accctaaagg gagcccccga    2040
tttagagctt gacggggaaa gccggcgaac gtggcgagaa aggaagggaa gaaagcgaaa    2100
ggagcgggcg ctagggcgct ggcaagtgta gcggtcacgc tgcgcgtaac caccacccc    2160 gccgcgctta atgcgccgct acagggcgcg tcaggtggca cttttcgggg aaatgtgcgc    2220 ggaacccta tttgtttatt tttctaaata cattcaaata tgtatccgct catgagacaa    2280
taaccctgat aaatgcttca ataatattga aaaaggaaga gtatgagtat caacatttc    2340 cgtgtcgccc ttattccctt ttttgcggca ttttgccttc ctgtttttgc tcacccagaa    2400
acgctggtga agtaaaaga tgctgaagat cagttgggtg cacgagtggg ttacatcgaa    2460
ctggatctca acagcggtaa gatccttgag agttttcgcc ccgaagaacg ttttccaatg    2520
atgagcactt ttaaagttct gctatgtggc gcggtattat cccgtattga cgccgggcaa    2580
gagcaactcg gtcgccgcat acactattct cagaatgact tggttgagta ctcaccagtc    2640
acagaaaagc atcttacgga tggcatgaca gtaagagaat tatgcagtgc tgccataacc    2700
atgagtgata acactgcggc caacttactt ctgacaacga tcggaggacc gaaggagcta    2760
accgcttttt tgcacaacat gggggatcat gtaactcgcc ttgatcgttg ggaaccggag    2820
ctgaatgaag ccataccaaa cgacgagcgt gacaccacga tgcctgtagc aatggcaaca    2880
acgttgcgca aactattaac tggcgaacta cttactctag cttcccggca acaattaata    2940
gactggatgg aggcggataa agttgcagga ccacttctgc gctcggccct tccggctggc    3000
tggtttattg ctgataaatc tggagccggt gagcgtgggt ctcgcggtat cattgcagca    3060
ctggggccag atggtaagcc ctcccgtatc gtagttatct acacgacggg gagtcaggca    3120
actatggatg aacgaaatag acagatcgct gagataggtg cctcactgat taagcattgg    3180
taactgtcag accaagttta ctcatatata ctttagattg atttaaaact tcatttttaa    3240
tttaaaagga tctaggtgaa gatcctttt gataatctca tgaccaaaat cccttaacgt    3300
gagttttcgt tccactgagc gtcagacccc gtagaaaaga tcaaaggatc ttcttgagat    3360
cctttttttc tgcgcgtaat ctgctgcttg caaacaaaaa aaccaccgct accagcggtg    3420
gtttgtttgc cggatcaaga gctaccaact ctttttccga aggtaactgg cttcagcaga    3480
gcgcagatac caaatactgt ccttctagtg tagccgtagt taggccacca cttcaagaac    3540
tctgtagcac cgcctacata cctcgctctg ctaatcctgt taccagtggc tgctgccagt    3600
ggcgataagt cgtgtcttac cgggttggac tcaagacgat agttaccgga taaggcgcag    3660
cggtcgggct gaacggggg ttcgtgcaca gcccagct tggagcgaac gacctacacc    3720
gaactgagat acctacagcg tgagctatga gaaagcgcca cgcttcccga agggagaaag    3780
gcggacaggt atccggtaag cggcagggtc ggaacaggag agcgcacgag ggagcttcca    3840
gggggaaacg cctggtatct ttatagtcct gtcgggtttc gccacctctg acttgagcgt    3900
cgatttttgt gatgctcgtc aggggggcgg agcctatgga aaaacgccag caacgcggcc    3960
```

```
ttttacggt tcctggcctt ttgctggcct tttgctcaca tgttcttcc tgcgttatcc    4020 cctgattctg tggataaccg tattaccgcc tttgagtgag ctgataccgc tcgccgcagc    4080
cgaacgaccg agcgcagcga gtcagtgagc gaggaagcgg aagagcgccc aatacgcaaa    4140
ccgcctctcc ccgcgcgttg gccgattcat taatgcagct ggcacgacag gtttcccgac    4200
tggaaagcgg gcagtgagcg caacgcaatt aatgtgagtt agctcactca ttaggcaccc    4260
caggctttac actttatgct tccggctcgt atgttgtgtg gaattgtgag cggataacaa    4320
tttcacacag gaaacagcta tgaccatgat tacgccaagc tcgaaattaa ccctcactaa    4380
agggaacaaa agctgggtac cgggccccc ctcgaggtcg acggtatcga taagcttgtt    4440
aaca                                                                 4444
```

<210> SEQ ID NO 45
<211> LENGTH: 5394
<212> TYPE: DNA
<213> ORGANISM: Artificial Sequence
<220> FEATURE:
<223> OTHER INFORMATION: donor construct QC460

<400> SEQUENCE: 45

```
gaagttccta ttccgaagtt cctattctct agaaagtata ggaacttcca ctagtgagga      60
tctgatcatg ccacacaaca caatggcggc caccgcttcc agaaccaccc gattctcttc     120
ttcctcttca caccccacct tccccaaacg cattactaga tccaccctcc ctctctctca     180
tcaaaccctc accaaaccca accacgctct caaaatcaaa tgttccatct ccaaaccccc     240
cacggcggcg cccttcacca aggaagcgcc gaccacggag cccttcgtgt cacggttcgc     300
ctccggcgaa cctcgcaagg gcgcggacat ccttgtggag gcgctggaga ggcagggcgt     360
gacgacggtg ttcgcgtacc ccggcggtgc gtcgatggag atccaccagg cgctcacgcg     420
ctccgccgcc atccgcaacg tgctcccgcg ccacgagcag ggcggcgtct tcgccgccga     480
aggctacgcg cgttcctccg gcctcccgg cgtctgcatt gccacctccg gccccggcgc     540
caccaacctc gtgagcggcc tcgccgacgc tttaatggac agcgtcccag tcgtcgccat     600
caccggccag gtcgcccgcc ggatgatcgg caccgacgcc ttccaagaaa ccccgatcgt     660
ggaggtgagc agatccatca cgaagcacaa ctacctcatc ctcgacgtcg acgacatccc     720
ccgcgtcgtc gccgaggctt tcttcgtcgc cacctccggc cgccccggtc cggtcctcat     780
cgacattccc aaagacgttc agcagcaact cgccgtgcct aattgggacg agcccgttaa     840
cctccccggt tacctcgcca ggctgcccag gccccccgcc gaggcccaat ggaacacat     900 tgtcagactc atcatggagg cccaaaagcc cgttctctac gtcggcggtg gcagtttgaa     960
ttccagtgct gaattgaggc gctttgttga actcactggt attcccgttg ctagcacttt    1020
aatgggtctt ggaactttc ctattggtga tgaatattcc cttcagatgc tgggtatgca    1080
tggtactgtt tatgctaact atgctgttga caatagtgat ttgttgcttg cctttgggt    1140 aaggtttgat gaccgtgtta ctgggaagct tgaggctttt gctagtaggg ctaagattgt    1200
tcacattgat attgattctg ccgagattgg gaagaacaag caggcgcacg tgtcggtttg    1260
cgcggatttg aagttggcct tgaagggaat taatatgatt ttggaggaga aaggagtgga    1320
gggtaagttt gatcttggag gttggagaga agagattaat gtgcagaaac acaagtttcc    1380
attgggttac aagacattcc aggacgcgat ttctccgcag catgctatcg aggttcttga    1440
tgagttgact aatggagatg ctattgttag tactggggtt gggcagcatc aaatgtgggc    1500
tgccgcagtt tacaagtaca agagaccgag gcagtggttg acctcagggg gtcttggagc    1560
```

```
catgggtttt ggattgcctg cggctattgg tgctgctgtt gctaaccctg gggctgttgt    1620
ggttgacatt gatggggatg gtagtttcat catgaatgtt caggagttgg ccactataag    1680
agtggagaat ctcccagtta agatattgtt gttgaacaat cagcatttgg gtatggtggt    1740
tcagttggag gataggttct acaagtccaa tagagctcac acctatcttg gagatccgtc    1800
tagcgagagc gagatattcc caaacatgct caagtttgct gatgcttgtg ggataccggc    1860
agcgcgagtg acgaagaagg aagagcttag agcggcaatt cagagaatgt tggacacccc    1920
tggcccctac cttcttgatg tcattgtgcc ccatcaggag catgtgttgc cgatgattcc    1980
cagtaatgga tccttcaagg atgtgataac tgagggtgat ggtagaacga ggtactgact    2040
agctagtcag ttaacctaga cttgtccatc ttctggattg ccaacttaa ttaatgtatg     2100 aaataaaagg atgcacacat agtgacatgc taatcactat aatgtgggca tcaaagttgt    2160
gtgttatgtg taattactag ttatctgaat aaaagagaaa gagatcatcc atatttctta    2220
tcctaaatga atgtcacgtg tctttataat tctttgatga accagatgca tttcattaac    2280
caaatccata tacatataaa tattaatcat atataattaa tatcaattgg gttagcaaaa    2340
caaatctagt ctaggtgtgt tttgccccca agcttatcga taccgtcggc gcggggtacc    2400
cgggccctag gaggccggcc cgaagttcct attccgaagt tcctattctt caaaaagtat    2460
aggaacttcc gatggccgcc accgcggtgg agctccaatt cgccctatag tgagtcgtat    2520
tacaattcac tggccgtcgt tttacaacgt cgtgactggg aaaaccctgg cgttacccaa    2580
cttaatcgcc ttgcagcaca tccccctttc gccagctggc gtaatagcga gaggcccgc    2640 accgatcgcc cttcccaaca gttgcgcagc ctgaatggcg aatggaaatt gtaagcgtta    2700
atattttgtt aaaattcgcg ttaaattttt gttaaatcag ctcatttttt aaccaatagg    2760
ccgaaatcgg caaaatccct tataaatcaa agaatagac cgagataggg ttgagtgttg     2820
ttccagtttg gaacaagagt ccactattaa agaacgtgga ctccaacgtc aaagggcgaa    2880
aaaccgtcta tcagggcgat ggcccactac gtgaaccatc accctaatca gttttttgg     2940 ggtcgaggtg ccgtaaagca ctaaatcgga accctaaagg agcccccga tttagagctt     3000 gacggggaaa gccggcgaac gtggcgagaa aggaagggaa gaaagcgaaa ggagcgggcg    3060
ctagggcgct ggcaagtgta gcggtcacgc tgcgcgtaac caccacaccc gccgcgctta    3120
atgcgccgct acagggcgcg tcaggtggca cttttcgggg aaatgtgcgc ggaaccccta    3180
tttgtttatt tttctaaata cattcaaata tgtatccgct catgagacaa taaccctgat    3240
aaatgcttca ataatattga aaaggaaga gtatgagtat tcaacatttc cgtgtcgccc     3300
ttattccctt ttttgcggca ttttgccttc ctgttttgc tcacccagaa acgctggtga    3360
aagtaaaaga tgctgaagat cagttgggtg cacgagtggg ttacatcgaa ctggatctca    3420
acagcggtaa gatccttgag agttttcgcc ccgaagaacg ttttccaatg atgagcactt    3480
ttaaagttct gctatgtggc gcggtattat cccgtattga cgccgggcaa gagcaactcg    3540
gtcgccgcat acactattct cagaatgact tggttgagta ctcaccagtc acagaaaagc    3600
atcttacgga tggcatgaca gtaagagaat tatgcagtgc tgccataacc atgagtgata    3660
acactgcggc caacttactt ctgacaacga tcggaggacc gaaggagcta accgcttttt    3720
tgcacaacat gggggatcat gtaactcgcc ttgatcgttg gaaccggag ctgaatgaag      3780 ccataccaaa cgacgagcgt gacaccacga tgcctgtagc aatggcaaca acgttgcgca    3840
aactattaac tggcgaacta cttactctag cttcccggca acaattaata gactggatgg    3900
aggcggataa agttgcagga ccacttctgc gctcggccct tccggctggc tggtttattg    3960
```

```
ctgataaatc tggagccggt gagcgtgggt ctcgcggtat cattgcagca ctggggccag    4020
atggtaagcc ctcccgtatc gtagttatct acacgacggg gagtcaggca actatggatg    4080
aacgaaatag acagatcgct gagataggtg cctcactgat taagcattgg taactgtcag    4140
accaagttta ctcatatata ctttagattg atttaaaact tcatttttaa tttaaaagga    4200
tctaggtgaa gatccttttt gataatctca tgaccaaaat cccttaacgt gagttttcgt    4260
tccactgagc gtcagacccc gtagaaaaga tcaaggatc ttcttgagat ccttttttc     4320 tgcgcgtaat ctgctgcttg caaacaaaaa aaccaccgct accagcggtg gtttgtttgc    4380
cggatcaaga gctaccaact cttttccga aggtaactgg cttcagcaga gcgcagatac    4440
caaatactgt ccttctagtg tagccgtagt taggccacca cttcaagaac tctgtagcac    4500
cgcctacata cctcgctctg ctaatcctgt taccagtggc tgctgccagt ggcgataagt    4560
cgtgtcttac cgggttggac tcaagacgat agttaccgga taaggcgcag cggtcgggct    4620 gaacggggg ttcgtgcaca cagcccagct tggagcgaac gacctacacc gaactgagat    4680
acctacagcg tgagctatga gaaagcgcca cgcttcccga agggagaaag gcggacaggt    4740
atccggtaag cggcagggtc ggaacaggag agcgcacgag ggagcttcca ggggggaaacg    4800 cctggtatct ttatagtcct gtcgggtttc gccacctctg acttgagcgt cgattttgt     4860 gatgctcgtc aggggggcgg agcctatgga aaaacgccag caacgcggcc ttttacggt    4920 tcctggcctt tgctggcct tttgctcaca tgttctttcc tgcgttatcc cctgattctg    4980
tggataaccg tattaccgcc tttgagtgag ctgataccgc tcgccgcagc cgaacgaccg    5040
agcgcagcga gtcagtgagc gaggaagcgg aagagcgccc aatacgcaaa ccgcctctcc    5100
ccgcgcgttg gccgattcat taatgcagct ggcacgacag gtttcccgac tggaaagcgg    5160
gcagtgagcg caacgcaatt aatgtgagtt agctcactca ttaggcaccc caggctttac    5220
actttatgct tccggctcgt atgttgtgtg gaattgtgag cggataacaa tttcacacag    5280
gaaacagcta tgaccatgat tacgccaagc tcgaaattaa ccctcactaa agggaacaaa    5340
agctgggtac cgggcccccc ctcgaggtcg acggtatcga taagcttgtt aaca          5394

<210> SEQ ID NO 46
<211> LENGTH: 3297
<212> TYPE: DNA
<213> ORGANISM: Artificial Sequence
<220> FEATURE:
<223> OTHER INFORMATION: QC288A422 DNA resulting from RMCE between
      QC288A and QC422

<400> SEQUENCE: 46
cgcgccggta ccgggccccc cctcgagcgg ccgcagattt aggtgacact atagaatatg     60
catcactagt aagcttgcat gcctgcaggt ttaaacagtc gactctagag atccgtcaac    120
atggtggagc acgacactct cgtctactcc aagaatatca aagatacagt ctcagaagac    180
caaagggcta ttgagacttt tcaacaaagg gtaatatcgg gaaacctcct cggattccat    240
tgcccagcta tctgtcactt catcaaaagg acagtagaaa aggaaggtgg cacctacaaa    300
tgccatcatt gcgataaagg aaaggctatc gttcaagatg cctctgccga cagtggtccc    360
aaagatggac ccccacccac gaggagcatc gtggaaaaag aagacgttcc aaccacgtct    420
tcaaagcaag tggattgatg tgatgatcct atgcgtatgg tatgacgtgt gttcaagatg    480
atgacttcaa acctacctat gacgtatggt atgacgtgtg tcgactgatg acttagatcc    540
actcgagcgg ctataaatac gtacctacgc accctgcgct accatcccta gagctgcagc    600
```

-continued

| | |
|---|---|
| ttatttttac aacaattacc aacaacaaca aacaacaaac aacattacaa ttactatttta | 660 |
| caattacagt cgacccaaca gaagttccta ttccgaagtt cctattctct agaaagtata | 720 |
| ggaacttcca ctagtgagga tctgatcatg ccacacaaca caatggcggc caccgcttcc | 780 |
| agaaccaccc gattctcttc ttcctcttca caccccacct tccccaaacg cattactaga | 840 |
| tccaccctcc ctctctctca tcaaaccctc accaaaccca accacgctct caaaatcaaa | 900 |
| tgttccatct ccaaaccccc cacggcggcg cccttcacca aggaagcgcc gaccacggag | 960 |
| cccttcgtgt cacggttcgc ctccggcgaa cctcgcaagg gcgcggacat ccttgtggag | 1020 |
| gcgctggaga ggcagggcgt gacgacggtg ttcgcgtacc ccggcggtgc gtcgatggag | 1080 |
| atccaccagg cgctcacgcg ctccgccgcc atccgcaacg tgctcccgcg ccacgagcag | 1140 |
| ggcggcgtct tcgccgccga aggctacgcg cgttcctccg gcctcccggg cgtctgcatt | 1200 |
| gccacctccg gccccggcgc caccaacctc gtgagcggcc tcgccgacgc tttaatggac | 1260 |
| agcgtcccag tcgtcgccat caccggccag gtcgcccgcc ggatgatcgg caccgacgcc | 1320 |
| ttccaagaaa ccccgatcgt ggaggtgagc agatccatca cgaagcacaa ctacctcatc | 1380 |
| ctcgacgtcg acgacatccc ccgcgtcgtc gccgaggctt tcttcgtcgc cacctccggc | 1440 |
| cgccccggtc cggtcctcat cgacattccc aaagacgttc agcagcaact cgccgtgcct | 1500 |
| aattgggacg agcccgttaa cctccccggt tacctcgcca ggctgcccag gccccccgcc | 1560 |
| gaggcccaat tggaacacat tgtcagactc atcatggagg cccaaaagcc cgttctctac | 1620 |
| gtcggcggtg gcagtttgaa ttccagtgct gaattgaggc gctttgttga actcactggt | 1680 |
| attcccgttg ctagcacttt aatgggtctt ggaacttttc ctattggtga tgaatattcc | 1740 |
| cttcagatgc tgggtatgca tggtactgtt tatgctaact atgctgttga caatagtgat | 1800 |
| ttgttgcttg cctttggggt aaggtttgat gaccgtgtta ctgggaagct tgaggctttt | 1860 |
| gctagtaggg ctaagattgt tcacattgat attgattctg ccgagattgg gaagaacaag | 1920 |
| caggcgcacg tgtcggtttg cgcggatttg aagttggcct tgaagggaat taatatgatt | 1980 |
| ttggaggaga aaggagtgga gggtaagttt gatcttggag gttggagaga agagattaat | 2040 |
| gtgcagaaac acaagtttcc attgggttac aagacattcc aggacgcgat ttctccgcag | 2100 |
| catgctatcg aggttcttga tgagttgact aatggagatg ctattgttag tactggggtt | 2160 |
| gggcagcatc aaatgtgggc tgcgcagttt tacaagtaca agagaccgag gcagtggttg | 2220 |
| acctcagggg gtcttggagc catgggtttt ggattgcctg cggctattgg tgctgctgtt | 2280 |
| gctaaccctg ggctgttgt ggttgacatt gatggggatg gtagtttcat catgaatgtt | 2340 |
| caggagttgg ccactataag agtggagaat ctcccagtta agatattgtt gttgaacaat | 2400 |
| cagcatttgg gtatggtggt tcagttggag gataggttct acaagtccaa tagagctcac | 2460 |
| acctatcttg gagatccgtc tagcgagagc gagatattcc caaacatgct caagtttgct | 2520 |
| gatgcttgtg gataccggc agcgcgagtg acgaagaagg aagagcttag agcggcaatt | 2580 |
| cagagaatgt tggacacccc tggcccctac cttcttgatg tcattgtgcc ccatcaggag | 2640 |
| catgtgttgc cgatgattcc cagtaatgga tccttcaagg atgtgataac tgagggtgat | 2700 |
| ggtagaacga ggtactgact agctagtcag ttaacctaga cttgtccatc ttctggattg | 2760 |
| gccaacttaa ttaatgtatg aaataaaagg atgcacacat agtgacatgc taatcactat | 2820 |
| aatgtgggca tcaaagttgt gtgttatgtg taattactag ttatctgaat aaaagagaaa | 2880 |
| gagatcatcc atatttctta tcctaaatga atgtcacgtg tctttataat tctttgatga | 2940 |
| accagatgca tttcattaac caaatccata tacatataaa tattaatcat atataattaa | 3000 |

```
tatcaattgg gttagcaaaa caaatctagt ctaggtgtgt tttgccccca agcttatcga      3060
taccgtcggc gcggggtacc cgggcagatc taggcgcgcc cgaagttcct attccgaagt      3120
tcctattcta catagagtat aggaacttcc gatatcactg cagtggccgg cccagctgat      3180
gatcccggtg aagttcctat tccgaagttc ctattctcca gaaagtatag gaacttcact      3240
agagcttgcg gccgcccct gggccggcca ctagtgagct cggtacccgg gtaccgg         3297
```

<210> SEQ ID NO 47
<211> LENGTH: 2275
<212> TYPE: DNA
<213> ORGANISM: Artificial Sequence
<220> FEATURE:
<223> OTHER INFORMATION: QC288A422-429 DNA resulting from RMCE between
      QC288A422 and QC429

<400> SEQUENCE: 47

```
cgcgccggta ccgggccccc cctcgagcgg ccgcagattt aggtgacact atagaatatg       60
catcactagt aagcttgcat gcctgcaggt ttaaacagtc gactctagag atccgtcaac      120
atggtggagc acgacactct cgtctactcc aagaatatca agatacagt ctcagaagac      180 caaagggcta ttgagacttt tcaacaaagg gtaatatcgg gaaacctcct cggattccat      240
tgcccagcta tctgtcactt catcaaaagg acagtagaaa aggaaggtgg cacctacaaa      300
tgccatcatt gcgataaagg aaaggctatc gttcaagatg cctctgccga cagtggtccc      360
aaagatggac ccccacccac gaggagcatc gtggaaaaag aagacgttcc aaccacgtct      420
tcaaagcaag tggattgatg tgatgatcct atgcgtatgg tatgacgtgt gttcaagatg      480
atgacttcaa acctacctat gacgtatggt atgacgtgtg tcgactgatg acttagatcc      540
actcgagcgg ctataaatac gtacctacgc accctgcgct accatcccta gagctgcagc      600
ttatttttac aacaattacc aacaacaaca acaacaaac aacattacaa ttactattta       660
caattacagt cgacccaaca gaagttccta ttccgaagtt cctattctct agaaagtata      720
ggaacttcca ctagtccatg aaaaagcctg aactcaccgc gacgtctgtc gagaagtttc      780
tgatcgaaaa gttcgacagc gtctccgacc tgatgcagct ctcggagggc gaagaatctc      840
gtgctttcag cttcgatgta ggagggcgtg gatatgtcct gcgggtaaat agctgcgccg      900
atggtttcta caaagatcgt tatgtttatc ggcactttgc atcggccgcg ctcccgattc      960
cggaagtgct tgacattggg gaattcagcg agagcctgac ctattgcatc tcccgccgtg     1020
cacagggtgt cacgttgcaa gacctgcctg aaaccgaact gcccgctgtt ctgcagccgg     1080
tcgcggaggc catggatgcg atcgctgcgg ccgatcttag ccagacgagc gggttcggcc     1140
cattcggacc gcaaggaatc ggtcaataca ctacatggcg tgatttcata tgcgcgattg     1200
ctgatcccca tgtgtatcac tggcaaactg tgatggacga caccgtcagt gcgtccgtcg     1260
cgcaggctct cgatgagctg atgctttggg ccgaggactg ccccgaagtc cggcacctcg     1320
tgcacgcgga tttcggctcc aacaatgtcc tgacggacaa tggccgcata acagcggtca     1380
ttgactggag cgaggcgatg ttcgggatt cccaatacga ggtcgccaac atcttcttct     1440
ggaggccgtg gttggcttgt atggagcagc agacgcgcta cttcgagcgg aggcatccgg     1500
agcttgcagg atcgccgcgg ctccgggcgt atatgctccg cattggtctt gaccaactct     1560
atcagagctt ggttgacggc aatttcgatg atgcagcttg ggcgcagggt cgatgcgacg     1620
caatcgtccg atccggagcc gggactgtcg ggcgtacaca aatcgcccgc agaagcgcgg     1680
ccgtctggac cgatgctgt gtagaagtac tcgccgatag tggaaaccga cgccccagca     1740
ctcgtccgag ggcaaaggaa tagtgaggta cctaaagaag gagtgcgtcg aagcagatcg     1800
```

```
ttcaaacatt tggcaataaa gtttcttaag attgaatcct gttgccggtc ttgcgatgat    1860
tatcatataa tttctgttga attacgttaa gcatgtaata attaacatgt aatgcatgac    1920
gttatttatg agatgggttt ttatgattag agtcccgcaa ttatacattt aatacgcgat    1980
agaaaacaaa atatagcgcg caaactagga taaattatcg cgcgcggtgt catctatgtt    2040
actagatcga tgtcgacccg ggcagatcta ggcgcgcccg aagttcctat tccgaagttc    2100
ctattctaca tagagtatag gaacttccga tatcactgca gtggccggcc cagctgatga    2160
tcccggtgaa gttcctattc cgaagttcct attctccaga agtatagga  acttcactag    2220 agcttgcggc cgcccctgg  gccggccact agtgagctcg gtacccgggt accgg         2275
```

<210> SEQ ID NO 48
<211> LENGTH: 2347
<212> TYPE: DNA
<213> ORGANISM: Artificial Sequence
<220> FEATURE:
<223> OTHER INFORMATION: QC288A422-459 DNA resulting from a RMCE between
      QC288A422 and QC459

<400> SEQUENCE: 48

```
cgcgccggta ccgggccccc cctcgagcgg ccgcagattt aggtgacact atagaatatg      60
catcactagt aagcttgcat gcctgcaggt ttaaacagtc gactctagag atccgtcaac     120
atggtggagc acgacactct cgtctactcc aagaatatca agatacagt  ctcagaagac    180 caaagggcta ttgagacttt tcaacaaagg gtaatatcgg gaaacctcct cggattccat    240
tgcccagcta tctgtcactt catcaaaagg acagtagaaa aggaaggtgg cacctacaaa    300
tgccatcatt gcgataaagg aaaggctatc gttcaagatg cctctgccga cagtggtccc    360
aaagatggac ccccacccac gaggagcatc gtggaaaaag aagacgttcc aaccacgtct    420
tcaaagcaag tggattgatg tgatgatcct atgcgtatgg tatgacgtgt gttcaagatg    480
atgacttcaa acctacctat gacgtatggt atgacgtgtg tcgactgatg acttagatcc    540
actcgagcgg ctataaatac gtacctacgc accctgcgct accatcccta gagctgcagc    600 ttattttttac aacaattacc aacaacaaca acaacaaac  aacattacaa ttactattta   660
caattacagt cgacccaaca gaagttccta ttccgaagtt cctattctct agaaagtata    720
ggaacttcca ctagtccatg aaaaagcctg aactcaccgc gacgtctgtc gagaagtttc    780
tgatcgaaaa gttcgacagc gtctccgacc tgatgcagct ctcggagggc gaagaatctc    840
gtgctttcag cttcgatgta ggagggcgtg gatatgtcct gcgggtaaat agctgcgccg    900
atggtttcta caaagatcgt tatgtttatc ggcactttgc atcggccgcg ctcccgattc    960
cggaagtgct tgacattggg gaattcagcg agagcctgac ctattgcatc tcccgccgtg    1020
cacagggtgt cacgttgcaa gacctgcctg aaaccgaact gcccgctgtt ctgcagccgg    1080
tcgcggaggc catggatgcg atcgctgcgg ccgatcttag ccagacgagc gggttcggcc    1140
cattcggacc gcaaggaatc ggtcaataca ctacatggcg tgatttcata tgcgcgattg    1200
ctgatcccca tgtgtatcac tggcaaactg tgatggacga caccgtcagt gcgtccgtcg    1260
cgcaggctct cgatgagctg atgctttggg ccgaggactg ccccgaagtc cggcacctcg    1320
tgcacgcgga tttcggctcc aacaatgtcc tgacggacaa tggccgcata acagcggtca    1380
ttgactggag cgaggcgatg ttcggggatt cccaatacga ggtcgccaac atcttcttct    1440
ggaggccgtg gttggcttgt atggagcagc agacgcgcta cttcgagcgg aggcatccgg    1500
agcttgcagg atcgccgcgg ctccgggcgt atatgctccg cattggtctt gaccaactct    1560
```

```
atcagagctt ggttgacggc aatttcgatg atgcagcttg ggcgcagggt cgatgcgacg    1620
caatcgtccg atccggagcc gggactgtcg ggcgtacaca aatcgcccgc agaagcgcgg    1680
ccgtctggac cgatggctgt gtagaagtac tcgccgatag tggaaaccga cgccccagca    1740
ctcgtccgag ggcaaaggaa tagtgaggta cctaaagaag gagtgcgtcg aagcagatcg    1800
ttcaaacatt tggcaataaa gtttcttaag attgaatcct gttgccggtc ttgcgatgat    1860
tatcatataa tttctgttga attacgttaa gcatgtaata attaacatgt aatgcatgac    1920
gttatttatg agatgggttt ttatgattag agtcccgcaa ttatacattt aatacgcgat    1980
agaaaacaaa atatagcgcg caaactagga taaattatcg cgcgcggtgt catctatgtt    2040
actagatcga tgtcgacccg ggccctagga ggccggcccg aagttcctat tccgaagttc    2100
ctattcttca aaaagtatag gaacttccga tatcacttaa gtggcgcgcc cgaagttcct    2160
attccgaagt tcctattcta catagagtat aggaacttcc gatatcactg cagtggccgg    2220
cccagctgat gatcccggtg aagttcctat tccgaagttc ctattctcca gaaagtatag    2280
gaacttcact agagcttgcg gccgccccct gggccggcca ctagtgagct cggtacccgg    2340
gtaccgg                                                              2347

<210> SEQ ID NO 49
<211> LENGTH: 3369
<212> TYPE: DNA
<213> ORGANISM: Artificial Sequence
<220> FEATURE:
<223> OTHER INFORMATION: QC288A422-459-460 DNA resulting from RMCE
      between QC288A422-459 and QC460

<400> SEQUENCE: 49
cgcgccggta ccgggccccc cctcgagcgg ccgcagattt aggtgacact atagaatatg      60
catcactagt aagcttgcat gcctgcaggt ttaaacagtc gactctagag atccgtcaac     120
atggtggagc acgacactct cgtctactcc aagaatatca agatacagt ctcagaagac     180 caaagggcta ttgagacttt tcaacaaagg gtaatatcgg gaaacctcct cggattccat     240
tgcccagcta tctgtcactt catcaaaagg acagtagaaa aggaaggtgg cacctacaaa     300
tgccatcatt gcgataaagg aaaggctatc gttcaagatg cctctgccga cagtggtccc     360
aaagatggac cccacccac gaggagcatc gtggaaaaag aagacgttcc aaccacgtct     420
tcaaagcaag tggattgatg tgatgatcct atgcgtatgg tatgacgtgt gttcaagatg     480
atgacttcaa acctacctat gacgtatggt atgacgtgtg tcgactgatg acttagatcc     540
actcgagcgg ctataaatac gtacctacgc accctgcgct accatcccta gagctgcagc     600 ttattttac aacaattacc aacaacaaca acaacaaac aacattacaa ttactattta       660
caattacagt cgacccaaca gaagttccta ttccgaagtt cctattctct agaaagtata    720
ggaacttcca ctagtgagga tctgatcatg ccacacaaca caatggcggc caccgcttcc    780
agaaccaccc gattctcttc ttcctcttca caccccacct tccccaaacg cattactaga    840
tccaccctcc ctctctctca tcaaaccctc accaaaccca accacgctct caaaatcaaa    900
tgttccatct ccaaaccccc cacggcggcg cccttcacca aggaagcgcc gaccacggag    960
cccttcgtgt cacggttcgc ctccggcgaa cctcgcaagg gcgcggacat ccttgtggag   1020
gcgctggaga ggcagggcgt gacgacggtg ttcgcgtacc ccggcggtgc gtcgatggag   1080
atccaccagg cgctcacgcg ctcgccgccg atccgcaacg tgctcccgcg ccacgagcag   1140
ggcggcgtct tcgccgccga aggctacgcg cgttcctccg gcctcccgg cgtctgcatt   1200 gccacctccg gccccggcgc caccaacctc gtgagcggcc tcgccgacgc tttaatggac   1260
```

```
agcgtcccag tcgtcgccat caccggccag gtcgcccgcc ggatgatcgg caccgacgcc    1320
ttccaagaaa ccccgatcgt ggaggtgagc agatccatca cgaagcacaa ctacctcatc    1380
ctcgacgtcg acgacatccc ccgcgtcgtc gccgaggctt tcttcgtcgc cacctccggc    1440
cgccccggtc cggtcctcat cgacattccc aaagacgttc agcagcaact cgccgtgcct    1500
aattgggacg agcccgttaa cctccccggt tacctcgcca ggctgccagg cccccccgcc    1560
gaggcccaat tggaacacat tgtcagactc atcatggagg cccaaaagcc cgttctctac    1620
gtcggcggtg gcagtttgaa ttccagtgct gaattgaggc gctttgttga actcactggt    1680
attcccgttg ctagcacttt aatgggtctt ggaacttttc ctattggtga tgaatattcc    1740
cttcagatgc tgggtatgca tggtactgtt tatgctaact atgctgttga caatagtgat    1800
ttgttgcttg cctttggggt aaggtttgat gaccgtgtta ctgggaagct tgaggctttt    1860
gctagtaggg ctaagattgt tcacattgat attgattctg ccgagattgg aagaacaag     1920 caggcgcacg tgtcggtttg cgcggatttg aagttggcct tgaagggaat taatatgatt    1980
ttggaggaga aaggagtgga gggtaagttt gatcttggag gttggagaga agagattaat    2040
gtgcagaaac acaagtttcc attgggttac aagacattcc aggacgcgat ttctccgcag    2100
catgctatcg aggttcttga tgagttgact aatggagatg ctattgttag tactggggtt    2160
gggcagcatc aaatgtgggc tgcgcagttt tacaagtaca agagaccgag gcagtggttg    2220
acctcagggg gtcttggagc catgggtttt ggattgcctg cggctattgg tgctgctgtt    2280
gctaaccctg gggctgttgt ggttgacatt gatgggatg gtagtttcat catgaatgtt     2340
caggagttgg ccactataag agtggagaat ctcccagtta agatattgtt gttgaacaat    2400
cagcatttgg gtatggtggt tcagttggag gataggttct acaagtccaa tagagctcac    2460
acctatcttg gagatccgtc tagcgagagc gagatattcc caaacatgct caagtttgct    2520
gatgcttgtg ggataccggc agcgcgagtg acgaagaagg aagagcttag agcggcaatt    2580
cagagaatgt tggacacccc tggcccctac cttcttgatg tcattgtgcc ccatcaggag    2640
catgtgttgc cgatgattcc cagtaatgga tccttcaagg atgtgataac tgagggtgat    2700
ggtagaacga ggtactgact agctagtcag ttaacctaga cttgtccatc ttctggattg    2760
gccaacttaa ttaatgtatg aaataaaagg atgcacacat agtgacatgc taatcactat    2820
aatgtgggca tcaaagttgt gtgttatgtg taattactag ttatctgaat aaaagagaaa    2880
gagatcatcc atatttctta tcctaaatga atgtcacgtg tctttataat tctttgatga    2940
accagatgca tttcattaac caaatccata tacatataaa tattaatcat atataattaa    3000
tatcaattgg gttagcaaaa caaatctagt ctaggtgtgt tttgcccca agcttatcga     3060 taccgtcggc gcggggtacc cgggccctag gaggccggcc cgaagttcct attccgaagt    3120
tcctattctt caaaaagtat aggaacttcc gatatcactt aagtggcgcg cccgaagttc    3180
ctattccgaa gttcctattc tacatagagt ataggaactt ccgatatcac tgcagtggcc    3240
ggcccagctg atgatcccgg tgaagttcct attccgaagt tcctattctc agaaagtat    3300 aggaacttca ctagagcttg cggccgcccc ctgggccggc cactagtgag ctcggtaccc    3360
gggtaccgg                                                           3369
```

<210> SEQ ID NO 50
<211> LENGTH: 30
<212> TYPE: DNA
<213> ORGANISM: Saccharomyces cerevisiae

<400> SEQUENCE: 50
agttcctatt ctctagaaag tataggaact                               30

<210> SEQ ID NO 51
<211> LENGTH: 30
<212> TYPE: DNA
<213> ORGANISM: Artificial Sequence
<220> FEATURE:
<223> OTHER INFORMATION: minimal FRT5 mutant recombination site

<400> SEQUENCE: 51
agttcctatt cttcaaaagg tataggaact                               30

<210> SEQ ID NO 52
<211> LENGTH: 30
<212> TYPE: DNA
<213> ORGANISM: Artificial Sequence
<220> FEATURE:
<223> OTHER INFORMATION: minimal FRT6 mutant recombination site

<400> SEQUENCE: 52
agttcctatt cttcaaaaag tataggaact                               30

<210> SEQ ID NO 53
<211> LENGTH: 30
<212> TYPE: DNA
<213> ORGANISM: Artificial Sequence
<220> FEATURE:
<223> OTHER INFORMATION: minimal FRT12 mutant recombination site

<400> SEQUENCE: 53
agttcctatt ctacatagag tataggaact                               30

<210> SEQ ID NO 54
<211> LENGTH: 30
<212> TYPE: DNA
<213> ORGANISM: Artificial Sequence
<220> FEATURE:
<223> OTHER INFORMATION: minimal FRT87 mutant recombination site

<400> SEQUENCE: 54
agttcctatt ctccagaaag tataggaact                               30

<210> SEQ ID NO 55
<211> LENGTH: 601
<212> TYPE: DNA
<213> ORGANISM: Glycine max
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (307)..(307)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t

<400> SEQUENCE: 55
acaattccaa attatgtatt acacaacttt tacttgttta tatacttttt ttcttttta       60 attaaataca aacagatatc tcttcaaaaa cttttgctgc acacaaacag atcatataac     120
cagaaaatgg agggaagaag aataaagcaa aaatagcaca acattacaaa tacgttatgt     180

```
gtaaaaattg gtgatgggag agacatatga aaaagaagc ataaaaggaa gccatgtctc    240
tctgaatttg taagaataag aaataggaat gaaattattt cctatgatcn tagattttcn    300
acgctcnant aactcctctc ctattgtttg ttgtttccaa gattgactgc ttaataattt    360
caatacttcc aatacaacaa taaatagtaa atattattac tatttccaac atgatcaaca    420
ctaacagttc aacacctcca taattgatgt gaaatctcac aacagtttta taacactcaa    480
taaaggtgat aatgatataa attgtttaa gattttaatt tttaaattag gtttcatgat    540
tttttattta ggggttttat ccctttggga ttatcttact ccagtataca gtagggttat    600
t                                                                   601
```

```
<210> SEQ ID NO 56
<211> LENGTH: 2588
<212> TYPE: DNA
<213> ORGANISM: Glycine max
<220> FEATURE:
<221> NAME/KEY: misc_feature
<222> LOCATION: (1312)..(1312)
<223> OTHER INFORMATION: n is a, c, g, or t
<220> FEATURE:
<221> NAME/KEY: misc_feature
<222> LOCATION: (2306)..(2306)
<223> OTHER INFORMATION: n is a, c, g, or t

<400> SEQUENCE: 56
```

```
cgcgtataga gattataaat ttaatcataa tatttgacta gttgaaagaa ttgtgtaata     60 agaacttta ttttaaatga cactatccag tttttcataa caaaacaaac accaaatatt    120
ggactaataa ccgtagttgg attcaattat caagtacata gtatttggat taagcatgga    180
attgtaatta gaaataaata ttttattcta aaatggattg atttagtgag atatgattag    240
tttggtgtca aatagaggtg ggtatatgag taagttggtc aatttaaact ggcacttgca    300
tagcccgcaa tctgtataac ccacctacta agccctcatc ttaaatgcgc ttcattttat    360
cttagtggat tggatagtta agggaaaaaa aaagaaaaag aaattatagg ttcaataggc    420
tctattaaaa gaaaactaat cttctaacaa ttaaatatttg tggataaaaa aattgacttc    480
atttaaacaa gcctttgttc agctcacata acccatgagc taaatgagtc aacctacatc    540
tatattaaaa aattaaaaaa tacgtgaaaa aaatctaaat tttaatattt tacttytacc    600 cgtattttt taagcatgtt caagtataaa tcaactttaa gtccttcaaa atcaagtgct    660
ttggtcaatc tagtttctaa ttaaaaacgt ttgacccaca acttttaaa gcggtggatc    720 acaaagctcc actaatttac aatattaata attcaagaaa aatatctcaa tcaaccaata    780
aatatcattt aagaaaattc aatcaatact caaaatatca acgatcacaa gtctacatca    840
aaataccata aatccaaaca taagaaagt acttaatgtt aacgcaaacc aatctattta    900
gctcgcaggt taaatacatt agattaaaaa actcacttt caaatagtct ttcaattgca    960
atgccccaaa tccacattta ttagactcta atgtcaaata agaaatctta gatatttcta   1020
gttgaacaaa aaaatatttt gactacatag ttatattaag tagttttatc aaatatgtac   1080 aaacccctaat tgtaaaaaag aagacaatca ttcttatatt atcaattttt tcttgatctc   1140
ataataaaaa ataataaaaa tgaactttc tccttaatta tgtattacta aataaaaaca   1200 aattttctc ctcaattatg tacacaatta aattcagggg agttggtcaa atgaagcaaa   1260
acaagatttt acatctaaca attcaaagtc tcactcagtc tcttgaaatg anggtaaaca   1320 agttttaaa cataagatat tgttttaaaa ttttcttgtc catttttata aaactttttc   1380
taattgtctc ttgcattatc tatttttttt accgaattat ccttaattat tttattacgc   1440
```

```
gtgcaattttt agtattaatt atttctttaa ttcataagcg agcatataat atatgtgtag    1500
tatttgcata attatatgat tatatccatg taagtctctt ataaatttca tttcatatct    1560
agaaaatcag agaatcaacg actatagttt tactgcaatc gaatcaacga atcataaact    1620
cgtaacttta ccgaataata acccatttag cattggattt tggacctatt tagatacaag    1680
gtataaatac ttttaaaagc tactctattg aaaatatagt ttttttttaat agagaaatcc    1740 tcaaaagttg tcaaagaac ttttaacttt gcatctaagt agatccttca tacatttatg    1800
gtttcacaat tgggacaaaa tcagaatgaa acatttaatg gcaaatatag cggaaagtag    1860
ggtaacgagc caaccaccat ttcaagacaa atgggtgaga tacttaatat aactccaaag    1920
tccaaattaa atcagagagg taattaataa aagagattaa acaaggatg tgtcacgccg    1980 tcgcccccta ctttctataa aatcaccgtt aattaatttg ccataattgt gtgcttaaaa    2040
aatgtcaact attattgctt taattttaga ttaccttaat gaatataatt ttttgtataa    2100
aaaaataaat tattaatata caaaaaaatt gtatgatttc ctacatcatc atatatttaa    2160
ttttgtttta gtacaaaatt ggtatatatg atcaaaacat tcaatcttaa tataaaaata    2220
gtactattaa tattaatcta aaatatttat atcaacagtt taatcttcgt ttaacaatat    2280
tatattaata aagatgattc taacanttac catttagagg gtaagtgtct atagaaaaaa    2340
agtaaattct aaagaatatt attattattt aatattctca taatatattt taaaaagaa    2400 gagttgtgaa ataaaataag tgatataatt aacgaggttt cggtccagcg aaaaaaattg    2460
gtctctcgtg tgacaaacca aagttcaaaa ttttgaccgg aaagctaccc gcatttagta    2520
ctcaattagt taatgtgaaa aataaggagt tatatataga ctattaagtc atatttgatt    2580
ggtcatga                                                              2588

<210> SEQ ID NO 57
<211> LENGTH: 984
<212> TYPE: DNA
<213> ORGANISM: Glycine max

<400> SEQUENCE: 57
aactcgcgct taagcttgag tttacttgca cttaagcctc aagattagta cacttcttcc      60
ctctgcaatt tgccctactt aagcgtgagt tactccatgc ttaagcatga ggaactttgt     120
ttttaccttg gcaaaaaaga taactttatt tttaccaaat aacgtaaatc cctagcaaat     180
taacatgggt aatgatgcta attatacata ttaaagagta atcacaaata ctcatacaca     240
aagtaaatct acacaatttg aatttacaat atctaaaatt acaaagtgta attttacata     300
gtgtaagaat catgttctaa agaaattttg atttctacta aacttatcac ataaaatagc     360
atgcatataa ctagaatttt aatcaattac ttgaattaaa tattcatgtt aattaatttc     420
aatatcaatt atatttccat agatcaccta aacacaaatt tttctagatc aagaacgtac     480
tcttttaggg atagaaaatc aagaaataaa tttagggacc aaatgcaaaa atccaaatat     540
ctctcaagga taaaaatata tttatgccca attaaaattt tcatacaatg attaatgaag     600
attttttttc caatctattc tacttagcac caaatatcca aatataacct aaaaaacatg     660
tgcagaacaa caatgcgagt tagataaatg atgctaatcc taaggattaa acctttttcc     720
ctccagctac ttaagttatc actgctaaat ccagcacata acctgaataa tgatcactta     780
ctaaccttca atttgcttca ggagttgttc ttctggaaca tagattcttt caagagtttt     840
aacaatcttt ccctcccaga gagtaacaag ctcattaaac gacaaggtat tagtgaagca     900
aatgttaata agaaaaatgt gacaagtaaa tttatagtaa tttctagtca atctttgata     960
```

```
caatactgca tcattcatag tata                                          984
```

<210> SEQ ID NO 58
<211> LENGTH: 1305
<212> TYPE: DNA
<213> ORGANISM: Glycine max

<400> SEQUENCE: 58

```
aatcaggaca acgtggcgcc gagccgcggg cgagccgatt ttggcttcga ggagagccac    60
gaaccacgcg ggaataacga ggttgatgtc aagctcgctc atgtagagga atcccctgtc   120
gctgcgcatg agaacgtggt cgtgggcgag ggcgagggtg tagccggcgg cggaggcgtg   180
gccggtgacg gcggcgatgg tcggcatcgg gagggtgagg agatcggaga cgacggagcg   240
gaggagggag tccatgagga tcatgcgctc tttgacctca tcggaggatc gggcccaggc   300
gatgtcgtag ccgttggaga agaatttgcc gtgcgcggtg gtgacgaggg cggaggaggc   360
ggtggcttct tggcggacgc ggcggaggga ggattggatg gaatcgagga gtgttgggtt   420
gagacggtgc tcgccatcgc cggtgagtgt taggatgaat atgctgcctc tcttctccaa   480
agtgcacatc tttgctttga attgaaggcg tggactccgc tggagaagtt ttttcttcct   540
gtatgatgat ggacaaacaa atataatcca ttgttgtaaa attttcttcc tattttgagt   600
ttttaaatg gcacaattat cattatgtca ttaattaatt caaaagacat tttttgttct    660
gtgtaattta atgactattt tacccattga gatagaaaga gaattttact ggtcaatata   720
ttcatgatat atgttaagga aaggtcaaga tagtaaaaca atatatgttc atgactattt   780
atatttaaaa taggtaaggg gtaaaacaat acaaaaacaa ctgtgtatta aaatatattt   840
aaccggtata aaaagtttcc tgaaagaaat ttgaccgtcc attataattt cataaatcca   900
acggtcaata atatttttt attacctcac caccaaacac aaatttaatt ccttgaccag   960
cctagcctag cctgaattga atggtatttt ctctgttttg attttgtttt catatataaa  1020
taaattaaaa aaaagctat ttaatgttag acgccggcga ataccatgac cttctctgca  1080
acttactttg aaacgcaaac atggttgaat aaataatact atgtgcctcg tcattacctc  1140
tatcagtgta ctaacatttc aaccatattg aaaacaatta ttgattacaa acactatttc  1200
aacaattttt ttatatcgaa tgcaaaaaca aattggtgta aaaaaaaaaa tagaccatca  1260
ctttaatcca aacatgcatt caaggtgtaa gagagaagac ctagg             1305
```

<210> SEQ ID NO 59
<211> LENGTH: 452
<212> TYPE: DNA
<213> ORGANISM: Glycine max

<400> SEQUENCE: 59

```
gtcggatacg atgtccagga catctggccc gaaaatactg gacacataaa tctgttatat    60
ctttaacaga ttattgtgca gttagcaaca gattagacga tctatcttta ggaacgaatt   120
aaaagataat taaagtacga attacaaact agaagagttc gttcagggat taaagattaa   180
agataaaagc taaagatca aactgtatct tttagatctt taagtgcaga ttttttcagaa  240
gaatgataga tctcttccag cacaagttgt tgcagcccag atacgcacac tgctatataa   300
acatgaaggc tgcacgagtt ttctaccaag tccaggattt aagagttatt ttgtgagttt   360
tgggacttga gtgttttgtg agccagaata actatttgtt gtggccatat tgttgtttat   420
catgaaccta aaccaactta ttctaatttt tt                                  452
```

<210> SEQ ID NO 60
<211> LENGTH: 377
<212> TYPE: DNA
<213> ORGANISM: Glycine max

<400> SEQUENCE: 60

| | | | | | |
|---|---|---|---|---|---|
| agaaagaggt | ttaaaattga | cacattgatt | cctttttgc | ttatatgatt | tttggtgaac | 60 |
| tgtatgcatc | aaaaggtgca | tgtacggctc | ttaaggaaac | aatcacagtg | acacgcttaa | 120 |
| accactttc | catcgggata | ggagttgcat | aataagcaaa | aaaaaaatca | taataattgc | 180 |
| tcgtgggaca | ttgagtggtt | gacattgagg | cggtgactca | agaaacaaa | aatgttgata | 240 |
| taattttac | ctttgttact | tcttctcttt | tcacgttctc | ttttttact | tttcacattt | 300 |
| tcgtccttac | atgtcctgta | gacagattgt | ctaacgttaa | catacaaatt | ttactagagg | 360 |
| ataaatttat | cttattc | | | | | 377 |

<210> SEQ ID NO 61
<211> LENGTH: 496
<212> TYPE: DNA
<213> ORGANISM: Glycine max

<400> SEQUENCE: 61

| | | | | | |
|---|---|---|---|---|---|
| aacaaaaact | aataatgata | atgaaaaaaa | aaaatttatg | aactttgatt | ggttaaaatt | 60 |
| taaattacat | actaaaaaca | taaattctaa | gaagtttgga | gataaaaaag | aataacatat | 120 |
| attctacttc | catcgtttgc | atgttatgca | tgatccttgc | attttcctct | gcaaaatgaa | 180 |
| ataaaaaaca | aaacaaaaaa | acaaaaaaag | tcacaaaaaa | gcatgagttt | acaccacatt | 240 |
| cttagttaca | tgtgttgggt | accataatga | tggccataaa | ccaaccatgt | tcgagtccaa | 300 |
| aatagaggat | tgggactcgt | cgtgcttaca | cgattacaag | ttacaaccga | accataggta | 360 |
| attggaaaac | tcgcatcttg | aactcattgt | gattggagaa | ctcgcatctc | aggctcgagc | 420 |
| cttcaaacct | gaggtgaagc | accgaactca | cgtctcgccc | tcaaccttca | caaccgaact | 480 |
| cgcatcttgc | atctcg | | | | | 496 |

<210> SEQ ID NO 62
<211> LENGTH: 543
<212> TYPE: DNA
<213> ORGANISM: Glycine max

<400> SEQUENCE: 62

| | | | | | |
|---|---|---|---|---|---|
| acgggactca | atcggacatc | cgagtaaaaa | gttttttgtcg | tttgaatttg | ctcggttctt | 60 |
| ctgttttcaa | tttcgagcgt | ctcgatatac | tacgggacac | aatcggaccc | tcgagattat | 120 |
| ttctccgaat | cggacatccg | tgttaaaagt | tatgaccatt | ttaatttctc | gaaagcttcc | 180 |
| gttgttgaat | ttctagcatc | tcgatatatt | atgtcaacaa | atccaacatc | ggtgtgaaaa | 240 |
| gttatgacca | ttcgaatttc | tcgatagctt | tcgctattca | atttcgagcg | ccttgacatt | 300 |
| catgggctc | cgaaaaaagt | ggagaatgga | gaattggcga | acagcgctac | gcaataactt | 360 |
| cgcgggctc | cagactcgaa | ggtggaggat | gcatgttgtg | gaattacagc | atacatagtg | 420 |
| ccttgctgga | accacactca | aagtgtgaaa | ggaacaaatt | cggatgcatt | tttcatattt | 480 |
| taatacaaat | caaatttgac | ccgggatgtc | gtgattacaa | gagtgagcta | gaaagatgaa | 540 |
| gtt | | | | | | 543 |

<210> SEQ ID NO 63
<211> LENGTH: 656
<212> TYPE: PRT
<213> ORGANISM: Glycine max

<400> SEQUENCE: 63

```
Met Pro His Asn Thr Met Ala Ala Thr Ala Ser Arg Thr Arg Phe
1               5                   10                  15

Ser Ser Ser Ser Ser His Pro Thr Phe Pro Lys Arg Ile Thr Arg Ser
            20                  25                  30

Thr Leu Pro Leu Ser His Gln Thr Leu Thr Lys Pro Asn His Ala Leu
            35                  40                  45

Lys Ile Lys Cys Ser Ile Ser Lys Pro Pro Thr Ala Ala Pro Phe Thr
    50                  55                  60

Lys Glu Ala Pro Thr Thr Glu Pro Phe Val Ser Arg Phe Ala Ser Gly
65                  70                  75                  80

Glu Pro Arg Lys Gly Ala Asp Ile Leu Val Glu Ala Leu Glu Arg Gln
                85                  90                  95

Gly Val Thr Thr Val Phe Ala Tyr Pro Gly Gly Ala Ser Met Glu Ile
            100                 105                 110

His Gln Ala Leu Thr Arg Ser Ala Ala Ile Arg Asn Val Leu Pro Arg
            115                 120                 125

His Glu Gln Gly Gly Val Phe Ala Ala Glu Gly Tyr Ala Arg Ser Ser
            130                 135                 140

Gly Leu Pro Gly Val Cys Ile Ala Thr Ser Gly Pro Gly Ala Thr Asn
145                 150                 155                 160

Leu Val Ser Gly Leu Ala Asp Ala Leu Met Asp Ser Val Pro Val Val
                165                 170                 175

Ala Ile Thr Gly Gln Val Ala Arg Arg Met Ile Gly Thr Asp Ala Phe
            180                 185                 190

Gln Glu Thr Pro Ile Val Glu Val Ser Arg Ser Ile Thr Lys His Asn
            195                 200                 205

Tyr Leu Ile Leu Asp Val Asp Asp Ile Pro Arg Val Val Ala Glu Ala
            210                 215                 220

Phe Phe Val Ala Thr Ser Gly Arg Pro Gly Pro Val Leu Ile Asp Ile
225                 230                 235                 240

Pro Lys Asp Val Gln Gln Gln Leu Ala Val Pro Asn Trp Asp Glu Pro
                245                 250                 255

Val Asn Leu Pro Gly Tyr Leu Ala Arg Leu Pro Arg Pro Pro Ala Glu
            260                 265                 270

Ala Gln Leu Glu His Ile Val Arg Leu Ile Met Glu Ala Gln Lys Pro
            275                 280                 285

Val Leu Tyr Val Gly Gly Gly Ser Leu Asn Ser Ser Ala Glu Leu Arg
            290                 295                 300

Arg Phe Val Glu Leu Thr Gly Ile Pro Val Ala Ser Thr Leu Met Gly
305                 310                 315                 320

Leu Gly Thr Phe Pro Ile Gly Asp Glu Tyr Ser Leu Gln Met Leu Gly
                325                 330                 335

Met His Gly Thr Val Tyr Ala Asn Tyr Ala Val Asp Asn Ser Asp Leu
            340                 345                 350

Leu Leu Ala Phe Gly Val Arg Phe Asp Asp Arg Val Thr Gly Lys Leu
            355                 360                 365

Glu Ala Phe Ala Ser Arg Ala Lys Ile Val His Ile Asp Ile Asp Ser
            370                 375                 380

Ala Glu Ile Gly Lys Asn Lys Gln Ala His Val Ser Val Cys Ala Asp
385                 390                 395                 400

Leu Lys Leu Ala Leu Lys Gly Ile Asn Met Ile Leu Glu Glu Lys Gly
                405                 410                 415
```

Val Glu Gly Lys Phe Asp Leu Gly Gly Trp Arg Glu Ile Asn Val
            420                 425                 430

Gln Lys His Lys Phe Pro Leu Gly Tyr Lys Thr Phe Gln Asp Ala Ile
            435                 440                 445

Ser Pro Gln His Ala Ile Glu Val Leu Asp Glu Leu Thr Asn Gly Asp
            450                 455                 460

Ala Ile Val Ser Thr Gly Val Gly Gln His Gln Met Trp Ala Ala Gln
465                 470                 475                 480

Phe Tyr Lys Tyr Lys Arg Pro Arg Gln Trp Leu Thr Ser Gly Gly Leu
                485                 490                 495

Gly Ala Met Gly Phe Gly Leu Pro Ala Ala Ile Gly Ala Ala Val Ala
            500                 505                 510

Asn Pro Gly Ala Val Val Asp Ile Asp Gly Asp Gly Ser Phe Ile
            515                 520                 525

Met Asn Val Gln Glu Leu Ala Thr Ile Arg Val Glu Asn Leu Pro Val
530                 535                 540

Lys Ile Leu Leu Leu Asn Asn Gln His Leu Gly Met Val Val Gln Leu
545                 550                 555                 560

Glu Asp Arg Phe Tyr Lys Ser Asn Arg Ala His Thr Tyr Leu Gly Asp
                565                 570                 575

Pro Ser Ser Glu Ser Glu Ile Phe Pro Asn Met Leu Lys Phe Ala Asp
            580                 585                 590

Ala Cys Gly Ile Pro Ala Ala Arg Val Thr Lys Lys Glu Glu Leu Arg
            595                 600                 605

Ala Ala Ile Gln Arg Met Leu Asp Thr Pro Gly Pro Tyr Leu Leu Asp
            610                 615                 620

Val Ile Val Pro His Gln Glu His Val Leu Pro Met Ile Pro Ser Asn
625                 630                 635                 640

Gly Ser Phe Lys Asp Val Ile Thr Glu Gly Asp Gly Arg Thr Arg Tyr
                645                 650                 655

<210> SEQ ID NO 64
<211> LENGTH: 670
<212> TYPE: PRT
<213> ORGANISM: Arabidopsis thaliana

<400> SEQUENCE: 64

Met Ala Ala Ala Thr Thr Thr Thr Thr Ser Ser Ser Ile Ser Phe
1               5                   10                  15

Ser Thr Lys Pro Ser Pro Ser Ser Lys Ser Pro Leu Pro Ile Ser
            20                  25                  30

Arg Phe Ser Leu Pro Phe Ser Leu Asn Pro Asn Lys Ser Ser Ser Ser
            35                  40                  45

Ser Arg Arg Arg Gly Ile Lys Ser Ser Pro Ser Ser Ile Ser Ala
50                  55                  60

Val Leu Asn Thr Thr Thr Asn Val Thr Thr Thr Pro Ser Pro Thr Lys
65                  70                  75                  80

Pro Thr Lys Pro Glu Thr Phe Ile Ser Arg Phe Ala Pro Asp Gln Pro
                85                  90                  95

Arg Lys Gly Ala Asp Ile Leu Val Glu Ala Leu Glu Arg Gln Gly Val
            100                 105                 110

Glu Thr Val Phe Ala Tyr Pro Gly Gly Ala Ser Met Glu Ile His Gln
            115                 120                 125

Ala Leu Thr Arg Ser Ser Ser Ile Arg Asn Val Leu Pro Arg His Glu
130                 135                 140

-continued

```
Gln Gly Gly Val Phe Ala Ala Glu Gly Tyr Ala Arg Ser Ser Gly Lys
145                 150                 155                 160

Pro Gly Ile Cys Ile Ala Thr Ser Gly Pro Ala Thr Asn Leu Val
                165                 170                 175

Ser Gly Leu Ala Asp Ala Leu Leu Asp Ser Val Pro Leu Val Ala Ile
                180                 185                 190

Thr Gly Gln Val Ala Arg Arg Met Ile Gly Thr Asp Ala Phe Gln Glu
                195                 200                 205

Thr Pro Ile Val Glu Val Thr Arg Ser Ile Thr Lys His Asn Tyr Leu
                210                 215                 220

Val Met Asp Val Glu Asp Ile Pro Arg Ile Ile Glu Glu Ala Phe Phe
225                 230                 235                 240

Leu Ala Thr Ser Gly Arg Pro Gly Pro Val Leu Val Asp Val Pro Lys
                245                 250                 255

Asp Ile Gln Gln Gln Leu Ala Ile Pro Asn Trp Glu Gln Ala Met Arg
                260                 265                 270

Leu Pro Gly Tyr Met Ser Arg Met Pro Lys Pro Pro Glu Asp Ser His
                275                 280                 285

Leu Glu Gln Ile Val Arg Leu Ile Ser Glu Ser Lys Lys Pro Val Leu
                290                 295                 300

Tyr Val Gly Gly Gly Cys Leu Asn Ser Ser Asp Glu Leu Gly Arg Phe
305                 310                 315                 320

Val Glu Leu Thr Gly Ile Pro Val Ala Ser Thr Leu Met Gly Leu Gly
                325                 330                 335

Ser Tyr Pro Cys Asp Asp Glu Leu Ser Leu His Met Leu Gly Met His
                340                 345                 350

Gly Thr Val Tyr Ala Asn Tyr Ala Val Glu His Ser Asp Leu Leu Leu
                355                 360                 365

Ala Phe Gly Val Arg Phe Asp Asp Arg Val Thr Gly Lys Leu Glu Ala
                370                 375                 380

Phe Ala Ser Arg Ala Lys Ile Val His Ile Asp Ile Asp Ser Ala Glu
385                 390                 395                 400

Ile Gly Lys Asn Lys Thr Pro His Val Ser Val Cys Gly Asp Val Lys
                405                 410                 415

Leu Ala Leu Gln Gly Met Asn Lys Val Leu Glu Asn Arg Ala Glu Glu
                420                 425                 430

Leu Lys Leu Asp Phe Gly Val Trp Arg Asn Glu Leu Asn Val Gln Lys
                435                 440                 445

Gln Lys Phe Pro Leu Ser Phe Lys Thr Phe Gly Glu Ala Ile Pro Pro
450                 455                 460

Gln Tyr Ala Ile Lys Val Leu Asp Glu Leu Thr Asp Gly Lys Ala Ile
465                 470                 475                 480

Ile Ser Thr Gly Val Gly Gln His Gln Met Trp Ala Ala Gln Phe Tyr
                485                 490                 495

Asn Tyr Lys Lys Pro Arg Gln Trp Leu Ser Ser Gly Gly Leu Gly Ala
                500                 505                 510

Met Gly Phe Gly Leu Pro Ala Ala Ile Gly Ala Ser Val Ala Asn Pro
                515                 520                 525

Asp Ala Ile Val Val Asp Ile Asp Gly Asp Gly Ser Phe Ile Met Asn
                530                 535                 540

Val Gln Glu Leu Ala Thr Ile Arg Val Glu Asn Leu Pro Val Lys Val
545                 550                 555                 560

Leu Leu Leu Asn Asn Gln His Leu Gly Met Val Met Gln Leu Glu Asp
```

```
                    565                 570                 575
Arg Phe Tyr Lys Ala Asn Arg Ala His Thr Phe Leu Gly Asp Pro Ala
            580                 585                 590

Gln Glu Asp Glu Ile Phe Pro Asn Met Leu Leu Phe Ala Ala Ala Cys
        595                 600                 605

Gly Ile Pro Ala Ala Arg Val Thr Lys Lys Ala Asp Leu Arg Glu Ala
    610                 615                 620

Ile Gln Thr Met Leu Asp Thr Pro Gly Pro Tyr Leu Leu Asp Val Ile
625                 630                 635                 640

Cys Pro His Gln Glu His Val Leu Pro Met Ile Pro Ser Gly Gly Thr
                645                 650                 655

Phe Asn Asp Val Ile Thr Glu Gly Asp Gly Arg Ile Lys Tyr
            660                 665                 670

<210> SEQ ID NO 65
<211> LENGTH: 25
<212> TYPE: DNA
<213> ORGANISM: Artificial Sequence
<220> FEATURE:
<223> OTHER INFORMATION: adaptor-specific primer AP1

<400> SEQUENCE: 65
gtaatacgac tcactatagg gcacg                                          25

<210> SEQ ID NO 66
<211> LENGTH: 26
<212> TYPE: DNA
<213> ORGANISM: Artificial Sequence
<220> FEATURE:
<223> OTHER INFORMATION: QC288A-specific primer Scp1-A

<400> SEQUENCE: 66
ctactgtcct tttgatgaag tgacag                                         26

<210> SEQ ID NO 67
<211> LENGTH: 22
<212> TYPE: DNA
<213> ORGANISM: Artificial Sequence
<220> FEATURE:
<223> OTHER INFORMATION: QC288A-specific primer Vec-S1

<400> SEQUENCE: 67
gatcgggaat tctagtggcc gg                                             22

<210> SEQ ID NO 68
<211> LENGTH: 22
<212> TYPE: DNA
<213> ORGANISM: Artificial Sequence
<220> FEATURE:
<223> OTHER INFORMATION: adaptor-specific primer AP2

<400> SEQUENCE: 68
ctatagggca cgcgtggtcg ac                                             22

<210> SEQ ID NO 69
<211> LENGTH: 22
<212> TYPE: DNA
<213> ORGANISM: Artificial Sequence
<220> FEATURE:
<223> OTHER INFORMATION: QC288A-specific primer Scp1-A4

<400> SEQUENCE: 69
ctgggcaatg gaatccgagg ag                                             22
```

<210> SEQ ID NO 70
<211> LENGTH: 23
<212> TYPE: DNA
<213> ORGANISM: Artificial Sequence
<220> FEATURE:
<223> OTHER INFORMATION: QC288A-specific primer Vec-S2

<400> SEQUENCE: 70
gctgatgatc ccggtgaagt tcc                                    23

<210> SEQ ID NO 71
<211> LENGTH: 30
<212> TYPE: DNA
<213> ORGANISM: Artificial Sequence
<220> FEATURE:
<223> OTHER INFORMATION: primer 288A-1F

<400> SEQUENCE: 71
attactattt acaattacag tcgacccaac                              30

<210> SEQ ID NO 72
<211> LENGTH: 22
<212> TYPE: DNA
<213> ORGANISM: Artificial Sequence
<220> FEATURE:
<223> OTHER INFORMATION: primer Als-163R

<400> SEQUENCE: 72
ggaagaagag aatcgggtgg tt                                      22

<210> SEQ ID NO 73
<211> LENGTH: 22
<212> TYPE: DNA
<213> ORGANISM: Artificial Sequence
<220> FEATURE:
<223> OTHER INFORMATION: probe Als-110T

<400> SEQUENCE: 73
ccacacaaca caatggcggc ca                                      22

<210> SEQ ID NO 74
<211> LENGTH: 21
<212> TYPE: DNA
<213> ORGANISM: Artificial Sequence
<220> FEATURE:
<223> OTHER INFORMATION: primer Hygro-116R

<400> SEQUENCE: 74
tcgaagctga aagcacgaga t                                       21

<210> SEQ ID NO 75
<211> LENGTH: 16
<212> TYPE: DNA
<213> ORGANISM: Artificial Sequence
<220> FEATURE:
<223> OTHER INFORMATION: probe Hygro-79T

<400> SEQUENCE: 75
ctctcggagg gcgaag                                             16

<210> SEQ ID NO 76
<211> LENGTH: 20
<212> TYPE: DNA
<213> ORGANISM: Artificial Sequence
<220> FEATURE:
<223> OTHER INFORMATION: primer 329-1F

```
<400> SEQUENCE: 76
aaacgacggc cagtgccaag                                              20

<210> SEQ ID NO 77
<211> LENGTH: 24
<212> TYPE: DNA
<213> ORGANISM: Artificial Sequence
<220> FEATURE:
<223> OTHER INFORMATION: primer Ucp3-57F

<400> SEQUENCE: 77
tcgagcggct ataaatacgt acct                                         24

<210> SEQ ID NO 78
<211> LENGTH: 24
<212> TYPE: DNA
<213> ORGANISM: Artificial Sequence
<220> FEATURE:
<223> OTHER INFORMATION: primer Flp-A

<400> SEQUENCE: 78
gtcttgcaga ggatgtcgaa ctgg                                         24

<210> SEQ ID NO 79
<211> LENGTH: 25
<212> TYPE: DNA
<213> ORGANISM: Artificial Sequence
<220> FEATURE:
<223> OTHER INFORMATION: probe OMEGA5UTR-87T

<400> SEQUENCE: 79
cctgcgctac catccctaga gctgc                                        25

<210> SEQ ID NO 80
<211> LENGTH: 26
<212> TYPE: DNA
<213> ORGANISM: Artificial Sequence
<220> FEATURE:
<223> OTHER INFORMATION: primer 53-1S1

<400> SEQUENCE: 80
tgtttgttgt ttccaagatt gactgc                                       26

<210> SEQ ID NO 81
<211> LENGTH: 26
<212> TYPE: DNA
<213> ORGANISM: Artificial Sequence
<220> FEATURE:
<223> OTHER INFORMATION: primer 70-1S

<400> SEQUENCE: 81
tctttccctc ccagagagta acaagc                                       26

<210> SEQ ID NO 82
<211> LENGTH: 24
<212> TYPE: DNA
<213> ORGANISM: Artificial Sequence
<220> FEATURE:
<223> OTHER INFORMATION: primer 8H-ScaS1

<400> SEQUENCE: 82
atagaggatt gggactcgtc gtgc                                         24

<210> SEQ ID NO 83
<211> LENGTH: 24
<212> TYPE: DNA
```

<213> ORGANISM: Artificial Sequence
<220> FEATURE:
<223> OTHER INFORMATION: primer Cyan-1

<400> SEQUENCE: 83
atggccctgt ccaacaagtt catc                                    24

<210> SEQ ID NO 84
<211> LENGTH: 33
<212> TYPE: DNA
<213> ORGANISM: Artificial Sequence
<220> FEATURE:
<223> OTHER INFORMATION: primer 53-1A

<400> SEQUENCE: 84
caccaaacta atcatatctc actaaatcaa tcc                          33

<210> SEQ ID NO 85
<211> LENGTH: 23
<212> TYPE: DNA
<213> ORGANISM: Artificial Sequence
<220> FEATURE:
<223> OTHER INFORMATION: primer 70-1A

<400> SEQUENCE: 85
gcagcgacag gggattcctc tac                                     23

<210> SEQ ID NO 86
<211> LENGTH: 27
<212> TYPE: DNA
<213> ORGANISM: Artificial Sequence
<220> FEATURE:
<223> OTHER INFORMATION: primer 8H-VecA

<400> SEQUENCE: 86
agatgctaga aattcaacaa cggaagc                                 27

<210> SEQ ID NO 87
<211> LENGTH: 16
<212> TYPE: DNA
<213> ORGANISM: Artificial Sequence
<220> FEATURE:
<223> OTHER INFORMATION: ORFSTOP-A oligonucleotide containing stop
      codons

<400> SEQUENCE: 87
tgacttaatc agctaa                                             16

<210> SEQ ID NO 88
<211> LENGTH: 17
<212> TYPE: DNA
<213> ORGANISM: Artificial Sequence
<220> FEATURE:
<223> OTHER INFORMATION: ORFSTOP-B oligonucleotide containing stop
      codons

<400> SEQUENCE: 88
tgaaattacc taattaa                                            17

<210> SEQ ID NO 89
<211> LENGTH: 788
<212> TYPE: DNA
<213> ORGANISM: Artificial Sequence
<220> FEATURE:
<223> OTHER INFORMATION: excision product QC288ME

<400> SEQUENCE: 89

-continued

| | |
|---|---|
| cgcgccggta ccgggccccc cctcgagcgg ccgcagattt aggtgacact atagaatatg | 60 |
| catcactagt aagcttgcat gcctgcaggt ttaaacagtc gactctagag atccgtcaac | 120 |
| atggtggagc acgacactct cgtctactcc aagaatatca agatacagt ctcagaagac | 180 |
| caaagggcta ttgagacttt tcaacaaagg gtaatatcgg gaaacctcct cggattccat | 240 |
| tgcccagcta tctgtcactt catcaaaagg acagtagaaa aggaaggtgg cacctacaaa | 300 |
| tgccatcatt gcgataaagg aaaggctatc gttcaagatg cctctgccga cagtggtccc | 360 |
| aaagatggac ccccacccac gaggagcatc gtggaaaaag aagacgttcc aaccacgtct | 420 |
| tcaaagcaag tggattgatg tgatgatcct atgcgtatgg tatgacgtgt gttcaagatg | 480 |
| atgacttcaa acctacctat gacgtatggt atgacgtgtg tcgactgatg acttagatcc | 540 |
| actcgagcgg ctataaatac gtacctacgc accctgcgct accatcccta gagctgcagc | 600 |
| ttatttttac aacaattacc aacaacaaca acaacaaac aacattacaa ttactattta | 660 |
| caattacagt cgacccaaca gaagttccta ttccgaagtt cctattctcc agaaagtata | 720 |
| ggaacttcac tagagcttgc ggccgccccc tgggccggcc actagtgagc tcggtacccg | 780 |
| ggtaccgg | 788 |

<210> SEQ ID NO 90
<211> LENGTH: 6721
<212> TYPE: DNA
<213> ORGANISM: Artificial Sequence
<220> FEATURE:
<223> OTHER INFORMATION: vector QC448

<400> SEQUENCE: 90

| | |
|---|---|
| ccgggtaccg agctcactag taacggccgc cagtgtgctg gaattcgccc ttcccaagct | 60 |
| ttgctctaga tcaaactcac atccaaacat aacatggata tcttccttac caatcatact | 120 |
| aattattttg ggttaaatat taatcattat ttttaagata ttaattaaga aattaaaaga | 180 |
| ttttttaaaa aaatgtataa aattatatta ttcatgattt ttcatacatt tgattttgat | 240 |
| aataaatata ttttttttaa tttcttaaaa aatgttgcaa gacacttatt agacatagtc | 300 |
| ttgttctgtt tacaaaagca ttcatcattt aatacattaa aaaatattta atactaacag | 360 |
| tagaatcttc ttgtgagtgg tgtgggagta ggcaacctgg cattgaaacg agagaaagag | 420 |
| agtcagaacc agaagacaaa taaaagtat gcaacaaaca atcaaaatc aaagggcaaa | 480 |
| ggctggggtt ggctcaattg gttgctacat tcaatttca actcagtcaa cggttgagat | 540 |
| tcactctgac ttccccaatc taagccgcgg atgcaaacgg ttgaatctaa cccacaatcc | 600 |
| aatctcgtta cttaggggct tttccgtcat taactcaccc ctgccacccg gtttccctat | 660 |
| aaattggaac tcaatgctcc cctctaaact cgtatcgctt cagagttgag accaagacac | 720 |
| actcgttcat atatctctct gctcttctct tctcttctac ctctcaaggt acttttcttc | 780 |
| tccctctacc aaatcctaga ttccgtggtt caatttcgga tcttgcactt ctggtttgct | 840 |
| ttgccttgct ttttcctcaa ctgggtccat ctaggatcca tgtgaaactc tactctttct | 900 |
| ttaatatctg cggaatacgc gtttgacttt cagatctagt cgaaatcatt tcataattgc | 960 |
| ctttctttct tttagcttat gagaaataaa atcacttttt tttatttca aaataaacct | 1020 |
| tgggccttgt gctgactgag atggggtttg tgattacag aatttagcg aattttgtaa | 1080 |
| ttgtacttgt ttgtctgtag ttttgttttg ttttcttgtt tctcatacat tccttaggct | 1140 |
| tcaatttat tcgagtatag gtcacaatag gaattcaaac tttgagcagg ggaattaatc | 1200 |
| ccttccttca aatccagttt gtttgtatat atgtttaaaa aatgaaactt ttgctttaaa | 1260 |

```
ttctattata acttttttta tggctgaaat ttttgcatgt gtctttgctc tctgttgtaa    1320
atttactgtt taggtactaa ctctaggctt gttgtgcagt ttttgaagta taaccatgaa    1380
cagaagttcc tattccgaag ttcctattct ctagaaagta taggaacttc cactagtgag    1440
gatctgatca tgccacacaa cacaatggcg gccaccgctt ccagaaccac ccgattctct    1500
tcttcctctt cacaccccac cttccccaaa cgcattacta gatccaccct ccctctctct    1560
catcaaaccc tcaccaaacc caaccacgct ctcaaaatca aatgttccat ctccaaaccc    1620
cccacggcgg cgcccttcac caaggaagcg ccgaccacgg agcccttcgt gtcacggttc    1680
gcctccggca aacctcgcaa gggcgcggac atccttgtgg aggcgctgga gaggcagggc    1740
gtgacgacgg tgttcgcgta ccccggcggt gcgtcgatgg agatccacca ggcgctcacg    1800
cgctccgccg ccatccgcaa cgtgctcccg cgccacgagc agggcggcgt cttcgccgcc    1860
gaaggctacg cgcgttcctc cggcctcccc ggcgtctgca ttgccacctc cggccccggc    1920
gccaccaacc tcgtgagcgg cctcgccgac gctttaatgg acagcgtccc agtcgtcgcc    1980
atcaccggcc aggtcgcccg ccggatgatc ggcaccgacg ccttccaaga aaccccgatc    2040
gtggaggtga gcagatccat cacgaagcac aactacctca tcctcgacgt cgacgacatc    2100
ccccgcgtcg tcgccgaggc tttcttcgtc gccacctccg gccgccccgg tccggtcctc    2160
atcgacattc ccaaagacgt tcagcagcaa ctcgccgtgc taattgggga cgagcccgtt    2220
aacctccccg gttacctcgc caggctgccc aggcccccg ccgaggccca attggaacac    2280
attgtcagac tcatcatgga ggcccaaaag cccgttctct acgtcggcgg tggcagtttg    2340
aattccagtg ctgaattgag gcgctttgtt gaactcactg gtattcccgt tgctagcact    2400
ttaatgggtc ttggaacttt tcctattggt gatgaatatt cccttcagat gctgggtatg    2460
catggtactg tttatgctaa ctatgctgtt gacaatagtg atttgttgct tgcctttggg    2520
gtaaggtttg atgaccgtgt tactgggaag cttgaggctt ttgctagtag gctaagatt    2580
gttcacattg atattgattc tgccgagatt gggaagaaca agcaggcgca cgtgtcggtt    2640
tgcgcggatt tgaagttggc cttgaaggga attaatatga ttttggagga gaaaggagtg    2700
gagggtaagt ttgatcttgg aggttggaga aagagattaa tgtgcagaa acacaagttt    2760
ccattgggtt acaagacatt ccaggacgcg atttctccgc agcatgctat cgaggttctt    2820
gatgagttga ctaatggaga tgctattgtt agtactgggg ttgggcagca tcaaatgtgg    2880
gctgcgcagt tttacaagta caagagaccg aggcagtggt tgacctcagg gggtcttgga    2940
gccatgggtt ttgattgcc tgcggctatt ggtgctgctg ttgctaaccc tggggctgtt    3000
gtggttgaca ttgatgggga tggtagtttc atcatgaatg ttcaggagtt ggccactata    3060
agagtggaga atctcccagt taagatattg ttgttgaaca atcagcatt gggtatggtg    3120
gttcagttgg aggataggtt ctacaagtcc aatagagctc acacctatct tggagatccg    3180
tctagcgaga gcgagatatt cccaaacatg ctcaagtttg ctgatgcttg tgggataccg    3240
gcagcgcgag tgacgaagaa ggaagagctt agagcggcaa ttcagagaat gttggacacc    3300
cctggcccct accttcttga tgtcattgtg ccccatcagg agcatgtgtt gccgatgatt    3360
cccagtaatg gatccttcaa ggatgtgata actgagggtg atggtagaac gaggtactga    3420
ttgcctagac caaatgttcc ttgatgcttg ttttgtacaa tatatataag ataatgctgt    3480
cctagttgca ggatttggcc tgtggtgagc atcatagtct gtagtagttt tggtagcaag    3540
acattttatt ttcctttat ttaacttact acatgcagta gcatctatct atctctgtag    3600
tctgatatct cctgttgtct gtattgtgcc gttggatttt ttgctgtagt gagactgaaa    3660
```

```
atgatgtgct agtaataata tttctgttag aaatctaagt agagaatctg ttgaagaagt   3720
caaaagctaa tggaatcagg ttacatattc aatgtttttc ttttttttagc ggttggtaga   3780
```

```
atgatgtgct agtaataata tttctgttag aaatctaagt agagaatctg ttgaagaagt   3720
caaaagctaa tggaatcagg ttacatattc aatgtttttc tttttttagc ggttggtaga   3780
cgtgtagatt caacttctct tggagctcac ctaggcaatc agtaaaatgc atattccttt   3840
tttaacttgc catttattta cttttagtgg aaattgtgac caatttgttc atgtagaacg   3900
gatttggacc attgcgtcca caaaacgtct cttttgctcg atcttcacaa agcgataccg   3960
aaatccagag atagttttca aaagtcagaa atggcaaagt tataaatagt aaaacagaat   4020
agatgctgta atcgacttca ataacaagtg gcatcacgtt tctagttcta gacccatcag   4080
ctgggccggc ccagctgatg atcccggtga agttcctatt ccgaagttcc tattctccag   4140
aaagtatagg aacttcacta gagcttgcgg ccgctcgagg ggggcccgg taccggcgcg   4200
ccgttctata gtgtcaccta aatcgtatgt gtatgataca taaggttatg tattaattgt   4260
agccgcgttc taacgacaat atgtccatat ggtgcactct cagtacaatc tgctctgatg   4320
ccgcatagtt aagccagccc cgacacccgc caacacccgc tgacgcgccc tgacgggctt   4380
gtctgctccc ggcatccgct tacagacaag ctgtgaccgt ctccgggagc tgcatgtgtc   4440
agaggttttc accgtcatca ccgaaacgcg cgagacgaaa gggcctcgtg atacgcctat   4500
ttttataggt taatgtcatg accaaaatcc cttaacgtga gttttcgttc cactgagcgt   4560
cagaccccgt agaaaagatc aaaggatctt cttgagatcc ttttttttctg cgcgtaatct   4620
gctgcttgca aacaaaaaaa ccaccgctac cagcggtggt ttgtttgccg gatcaagagc   4680
taccaactct ttttccgaag gtaactggct tcagcagagc gcagatacca atactgtcc   4740
ttctagtgta gccgtagtta ggccaccact tcaagaactc tgtagcaccg cctacatacc   4800
tcgctctgct aatcctgtta ccagtggctg ctgccagtgg cgataagtcg tgtcttaccg   4860
ggttggactc aagacgatag ttaccggata aggcgcagcg gtcgggctga acggggggtt   4920
cgtgcacaca gcccagcttg gagcgaacga cctacaccga actgagatac ctacagcgtg   4980
agcattgaga aagcgccacg cttcccgaag ggagaaaggc ggacaggtat ccggtaagcg   5040
gcagggtcgg aacaggagag cgcacgaggg agcttccagg gggaaacgcc tggtatcttt   5100
atagtcctgt cgggtttcgc cacctctgac ttgagcgtcg attttttgtga tgctcgtcag   5160
gggggcggag cctatggaaa aacgccagca acgcggcctt tttacggttc ctggccttt   5220
gctggccttt tgctcacatg ttctttcctg cgttatcccc tgattctgtg ataaccgta   5280
ttaccgcctt tgagtgagct gataccgctc gccgcagccg aacgaccgag cgcagcgagt   5340
cagtgagcga ggaagcggaa gagcgcccaa tacgcaaacc gcctctcccc gcgcgttggc   5400
cgattcatta atgcaggttg atcagatctc gatcccgcga aattaatacg actcactata   5460
gggagaccac aacggtttcc ctctagaaat aattttgttt aactttaaga aggagatata   5520
cccatggaaa agcctgaact caccgcgacg tctgtcgaga gtttctgat cgaaaagttc   5580
gacagcgtct ccgacctgat gcagctctcg gagggcgaag aatctcgtgc tttcagcttc   5640
gatgtaggag ggcgtggata tgtcctgcgg gtaaatagct gcgccgatgg tttctacaaa   5700
gatcgttatg tttatcggca ctttgcatcg gccgcgctcc cgattccgga agtgcttgac   5760
attggggaat tcagcgagag cctgacctat tgcatctccc gccgtgcaca gggtgtcacg   5820
ttgcaagacc tgcctgaaac cgaactgccc gctgttctgc agccggtcgc ggaggctatg   5880
gatgcgatcg ctgcggccga tcttagccag acgagcgggt tcggcccatt cggaccgcaa   5940
ggaatcggtc aatacactac atggcgtgat ttcatatgcg cgattgctga tccccatgtg   6000
tatcactggc aaactgtgat ggacgacacc gtcagtgcgt ccgtcgcgca ggctctcgat   6060
```

-continued

| | |
|---|---|
| gagctgatgc tttgggccga ggactgcccc gaagtccggc acctcgtgca cgcggatttc | 6120 |
| ggctccaaca atgtcctgac ggacaatggc cgcataacag cggtcattga ctggagcgag | 6180 |
| gcgatgttcg gggattccca atacgaggtc gccaacatct tcttctggag gccgtggttg | 6240 |
| gcttgtatgg agcagcagac gcgctacttc gagcggaggc atccggagct tgcaggatcg | 6300 |
| ccgcggctcc gggcgtatat gctccgcatt ggtcttgacc aactctatca gagcttggtt | 6360 |
| gacggcaatt tcgatgatgc agcttgggcg cagggtcgat gcgacgcaat cgtccgatcc | 6420 |
| ggagccggga ctgtcgggcg tacacaaatc gcccgcagaa gcgcggccgt ctggaccgat | 6480 |
| ggctgtgtag aagtactcgc cgatagtgga accgacgcc ccagcactcg tccgagggca | 6540 |
| aaggaatagt gaggtacagc ttggatcgat ccggctgcta acaaagcccg aaaggaagct | 6600 |
| gagttggctg ctgccaccgc tgagcaataa ctagcataac cccttgggc ctctaaacgg | 6660 |
| gtcttgaggg gttttttgct gaaaggagga actatatccg gatgatcggg cgcgccggta | 6720 |
| c | 6721 |

<210> SEQ ID NO 91
<211> LENGTH: 8435
<212> TYPE: DNA
<213> ORGANISM: Artificial Sequence
<220> FEATURE:
<223> OTHER INFORMATION: vector QC449

<400> SEQUENCE: 91

| | |
|---|---|
| gggtaccgag ctcactagta acggccgcca gtgtgctgga attcgccctt cccaagcttt | 60 |
| gctctagatc aaactcacat ccaaacataa catggatatc ttccttacca atcatactaa | 120 |
| ttatttggg ttaaatatta atcattattt ttaagatatt aattaagaaa ttaaagatt | 180 |
| ttttaaaaaa atgtataaaa ttatattatt catgattttt catacatttg attttgataa | 240 |
| taaatatatt ttttttaatt tcttaaaaaa tgttgcaaga cacttattag acatagtctt | 300 |
| gttctgttta caaaagcatt catcatttaa tacattaaaa aatatttaat actaacagta | 360 |
| gaatcttctt gtgagtggtg tgggagtagg caacctggca ttgaaacgag agaaagagag | 420 |
| tcagaaccag aagacaaata aaagtatgc aacaaacaaa tcaaaatcaa agggcaaagg | 480 |
| ctggggttgg ctcaattggt tgctacattc aattttcaac tcagtcaacg gttgagattc | 540 |
| actctgactt ccccaatcta agccgcggat gcaacggtt gaatctaacc cacaatccaa | 600 |
| tctcgttact taggggcttt tccgtcatta actcacccct gccacccggt ttccctataa | 660 |
| attgaaactc aatgctcccc tctaaactcg tatcgcttca gagttgagac caagacacac | 720 |
| tcgttcatat atctctctgc tcttctcttc tcttctacct ctcaaggtac ttttcttctc | 780 |
| cctctaccaa atcctagatt ccgtggttca atttcggatc ttgcacttct ggtttgcttt | 840 |
| gccttgcttt ttcctcaact gggtccatct aggatccatg tgaaactcta ctctttcttt | 900 |
| aatatctgcg gaatacgcgt ttgactttca gatctagtcg aaatcatttc ataattgcct | 960 |
| ttctttcttt tagcttatga gaaataaaat cacttttttt ttatttcaaa ataaaccttg | 1020 |
| ggccttgtgc tgactgagat ggggtttggt gattacagaa ttttagcgaa ttttgtaatt | 1080 |
| gtacttgttt gtctgtagtt ttgttttgtt ttcttgtttc tcatacattc cttaggcttc | 1140 |
| aattttattc gagtataggt cacaatagga attcaaactt tgagcagggg aattaatccc | 1200 |
| ttccttcaaa tccagtttgt ttgtatatat gtttaaaaaa tgaaactttt gctttaaatt | 1260 |
| ctattataac ttttttttatg ctgaaattt ttgcatgtgt ctttgctctc tgttgtaaat | 1320 |
| ttactgttta ggtactaact ctaggcttgt tgtgcagttt ttgaagtata accatgaaca | 1380 |

```
gaagttccta ttccgaagtt cctattctct agaaagtata ggaacttcca ctagtgagga    1440
tctgatcatg ccacacaaca caatggcggc caccgcttcc agaaccaccc gattctcttc    1500
ttcctcttca caccccacct tccccaaacg cattactaga tccaccctcc ctctctctca    1560
tcaaaccctc accaaaccca accacgctct caaaatcaaa tgttccatct ccaaaccccc    1620
cacggcggcg cccttcacca aggaagcgcc gaccacggag cccttcgtgt cacggttcgc    1680
ctccggcgaa cctcgcaagg gcgcggacat ccttgtggag gcgctggaga ggcagggcgt    1740
gacgacggtg ttcgcgtacc ccggcggtgc gtcgatggag atccaccagg cgctcacgcg    1800
ctccgccgcc atccgcaacg tgctcccgcg ccacgagcag ggcggcgtct cgccgccga    1860 aggctacgcg cgttcctccg gcctccccgg cgtctgcatt gccacctccg ccccggcgc    1920 caccaacctc gtgagcggcc tcgccgacgc tttaatggac agcgtcccag tcgtcgccat    1980
caccggccag gtcgcccgcc ggatgatcgg caccgacgcc ttccaagaaa ccccgatcgt    2040
ggaggtgagc agatccatca cgaagcacaa ctacctcatc ctcgacgtcg acgacatccc    2100
ccgcgtcgtc gccgaggctt tcttcgtcgc cacctccggc cgccccggtc cggtcctcat    2160
cgacattccc aaagacgttc agcagcaact cgccgtgcct aattgggacg agcccgttaa    2220
cctccccggt tacctcgcca ggctgcccag gccccccgcc gaggcccaat tggaacacat    2280
tgtcagactc atcatggagg cccaaaagcc cgttctctac gtcggcggtg gcagtttgaa    2340
ttccagtgct gaattgaggc gctttgttga actcactggt attcccgttg ctagcacttt    2400
aatgggtctt ggaacttttc ctattggtga tgaatattcc cttcagatgc tgggtatgca    2460
tggtactgtt tatgctaact atgctgttga caatagtgat ttgttgcttg cctttggggt    2520
aaggtttgat gaccgtgtta ctgggaagct tgaggctttt gctagtaggg ctaagattgt    2580
tcacattgat attgattctg ccgagattgg gaagaacaag caggcgcacg tgtcggtttg    2640
cgcggatttg aagttggcct tgaagggaat taatatgatt ttggaggaga aaggagtgga    2700
gggtaagttt gatcttggag gttggagaga agagattaat gtgcagaaac acaagtttcc    2760
attgggttac aagacattcc aggacgcgat ttctccgcag catgctatcg aggttcttga    2820
tgagttgact aatggagatg ctattgttag tactgggggtt gggcagcatc aaatgtgggc    2880
tgcgcagttt tacaagtaca agagaccgag gcagtggttg acctcagggg gtcttggagc    2940
catgggtttt ggattgcctg cggctattgg tgctgctgtt gctaaccctg gggctgttgt    3000
ggttgacatt gatggggatg gtagtttcat catgaatgtt caggagttgg ccactataag    3060
agtggagaat ctcccagtta agatattgtt gttgaacaat cagcatttgg gtatggtggt    3120
tcagttggag gataggttct acaagtccaa tagagctcac acctatcttg gagatccgtc    3180
tagcgagagc gagatattcc caaacatgct caagtttgct gatgcttgtg ggataccggc    3240
agcgcgagtg acgaagaagg aagagcttag agcggcaatt cagagaatgt ggacacccc    3300 tggccctac cttcttgatg tcattgtgcc ccatcaggag catgtgttgc cgatgattcc    3360
cagtaatgga tccttcaagg atgtgataac tgagggtgat ggtagaacga ggtactgatt    3420
gcctagacca aatgttcctt gatgcttgtt ttgtacaata tatataagat aatgctgtcc    3480
tagttgcagg atttggcctg tggtgagcat catagtctgt agtagttttg gtagcaagac    3540
attttatttt ccttttattt aacttactac atgcagtagc atctatctat ctctgtagtc    3600
tgatatctcc tgttgtctgt attgtgccgt tggattttt gctgtagtga gactgaaaat    3660
gatgtgctag taataatatt tctgttagaa atctaagtag agaatctgtt gaagaagtca    3720
aaagctaatg gaatcaggtt acatattcaa tgttttcctt tttttagcgg ttggtagacg    3780
```

```
tgtagattca acttctcttg gagctcacct aggcaatcag taaaatgcat attccttttt    3840
taacttgcca tttatttact tttagtggaa attgtgacca atttgttcat gtagaacgga    3900
tttggaccat tgcgtccaca aaacgtctct tttgctcgat cttcacaaag cgataccgaa    3960
atccagagat agttttcaaa agtcagaaat ggcaaagtta taaatagtaa aacagaatag    4020
atgctgtaat cgacttcaat aacaagtggc atcacgtttc tagttctaga cccatcagct    4080
gggccggccc agctgatgat cccggtgaag ttcctattcc gaagttccta ttctccagaa    4140
agtataggaa cttcactaga gcttgcggcc gctcgagggg gggcccggta ccggcgcgcc    4200
gttctatagt gtcacctaaa tcgtatgtgt atgatacata aggttatgta ttaattgtag    4260
ccgcgttcta acgacaatat gtccatatgg tgcactctca gtacaatctg ctctgatgcc    4320
gcatagttaa gccagcccg acacccgcca cacccgctg acgcgccctg acgggcttgt    4380
ctgctcccgg catccgctta cagacaagct gtgaccgtct ccgggagctg catgtgtcag    4440
aggttttcac cgtcatcacc gaaacgcgcg agacgaaagg gcctcgtgat acgcctattt    4500
ttataggtta atgtcatgac caaaatccct taacgtgagt tttcgttcca ctgagcgtca    4560 gacccgtag aaaagatcaa aggatcttct tgagatcctt ttttctgcg cgtaatctgc    4620 tgcttgcaaa caaaaaaacc accgctacca gcggtggttt gtttgccgga tcaagagcta    4680
ccaactcttt ttccgaaggt aactggcttc agcagagcgc agataccaaa tactgtcctt    4740
ctagtgtagc cgtagttagg ccaccacttc aagaactctg tagcaccgcc tacatacctc    4800
gctctgctaa tcctgttacc agtggctgct gccagtggcg ataagtcgtg tcttaccggg    4860
ttggactcaa gacgatagtt accggataag gcgcagcggt cgggctgaac ggggggttcg    4920
tgcacacagc ccagcttgga gcgaacgacc tacaccgaac tgagatacct acagcgtgag    4980
cattgagaaa gcgccacgct tcccgaaggg agaaaggcgg acaggtatcc ggtaagcggc    5040
agggtcggaa caggagagcg cacgaggag cttccagggg gaaacgcctg gtatctttat    5100
agtcctgtcg ggtttcgcca cctctgactt gagcgtcgat ttttgtgatg ctcgtcaggg    5160
gggcggagcc tatggaaaaa cgccagcaac gcggcctttt tacggttcct ggccttttgc    5220
tggccttttg ctcacatgtt ctttcctgcg ttatccctg attctgtgga taccgtatt    5280 accgcctttg agtgagctga taccgctcgc cgcagccgaa cgaccgagcg cagcgagtca    5340
gtgagcgagg aagcggaaga gcgcccaata cgcaaaccgc ctctccccgc gcgttggccg    5400
attcattaat gcaggttgat cagatctcga tcccgcgaaa ttaatacgac tcactatagg    5460
gagaccacaa cggtttccct ctagaaataa ttttgtttaa cttaagaag gagatatacc    5520 catggaaaag cctgaactca ccgcgacgtc tgtcgagaag tttctgatcg aaaagttcga    5580
cagcgtctcc gacctgatgc agctctcgga gggcgaagaa tctcgtgctt tcagcttcga    5640
tgtaggaggg cgtggatatg tcctgcgggt aaatagctgc gccgatggtt tctacaaaga    5700
tcgttatgtt tatcggcact ttgcatcggc cgcgctcccg attccggaag tgcttgacat    5760
tggggaattc agcgagagcc tgacctattg catctcccgc cgtgcacagg gtgtcacgtt    5820
gcaagacctg cctgaaaccg aactgcccgc tgttctgcag ccggtcgcgg aggctatgga    5880
tgcgatcgct gcggccgatc ttagccagac gagcgggttc ggcccattcg gaccgcaagg    5940
aatcggtcaa tacactacat ggcgtgattt catatgcgcg attgctgatc ccatgtgta    6000 tcactggcaa actgtgatgg acgacaccgt cagtgcgtcc gtcgcgcagg ctctcgatga    6060
gctgatgctt tgggccgagg actgccccga agtccggcac ctcgtgcacg cggatttcgg    6120
ctccaacaat gtcctgacgg acaatggccg cataacagcg gtcattgact ggagcgaggc    6180
```

```
gatgttcggg gattcccaat acgaggtcgc caacatcttc ttctggaggc cgtggttggc    6240
ttgtatggag cagcagacgc gctacttcga gcggaggcat ccggagcttg caggatcgcc    6300
gcggctccgg gcgtatatgc tccgcattgg tcttgaccaa ctctatcaga gcttggttga    6360
cggcaatttc gatgatgcag cttgggcgca gggtcgatgc gacgcaatcg tccgatccgg    6420
agccgggact gtcgggcgta cacaaatcgc ccgcagaagc gcggccgtct ggaccgatgg    6480
ctgtgtagaa gtactcgccg atagtggaaa ccgacgcccc agcactcgtc cgagggcaaa    6540
ggaatagtga ggtacagctt ggatcgatcc ggctgctaac aaagcccgaa aggaagctga    6600
gttggctgct gccaccgctg agcaataact agcataaccc cttggggcct ctaaacgggt    6660
cttgaggggt tttttgctga aggaggaac tatatccgga tgatcgggcg cgccggtacc     6720
catcaaacaa gtttgtacaa aaaagctgaa cgagaaacgt aaaatgatat aaatatcaat    6780
atattaaatt agattttgca taaaaaacag actacataat actgtaaaac acaacatatc    6840
cagtcactat ggcggccgca ttaggcaccc caggctttac actttatgct tccggctcgt    6900
ataatgtgtg gattttgagt taggatccgt cgagattttc aggagctaag gaagctaaaa    6960
tggagaaaaa aatcactgga tataccaccg ttgatatatc ccaatggcat cgtaaagaac    7020
attttgaggc atttcagtca gttgctcaat gtacctataa ccagaccgtt cagctggata    7080
ttacggcctt tttaaagacc gtaaagaaaa ataagcacaa gttttatccg gcctttattc    7140
acattcttgc ccgcctgatg aatgctcatc cggaattccg tatggcaatg aaagacggtg    7200
agctggtgat atgggatagt gttcacccct gttacaccgt tttccatgag caaactgaaa    7260
cgttttcatc gctctggagt gaataccacg acgatttccg gcagtttcta cacatatatt    7320
cgcaagatgt ggcgtgttac ggtgaaaacc tggcctattt ccctaaaggg tttattgaga    7380
atatgttttt cgtctcagcc aatccctggg tgagtttcac cagttttgat ttaaacgtgg    7440
ccaatatgga caacttcttc gcccccgttt tcaccatggg caaatattat acgcaaggcg    7500
acaaggtgct gatgccgctg gcgattcagg ttcatcatgc cgtttgtgat ggcttccatg    7560
tcggcagaat gcttaatgaa ttacaacagt actgcgatga gtggcaggcg gggcgtaatc    7620
tagaggatcc ggcttactaa aagccagata acagtatgcg tatttgcgcg ctgatttttg    7680
cggtataaga atatatactg atatgtatac ccgaagtatg tcaaaaagag gtatgctatg    7740
aagcagcgta ttacagtgac agttgacagc gacagctatc agttgctcaa ggcatatatg    7800
atgtcaatat ctccggtctg gtaagcacaa ccatgcagaa tgaagcccgt cgtctgcgtg    7860
ccgaacgctg gaaagcggaa atcaggaag ggatggctga ggtcgcccgg tttattgaaa     7920
tgaacggctc ttttgctgac gagaacaggg gctggtgaaa tgcagtttaa ggtttacacc    7980
tataaaagag agagccgtta tcgtctgttt gtggatgtac agagtgatat tattgacacg    8040
cccgggcgac ggatggtgat cccctggcc agtgcacgtc tgctgtcaga taaagtcccc     8100
cgtgaacttt acccggtggt gcatatcggg gatgaaagct ggcgcatgat gaccaccgat    8160
atggccagtg tgccggtctc cgttatcggg gaagaagtgg ctgatctcag ccaccgcgaa    8220
aatgacatca aaaacgccat taacctgatg ttctggggaa tataaatgtc aggctcccct    8280
atacacagcc agtctgcagg tcgaccatag tgactggata tgttgtgttt tacagtatta    8340
tgtagtctgt ttttatgca aaatctaatt taatatattg atatttatat cattttacgt     8400
ttctcgttca gctttcttgt acaaagtggt tcgat                              8435
```

<210> SEQ ID NO 92
<211> LENGTH: 6768
<212> TYPE: DNA

<213> ORGANISM: Artificial Sequence
<220> FEATURE:
<223> OTHER INFORMATION: vector QC477

<400> SEQUENCE: 92

```
ggcgcgccgg tacccgggta ccgagctcac tagacgcggt gaaattacct aattaacacc      60 ggtgttaaa cactagtaac ggccgccagt gtgctggaat tcgcccttcc caagctttgc     120
tctagatcaa actcacatcc aaacataaca tggatatctt ccttaccaat catactaatt     180
attttgggtt aaatattaat cattattttt aagatattaa ttaagaaatt aaaagatttt     240 ttaaaaaat gtataaaatt atattattca tgattttca tacatttgat tttgataata      300
aatatatttt ttttaatttc ttaaaaaatg ttgcaagaca cttattagac atagtcttgt     360
tctgtttaca aaagcattca tcatttaata cattaaaaaa tatttaatac taacagtaga     420
atcttcttgt gagtggtgtg ggagtaggca acctggcatt gaaacgagag aaagagagtc     480
agaaccagaa gacaaataaa aagtatgcaa caaacaaatc aaaatcaaag ggcaaaggct     540
ggggttggct caattggttg ctacattcaa ttttcaactc agtcaacggt tgagattcac     600
tctgacttcc ccaatctaag ccgcggatgc aaacggttga atctaaccca caatccaatc     660
tcgttactta ggggcttttc cgtcattaac tcacccctgc cacccggttt ccctataaat     720
tggaactcaa tgctcccctc taaactcgta tcgcttcaga gttgagacca agacacactc     780
gttcatatat ctctctgctc ttctcttctc ttctacctct caaggtactt tcttctccc     840 tctaccaaat cctagattcc gtggttcaat ttcggatctt gcacttctgg tttgctttgc     900
cttgcttttt cctcaactgg gtccatctag gatccatgtg aaactctact ctttctttaa     960
tatctgcgga atacgcgttt gactttcaga tctagtcgaa atcatttcat aattgccttt    1020
ctttctttta gcttatgaga aataaaatca cttttttttt atttcaaaat aaaccttggg    1080
ccttgtgctg actgagatgg ggtttggtga ttacagaatt ttagcgaatt ttgtaattgt    1140
acttgtttgt ctgtagtttt gttttgtttt cttgtttctc atacattcct taggcttcaa    1200
ttttattcga gtataggtca caataggaat tcaaactttg agcaggggaa ttaatccctt    1260
ccttcaaatc cagtttgttt gtatatatgt ttaaaaaatg aaacttttgc tttaaattct    1320
attataactt tttttatggc tgaaattttt gcatgtgtct ttgctctctg ttgtaaattt    1380
actgtttagg tactaactct aggcttgttg tgcagttttt gaagtataac aacagaagtt    1440
cctattccga agttcctatt ctctagaaag tataggaact tccaccacac aacacaatgg    1500
cggccaccgc ttcagaacc acccgattct cttcttcctc ttcacacccc accttcccca    1560
aacgcattac tagatccacc ctccctctct ctcatcaaac cctcaccaaa cccaaccacg    1620
ctctcaaaat caaatgttcc atctccaaac ccccacggc ggcgcccttc accaaggaag    1680
cgccgaccac ggagcccttc gtgtcacggt tcgcctccgg cgaacctcgc aagggcgcgg    1740
acatccttgt ggaggcgctg gagaggcagg gcgtgacgac ggtgttcgcg taccccggcg    1800
gtgcgtcgat ggagatccac caggcgctca cgcgctccgc cgccatccgc aacgtgctcc    1860
cgcgccacga gcagggcggc gtcttcgccc ccgaaggcta cgcgcgttcc tccggcctcc    1920
ccggcgtctg cattgccacc tccggccccg cgccaccaa cctcgtgagc ggcctcgccg    1980
acgctttaat ggacagcgtc ccagtcgtcg ccatcaccgg ccaggtcgcc cgccggatga    2040
tcggcaccga cgccttccaa gaaaccccga tcgtggaggt gagcagatcc atcacgaagc    2100
acaactacct catcctcgac gtcgacgaca tccccgcgt cgtcgccgag gctttcttcg    2160
tcgccacctc cggccgcccc ggtccggtcc tcatcgacat tcccaaagac gttcagcagc    2220
```

```
aactcgccgt gcctaattgg gacgagcccg ttaacctccc cggttacctc gccaggctgc   2280
ccaggccccc cgccgaggcc caattggaac acattgtcag actcatcatg gaggcccaaa   2340
agcccgttct ctacgtcggc ggtggcagtt tgaattccag tgctgaattg aggcgctttg   2400
ttgaactcac tggtattccc gttgctagca ctttaatggg tcttggaact tttcctattg   2460
gtgatgaata ttcccttcag atgctgggta tgcatggtac tgtttatgct aactatgctg   2520
ttgacaatag tgatttgttg cttgcctttg gggtaaggtt tgatgaccgt gttactggga   2580
agcttgaggc ttttgctagt agggctaaga ttgttcacat tgatattgat tctgccgaga   2640
ttgggaagaa caagcaggcg cacgtgtcgg tttgcgcgga tttgaagttg gccttgaagg   2700
gaattaatat gattttggag gagaaaggag tggagggtaa gtttgatctt ggaggttgga   2760
gagaagagat taatgtgcag aaacacaagt ttccattggg ttacaagaca ttccaggacg   2820
cgatttctcc gcagcatgct atcgaggttc ttgatgagtt gactaatgga gatgctattg   2880
ttagtactgg ggttgggcag catcaaatgt gggctgcgca gttttacaag tacaagagac   2940
cgaggcagtg gttgacctca gggggtcttg gagccatggg ttttggattg cctgcggcta   3000
ttggtgctgc tgttgctaac cctggggctg ttgtggttga cattgatggg gatggtagtt   3060
tcatcatgaa tgttcaggag ttggccacta taagagtgga gaatctccca gttaagatat   3120
tgttgttgaa caatcagcat ttgggtatgg tggttcagtt ggaggatagg ttctacaagt   3180
ccaatagagc tcacacctat cttggagatc cgtctagcga gagcgagata ttcccaaaca   3240
tgctcaagtt tgctgatgct tgtgggatac cggcagcgcg agtgacgaag aaggaagagc   3300
ttagagcggc aattcagaga atgttggaca ccccctggccc ctaccttctt gatgtcattg   3360
tgccccatca ggagcatgtg ttgccgatga ttcccagtaa tggatccttc aaggatgtga   3420
taactgaggg tgatggtaga acgaggtact gattgcctag accaaatgtt ccttgatgct   3480
tgttttgtac aatatatata agataatgct gtcctagttg caggatttgg cctgtggtga   3540
gcatcatagt ctgtagtagt tttggtagca agacatttta tttttccttt atttaactta   3600
ctacatgcag tagcatctat ctatctctgt agtctgatat ctcctgttgt ctgtattgtg   3660
ccgttggatt ttttgctgta gtgagactga aaatgatgtg ctagtaataa tatttctgtt   3720
agaaatctaa gtagagaatc tgttgaagaa gtcaaaagct aatggaatca ggttacatat   3780
tcaatgtttt tctttttta gcggttggta gacgtgtaga ttcaacttct cttggagctc   3840
acctaggcaa tcagtaaaat gcatattcct ttttaactt gccatttatt tacttttagt   3900
ggaaattgtg accaatttgt tcatgtagaa cggatttgga ccattgcgtc cacaaaacgt   3960
ctcttttgct cgatcttcac aaaagcgatac cgaaatccag agatagtttt caaaagtcag   4020
aaatggcaaa gttataaata gtaaaacaga atagatgctg taatcgactt caataacaag   4080
tggcatcacg tttctagttc tagacccatc agctgggccg gcccagctga tgatcccggt   4140
gaagttccta ttccgaagtt cctattctcc agaaagtata ggaacttcac tagagcttgc   4200
ggccgcgcat gctgacttaa tcagctaacg ccactcgagg gggggcccgg taccggcgcg   4260
ccgttctata gtgtcaccta atcgtatgt gtatgataca taaggttatg tattaattgt   4320
agccgcgttc taacgacaat atgtccatat ggtgcactct cagtacaatc tgctctgatg   4380
ccgcatagtt aagccagccc cgacacccgc caacacccgc tgacgcgccc tgacgggctt   4440
gtctgctccc ggcatccgct tacagacaag ctgtgaccgt ctccgggagc tgcatgtgtc   4500
agaggttttc accgtcatca ccgaaacgcg cgagacgaaa gggcctcgtg atacgcctat   4560
ttttataggt taatgtcatg accaaaatcc cttaacgtga gttttcgttc cactgagcgt   4620
```

```
cagaccccgt agaaaagatc aaaggatctt cttgagatcc ttttttttctg cgcgtaatct   4680
gctgcttgca aacaaaaaaa ccaccgctac cagcggtggt ttgtttgccg gatcaagagc   4740
taccaactct ttttccgaag gtaactggct tcagcagagc gcagatacca aatactgtcc   4800
ttctagtgta gccgtagtta ggccaccact tcaagaactc tgtagcaccg cctacatacc   4860
tcgctctgct aatcctgtta ccagtggctg ctgccagtgg cgataagtcg tgtcttaccg   4920
ggttggactc aagacgatag ttaccggata aggcgcagcg gtcgggctga acggggggtt   4980
cgtgcacaca gcccagcttg gagcgaacga cctacaccga actgagatac ctacagcgtg   5040
agcattgaga aagcgccacg cttcccgaag ggagaaaggc ggacaggtat ccggtaagcg   5100
gcagggtcgg aacaggagag cgcacgaggg agcttccagg gggaaacgcc tggtatcttt   5160
atagtcctgt cgggtttcgc cacctctgac ttgagcgtcg atttttgtga tgctcgtcag   5220
gggggcggag cctatggaaa aacgccagca acgcggcctt tttacggttc ctggccttt   5280
gctggccttt tgctcacatg ttctttcctg cgttatcccc tgattctgtg gataaccgta   5340
ttaccgcctt tgagtgagct gataccgctc gccgcagccg aacgaccgag cgcagcgagt   5400
cagtgagcga ggaagcggaa gagcgcccaa tacgcaaacc gcctctcccc gcgcgttggc   5460
cgattcatta atgcaggttg atcagatctc gatcccgcga aattaatacg actcactata   5520
gggagaccac aacggtttcc ctctagaaat aattttgttt aactttaaga aggagatata   5580
cccatggaaa agcctgaact caccgcgacg tctgtcgaga agtttctgat cgaaaagttc   5640
gacagcgtct ccgacctgat gcagctctcg gagggcgaag aatctcgtgc tttcagcttc   5700
gatgtaggag ggcgtggata tgtcctgcgg gtaaatagct gcgccgatgg tttctacaaa   5760
gatcgttatg tttatcggca ctttgcatcg gccgcgctcc cgattccgga agtgcttgac   5820
attggggaat tcagcgagag cctgacctat tgcatctccc gccgtgcaca gggtgtcacg   5880
ttgcaagacc tgcctgaaac cgaactgccc gctgttctgc agccggtcgc ggaggctatg   5940
gatgcgatcg ctgcggccga tcttagccag acgagcgggt tcggcccatt cggaccgcaa   6000
ggaatcggtc aatacactac atggcgtgat ttcatatgcg cgattgctga tccccatgtg   6060
tatcactggc aaactgtgat ggacgacacc gtcagtgcgt ccgtcgcgca ggctctcgat   6120
gagctgatgc tttgggccga ggactgcccc gaagtccggc acctcgtgca cgcggatttc   6180
ggctccaaca atgtcctgac ggacaatggc cgcataacag cggtcattga ctggagcgag   6240
gcgatgttcg gggattccca atacgaggtc gccaacatct tcttctggag gccgtggttg   6300
gcttgtatgg agcagcagac gcgctacttc gagcggaggc atccggagct tgcaggatcg   6360
ccgcggctcc gggcgtatat gctccgcatt ggtcttgacc aactctatca gagcttggtt   6420
gacggcaatt tcgatgatgc agcttgggcg cagggtcgat gcgacgcaat cgtccgatcc   6480
ggagccggga ctgtcgggcg tacacaaatc gcccgcagaa gcgcggccgt ctggaccgat   6540
ggctgtgtag aagtactcgc cgatagtgga aaccgacgcc ccagcactcg tccgagggca   6600
aaggaatagt gaggtacagc ttggatcgat ccggctgcta caaagcccg aaaggaagct   6660
gagttggctg ctgccaccgc tgagcaataa ctagcataac cccttgggc ctctaaacgg   6720
gtcttgaggg gttttttgct gaaaggagga actatatccg gatgctcg             6768
```

<210> SEQ ID NO 93
<211> LENGTH: 8482
<212> TYPE: DNA
<213> ORGANISM: Artificial Sequence
<220> FEATURE:
<223> OTHER INFORMATION: vector QC478

<400> SEQUENCE: 93

```
aaacactagt aacggccgcc agtgtgctgg aattcgccct tcccaagctt tgctctagat    60
caaactcaca tccaaacata acatggatat cttccttacc aatcatacta attattttgg   120
gttaaatatt aatcattatt tttaagatat taattaagaa attaaaagat tttttaaaaa   180
aatgtataaa attatattat tcatgatttt tcatacattt gattttgata ataaatatat   240
ttttttaat ttcttaaaaa atgttgcaag acacttatta gacatagtct tgttctgttt    300
acaaaagcat tcatcattta atacattaaa aaatatttaa tactaacagt agaatcttct   360
tgtgagtggt gtgggagtag gcaacctggc attgaaacga gagaaagaga gtcagaacca   420
gaagacaaat aaaaagtatg caacaaacaa atcaaaatca aagggcaaag gctggggttg   480
gctcaattgg ttgctacatt caattttcaa ctcagtcaac ggttgagatt cactctgact   540
tccccaatct aagccgcgga tgcaaacggt tgaatctaac ccacaatcca atctcgttac   600
ttaggggctt ttccgtcatt aactcacccc tgccacccgg tttccctata aattggaact   660
caatgctccc ctctaaactc gtatcgcttc agagttgaga ccaagacaca ctcgttcata   720
tatctctctg ctcttctctt ctcttctacc tctcaaggta cttttcttct ccctctacca   780
aatcctagat tccgtggttc aatttcggat cttgcacttc tggtttgctt tgccttgctt   840
tttcctcaac tgggtccatc taggatccat gtgaaactct actctttctt taatatctgc   900
ggaatacgcg tttgactttc agatctagtc gaaatcattt cataattgcc tttctttctt   960
ttagcttatg agaaataaaa tcactttttt tttatttcaa aataaacctt gggccttgtg  1020
ctgactgaga tgggggtttgg tgattacaga attttagcga attttgtaat tgtacttgtt  1080
tgtctgtagt tttgtttttgt tttcttgttt ctcatacatt ccttaggctt caattttatt  1140
cgagtatagg tcacaatagg aattcaaact ttgagcaggg gaattaatcc cttccttcaa  1200
atccagtttg tttgtatata tgtttaaaaa atgaaacttt tgcttaaat tctattataa   1260
cttttttat ggctgaaatt tttgcatgtg tctttgctct ctgttgtaaa tttactgttt   1320
aggtactaac tctaggcttg ttgtgcagtt tttgaagtat aacaacagaa gttcctattc  1380
cgaagttcct attctctaga aagtatagga acttccacca cacaacacaa tggcggccac  1440
cgcttccaga accacccgat tctcttcttc ctcttcacac cccaccttcc ccaaacgcat  1500
tactagatcc accctccctc tctctcatca accctcacc aaacccaacc acgtctcaa   1560
aatcaaatgt tccatctcca aaccccccac ggcggcgccc ttcaccaagg aagcgccgac  1620
cacgagccc ttcgtgtcac ggttcgcctc cggcgaacct cgcaagggcg cggacatcct   1680
tgtggaggcg ctggagaggc agggcgtgac gacggtgttc gcgtaccccg gcggtgcgtc  1740
gatggagatc caccaggcgc tcacgcgctc cgccgccatc cgcaacgtgc tcccgcgcca  1800
cgagcagggc ggcgtcttcg ccgccgaagg ctacgcgcgt tcctccggcc tccccggcgt  1860
ctgcattgcc acctccggcc ccggcgccac caacctcgtg agcggcctcg ccgacgcttt  1920
aatggacagc gtcccagtcg tcgccatcac cggccaggtc gcccgccgga tgatcggcac  1980
cgacgccttc caagaaaccc cgatcgtgga ggtgagcaga tccatcacga agcacaacta  2040
cctcatcctc gacgtcgacg acatcccccg cgtcgtcgcc gaggctttct tcgtcgccac  2100
ctccggccgc cccggtccgg tcctcatcga cattcccaaa gacgttcagc agcaactcgc  2160
cgtgcctaat tgggacgagc ccgttaacct ccccggttac ctcgccaggc tgcccaggcc  2220
ccccgccgag gcccaattgg aacacattgt cagactcatc atggaggccc aaaagcccgt  2280
tctctacgtc ggcggtggca gtttgaattc cagtgctgaa ttgaggcgct tgttgaact   2340
```

```
cactggtatt cccgttgcta gcactttaat gggtcttgga acttttccta ttggtgatga    2400
atattcccctt cagatgctgg gtatgcatgg tactgtttat gctaactatg ctgttgacaa    2460
tagtgatttg ttgcttgcct ttggggtaag gtttgatgac cgtgttactg ggaagcttga    2520
ggcttttgct agtagggcta agattgttca cattgatatt gattctgccg agattgggaa    2580
gaacaagcag gcgcacgtgt cggtttgcgc ggatttgaag ttggccttga agggaattaa    2640
tatgattttg gaggagaaag gagtggaggg taagtttgat cttggaggtt ggagagaaga    2700
gattaatgtg cagaaacaca gtttccatt gggttacaag acattccagg acgcgatttc    2760
tccgcagcat gctatcgagg ttcttgatga gttgactaat ggagatgcta ttgttagtac    2820
tggggttggg cagcatcaaa tgtgggctgc gcagttttac aagtacaaga gaccgaggca    2880
gtggttgacc tcaggggggtc ttggagccat gggttttgga ttgcctgcgg ctattggtgc    2940
tgctgttgct aaccctgggg ctgttgtggt tgacattgat ggggatggta gtttcatcat    3000
gaatgttcag gagttggcca ctataagagt ggagaatctc ccagttaaga tattgttgtt    3060
gaacaatcag catttgggta tggtggttca gttggaggat aggttctaca gtccaatag    3120
agctcacacc tatcttggag atccgtctag cgagagcgag atattcccaa acatgctcaa    3180
gtttgctgat gcttgtggga taccggcagc gcgagtgacg aagaaggaag agcttagagc    3240
ggcaattcag agaatgttgg acaccctgg ccccctacctt cttgatgtca ttgtgcccca    3300
tcaggagcat gtgttgccga tgattcccag taatggatcc ttcaaggatg tgataactga    3360
gggtgatggt agaacgaggt actgattgcc tagaccaaat gttccttgat gcttgttttg    3420
tacaatatat ataagataat gctgtcctag ttgcaggatt tggcctgtgg tgagcatcat    3480
agtctgtagt agttttggta gcaagacatt ttattttcct tttatttaac ttactacatg    3540
cagtagcatc tatctatctc tgtagtctga tatctcctgt tgtctgtatt gtgccgttgg    3600
attttttgct gtagtgagac tgaaaatgat gtgctagtaa taatatttct gttagaaatc    3660
taagtagaga atctgttgaa gaagtcaaaa gctaatggaa tcaggttaca tattcaatgt    3720
ttttctttt ttagcggttg gtagacgtgt agattcaact tctcttggag ctcacctagg    3780
caatcagtaa aatgcatatt ccttttttaa cttgccatt atttacttt agtggaaatt    3840
gtgaccaatt tgttcatgta aacggattt ggaccattgc gtccacaaaa cgtctctttt    3900
gctcgatctt cacaaagcga taccgaaatc cagagatagt tttcaaaagt cagaaatggc    3960
aaagttataa atagtaaaac agaatagatg ctgtaatcga cttcaataac aagtggcatc    4020
acgtttctag ttctagaccc atcagctggg ccggcccagc tgatgatccc ggtgaagttc    4080
ctattccgaa gttcctattc tccagaaagt ataggaactt cactagagct tgcggccgcg    4140
catgctgact taatcagcta acgccactcg agggggggcc cggtaccggc gcgccgttct    4200
atagtgtcac ctaaatcgta tgtgtatgat acataaggtt atgtattaat tgtagccgcg    4260
ttctaacgac aatatgtcca tatggtgcac tctcagtaca atctgctctg atgccgcata    4320
gttaagccag ccccgacacc cgccaacacc cgctgacgcg ccctgacggg cttgtctgct    4380
cccggcatcc gcttacagac aagctgtgac cgtctccggg agctgcatgt gtcagaggtt    4440
ttcaccgtca tcaccgaaac gcgcgagacg aaagggcctc gtgatacgcc tatttttata    4500
ggttaatgtc atgaccaaaa tcccttaacg tgagttttcg ttccactgag cgtcagaccc    4560
cgtagaaaag atcaaaggat cttcttgaga tcctttttt ctgcgcgtaa tctgctgctt    4620
gcaaacaaaa aaaccaccgc taccagcggt ggtttgtttg ccggatcaag agctaccaac    4680
tctttttccg aaggtaactg gcttcagcag agcgcagata ccaaatactg tccttctagt    4740
```

```
gtagccgtag ttaggccacc acttcaagaa ctctgtagca ccgcctacat acctcgctct   4800
gctaatcctg ttaccagtgg ctgctgccag tggcgataag tcgtgtctta ccgggttgga   4860
ctcaagacga tagttaccgg ataaggcgca gcggtcgggc tgaacggggg gttcgtgcac   4920
acagcccagc ttggagcgaa cgacctacac cgaactgaga tacctacagc gtgagcattg   4980
agaaagcgcc acgcttcccg aagggagaaa ggcggacagg tatccggtaa gcggcagggt   5040
cggaacagga gagcgcacga gggagcttcc aggggggaaac gcctggtatc tttatagtcc   5100
tgtcgggttt cgccacctct gacttgagcg tcgattttg tgatgctcgt caggggggcg   5160
gagcctatgg aaaaacgcca gcaacgcggc cttttttacgg ttcctggcct tttgctggcc   5220
ttttgctcac atgttctttc ctgcgttatc ccctgattct gtggataacc gtattaccgc   5280
ctttgagtga gctgataccg ctcgccgcag ccgaacgacc gagcgcagcg agtcagtgag   5340
cgaggaagcg gaagagcgcc caatacgcaa accgcctctc cccgcgcgtt ggccgattca   5400
ttaatgcagg ttgatcagat ctcgatcccg cgaaattaat acgactcact atagggagac   5460
cacaacggtt tccctctaga ataattttg tttaacttta agaaggagat atacccatgg   5520
aaaagcctga actcaccgcg acgtctgtcg agaagtttct gatcgaaaag ttcgacagcg   5580
tctccgacct gatgcagctc tcggagggcg aagaatctcg tgctttcagc ttcgatgtag   5640
gagggcgtgg atatgtcctg cgggtaaata gctgcgccga tggtttctac aaagatcgtt   5700
atgtttatcg gcactttgca tcggccgcgc tcccgattcc ggaagtgctt gacattgggg   5760
aattcagcga gagcctgacc tattgcatct cccgccgtgc acagggtgtc acgttgcaag   5820
acctgcctga aaccgaactg cccgctgttc tgcagccggt cgcggaggct atggatgcga   5880
tcgctgcggc cgatcttagc cagacgagcg ggttcggccc attcggaccg caaggaatcg   5940
gtcaatacac tacatggcgt gatttcatat gcgcgattgc tgatccccat gtgtatcact   6000
ggcaaactgt gatggacgac accgtcagtg cgtccgtcgc gcaggctctc gatgagctga   6060
tgctttgggc cgaggactgc cccgaagtcc ggcacctcgt gcacgcggat ttcggctcca   6120
acaatgtcct gacggacaat ggccgcataa cagcggtcat tgactggagc gaggcgatgt   6180
tcggggattc ccaatacgag gtcgccaaca tcttcttctg gaggccgtgg ttggcttgta   6240
tggagcagca gacgcgctac ttcgagcgga ggcatccgga gcttgcagga tcgccgcggc   6300
tccgggcgta tatgctccgc attggtcttg accaactcta tcagagcttg gttgacggca   6360
atttcgatga tgcagcttgg gcgcagggtc gatgcgacgc aatcgtccga tccggagccg   6420
ggactgtcgg gcgtacacaa atcgcccgca gaagcgcggc cgtctggacc gatggctgtg   6480
tagaagtact cgccgatagt ggaaaccgac gccccagcac tcgtccgagg gcaaaggaat   6540
agtgaggtac agcttggatc gatccggctg ctaacaaagc ccgaaaggaa gctgagttgg   6600
ctgctgccac cgctgagcaa taactagcat aaccccttgg ggcctctaaa cgggtcttga   6660
ggggtttttt gctgaaagga ggaactatat ccggatgctc gggcgcgccg gtacccgggt   6720
accgagctca ctagacgcgg tgaaattacc taattaacac cggtgtttat caaacaagtt   6780
tgtacaaaaa agctgaacga gaaacgtaaa atgatataaa tatcaatata ttaaattaga   6840
ttttgcataa aaaacagact acataatact gtaaaacaca acatatccag tcactatggc   6900
ggccgcatta ggcaccccag gctttacact ttatgcttcc ggctcgtata atgtgtggat   6960
tttgagttag gatccgtcga gattttcagg agctaaggaa gctaaaatgg agaaaaaaat   7020
cactggatat accaccgttg atatatccca atggcatcgt aaagaacatt ttgaggcatt   7080
tcagtcagtt gctcaatgta cctataacca gaccgttcag ctggatatta cggcctttt   7140
```

| | |
|---|---|
| aaagaccgta aagaaaaata agcacaagtt ttatccggcc tttattcaca ttcttgcccg | 7200 |
| cctgatgaat gctcatccgg aattccgtat ggcaatgaaa gacggtgagc tggtgatatg | 7260 |
| ggatagtgtt caccctttgtt acaccgtttt ccatgagcaa actgaaacgt tttcatcgct | 7320 |
| ctggagtgaa taccacgacg atttccggca gtttctacac atatattcgc aagatgtggc | 7380 |
| gtgttacggt gaaaacctgg cctatttccc taaagggttt attgagaata tgttttcgt | 7440 |
| ctcagccaat ccctgggtga gtttcaccag ttttgattta aacgtggcca atatggacaa | 7500 |
| cttcttcgcc cccgttttca ccatgggcaa atattatacg caaggcgaca aggtgctgat | 7560 |
| gccgctggcg attcaggttc atcatgccgt ttgtgatggc ttccatgtcg gcagaatgct | 7620 |
| taatgaatta caacagtact gcgatgagtg gcaggcgggg cgtaatctag aggatccggc | 7680 |
| ttactaaaag ccagataaca gtatgcgtat ttgcgcgctg attttgcggg tataagaata | 7740 |
| tatactgata tgtataccccg aagtatgtca aaaagaggta tgctatgaag cagcgtatta | 7800 |
| cagtgacagt tgacagcgac agctatcagt tgctcaaggc atatatgatg tcaatatctc | 7860 |
| cggtctggta agcacaacca tgcagaatga agcccgtcgt ctgcgtgccg aacgctggaa | 7920 |
| agcggaaaat caggaaggga tggctgaggt cgcccggttt attgaaatga acggctcttt | 7980 |
| tgctgacgag aacaggggct ggtgaaatgc agtttaaggt ttacacctat aaaagagaga | 8040 |
| gccgttatcg tctgttttgtg gatgtacaga gtgatattat tgacacgccc gggcgacgga | 8100 |
| tggtgatccc cctggccagt gcacgtctgc tgtcagataa agtcccccgt gaactttacc | 8160 |
| cggtggtgca tatcggggat gaaagctggc gcatgatgac caccgatatg gccagtgtgc | 8220 |
| cggtctccgt tatcggggaa gaagtggctg atctcagcca ccgcgaaaat gacatcaaaa | 8280 |
| acgccattaa cctgatgttc tggggaatat aaatgtcagg ctccctttata cacagccagt | 8340 |
| ctgcaggtcg accatagtga ctggatatgt tgtgttttac agtattatgt agtctgtttt | 8400 |
| ttatgcaaaa tctaatttaa tatattgata tttatatcat tttacgtttc tcgttcagct | 8460 |
| ttcttgtaca aagtggttcg at | 8482 |

<210> SEQ ID NO 94
<211> LENGTH: 8484
<212> TYPE: DNA
<213> ORGANISM: Artificial Sequence
<220> FEATURE:
<223> OTHER INFORMATION: vector QC479

<400> SEQUENCE: 94

| | |
|---|---|
| aaacactagt aacggccgcc agtgtgctgg aattcgccct tcccaagctt tgctctagat | 60 |
| caaactcaca tccaaacata acatggatat cttccttacc aatcatacta attatttggg | 120 |
| gttaaatatt aatcattatt tttaagatat taattaagaa attaaagat ttttaaaaa | 180 |
| aatgtataaa attatattat tcatgatttt tcatacattt gatttttgata ataaatatat | 240 |
| ttttttaat ttcttaaaaa atgttgcaag acacttatta gacatagtct tgttctgttt | 300 |
| acaaaagcat tcatcattta atacattaaa aaatatttaa tactaacagt agaatcttct | 360 |
| tgtgagtggt gtgggagtag gcaacctggc attgaaacga gagaaagaga gtcagaacca | 420 |
| gaagacaaat aaaagtatg caacaaacaa atcaaaatca aagggcaaag gctggggttg | 480 |
| gctcaattgg ttgctacatt caattttcaa ctcagtcaac ggttgagatt cactctgact | 540 |
| tccccaatct aagccgcgga tgcaaacggt tgaatctaac ccacaatcca atctcgttac | 600 |
| ttaggggctt ttccgtcatt aactcacccc tgccacccgg tttccctata aattggaact | 660 |
| caatgctccc ctctaaactc gtatcgcttc agagttgaga ccaagacaca ctcgttcata | 720 |

```
tatctctctg ctcttctctt ctcttctacc tctcaaggta cttttcttct ccctctacca      780
aatcctagat tccgtggttc aatttcggat cttgcacttc tggtttgctt tgccttgctt      840
tttcctcaac tgggtccatc taggatccat gtgaaactct actctttctt taatatctgc      900
ggaatacgcg tttgactttc agatctagtc gaaatcattt cataattgcc tttctttctt      960
ttagcttatg agaaataaaa tcactttttt tttatttcaa ataaaccttg ggccttgtg      1020 ctgactgaga tggggtttgg tgattacaga attttagcga attttgtaat tgtacttgtt     1080
tgtctgtagt tttgttttgt tttcttgttt ctcatacatt ccttaggctt caattttatt     1140
cgagtatagg tcacaatagg aattcaaact ttgagcaggg gaattaatcc cttccttcaa     1200
atccagtttg tttgtatata tgtttaaaaa atgaaacttt tgctttaaat tctattataa     1260 cttttttttat ggctgaaatt tttgcatgtg tctttgctct ctgttgtaaa tttactgttt    1320
aggtactaac tctaggcttg ttgtgcagtt tttgaagtat aacaacagaa gttcctattc     1380
cgaagttcct attctctaga aagtatagga acttccacca cacaacacaa tggcggccac     1440
cgcttccaga accacccgat tctcttcttc ctcttcacac cccaccttcc ccaaacgcat     1500
tactagatcc accctccctc tctctcatca aaccctcacc aaacccaacc acgtctcaa     1560 aatcaaatgt tccatctcca aaccccccac ggcggcgccc ttcaccaagg aagcgccgac    1620
cacggagccc ttcgtgtcac ggttcgcctc cggcgaacct cgcaagggcg cggacatcct    1680
tgtggaggcg ctggagaggc agggcgtgac gacggtgttc gcgtaccccg gcggtgcgtc    1740
gatggagatc caccaggcgc tcacgcgctc cgccgccatc cgcaacgtgc tcccgcgcca    1800
cgagcagggc ggcgtcttcg ccgccgaagg ctacgcgcgt tcctccggcc tccccggcgt    1860
ctgcattgcc acctccggcc ccggcgccac caacctcgtg agcggcctcg ccgacgcttt    1920
aatggacagc gtcccagtcg tcgccatcac cggccaggtc gcccgccgga tgatcggcac    1980
cgacgccttc caagaaaccc cgatcgtgga ggtgagcaga tccatcacga agcacaacta    2040
cctcatcctc gacgtcgacg acatcccccg cgtcgtcgcc gaggctttct tcgtcgccac    2100
ctccggccgc cccggtccgg tcctcatcga cattcccaaa gacgttcagc agcaactcgc    2160
cgtgcctaat tgggacgagc ccgttaacct ccccggttac ctcgccaggc tgcccaggcc    2220
ccccgccgag gcccaattgg aacacattgt cagactcatc atggaggccc aaaagcccgt    2280
tctctacgtc ggcggtggca gtttgaattc cagtgctgaa ttgaggcgct tgttgaact    2340 cactggtatt cccgttgcta gcactttaat gggtcttgga acttttccta ttggtgatga    2400
atattccctt cagatgctgg gtatgcatgg tactgtttat gctaactatg ctgttgacaa    2460
tagtgatttg ttgcttgcct ttggggtaag gtttgatgac cgtgttactg ggaagcttga    2520
ggcttttgct agtagggcta agattgttca cattgatatt gattctgccg agattgggaa    2580
gaacaagcag gcgcacgtgt cggtttgcgc ggatttgaag ttggccttga agggaattaa    2640
tatgattttg gaggagaaag gagtggaggg taagtttgat cttggaggtt ggagagaaga    2700
gattaatgtg cagaaacaca gtttccatt gggttacaag acattccagg acgcgatttc    2760
tccgcagcat gctatcgagg ttcttgatga gttgactaat ggagatgcta ttgttagtac    2820
tggggttggg cagcatcaaa tgtgggctgc gcagttttac aagtacaaga gaccgaggca    2880
gtggttgacc tcaggggtc ttggagccat gggttttgga ttgcctgcgg ctattggtgc    2940
tgctgttgct aaccctgggg ctgttgtggt tgacattgat ggggatggta gtttcatcat    3000
gaatgttcag gagttggcca ctataagagt ggagaatctc ccagttaaga tattgttgtt    3060
gaacaatcag catttgggta tggtggttca gttggaggat aggttctaca agtccaatag    3120
```

```
agctcacacc tatcttggag atccgtctag cgagagcgag atattcccaa acatgctcaa    3180
gtttgctgat gcttgtggga taccggcagc gcgagtgacg aagaaggaag agcttagagc    3240
ggcaattcag agaatgttgg acaccctgg cccctacctt cttgatgtca ttgtgcccca    3300
tcaggagcat gtgttgccga tgattcccag taatggatcc ttcaaggatg tgataactga    3360
gggtgatggt agaacgaggt actgattgcc tagaccaaat gttccttgat gcttgttttg    3420
tacaatatat ataagataat gctgtcctag ttgcaggatt tggcctgtgg tgagcatcat    3480
agtctgtagt agttttggta gcaagacatt ttattttcct tttatttaac ttactacatg    3540
cagtagcatc tatctatctc tgtagtctga tatctcctgt tgtctgtatt gtgccgttgg    3600 atttttgct gtagtgagac tgaaaatgat gtgctagtaa taatatttct gttagaaatc    3660
taagtagaga atctgttgaa gaagtcaaaa gctaatggaa tcaggttaca tattcaatgt    3720
ttttcttttt ttagcggttg gtagacgtgt agattcaact tctcttggag ctcacctagg    3780
caatcagtaa aatgcatatt cctttttaa cttgccattt atttactttt agtggaaatt    3840
gtgaccaatt tgttcatgta gaacggattt ggaccattgc gtccacaaaa cgtctctttt    3900
gctcgatctt cacaaagcga taccgaaatc cagagatagt tttcaaaagt cagaaatggc    3960
aaagttataa atagtaaaac agaatagatg ctgtaatcga cttcaataac aagtggcatc    4020
acgtttctag ttctagaccc atcagctggg ccggcccagc tgatgatccc ggtgaagttc    4080
ctattccgaa gttcctattc tccagaaagt ataggaactt cactagagct tgcggccgcg    4140
catgctgact taatcagcta acgccactcg agggggggcc cggtaccggc gcgccgttct    4200
atagtgtcac ctaaatcgta tgtgtatgat acataaggtt atgtattaat tgtagccgcg    4260
ttctaacgac aatatgtcca tatggtgcac tctcagtaca atctgctctg atgccgcata    4320
gttaagccag ccccgacacc cgccaacacc cgctgacgcg ccctgacggg cttgtctgct    4380
cccggcatcc gcttacagac aagctgtgac cgtctccggg agctgcatgt gtcagaggtt    4440
ttcaccgtca tcaccgaaac gcgcgagacg aaagggcctc gtgatacgcc tatttttata    4500
ggttaatgtc atgaccaaaa tcccttaacg tgagttttcg ttccactgag cgtcagaccc    4560
cgtagaaaag atcaaaggat cttcttgaga tccttttttt ctgcgcgtaa tctgctgctt    4620
gcaaacaaaa aaaccaccgc taccagcggt ggtttgtttg ccggatcaag agctaccaac    4680 tcttttccg aaggtaactg gcttcagcag agcgcagata ccaaatactg tccttctagt    4740
gtagccgtag ttaggccacc acttcaagaa ctctgtagca ccgcctacat acctcgctct    4800
gctaatcctg ttaccagtgg ctgctgccag tggcgataag tcgtgtctta ccgggttgga    4860
ctcaagacga tagttaccgg ataaggcgca gcggtcgggc tgaacggggg gttcgtgcac    4920
acagcccagc ttggagcgaa cgacctacac cgaactgaga tacctacagc gtgagcattg    4980
agaaagcgcc acgcttcccg aagggagaaa ggcggacagg tatccggtaa gcggcagggt    5040
cggaacagga gagcgcacga gggagcttcc agggggaaac gcctggtatc tttatagtcc    5100
tgtcgggttt cgccacctct gacttgagcg tcgatttttg tgatgctcgt caggggggcg    5160
gagcctatgg aaaaacgcca gcaacgcggc ctttttacgg ttcctggcct tttgctggcc    5220
ttttgctcac atgttctttc ctgcgttatc ccctgattct gtggataacc gtattaccgc    5280
ctttgagtga gctgataccg ctcgccgcag ccgaacgacc gagcgcagcg agtcagtgag    5340
cgaggaagcg gaagagcgcc caatacgcaa accgcctctc cccgcgcgtt ggccgattca    5400
ttaatgcagg ttgatcagat ctcgatcccg cgaaattaat acgactcact atagggagac    5460
cacaacggtt ccctctaga aataattttg tttaacttta agaaggagat atacccatgg    5520
```

```
aaaagcctga actcaccgcg acgtctgtcg agaagtttct gatcgaaaag ttcgacagcg   5580
tctccgacct gatgcagctc tcggagggcg aagaatctcg tgctttcagc ttcgatgtag   5640
gagggcgtgg atatgtcctg cgggtaaata gctgcgccga tggtttctac aaagatcgtt   5700
atgtttatcg gcactttgca tcggccgcgc tcccgattcc ggaagtgctt gacattgggg   5760
aattcagcga gagcctgacc tattgcatct cccgccgtgc acagggtgtc acgttgcaag   5820
acctgcctga aaccgaactg cccgctgttc tgcagccggt cgcggaggct atggatgcga   5880
tcgctgcggc cgatcttagc cagacgagcg ggttcggccc attcggaccg caaggaatcg   5940
gtcaatacac tacatggcgt gatttcatat gcgcgattgc tgatccccat gtgtatcact   6000
ggcaaactgt gatggacgac accgtcagtg cgtccgtcgc gcaggctctc gatgagctga   6060
tgctttgggc cgaggactgc cccgaagtcc ggcacctcgt gcacgcggat ttcggctcca   6120
acaatgtcct gacggacaat ggccgcataa cagcggtcat tgactggagc gaggcgatgt   6180
tcggggattc ccaatacgag gtcgccaaca tcttcttctg gaggccgtgg ttggcttgta   6240
tggagcagca gacgcgctac ttcgagcgga ggcatccgga gcttgcagga tcgccgcggc   6300
tccgggcgta tatgctccgc attggtcttg accaactcta tcagagcttg gttgacggca   6360
atttcgatga tgcagcttgg gcgcagggtc gatgcgacgc aatcgtccga tccggagccg   6420
ggactgtcgg gcgtacacaa atcgcccgca gaagcgcggc cgtctggacc gatggctgtg   6480
tagaagtact cgccgatagt ggaaaccgac gccccagcac tcgtccgagg gcaaaggaat   6540
agtgaggtac agcttggatc gatccggctg ctaacaaagc ccgaaaggaa gctgagttgg   6600
ctgctgccac cgctgagcaa taactagcat aaccccttgg ggcctctaaa cgggtcttga   6660 ggggttttt gctgaaagga ggaactatat ccggatgctc gggcgcgccg gtacccgggt   6720
accgagctca ctagacgcgg tgaaattacc taattaacac cggtgtttat ctatcaactt   6780
tgtataataa agttaacga gaaacgtaaa atgatataaa tatcaatata ttaaattaga   6840
ttttgcataa aaaacagact acataatact gtaaaacaca acatatccag tcactatggc   6900
ggccgcatta ggcaccccag gctttacact ttatgcttcc ggctcgtata atgtgtggat   6960
tttgagttag gatccgtcga gattttcagg agctaaggaa gctaaaatgg agaaaaaaat   7020
cactggatat accaccgttg atatatccca atggcatcgt aaagaacatt ttgaggcatt   7080
tcagtcagtt gctcaatgta cctataacca gaccgttcag ctggatatta cggcctttt   7140 aaagaccgta agaaaaata agcacaagtt ttatccggcc tttattcaca ttcttgcccg   7200
cctgatgaat gctcatccgg aattccgtat ggcaatgaaa gacggtgagc tggtgatatg   7260
ggatagtgtt cacccttgtt acaccgtttt ccatgagcaa actgaaacgt tttcatcgct   7320
ctggagtgaa taccacgacg atttccggca gtttctacac atatattcgc aagatgtggc   7380
gtgttacggt gaaaacctgg cctatttccc taaagggttt attgagaata tgttttcgt   7440 ctcagccaat ccctgggtga gtttcaccag ttttgattta aacgtggcca atatggacaa   7500
cttcttcgcc cccgttttca ccatgggcaa atattatacg caaggcgaca aggtgctgat   7560
gccgctggcg attcaggttc atcatgccgt ttgtgatggc ttccatgtcg cagaatgct   7620 taatgaatta caacagtact gcgatgagtg gcaggcgggg cgtaatctag aggatccggc   7680
ttactaaaag ccagataaca gtatgcgtat ttgcgcgctg attttgcgg tataagaata   7740 tatactgata tgtatacccg aagtatgtca aaaagaggta tgctatgaag cagcgtatta   7800
cagtgacagt tgacagcgac agctatcagt tgctcaaggc atatatgatg tcaatatctc   7860
cggttcggta agcacaacca tgcagaatga agcccgtcgt ctgcgtgccg aacgctggaa   7920
```

```
agcggaaaat caggaaggga tggctgaggt cgcccggttt attgaaatga acggctcttt    7980
tgccgacgag aacaggggct ggtgaaatgc agtttaaggt ttacacctat aaaagagaga    8040
gccgttatcg tctgtttgtg gatgtacaga gtgatattat tgacacgccc gggcgacgga    8100
tggtgatccc cctggccagt gcacgtctgc tgtcagataa agtcccccgt gaactttacc    8160
cggtggtgca tatcggggat gaaagctggc gcatgatgac caccgatatg gccagtgtgc    8220
cggtctccgt tatcggggaa gaagtggctg atctcagcca ccgcgaaaat gacatcaaaa    8280
acgccattaa cctgatgttc tggggaatat aaatgtcagg ctcccttata cacagccagt    8340
ctgcaggtcg accatagtga ctggatatgt tgtgttttac agtattatgt agtctgtttt    8400
ttatgcaaaa tctaatttaa tatattgata tttatatcat tttacgtttc tcgttcaact    8460
tttctataca aagttgatag cgat                                           8484
```

SITE-SPECIFIC INTEGRATION AND STACKING OF TRANSGENES IN SOYBEAN VIA DNA RECOMBINASE MEDIATED CASSETTE EXCHANGE

FIELD OF THE INVENTION

The present invention relates to the field of plant molecular biology, more particularly to site-specific integration and stacking of transgenes in soybean.

BACKGROUND OF THE INVENTION

Current transformation methods using *Agrobacterium* or biolistic bombardment have challenges such as random integration, multiple transgene copies, and unpredicted integration sites. Acting alone or combined, these challenges could lead to unpredictable expression or silencing of introduced transgenes. Though homologous recombination can be explored to address these challenges (Iida and Terada, (2005) Plant Mol. Biol. 59:205-219; Wright et al. (2005) Plant J. 44:693-705), site-specific integration (SSI) mediated by DNA recombinase is practically a more promising approach to eliminate random integration of unpredictable copies of a transgene by placing single copy transgene into a pre-characterized site in plant genome.

Several site-specific DNA recombination systems, such as the Cre/lox of bacteriophage P1, the FLP/FRT of *Sacchromyces cerevisiae*, and the R/RS of *Zygosacchromyces rouxii* have been used in site-specific gene integration studies (Groth and Calos, (2003) J. Mol. Biol. 335:667-678; Ow, (2003) Plant Mol. Biol. 48:183-200). A common feature of these systems is that each system consists of a single polypeptide recombinase Cre, FLP, or R, and two identical or almost identical palindromic recognition sites lox, FRT, or RS. Each recognition site contains a short asymmetric spacer sequence where DNA strand exchange takes place, flanked on each side by an inverted repeat sequence where the corresponding recombinase specifically binds. If two recognitions sites are located in cis on the same DNA molecule, DNA segment flanked by the two sites can be excised if the two sites are in the same orientation, or be inverted if the two sites are in opposite orientations. If two recognitions sites are each located in trans on two different DNA molecules, a reciprocal translocation can happen between the two linear DNA molecules, or the two molecules can integrate if at least one of them is a circular DNA (Groth and Calos, J. Mol. Biol. 335: 667-678 (2003); Ow, Plant Mol. Biol. 48:183-200 (2003)).

A simple SSI can target DNA into single recombination site previously placed in a plant genome. Improvement of the single site integration approach involved transient Cre expression and the use of mutant lox sites to recreate two less compatible lox sites after integration to reduce subsequent excision of the integrated gene in tobacco (Albert et al. (1995) Plant J. 7:649-659; Day et al. (2000) Genes Dev. 14:2869-2880). Similar approach was used to produce SSI events in rice by biolistic bombardment transformation method and the transgene was proven to be stable and consistently expressed over generations (Srivastava and Ow, (2001) Mol. Breed. 8:345-350; Srivastava et al. (2004) Plant Biotechnol. J. 2:169-179). Using *Agrobacterium* T-DNA for donor DNA delivery and a promoter trap to activate selectable marker gene and to displace Cre expression upon DNA recombination, ~2% single lox site SSI was achieved in *Arabidopsis* (Vergunst et al. (1998) Nucleic Acids Res. 26:2729-2734). The process of SSI is basically irreversible and thus the genomic site can not be recovered for repeated use. Additionally, since SSI will integrate the entire circular DNA, unwanted components such as the vector backbone is also integrated unless the integration DNA can be circulated by Cre recombinase to remove unwanted DNA prior to SSI (Srivastava et al. (2004) Plant Biotechnol J. 2:169-179; Chawla et al. (2006) Plant Biotechnol. J. 4:209-218; Vergunst et al. (1998) Nucleic Acids Res. 26:2729-2734). To achieve marker-free site-specific gene integration, a two-step approach was proposed to combine gene integration using one recombinase system such as Cre/lox followed by gene excision using another system such as FLP/FRT that is also conditionally controlled by an inducible promoter (Srivastava and Ow, (2004) Trends Biotech. 22:627-629).

If two incompatible recognition sites, which are similar enough to be recognized by the same recombinase but also different enough to prevent DNA recombination from happening between them, are located on a linear DNA molecule, DNA segment between the two sites will not be either excised or inverted. When a circular DNA molecule carrying an identical pair of the incompatible sites is introduced, the circular DNA can integrate by the corresponding recombinase at either site on the linear DNA to create a collinear DNA molecule with four recognition sites, two from the original linear DNA and two from the circular DNA. DNA excision can subsequently happen between any pair of compatible sites and result in the restoration of the original two DNA molecules or the exchange of the intervening DNA segments between the two DNA molecules. The latter process termed recombinase mediated cassette exchange (RMCE) can be employed to integrate transgenes directionally into pre-defined genome sites (Baer and Bode, (2001) Curr. Opin. Biotechnol. 12:473-480; Trinh and Morrision, (2000) J. Immunol. Methods 244:185-193).

RMCE using two identical but oppositely orientated RS sites resulted in donor cassette exchange into the previously placed target site in tobacco (Nanto et al. (2005) Plant Biotechnol. J. 3:203-214). The donor vector containing the R recombinase gene and a third RS site to help eliminating random integration was delivered by *Agrobacterium* transformation. RMCE utilizing both the Cre/lox and FLP/FRT systems was used in animal cell cultures to improve RMCE frequency (Lauth et al. (2002) Nucleic Acids Res. 30:e115). RMCE using two directional incompatible FRT sites was used in *Drosophila* to achieve cassette exchange by transiently expressed FLP recombinase between a target DNA previously placed in the genome and a donor introduced as a circular DNA (Horn and Handler, (2005) Proc. Natl. Acad. Sci. 102:12483-12488). A complex gene conversion approach involving Cre/lox and FLP/FRT mediated site-specific integration, RMCE, and homologous recombination was explored in maize (Djukanovic et al. (2006) Plant Biotechnol. J. 4:345-357).

SUMMARY OF THE INVENTION

The present invention includes:

In one embodiment, a method for stacking multiple expression cassettes of interest into a specific chromosomal site in a soybean genome, said method comprising: (a) transforming a first soybean cell with an isolated nucleic acid fragment comprising at least one first expression cassette of interest adjacent to a target site, wherein said target site comprises a first selectable marker protein-coding sequence, wherein the first selectable marker protein-coding sequence is bounded by a first recombination site and a second non-identical recombination site; (b) regenerating a transgenic plant from the transformed soybean cell of step (a); (c) introducing into a second soybean cell from the transgenic plant of step (b) a transfer cassette, wherein said transfer cassette comprises a second selectable marker protein-coding sequence, wherein the second selectable marker protein-coding sequence is bounded by the first recombination site and the second non-identical recombination sites of the target site, and further wherein the transfer cassette further comprises at least one second expression cassette of interest, wherein the at least one second expression cassette of interest is bounded by the second selectable marker protein-coding sequence and the second non-identical recombination site; and (d) providing a recombinase that recognizes and implements recombination at the non-identical recombination sites.

In another embodiment, the transfer cassette of the method may further comprise a third non-identical recombination site bounded by the second selectable marker protein-coding sequence and the at least one second expression cassette of interest.

In another embodiment, the method may further comprise between steps (b) and (c), identifying a transgenic plant of step (b), wherein the transgenic plant has desirable levels of gene expression for the at least one first expression cassette of interest.

In another embodiment, the non-identical recombination sites of the method are selected from the group consisting of FRT1 (SEQ ID NO:50), FRT5 (SEQ ID NO:51), FRT6 (SEQ ID NO:52), FRT12 (SEQ ID NO:53) and FRT87 (SEQ ID NO:54).

In another embodiment, the soybean cell of step (a) is transformed with the isolated nucleic acid fragment by gene bombardment and the transfer cassette of step (c) is introduced into the soybean cell by gene bombardment.

In another embodiment, providing of said recombinase in step (d) comprises transiently expressing within said soybean cell an expression cassette comprising a polynucleotide encoding said recombinase. The recombinase may be FLP. The FLP recombinase may be synthesized using maize preferred codons.

In another embodiment, the first selectable marker protein-coding sequence of the method encodes a protein selected from the group consisting of a hygromycin phosphotransferase, a sulfonylurea-tolerant acetolactate synthase, and a sulfonylurea-tolerant acetolactate synthase that has an amino acid sequence comprising SEQ ID NO:63 or SEQ ID NO:64.

In another embodiment, the target site of the method comprises a promoter operably linked to the first selectable marker protein-coding sequence, and the first recombination site is between the promoter and the first selectable marker protein-coding sequence.

In another embodiment, a soybean cell, plant or seed having stably incorporated in its genome a transfer cassette comprising at least three non-identical recombination sites, where the transfer cassette comprises a polynucleotide encoding a selectable marker protein-coding sequence bounded by a first recombination site and a second non-identical recombination site, wherein the transfer cassette further comprises a third non-identical recombination site bounded by the selectable marker protein-coding sequence and the second non-identical recombination site, wherein the transfer cassette further comprises at least one expression cassette of interest, wherein the at least one expression cassette of interest is bounded by the third non-identical recombination site and the second non-identical recombination site. The non-identical FRT recombination sites may be selected from the group consisting of FRT1 (SEQ ID NO:50), FRT5 (SEQ ID NO:51), FRT6 (SEQ ID NO:52), FRT12 (SEQ ID NO:53) and FRT87 (SEQ ID NO:54). The transfer cassette ma be genetically linked to a chromosomal region comprising a sequence selected from the group consisting of SEQ ID NO:55, SEQ ID NO:56, SEQ ID NO:57, SEQ ID NO:58, SEQ ID NO:59, SEQ ID NO:60, SEQ ID NO:61 and SEQ ID NO:62.

In another embodiment, a method for stacking of multiple expression cassettes of interest into a specific chromosomal site in a soybean genome, said method comprising: (a) obtaining a transgenic soybean cell comprising a target site, wherein said target site comprises a first selectable marker protein-coding sequence, wherein the first selectable marker protein-coding sequence is bounded by a first recombination site and a second non-identical recombination site; (b) introducing into the transgenic soybean cell of step (a) a transfer cassette, wherein said transfer cassette comprises a second selectable marker protein-coding sequence, wherein the second selectable marker protein-coding sequence is bounded by the first recombination site and the second non-identical recombination site, and further wherein the transfer cassette further comprises at least one expression cassette of interest, wherein the at least one expression cassette of interest is bounded by the second selectable marker protein-coding sequence and the second non-identical recombination site; and (c) providing a recombinase that recognizes and implements recombination at the non-identical recombination sites. The transfer cassette may further comprise a third non-identical recombination site bounded by the second selectable marker gene and the at least one expression cassette of interest. The non-identical FRT recombination sites may be selected from the group consisting of FRT1 (SEQ ID NO:50), FRT5 (SEQ ID NO:51), FRT6 (SEQ ID NO:52), FRT12 (SEQ ID NO:53) and FRT87 (SEQ ID NO:54). The transfer cassette may be genetically linked to a chromosomal region comprising a sequence selected from the group consisting of SEQ ID NO:55, SEQ ID NO:56, SEQ ID NO:57, SEQ ID NO:58, SEQ ID NO:59, SEQ ID NO:60, SEQ ID NO:61 and SEQ ID NO:62.

In another embodiment, a method for creating a transgenic soybean cell comprising a target site suitable for stacking of multiple expression cassettes of interest into a specific chromosomal site in a soybean genome, said method comprising transforming a soybean cell with an isolated nucleic acid fragment comprising at least one first expression cassette of interest adjacent to a target site, wherein said target site comprises a selectable marker protein-coding sequence, wherein the selectable marker protein-coding sequence is bounded by a first recombination site and a second non-identical recombination site. The non-identical recombination sites may be selected from the group consisting of FRT1 (SEQ ID NO:50), FRT5 (SEQ ID NO:51), FRT6 (SEQ ID NO:52), FRT12 (SEQ ID NO:53) and FRT87 (SEQ ID NO:54).

In another embodiment, a soybean cell, plant or seed having stably incorporated in its genome an isolated nucleic acid fragment comprising at least one first expression cassette of interest adjacent to a target site, wherein said target site comprises a selectable marker protein-coding sequence, wherein the selectable marker protein-coding sequence is bounded by a first recombination site and a second non-identical recombination site. The non-identical recombination sites may be selected from the group consisting of FRT1 (SEQ ID NO:50), FRT5 (SEQ ID N0:51), FRT6 (SEQ ID NO:52), FRT12 (SEQ ID NO:53) and FRT87 (SEQ ID NO:54).

In another embodiment, a soybean cell, plant or seed having stably incorporated in its genome an isolated nucleic acid fragment comprising a target site, wherein said target site comprises a promoter operably linked to a selectable marker protein-coding sequence, wherein the selectable marker protein-coding sequence is bounded by a first recombination site and a second non-identical recombination site, further wherein the first recombination site is between the promoter and the selectable marker protein-coding sequence. The target site may further comprise at least one additional non-identical recombination site, wherein the at least one additional non-identical recombination site is bounded by the selectable marker protein-coding sequence and the second non-identical recombination site. The non-identical recombination sites may be selected from the group consisting of FRT1 (SEQ ID NO:50), FRT5 (SEQ ID NO:51), FRT6 (SEQ ID NO:52), FRT12 (SEQ ID NO:53) and FRT87 (SEQ ID NO:54).

BRIEF DESCRIPTION OF THE DRAWINGS AND SEQUENCES

The invention can be more fully understood from the following detailed description, the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

SEQ ID NO:1 is the DNA sequence comprising the 4544 bp (base pair) target DNA fragment QC288A. Sequence 109-594 is a synthetic constitutive promoter SCP1. Sequence 601-673 is the OMEGA 5' Un-Translated Region (UTR). Sequence 681-728 is a FLP recombinase recognition site FRT1. Sequence 738-1763 is the hygromycin phosphotransferase (hpt) gene coding region. Sequence 1772-2052 is the nopaline synthase (NOS) terminator. Sequence 2081-3416 is the *Arabidopsis* ubiquitin 10 gene promoter AT-UBIQ10 PRO including a 5' UTR intron sequence 3112-3415. Sequence 3435-4130 is a yellow fluorescent reporter gene ZS-YELLOW1 N1 (YFP) coding region. Sequence 4136-4402 is another NOS terminator. Sequence 4437-4484 is a FLP recombinase recognition site FRT87. See the map of QC288 in FIG. 2A.

SEQ ID NO:2 is the 7058 bp complete sequence of the target construct QC288 from which SEQ ID NO:1 was isolated as a 4544 bp DNA fragment QC288A by AscI digestion.

SEQ ID NO:3 is the 8533 bp complete sequence of the donor construct QC329. Sequence 1-48 is a FLP recombinase recognition site FRT1. Sequence 68-2038 is a soybean acetolactate synthase (als) gene coding region encoding a mutant ALS enzyme insensitive to sulfonylurea herbicides. Sequence 2055-2365 is the potato proteinase II inhibitor gene (PINII) terminator. Sequence 2400-4347 is the soybean ubiquitin gene promoter including a 5' UTR intron 3816-4347. Sequence 4350-5039 is a cyan fluorescent reporter gene AM-CYAN1 (CFP) coding region. Sequence 5045-5311 is a NOS terminator. Sequence 5346-5393 is a FLP recombinase recognition site FRT87. See the map of QC329 in FIG. 2B.

SEQ ID NO:4 is the 6133 bp sequence of the predicted product DNA QC288A329 of RMCE (recombinase mediated cassette exchange) between QC288A and QC329. The sequence between the FRT1 and FRT87 sites of QC288A is replaced by the sequence between the FRT1 and FRT87 sites of QC329. See the predicted map of QC288A329 in FIG. 3A.

SEQ ID NO:5 is the 4860 bp complete sequence of the FLP recombinase expression construct QC292. Sequence 38-523 is the constitutive promoter SCP1. Sequence 530-602 is the OMEGA 5' UTR. Sequence 617-1888 is a codon optimized FLP recombinase coding region. Sequence 1895-2204 is the PINII terminator.

SEQ ID NO:6 is an oligonucleotide that can anneal to SEQ ID NO:7 to make FRT1 DNA duplex. Restriction enzyme recognition sites are engineered on both sites of the 48 bp FRT1 sequence for subsequent cloning.

SEQ ID NO:7 is an oligonucleotide complementary to SEQ ID NO:6.

SEQ ID NO:8 is a primer, HSP-F1, specific to a quantitative PCR (qPCR) endogenous control heat shock protein (HSP) gene.

SEQ ID NO:9 is a primer, HSP-R1, specific to a qPCR endogenous control heat shock protein (HSP) gene.

SEQ ID NO:10 is a VIC labeled MGB fluorescent probe, VIC-MGB, specific to a qPCR endogenous control heat shock protein (HSP) gene.

SEQ ID NO:11 is a primer, 35S-277F, specific to the SCP1 promoter.

SEQ ID NO:12 is a primer, 35S-345R, specific to the SCP1 promoter.

SEQ ID NO:13 is a FAM labeled BHQ1 fluorescent probe 35S-399T specific to the SCP1 promoter for qPCR analysis.

SEQ ID NO:14 is a primer, Hygro-591F, specific to the hpt gene coding region.

SEQ ID NO:15 is a primer, Hygro-659R, specific to the hpt gene coding region.

SEQ ID NO:16 is a FAM labeled BHQ1 fluorescent probe, Hygro-612T, specific to the hpt gene coding region.

SEQ ID NO:17 is a primer, Yfp-67F, specific to the YFP gene coding region. SEQ ID NO:18 is a primer, Yfp-130R, specific to the YFP gene coding region.

SEQ ID NO:19 is a FAM labeled BHQ1 fluorescent probe, Yfp-88T, specific to the YFP gene coding region.

SEQ ID NO:20 is a primer, Cfp-F, specific to the CFP gene coding region.

SEQ ID NO:21 is a primer, Cfp-R, specific to the CFP gene coding region.

SEQ ID NO:22 is a FAM labeled MGB fluorescent probe, Cfp-T, specific to the CFP gene coding region.

SEQ ID NO:23 is a primer, Scp1-S, specific to the SCP1 promoter.

SEQ ID NO:24 is a primer, Hygro-A, specific to the hpt gene coding region.

SEQ ID NO:25 is a primer, Yfp-3, specific to the YFP gene coding region.

SEQ ID NO:26 is a primer, Frt87-A, specific to a part of the FRT87 site and its downstream sequence in DNA constructs QC288 and QC329.

SEQ ID NO:27 is a primer, Als-3, specific to the als gene coding region.

SEQ ID NO:28 is a primer, Hpt-1, specific to the hpt gene coding region.

SEQ ID NO:29 is a primer, Hygro-2, specific to the hpt gene coding region.

SEQ ID NO:30 is a primer, Yfp-1, specific to the YFP gene coding region.

SEQ ID NO:31 is a primer, Yfp-2, specific to the YFP gene coding region.

SEQ ID NO:32 is a primer, Cyan-1, specific to the CFP gene coding region.

SEQ ID NO:33 is a primer, Cyan-2, specific to the CFP gene coding region.

SEQ ID NO:34 is a primer, PinII-100R, specific to the PINII terminator.

SEQ ID NO:35 is a primer, PinII-2F, specific to the PINII terminator.

SEQ ID NO:36 is a primer, Vec81, specific to the vector backbone of constructs QC288, QC292, and QC329.

SEQ ID NO:37 is a primer, Flp-A, specific to the FLP gene coding region.

SEQ ID NO:38 is an oligonucleotide that can anneal to SEQ ID NO:39 to make FRT12 DNA duplex. Restriction enzyme recognition sites are engineered on both sites of the 48 bp FRT12 sequence for subsequent cloning.

SEQ ID NO:39 is an oligonucleotide complementary to SEQ ID NO:38.

SEQ ID NO:40 is an oligonucleotide that can anneal to SEQ ID NO:41 to make FRT6 DNA duplex. Restriction enzyme recognition sites are engineered on both sites of the 48 bp FRT6 sequence for subsequent cloning.

SEQ ID NO:41 is an oligonucleotide complementary to SEQ ID NO:40.

SEQ ID NO:42 is the DNA sequence comprising a 5490 bp basic donor construct QC422 for transgene stacking. Sequence 1-48 is a FLP recombinase recognition site FRT1. Sequence 68-2038 is the soybean acetolactate synthase (als) gene coding region encoding a mutant ALS enzyme insensitive to sulfonylurea herbicides. Sequence 2055-2365 is the potato proteinase II inhibitor gene (PINII) terminator. Sequence 2422-2469 is a FLP recombinase recognition site FRT12. Sequence 2510-2557 is another FLP recombinase recognition site FRT87. Multiple restriction enzyme recognition sites are engineered between the FRT12 and FRT87 sites for the insertion of trait genes. See the map of QC422 in FIG. 11A.

SEQ ID NO:43 is the DNA sequence comprising a 4372 bp basic donor construct QC429 for transgene stacking. Sequence 1-48 is a FLP recombinase recognition site FRT1. Sequence 58-1083 is the hygromycin phosphotransferase (hpt) gene coding region. Sequence 1092-1372 is the nopaline synthase (NOS) terminator. Sequence 1400-1447 is a FLP recombinase recognition site FRT12. Multiple restriction enzyme recognition sites are engineered upstream of the FRT12 site for the insertion of trait genes. See the map of QC429 in FIG. 11B.

SEQ ID NO:44 is the DNA sequence comprising a 4444 bp basic donor construct QC459 for transgene stacking. Sequence 1-48 is a FLP recombinase recognition site FRT1. Sequence 58-1083 is the hygromycin phosphotransferase (hpt) gene coding region. Sequence 1092-1372 is the nopaline synthase (NOS) terminator. Sequence 1400-1447 is a FLP recombinase recognition site FRT6. Sequence 1472-1519 is another FLP recombinase recognition site FRT87. Multiple restriction enzyme recognition sites are engineered between the FRT6 and FRT87 sites for the insertion of trait genes. See the map of QC459 in FIG. 13A.

SEQ ID NO:45 is the DNA sequence comprising a 5394 bp basic donor construct QC428 for transgene stacking. Sequence 1-48 is a FLP recombinase recognition site FRT1. Sequence 68-2038 is the soybean acetolactate synthase (als) gene coding region encoding a mutant ALS enzyme insensitive to sulfonylurea herbicides. Sequence 2055-2365 is the potato proteinase II inhibitor gene (PINII) terminator. Sequence 2422-2469 is a FLP recombinase recognition site FRT6. Multiple restriction enzyme recognition sites are engineered upstream of the FRT6 site for the insertion of trait genes. See the map of QC428 in FIG. 13B.

SEQ ID NO:46 is the predicted QC288A422 DNA resulted from a RMCE between QC288A and QC422. Sequence 109-594 is a synthetic constitutive promoter SCP1. Sequence 601-673 is the OMEGA 5' Un-Translated Region (UTR). Sequence 681-728 is a FLP recombinase recognition site FRT1. Sequence 748-2178 is the soybean acetolactate synthase (als) gene coding region encoding a mutant ALS enzyme insensitive to sulfonylurea herbicides. Sequence 2735-3045 is the potato proteinase II inhibitor gene (PINII) terminator. Sequence 3102-3149 is a FLP recombinase recognition site FRT12. Sequence 3190-3237 is a FLP recombinase recognition site FRT87. The sequences of group 1 transgenes which can be any trait genes of choice are not included.

SEQ ID NO:47 is the predicted QC288A422-429 DNA resulted from a RMCE between QC288A422 and QC429. Sequence 109-594 is a synthetic constitutive promoter SCP1. Sequence 601-673 is the OMEGA 5' Un-Translated Region (UTR). Sequence 681-728 is a FLP recombinase recognition site FRT1. Sequence 738-1763 is the hygromycin phosphotransferase (hpt) gene coding region. Sequence 1772-2052 is the nopaline synthase (NOS) terminator. Sequence 2080-2127 is a FLP recombinase recognition site FRT12. Sequence 2168-2215 is a FLP recombinase recognition site FRT87. The sequences of group 1 and group 2 transgenes which can be any trait genes of choice are not included.

SEQ ID NO:48 is the predicted QC288A422-459 DNA resulted from a RMCE between QC288A422 and QC459. Sequence 109-594 is a synthetic constitutive promoter SCP1. Sequence 601-673 is the OMEGA 5' Un-Translated Region (UTR). Sequence 681-728 is a FLP recombinase recognition site FRT1. Sequence 738-1763 is the hygromycin phosphotransferase (hpt) gene coding region. Sequence 1772-2052 is the nopaline synthase (NOS) terminator. Sequence 2080-2127 is a FLP recombinase recognition site FRT6. Sequence 2152-2199 is a FLP recombinase recognition site FRT12. Sequence 2240-2287 is a FLP recombinase recognition site FRT87. The sequences of group 1 and group 2 transgenes which can be any trait genes of choice are not included.

SEQ ID NO:49 is the predicted QC288A422-459-460 DNA resulted from a RMCE between QC288A422-459 and QC428. Sequence 109-594 is a synthetic constitutive promoter SCP1. Sequence 601-673 is the OMEGA 5' Un-Translated Region (UTR). Sequence 681-728 is a FLP recombinase recognition site FRT1. Sequence 748-2178 is the soybean acetolactate synthase (als) gene coding region encoding a mutant ALS enzyme insensitive to sulfonylurea herbicides. Sequence 2735-3045 is the potato proteinase II inhibitor gene (PINII) terminator. Sequence 3102-3149 is a FLP recombinase recognition site FRT6. Sequence 3174-3221 is a FLP recombinase recognition site FRT12. Sequence 3262-3309 is a FLP recombinase recognition site FRT87. The sequences of group 1, group 2, and group 3 transgenes which can be any trait genes of choice are not included.

SEQ ID NO:50 is the nucleotide sequence of the minimal wild-type FRT recombination site, designated FRT1.

SEQ ID NO:51 is the nucleotide sequence of the minimal FRT5 mutant recombination site.

SEQ ID NO:52 is the nucleotide sequence of the minimal FRT6 mutant recombination site.

SEQ ID NO:53 is the nucleotide sequence of the minimal FRT12 mutant recombination site.

SEQ ID NO:54 is the nucleotide sequence of the minimal FRT87 mutant recombination site.

SEQ ID NO:55 is 601 nucleotides of 5' genomic sequence from target line 4729.5.1, also called the "A" line.

SEQ ID NO:56 is 2588 nucleotides of 3' genomic sequence from the target line 4729.1.

SEQ ID NO:57 is 984 nucleotides of 5' genomic sequence from the target line 4729.5.2, also called the "B" line.

SEQ ID NO:58 is 1305 nucleotides of 3' genomic sequence from the target line 4729.5.2.

SEQ ID NO:59 is 452 nucleotides of 5' genomic sequence from the target line 4729.7.1, also called the "N" line.

SEQ ID NO:60 is 377 nucleotides of 3' genomic sequence from the target line 4729.7.1.

SEQ ID NO:61 is 496 nucleotides of 5' genomic sequence from the target line 4730.3.1, also called the "C" line.

SEQ ID NO:62 is 543 nucleotides of 3' genomic sequence from the target line 4730.3.1.

SEQ ID NO:63 is the amino acid sequence of a herbicide-tolerant soybean ALS protein.

SEQ ID NO:64 is the amino acid sequence of a herbicide-tolerant *Arabidopsis* ALS protein.

SEQ ID NO:65 is the nucleotide sequence of the adaptor-specific primer AP1 used to amplify genomic DNA sequence bordering the transgenic region of a target line.

SEQ ID NO:66 is the nucleotide sequence of the QC288A-specific primer, Scp1-A, used to amplify 5' genomic DNA sequence bordering the transgenic region of a target line.

SEQ ID NO:67 is the nucleotide sequence of the QC288A-specific primer, Vec-S1, used to amplify 3' genomic DNA sequence bordering the transgenic region of a target line.

SEQ ID NO:68 is the nucleotide sequence of the adaptor-specific primer AP2 used to amplify genomic DNA sequence bordering the transgenic region of a target line.

SEQ ID NO:69 is the nucleotide sequence of the QC288A-specific primer, Scp1-A4, used to amplify 5' genomic DNA sequence bordering the transgenic region of a target line.

SEQ ID NO:70 is the nucleotide sequence of the QC288A-specific primer, Vec-S2, used to amplify 3' genomic DNA sequence bordering the transgenic region of a target line.

SEQ ID NO:71 is the nucleotide sequence of the 288A-1F primer used for RMCE-specific qPCR.

SEQ ID NO:72 is the nucleotide sequence of the Als-163R primer used for RMCE-specific qPCR.

SEQ ID NO:73 is the nucleotide sequence of the FAM-labeled BHQ1 probe Als-110T.

SEQ ID NO:74 is the nucleotide sequence of the Hygro-116R primer used for Target-specific qPCR.

SEQ ID NO:75 is the nucleotide sequence of the FAM-labeled BHQ1 probe Hygro-79T.

SEQ ID NO:76 is the nucleotide sequence of the 329-1F primer used for donor-specific qPCR.

SEQ ID NO:77 is the nucleotide sequence of the QC292 primer used for qPCR assay of the Flp construct QC292.

SEQ ID NO:78 is the nucleotide sequence of the Flp-A primer used for qPCR assay of the Flp construct QC292.

SEQ ID NO:79 is the nucleotide sequence of the FAM-labeled BHQ1 probe OMEGA5UTR-87T used for qPCR assay of the Flp construct QC292.

SEQ ID NO:80 is the nucleotide sequence of the 5' border sequence-specific sense primer 53-1S1 used for PCR analysis of target line A.

SEQ ID NO:81 is the nucleotide sequence of the 5' border sequence-specific sense primer 70-1S used for PCR analysis of target line B.

SEQ ID NO:82 is the nucleotide sequence of the 5' border sequence-specific sense primer 8H-ScaS1 used for PCR analysis of target line C.

SEQ ID NO:83 is the nucleotide sequence of the common sense primer Cyan-1 used for RMCE 3' border-specific PCR.

SEQ ID NO:84 is the nucleotide sequence of the 3' border sequence-specific antisense primer 53-1A used for PCR analysis of target line A.

SEQ ID NO:85 is the nucleotide sequence of the 3' border sequence-specific antisense primer 70-1A used for PCR analysis of target line B.

SEQ ID NO:86 is the nucleotide sequence of the 3' border sequence-specific antisense primer 8H-VecA used for PCR analysis of target line C.

SEQ ID NO:87 is the nucleotide sequence of ORFSTOP-A which contains stop codons in all open reading frames.

SEQ ID NO:88 is the nucleotide sequence of ORFSTOP-B which contains stop codons in all open reading frames.

SEQ ID NO:89 is the nucleotide sequence of excision product QC288ME.

SEQ ID NO:90 is the nucleotide sequence of vector QC448.

SEQ ID NO:91 is the nucleotide sequence of vector QC449.

SEQ ID NO:92 is the nucleotide sequence of vector QC477.

SEQ ID NO:93 is the nucleotide sequence of vector QC478.

SEQ ID NO:94 is the nucleotide sequence of vector QC479.

SEQ ID NO:95 is the predicted 8910 bp QC288A436A DNA resulting from a RMCE between QC288A329A and QC436. All components derived from QC329 in QC288A329A are exchanged with components from the donor DNA QC436. Sequence 109-594 is a synthetic constitutive promoter SCP1. Sequence 601-673 is the OMEGA 5' Un-Translated Region (UTR). Sequence 681-728 is a FLP recombinase recognition site FRT1. Sequence 748-1763 is the hygromycin phosphotransferase gene (HPT). Sequence 1772-2052 is the nopaline synthase gene terminator (NOS TERM). Sequence 2080-2127 is a FLP recombinase recognition site FRT12. Sequence 2147-4233 is the soybean Kunitz proteinase inhibitor gene promoter (KTI3 PRO). Sequence 4256-5291 is a fragment of soybean FAD2 desaturase gene (FAD2-1 (TR1)). Sequence 5302-6012 is a fragment of soybean thioesterase gene (TE2 (TR4)). Sequence 6022-6481 is a fragment of soybean thioesterase gene (TE2 (TR5)). Sequence 6502-7212 is an inverted copy of the soybean thioesterase gene fragment (TE2 (TR4)). Sequence 7223-8258 is an inverted copy of the soybean FAD2 desaturase gene fragment (FAD2-1 (TR1)). Sequence 8277-8478 is the soybean Kunitz proteinase inhibitor gene terminator (KTI3 TERM). Sequence 8488-8755 is the soybean albumin gene terminator (ALB TERM). Sequence 8803-8850 is a FLP recombinase recognition site FRT87.

SEQ ID NO:96 is the predicted 21727 bp QC288A436A438A DNA resulting from a RMCE between QC288A436A and QC438. All components derived from QC436 in QC288A436A are retained and components from the donor DNA QC438 are stacked. Sequence 109-594 is a synthetic constitutive promoter SCP1. Sequence 601-673 is the OMEGA 5' Un-Translated Region (UTR). Sequence 681-728 is a FLP recombinase recognition site FRT1. Sequence 748-2718 is the mutant soybean acetolactate synthase gene (ALS). Sequence 2735-3045 is the potato proteinase II inhibitor gene terminator (PINII TERM). Sequence 3096-3861 is the pea legumin gene terminator (PS-LEG TERM). Sequence 3866-5443 is the *Yarrowia* diacylglycerol acyltransferase gene (YL-DGAT1). Sequence 5455-6150 is the soybean glycinin 1 gene promoter (GY1 PRO). Sequence 6190-6799 is the soybean beta conglycinin gene promoter (B-CONGLYCININ PRO). Sequence 6815-6919 is the soybean lectin signal peptide (LECTIN SP). Sequence 6920-7123 is the barley high lysine protein gene (BHL8). Sequence 7126-8290 is the French bean phaseolin gene terminator (PHASEOLIN TERM). Sequence 8322-9349 is the soybean albumin gene promoter (ALB PRO). Sequence 9352-9516 is the soybean ribulose-1,5-bisphosphate carboxylase small subunit transit peptide (SSU TP). Sequence 9517-10422 is the *Corynebacterium glutamicum* dihydrodipicolinate synthetase gene (CORYNE DAP A). Sequence 10432-10956 is a soybean MYB2 gene terminator (MYB2 TERM). Sequence 10974-11976 is the *Arabidopsis* ubiquitin gene promoter (UBIQ10 PRO). Sequence 11977-12280 is an intron of the *Arabidopsis* ubiquitin gene promoter (AT-UBQ10 INTRON). Sequence 12298-12462 is the soybean ribulose-1,5-bisphosphate carboxylase small subunit transit peptide (SSU TP). Sequence 12463-13644 is a soybean cysteine synthase gene fragment (CGS (TR1)). Sequence 13647-14811 is the French bean phaseolin gene terminator (PHASEOLIN TERM). Sequence 14897-14944 is a FLP recombinase recognition site FRT12. Sequence 14964-17050 is the soybean Kunitz proteinase inhibitor gene promoter (KTI3 PRO). Sequence 17073-18108 is a fragment of soybean FAD2 desaturase gene (FAD2-1 (TR1)). Sequence 18119-18829 is a fragment of soybean thioesterase gene (TE2 (TR4)). Sequence 18839-19298 is a fragment of soybean thioesterase gene (TE2 (TR5)). Sequence 19319-20029 is an inverted copy of the soybean thioesterase gene fragment (TE2 (TR4)). Sequence 20040-21075 is an inverted copy of the soybean FAD2 desaturase gene fragment (FAD2-1 (TR1)). Sequence 21094-21295 is the soybean Kunitz proteinase inhibitor gene terminator (KTI3 TERM). Sequence 21305-21572 is the soybean albumin gene terminator (ALB TERM). Sequence 21620-21667 is a FLP recombinase recognition site FRT87.

FIG. 1A-1E are schematic descriptions of DNA constructs, relative PCR primer and Southern probe positions. FIG. 1A: Target DNA fragment QC288A contains a constitutive promoter scp1 driving the hpt gene for transformation selection. A FRT1 site (solid triangle) is placed between the scp1 promoter and the hpt coding sequence, a FRT87 (open triangle) site is placed at the 3' end. A fluorescent reporter gene yfp driven by an *Arabidopsis* ubiquitin gene promoter ubiq10 is included between the two FRT sites. FIG. 1B: Donor construct QC329 contains an identical pair of FRT1-FRT87 sites flanking a promoter-less mutated soybean acetolactate synthase (als) gene, which can give chlorsulfuron resistance if expressed, and a cyan florescent reporter gene cfp driven by a soybean ubiquitin promoter ubq. If RMCE happens between the target and donor DNA, the als gene will be linked to the scp1 promoter in the target locus to be expressed and only RMCE events can be selected by chlorsulfuron resistance. FIG. 1C: RMCE product DNA QC288A329 has the same structure as the target DNA QC288A described in FIG. 1A except that all the components between the FRT1 and FRT87 sites of QC288A are replaced by the components between the FRT1 and FRT87 sites of the donor DNA QC329 described in FIG. 1B. FIG. 1D: FLP construct QC292 contains a constitutive scp1 promoter to drive the flp gene expression to make the FLP recombinase needed for RMCE. FIG. 1E: A RMCE PCR positive control construct QC165 is unrelated to RMCE but contains a scp1:als cassette that is similar to the scp1-FRT1:als cassette in the RMCE DNA QC288A329. Construct-specific PCR primers and expected PCR product sizes, Southern probes and restriction enzyme recognition sites are depicted.

FIG. 3A-3D shows the maps of predicted RMCE DNA QC288A329, FRT1 site SSI DNA QC288A329FRT1, FRT87 site SSI DNA QC288A329FRT87, and excision product QC288ME.

FIG. 4A-4E show PCR detection and confirmation of RMCE. FIG. 4A-4D: Seven putative RMCE events at somatic embryo stage were analyzed by PCR with four sets of primers specific to the target QC288A, RMCE QC288A329, donor QC329, and FLP QC292 DNA, respectively. Plasmid DNA QC288, QC329, QC292, and QC165 in place of QC288A329, were included as positive controls. The wt and No DNA lanes are wild type and no template negative controls. Positions of the primers and sizes of expected PCR products are depicted in FIG. 1. Three events A-1, B-2, and N-1 were false events having only the QC288A-specific band. A faint QC329-specific band detected in event M-1 suggested that M-1 might as a chimeric event contain randomly integrated QC329 DNA in some cells. QC288A329-specific band was detected in three events M-2, M-3, and B-1. No QC288A-specific band was detected in events M-2 and M-3 suggesting that they were complete RMCE events. A weak QC288A-specific band was detected in event B-1 suggesting that some cells of this event still contain the original QC288A DNA. A faint QC292-specific band was detected in event M-3 suggesting that this event might contain QC292 DNA in some cells. FIG. 4E: The three QC288A329 positive events M-2, M-3, and B-1 were analyzed by PCR with primers Scp1-S (SEQ ID NO:23) and Frt87-A (SEQ ID NO:26) to amplify a 5982 bp band, almost the entire length of predicted QC288A329 transgene. Their parent events M and B containing the QC288A transgene were included as controls since the same primers would amplify a 4393 bp band from QC288A. The expected bands were amplified from all the five events. The wt and No DNA lanes are wild type and no template negative controls.

Figure 5A:
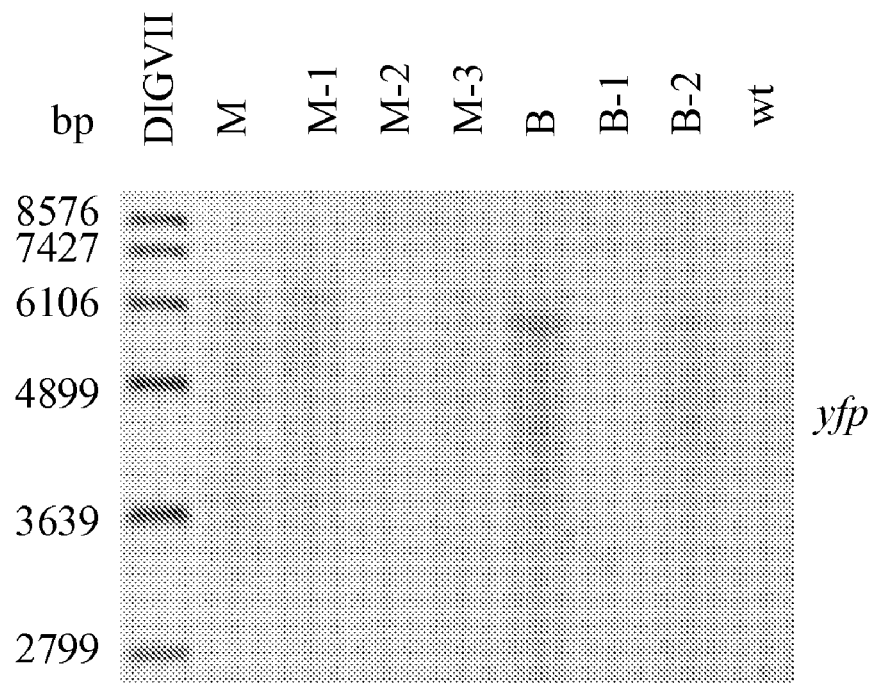
Figure 5B:
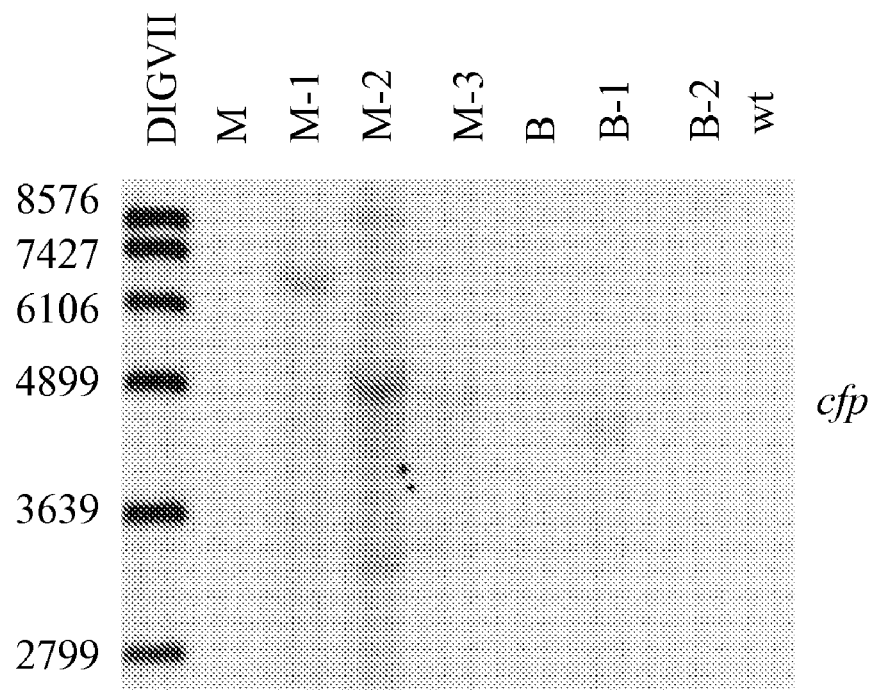

FIG. 5A-5B show Southern confirmation of RMCE. Leaf genomic DNA extracted from the T0 plants of five selected retransformation events M-1, M-2, M-3, B-1, and B-2 were digested with NdeI to make a Southern blot that was sequentially hybridized with yfp, and cfp probes. T1 plants of their target parents M and B and wild type plant were included as controls. FIG. 5A: The yfp probe hybridized to the target events M, B, the random integration event M-1, the SSI event M-3, and the false event B-2. No yfp band was detected in the two RMCE events M-2 and B-1 indicating that the yfp gene had been displaced. FIG. 5B: The cfp probe did not hybridize to the target events M, B, or the false event B-2. As expected, the cfp probe hybridized to the random integration event M-1, the SSI event M-3, and the two RMCE events M-2 and B-1. The cfp bands in the RMCE events M-2 and B-1 are ~1617 bp smaller than the corresponding yfp bands in their target parents M and B as predicted from QC288A and QC288A329 maps (FIG. 1A; FIG. 1C). In addition to the middle band that is ~1617 bp smaller than the corresponding yfp bands in its parent M, the RMCE event M-2 has two extra cfp bands of random sizes.

FIG. 6 shows the analyses of putative RMCE events at the somatic embryo stage. Putative RMCE events from the retransformation of the target lines were selected by their resistance to chlorsulfuron and identified by CFP expression. One CFP negative event A3 was included as negative controls for subsequent analyses. The events were first screened with a PCR using 35S-277F (SEQ ID NO:11) and Als-3 (SEQ ID NO:27) primers common to all three target lines. The events were analyzed by construct-specific qPCR to confirm RMCE and to check donor and Flp integration. Border-specific PCR analyses including RMCE-specific, target-specific, and full length PCR were done using various combinations of the 5' border-specific, 3' border-specific, and transgene-specific primers. Expected sizes of the RMCE 5' end-specific, RMCE 3' end-specific, Target 5' end-specific, Target 3' end-specific, full length Excision, full length Target, and full length RMCE PCR are 1117, 1351, 1036, 732, 1307, 5063, and 6652 bp for target line A events; 967, 1180, 886, 561, 986, 4742, and 6331 bp for target line B events; and 1018, 1294, 937, 675, 1151, 4907, and 6496 bp for target line C events.

Figure 7A:
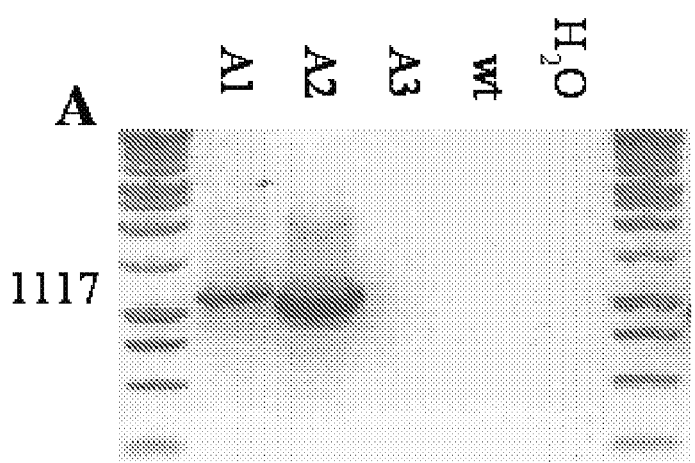
Figure 7B:
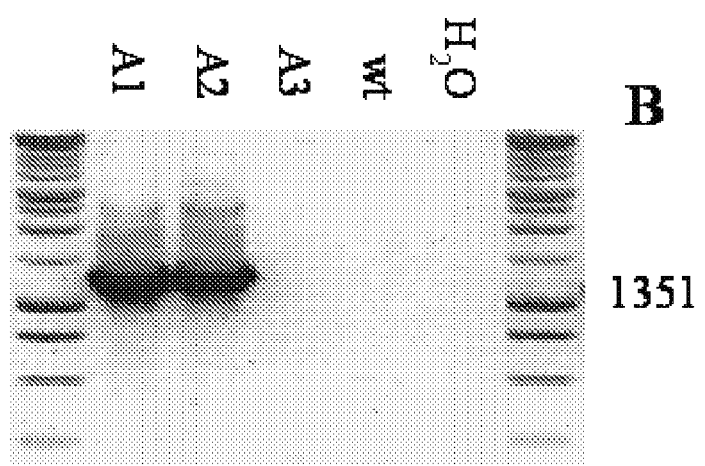
Figure 7C:
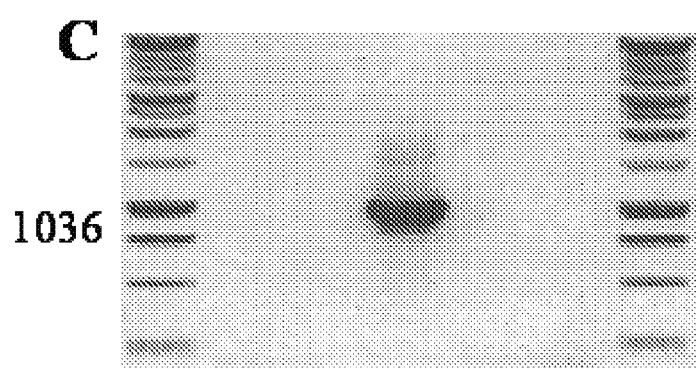
Figure 7D:
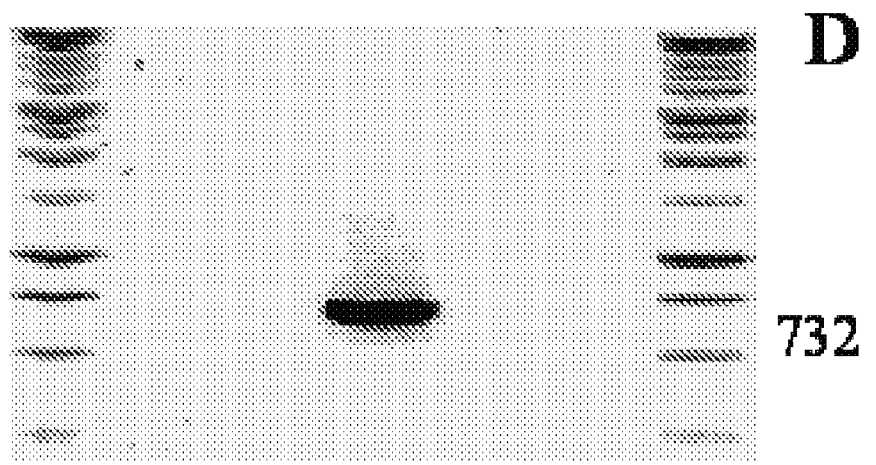
Figure 7E:
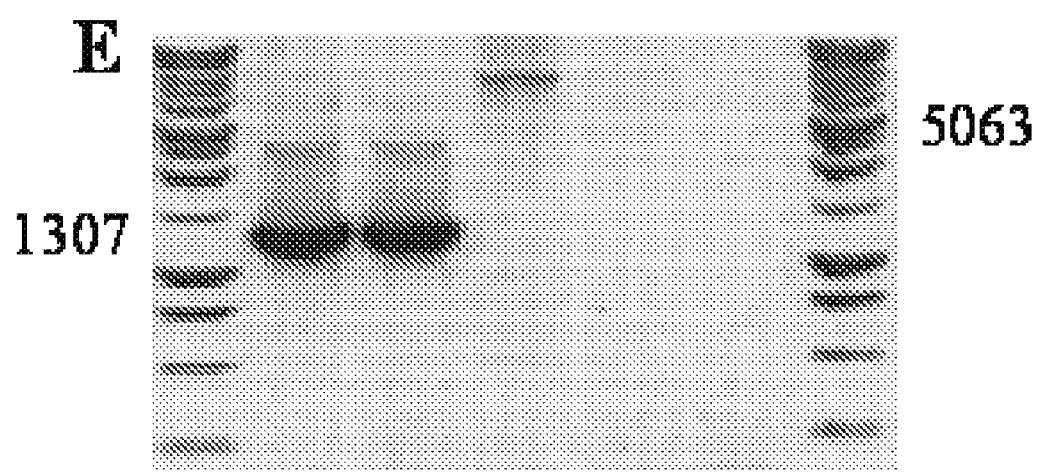

FIG. 7A-7E show border-specific PCR confirmation of RMCE at the somatic embryo stage. Two RMCE events A1 (lane 2), A2 (lane 3) and one escape event A3 (lane 4) derived from target line A were analyzed by PCR using combinations of gene-specific and border-specific primers. Wild-type DNA (wt; lane 5) and no template ($H_2O$; lane 6) negative controls were included. The size of each PCR band is given in by next to the 1 Kb DNA ladder (lanes 1 and 7). FIG. 7A: RMCE 5' border-specific PCR with primers 53-1S1 and Als-3. FIG. 7B: RMCE 3' border-specific PCR with primers 53-1A and Cyan-1. FIG. 7C: Target 5' border-specific PCR with primers 53-1S1 and Hygro-A. FIG. 7D: Target 3' border-specific PCR with primers Yfp-3 and 53-1A. FIG. 7E: Full-length PCR with two border-specific primers 53-1 S1 and 53-1A. The same PCR experiment amplified the 1307 bp excision-specific band for events A1 and A2, the 5063 bp target-specific band for event A3 but not the expected 6652 bp RMCE-specific band in the presence of the smaller excision band for events A1 and A2.

FIG. 8 shows PCR and qPCR analyses of selected T0 plants from various RMCE events. Multiple T0 plants regenerated from three RMCE events derived from two target lines A and C were analyzed with the same construct-specific qPCR and border-specific PCR analyses described in FIG. 6.

Figure 9A:
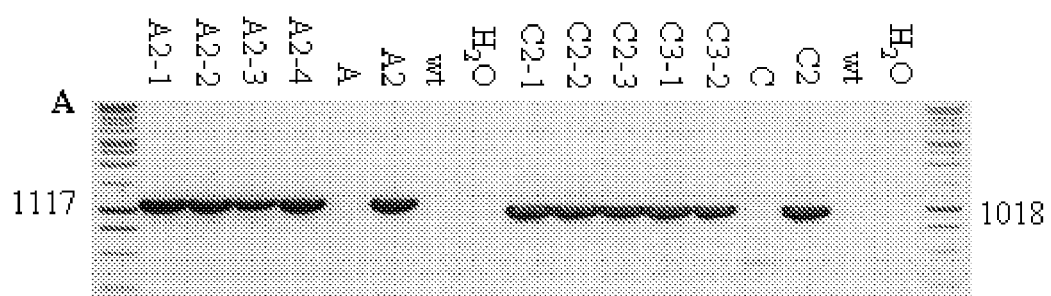
Figure 9B:
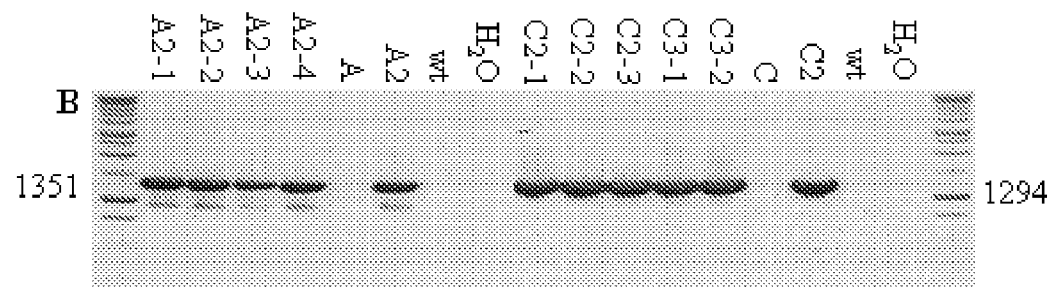
Figure 9C:
Figure 9D:
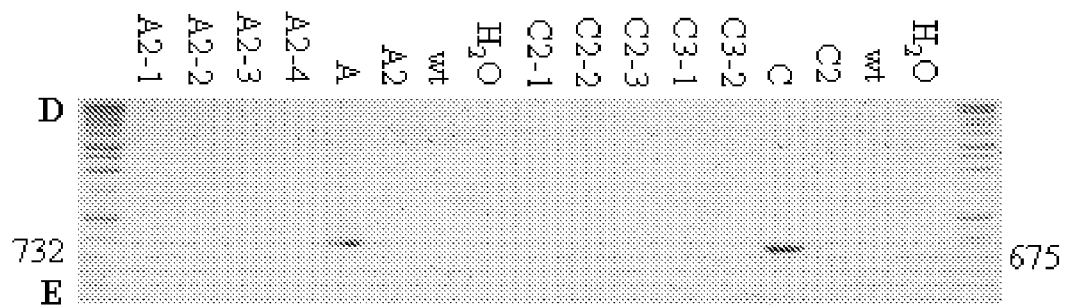
Figure 9E:
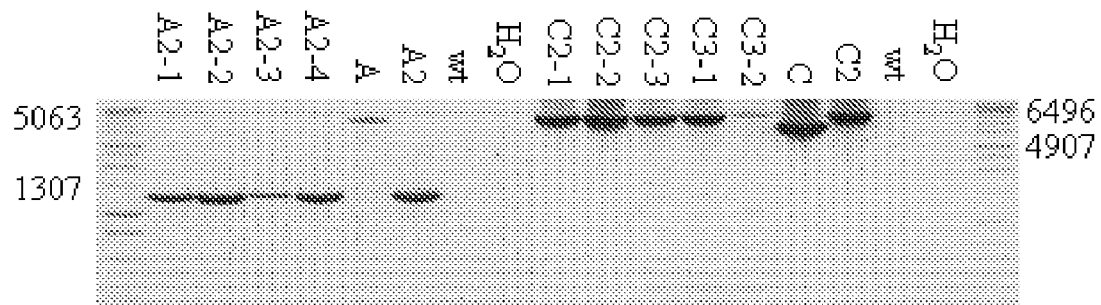

FIG. 9A-9E show border-specific PCR confirmation of RMCE at the T0 plant stage. Four T0 plants regenerated from event A2 were analyzed by border-specific PCR analyses with the same primers used in FIGS. 7A-7E. Five T0 plants regenerated from events C2 and C3 were analyzed by similar border-specific PCR analyses except using 5' border-specific primer 8H-ScaS1 and 3' border-specific 8H-VecA specific to the target line C. Target parent DNA A and C, RMCE events somatic embryo DNA A2 and C2, wild-type (wt) and no template ($H_2O$) were included as controls. The size of each PCR band is given in by next to the 1 Kb DNA ladder. FIG. 9A: RMCE 5' border-specific PCR. FIG. 9B: RMCE 3' border-specific PCR. FIG. 9C: Target 5' border-specific PCR. FIG. 9D: Target 3' border-specific PCR. FIG. 9E: Full length PCR. The PCR failed to amplify the expected 6652 bp RMCE-band for the target line A derived hemizygous RMCE event A2 and T0 plants A2-1, A2-2, A2-3, and A2-4 in the presence of the 1307 bp Excision-specific band. The PCR amplified the 6496 bp RMCE-specific band for target line C derived homologous RMCE events C2, C3 and T0 plants C2-1, C2-2, C2-3, C3-1, and C3-2 in the absence of a small Excision-specific band.

FIG. 10A and FIG. 10B show an alignment of predicted Target, RMCE, and Excision sequences surrounding the recombination sites. FIG. 10A: Sequences surrounding the 5' end recombination site. Excision resulting from the recombination between FRT1 and FRT87 sites could restore either the FRT87 site or the FRT1 site depending on the crossing-over position. FIG. 10B: Sequences surrounding the 3' end recombination site. Sequences originated from the donor are capitalized. Sequences different from the Target sequence in the alignments are underlined. Sequences of the transgene DNA fragments from the border-specific PCR analyses (FIGS. 9A-9E) matched, respectively, the predicted Target, RMCE, or Excision sequences and are thus not shown.

Figure 11A:
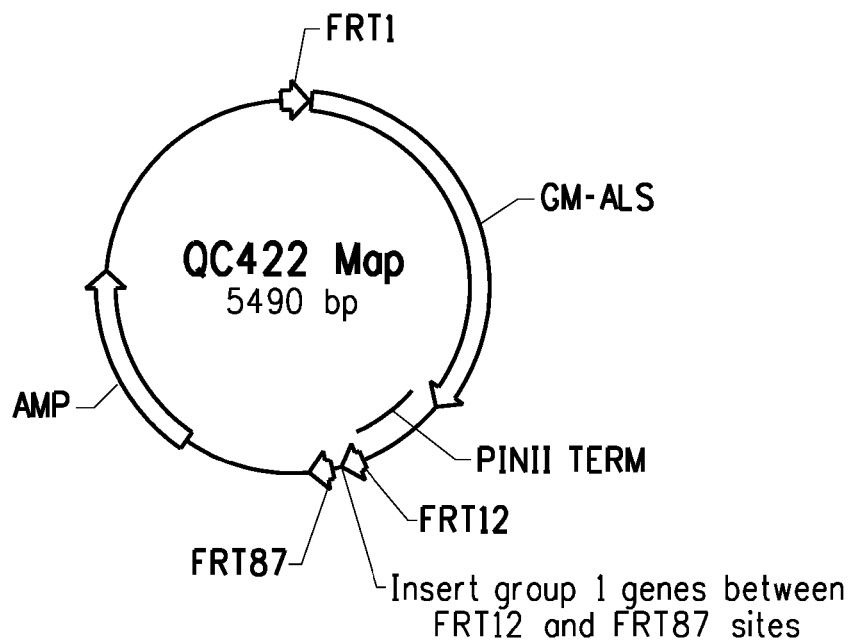
Figure 11B:
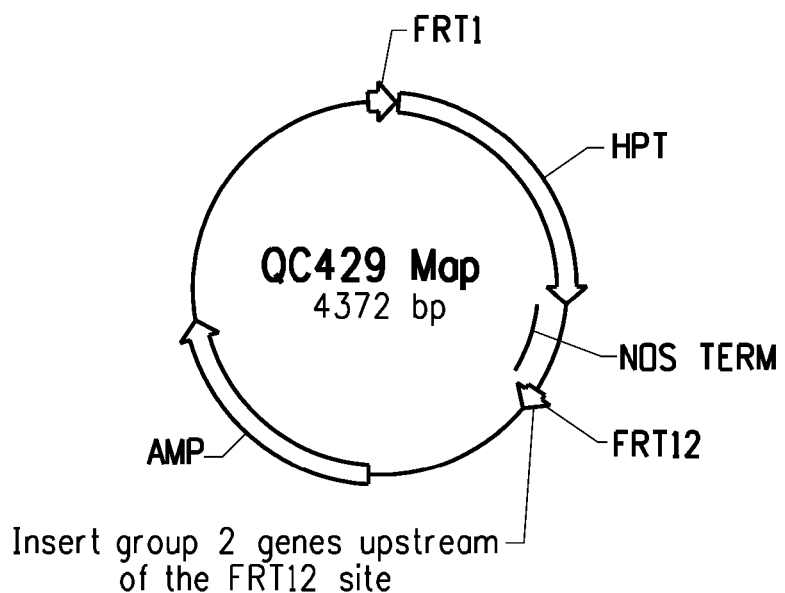

FIG. 11A and FIG. 11B show the maps of the donor DNA construct QC422 which contains three FRT sites designed for the first round of RMCE and the donor DNA construct QC429 which contains two FRT sites designed for the second round of RMCE in the approach to stack two groups of transgenes. The insertion sites of transgene groups are indicated.

Figure 12A:
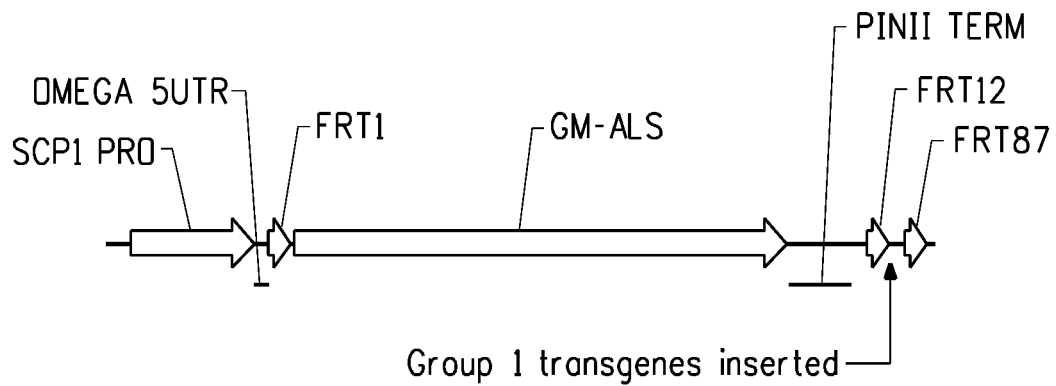
Figure 12B:
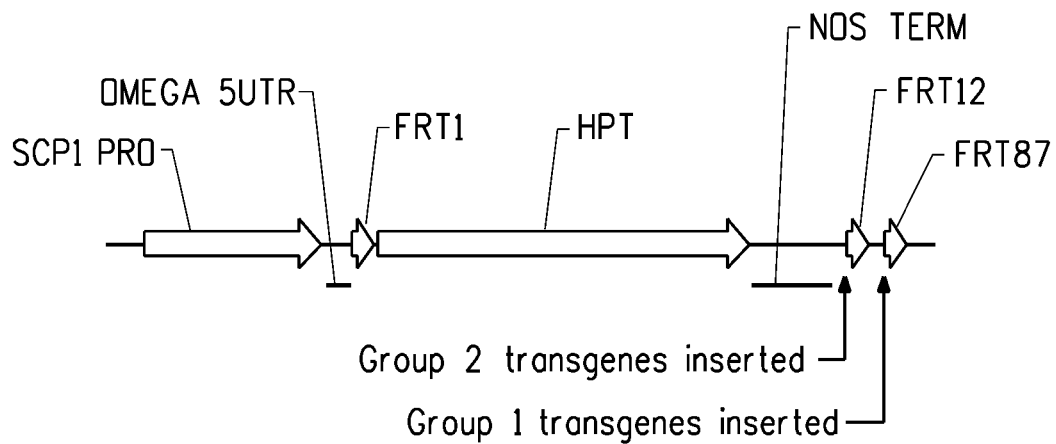

FIG. 12A and FIG. 12B show the maps of predicted first round RMCE DNA QC288A422 and predicted second round RMCE DNA QC288A422-429 in the approach to stack two groups of transgenes. The insertion sites of transgene groups are indicated.

Figure 13A:
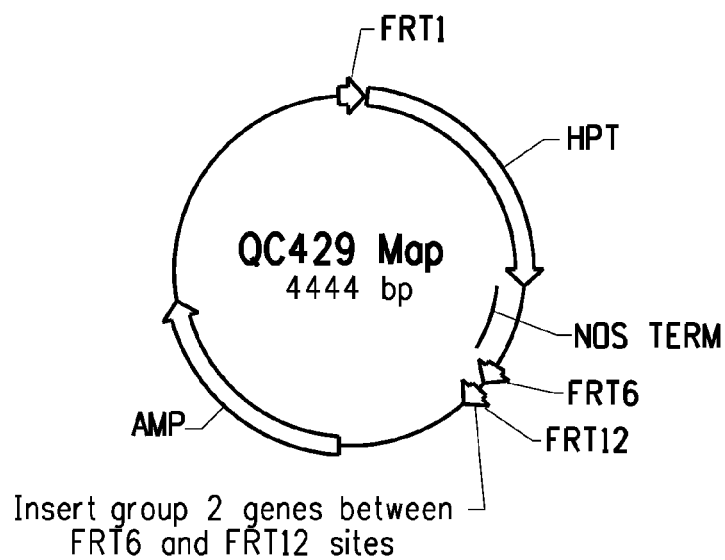
Figure 13B:
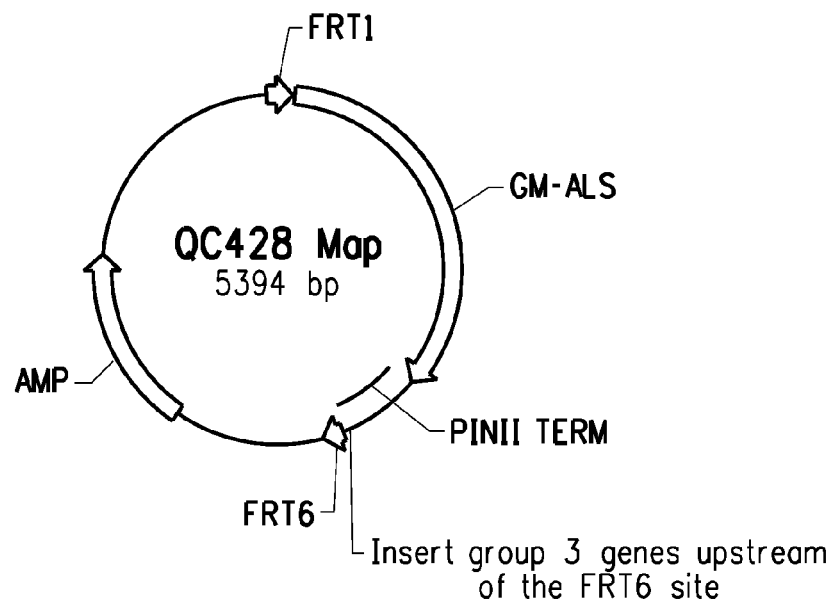

FIG. 13A and FIG. 13B show the maps of the donor DNA construct QC459 which contains three FRT sites designed for the second round of RMCE and the donor DNA construct QC428 which contains two FRT sites designed for the third round of RMCE in the approach to stack three groups of transgenes. The insertion sites of transgene groups are indicated.

Figure 14A:
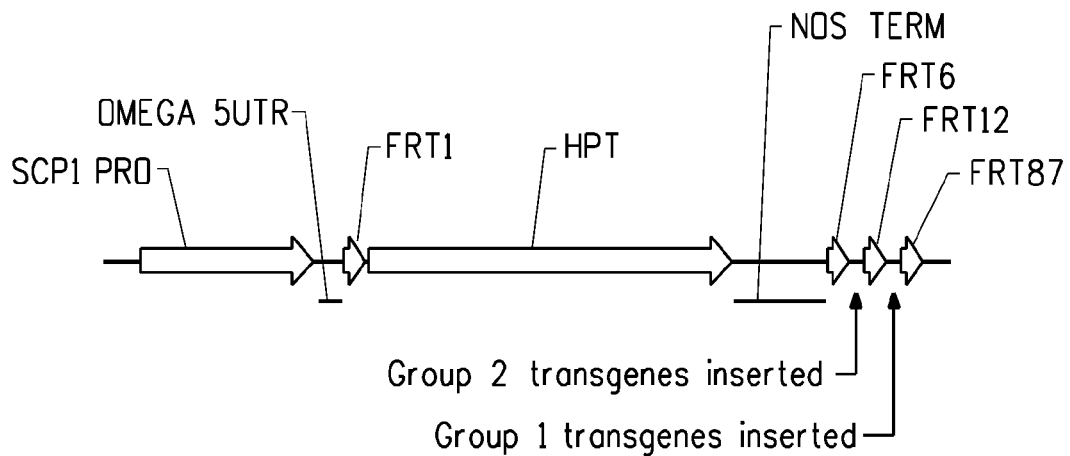
Figure 14B:
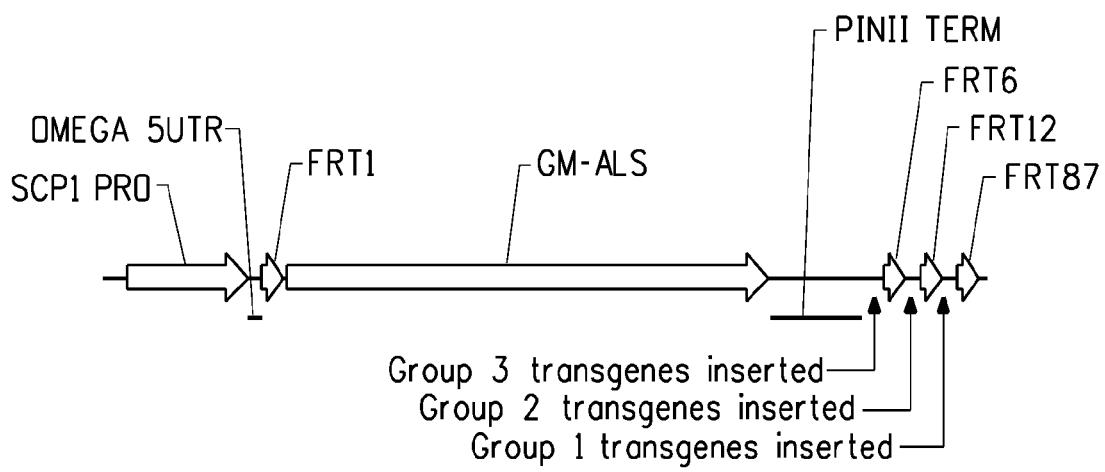

FIG. 14A and FIG. 14B show the maps of predicted second round RMCE DNA QC288A422-459 and predicted third round RMCE DNA QC288A422-459-460 in the approach to stack three groups of transgenes. The insertion sites of transgene groups are indicated.

Figure 15A:
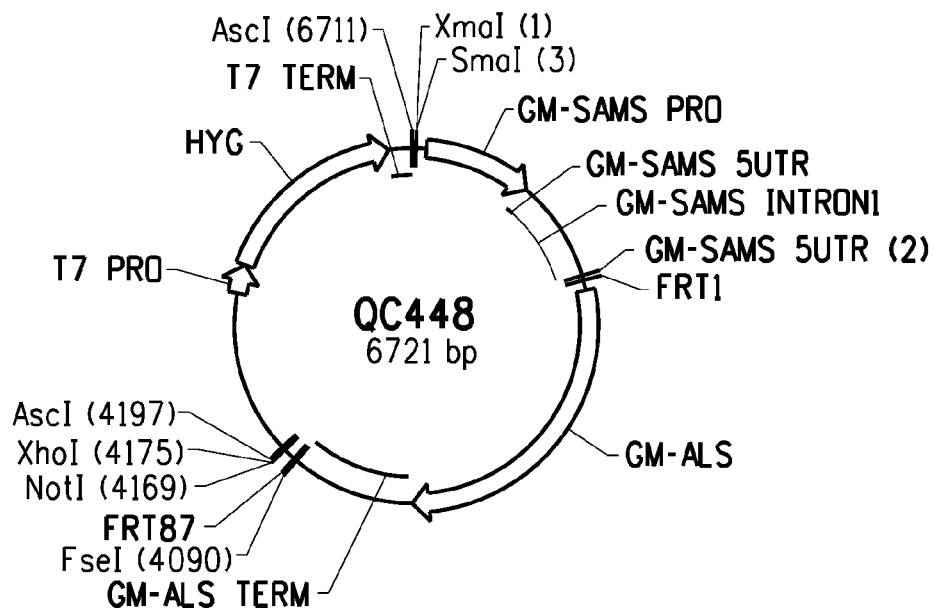
Figure 15B:
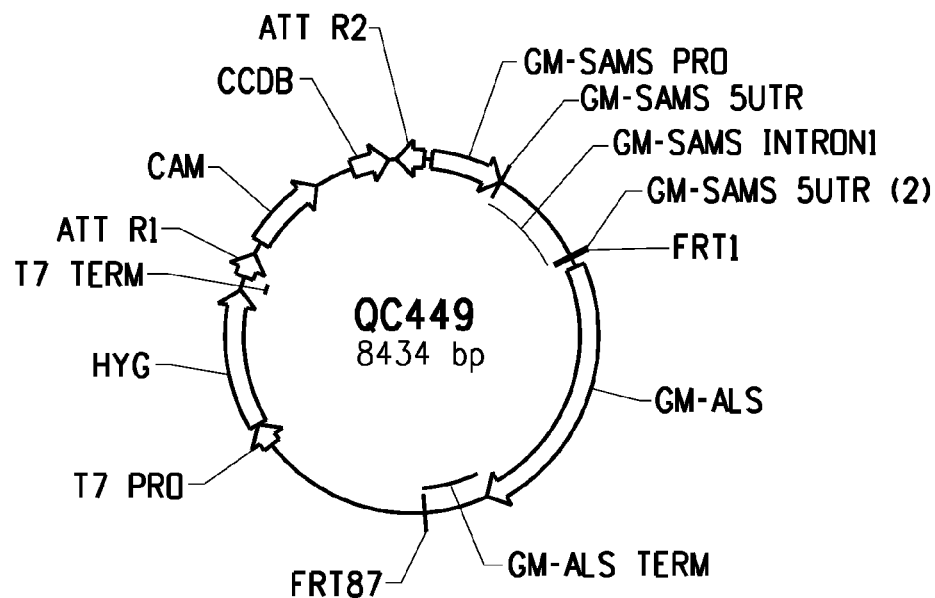
Figure 15C:
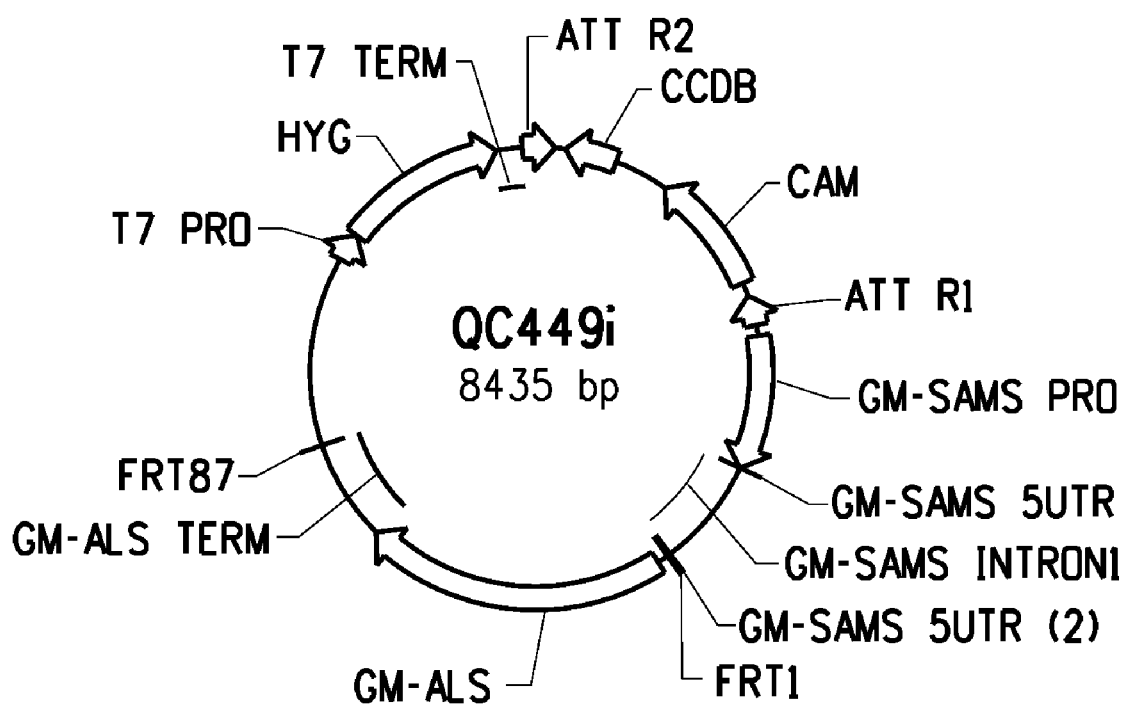

FIG. 15A-15C show vectors QC448 and its Gateway versions QC449 and QC449i that are useful for creation of target sites during development of trait-containing transgenic product lines. Unique cloning sites XmaI, SmaI, FseI, NotI, and XhoI are labeled. The two AscI sites can be used to prepare DNA fragments free of the vector backbone. QC449 and QC449i (inverted) are made by inserting the ATTR1/R2Gateway fragment at the SmaI site of QC448.

FIG. 16A-16E show vectors QC477 and its Gateway versions QC478, QC478i, QC479, QC479i that are useful for creation of target sites during development of trait-containing transgenic product lines. ORFSTOP-A (SEQ ID NO:87) and ORFSTOP-B (SEQ ID NO:88) on each end of the sams:als cassette are different short sequences containing stop codons in all open reading frames. Unique cloning sites XmaI, SmaI, AgeI, PmeI, SpeI, FseI, NotI, and XhoI are labeled. The two AscI sites can be used to prepare DNA fragments free of the vector backbone. The four Gateway versions are created for easy cloning to link trait genes to the sams:als cassette. The Gateway fragment ATTR1/R2 in QC478, 478i (inverted), or Gateway fragment ATTR3/R4 in QC479, 479i (inverted), is inserted at the PmeI site of QC477.

Figure 17A:
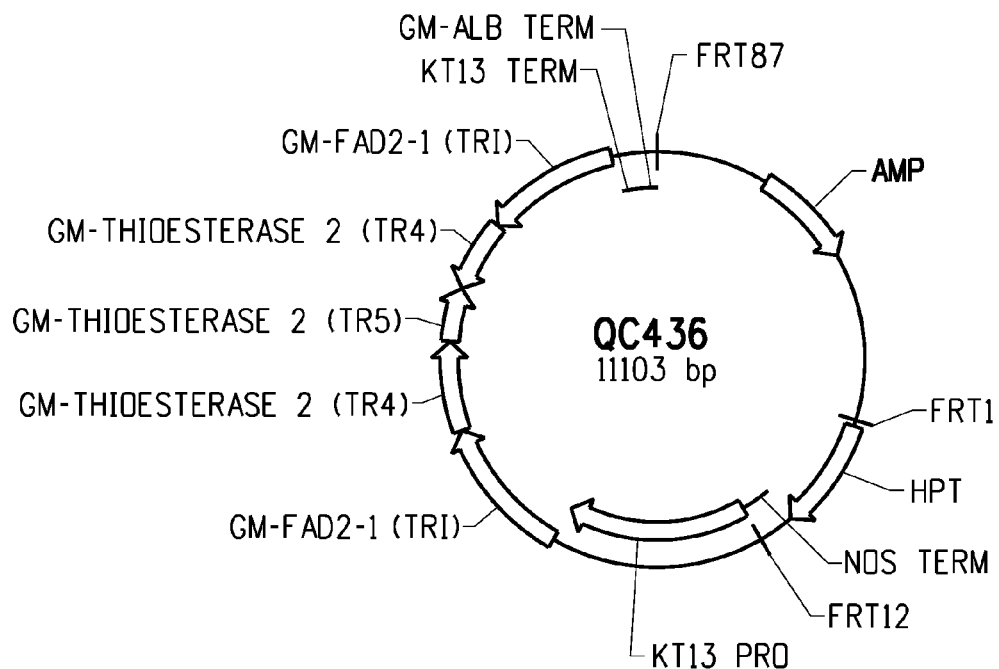
Figure 17B:
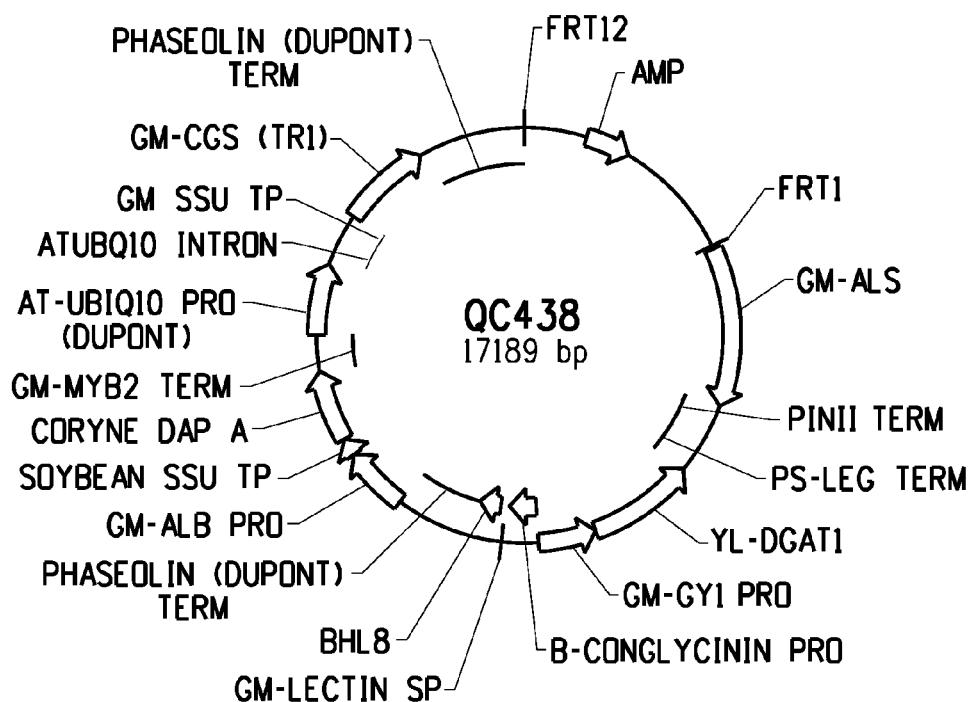
Figure 17C:
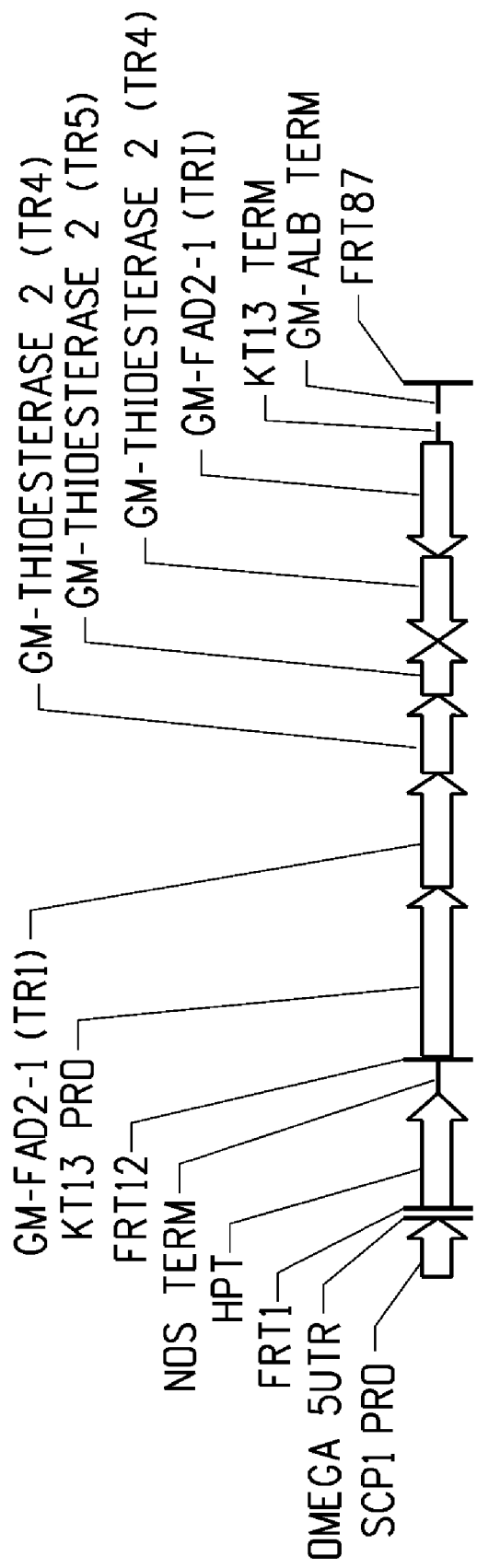

FIG. 17A-17D are schematic descriptions of donor DNA constructs for gene stacking and predicted RMCE products. FIG. 17A: Donor DNA QC436 for the first round of SSI. A third recombination site FRT12 is introduced between the FRT1 and FRT87 sites. The promoter-less selectable marker gene HPT is placed between the FRT1 and FRT12 sites. Inverted repeats of the soybean delta9 desaturase gene fragment (GM-FAD2-1 (TR1)) and thioesterase gene fragment (GM-THIOESTERASE 2 (TR4)) controlled by the common KTI3 promoter are placed between the FRT12 and FRT87 sites. FIG. 17B: Donor DNA QC438 for the second round of SSI. Only two recombination sites FRT1 and FRTa2 are kept. The promoter-less selectable marker gene GM-ALS and several trait genes controlled by various promoters and terminators are placed between the FRT1 and FRT12 sites. FIG. 17C: Predicted QC288A436 DNA of RMCE involving the FRT1 and FRT87 sites between the target QC288A329 DNA (FIG. 1C) and the QC436 donor DNA. All the components between the FRT1 and FRT87 sites of QC288A329 are replaced by the components between the FRT1 and FRT87 sites of the donor DNA QC436. FIG. 17D: Predicted QC288A436A438 DNA of RMCE involving the FRT1 and FRT12 sites between the target QC288A436 DNA (FIG. 17C) and the QC438 donor DNA. The promoter-less HPT gene between the FRT1 and FRT12 sites of QC288A436 is replaced by the components between the FRT1 and FRT12 sites of the donor DNA QC438. All the components between the FRT12 and FRT87 sites of QC288A436 are retained in QC288A436A438.

DETAILED DESCRIPTION OF THE INVENTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

A "target site" comprises a nucleotide sequence flanked by two non-identical recombination sites. A target site provides a "specific chromosomal site" for stacking multiple expression cassettes of interest.

A "transfer cassette" for use with a given target site comprises a nucleotide sequence flanked by the same two non-identical recombination sites present in the corresponding target site. The terms "transfer cassette", "donor cassette" and "targeting cassette" are used interchangeably herein.

A target site and a transfer cassette may each comprise more than two non-identical recombination sites.

A "donor construct" is a recombinant construct that contains a transfer cassette. The terms "donor construct" and "donor vector" are used interchangeably herein.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase I.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/ transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably, and refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

Sequence alignments and percent identity calculations may be determined using a variety of comparison methods designed to detect homologous sequences including, but not limited to, the MEGALIGN® program of the LASER-GENE® bioinformatics computing suite (DNASTAR® Inc., Madison, Wis.). Unless stated otherwise, multiple alignment of the sequences provided herein were performed using the Clustal V method of alignment (Higgins and Sharp (1989) CABIOS. 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 (hereinafter "Sambrook").

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al. (1998) Plant J. 16:651-659; and Gura, (2000) Nature 404:804-808).

"Selection agent" refers to a compound which is toxic to non-transformed plant cells and which kills non-transformed tissues when it is incorporated in the culture medium in an "effective amount", i.e., an amount equal to or greater than the minimal amount necessary to kill non-transformed tissues. Cells can be transformed with an appropriate gene, such that expression of that transgene confers resistance to the corresponding selection agent, via de-toxification or another mechanism, so that these cells continue to grow and are subsequently able to regenerate plants. The gene conferring resistance to the selection agent is termed the "selectable marker gene", "selectable marker" or "resistance gene". Transgenic cells that lack a functional selectable marker gene will be killed by the selection agent. Selectable marker genes include genes conferring resistance to herbicidal compounds. Herbicide resistance genes generally code for a modified target protein insensitive to the herbicide or for an enzyme that degrades or detoxifies the herbicide in the plant before it can act (DeBlock et al. (1987) EMBO J. 6:2513-2518, DeBlock et al. (1989) Plant Physiol., 91: 691-704). For example, resistance to glyphosate or sulfonylurea herbicides has been obtained by using genes coding for mutant versions of the target enzymes, 5-enolpyruvylshikimate-3-phosphate synthase (EPSPS) and acetolactate synthase (ALS), respectively. Resistance to glufosinate ammonium, bromoxynil and 2,4-dichlorophenoxyacetic acid (2,4-D) has been obtained by using bacterial genes encoding a phosphinothricin acetyl-transferase, a nitrilase, or a 2,4-dichlorophenoxyacetate monooxygenase, respectively, which detoxify the respective herbicide. "Sulfonylurea herbicides" include but are not limited to chlorsulfuron, rimsulfuron, nicosulfuron, Classic®, and Oust®. A specific selection agent may have one or more corresponding selectable marker genes. Likewise, a specific selectable marker gene may have one or more corresponding selection agents. It is appreciated by one skilled in the art that a selection agent may not be toxic to all plant species or to all cell types within a given plant. For a plant species susceptible to a given selection agent, it is also appreciated that resistance cells, tissues or whole plants may be obtained independent of the transformation process, e.g., through chemical mutagenesis of the target gene or gene amplification of the target gene during tissue culture.

Examples of suitable selection agents, include but are not limited to, cytotoxic agents such as hygromycin, sulfonylurea herbicides such as chlorsulfuron, nicosulfuron and rimsulfuron, and other herbicides which act by inhibition of the enzyme acetolactate synthase (ALS), glyphosate, bialaphos and phosphinothricin (PPT). It is also possible to use positive selection marker systems such as phospho-mannose isomerase and similar systems which confer positive growth advantage to transgenic cells.

Any regenerable plant tissue can be used in accordance with the present invention. Regenerable plant tissue generally refers to tissue which can be regenerated into a differentiated plant. For example, such tissues can include calluses and/or somatic embryos derived from whole zygotic embryos, isolated scutella, anthers, inflorescences and leaf and meristematic tissues.

Many of the problems associated with random gene integration, such as multiple transgene copies, unknown integration sites, unpredicted transgene expression, may be overcome by site-specific integration transformation. Various position effects influencing the expression of randomly integrated transgenes may be eliminated and as a result, the effects of regulatory elements such as promoters, terminators, enhancers, and insulators on gene expression may be comparatively analyzed. Transgene integration sites may also be characterized and selected for different applications prior to retransformation.

The RMCE approach using two incompatible recombination sites for double crossover provides a more controlled way for gene targeting. The RMCE approach employs a transgenic plant which comprises a first sequence encoding a first recombination site and a second sequence comprising a second non-identical recombination site. A transfer cassette is then introduced into the transgenic plant, wherein the transfer cassette comprises the same first sequence encoding the same first recombination site and the same second sequence comprising the same second non-identical recombination site. Recombination is then accomplished by a recombinase that recognizes and implements recombination at the non-identical recombination sites. An advantage of the directional RMCE is that DNA cassette exchange is reversible so the RMCE product can be used as new target for next round RMCE using additional recombination sites to successively stack multiple transgenes at the same locus to generate allelic transgenes. Furthermore, since RMCE places only one copy of a transgene at a selected locus, only one transgenic event is needed for each locus. The cost associated with the production, maintenance, and characterization of large numbers of transgenic events with the transgene at unpredicted multiple loci can be eliminated.

Recently, single copy RMCE plants were obtained in *Arabidopsis* from the retransformation of target plants by T-DNA delivery of a donor cassette. Both the target and donor cassettes were flanked by two incompatible lox sites in inverted orientation. The Cre recombinase was provided on a co-transformed T-DNA (Louwerse, J. D., et al. (2007) *Plant Physiol.* 145:1282-1293).

To develop FLP/FRT mediated RMCE technology in soybean, we first created transgenic target lines containing a hygromycin selection gene flanked by two incompatible FRT sites via biolistic random integration transformation. Homozygous target lines were obtained and retransformed with a donor DNA containing a chlorsulfuron selection gene flanked by the same pair of FRT sites. A FLP expression DNA construct was co-bombarded with the donor DNA to transiently provide FLP recombinase required for DNA recombination between the target and donor DNA molecules. RMCE events were produced from multiple target lines and confirmed at both somatic embryo and plant stages by extensive molecular characterizations.

The success of the current invention opens new ways for transgenic product development and transgene expression research. Various target lines can be produced and selected with respect to parameters, such as gene silencing, tissue-specific expression, agronomic performance, etc. and maintained as production target lines to accept transgenes with different expression preferences. By engineering more FRT sites in specific arrangements in target or donor constructs, multiple genes can be stacked reversibly at the same genetic locus by repeated RMCE. Integration of large DNA molecules, such as bacterial artificial chromosomes, could be feasible via RMCE which relies only on the FLP recombinase catalyzed interactions between FRT sites.

Compositions and methods for the directional, targeted integration of exogenous nucleotides into a transformed soybean plant are provided. The methods use non-identical recombination sites in a gene targeting system which facilitates directional targeting of desired genes and nucleotide sequences into corresponding recombination sites previously introduced into the target plant genome.

In the methods of the invention, a nucleotide sequence flanked by two non-identical recombination sites is introduced into the target organism's genome establishing a target site for insertion of nucleotide sequences of interest. Once a stable plant or cultured tissue is established a second construct, or nucleotide sequence of interest, flanked by corresponding recombination sites as those flanking the target site, is introduced into the stably transformed plant or tissues in the presence of a recombinase protein. This process results in exchange of the nucleotide sequences between the non-identical recombination sites of the target site and the transfer cassette.

It is recognized that the transformed plant may comprise multiple target sites; i.e., sets of non-identical recombination sites. In this manner, multiple manipulations of the target site in the transformed plant are available. By target site in the transformed plant is intended a DNA sequence that has been inserted into the transformed plant's genome and comprises non-identical recombination sites.

The two-micron plasmid found in most naturally occurring strains of *Saccharomyces cerevisiae*, encodes a site-specific recombinase that promotes an inversion of the DNA between two inverted repeats. This inversion plays a central role in plasmid copy-number amplification. The protein, designated FLP protein, catalyzes site-specific recombination events. The minimal recombination site (FRT) has been defined and contains two inverted 13-base pair (bp) repeats surrounding an asymmetric 8-bp spacer. The FLP protein cleaves the site at the junctions of the repeats and the spacer and is covalently linked to the DNA via a 3' phosphate.

Site specific recombinases like FLP cleave and religate DNA at specific target sequences, resulting in a precisely defined recombination between two identical sites. To function, the system needs the recombination sites and the recombinase. No auxiliary factors are needed. Thus, the entire system can be inserted into and function in plant cells.

The yeast FLP/FRT site specific recombination system has been shown to function in plants. Earlier, the system was utilized for excision of unwanted DNA. See, Lyznik et al. (1993) *Nucleic Acid Res.* 21:969-975. Subsequently, non-identical FRTs were used for the exchange, targeting, arrangement, insertion and control of expression of nucleotide sequences into the plant genome (PCT Publication No. WO1999025821; PCT Publication No. WO1999025840; PCT Publication No. WO1999025854; PCT Publication No. 1999025855; and PCT Publication No. WO2007011733; the contents of all are herein incorporated by reference).

To practice the methods of the invention, a transformed organism of interest, particularly a soybean plant, containing a target site integrated into its genome is needed. The target site is characterized by being flanked by non-identical recombination sites. A targeting cassette is additionally required containing a nucleotide sequence flanked by corresponding non-identical recombination sites as those sites contained in the target site of the transformed organism. A recombinase which recognizes the non-identical recombination sites and catalyzes site-specific recombination is required.

It is recognized that the recombinase can be provided by any means known in the art. That is, it can be provided in the organism or plant cell by transforming the organism with an expression cassette capable of expressing the recombinase in the organism, by transient expression; or by providing messenger RNA (mRNA) for the recombinase or the recombinase protein.

By "non-identical recombination sites" is intended that the flanking recombination sites are not identical in sequence and will not recombine or recombination between the non-identical sites will be reduced compared to recombination between identical sites. That is, one flanking recombination site may be a FRT site where the second recombination site may be a mutated FRT site. The non-identical recombination sites used in the methods of the invention prevent or greatly suppress recombination between the two flanking recombination sites and excision of the nucleotide sequence contained therein. Accordingly, it is recognized that any suitable non-identical recombination sites may be utilized in the invention, including FRT and mutant FRT sites, FRT and lox sites, 10× and mutant lox sites, as well as other recombination sites known in the art.

Suitable non-identical recombination site implies that in the presence of active recombinase, excision of sequences between two non-identical recombination sites occurs, if at all, with an efficiency considerably lower than the recombinationally-mediated cassette exchange targeting arrangement of nucleotide sequences into the plant genome. Thus, suitable non-identical sites for use in the invention include those sites where the efficiency of recombination between the sites is low; for example, where the efficiency is less than about 30 to about 50%, in another embodiment less than about 10 to about 30%, in another embodiment less than about 5 to about 10%. As noted above, the recombination sites in the targeting cassette correspond to those in the target site of the transformed plant. That is, if the target site of the transformed plant contains flanking non-identical recombination sites of FRTA and FRTB, the targeting cassette will contain the same FRTA and FRTB non-identical recombination sites.

Sequences of minimal and larger than minimal non-identical FRTs sites have been described for the exchange, targeting, arrangement, insertion and control of expression of nucleotide sequences into the plant genome (PCT Publication No. WO1999025821; PCT Publication No. WO1999025840; PCT Publication No. WO1999025854; PCT Publication No. 1999025855; and PCT Publication No. WO2007011733; the contents of all are herein incorporated by reference).

It is furthermore recognized that the recombinase, which is used in the invention, will depend upon the recombination sites in the target site of the transformed plant and the targeting cassette. That is, if FRT sites are utilized, the FLP recombinase will be needed. In the same manner, where lox sites are utilized, the Cre recombinase is required. If the non-identical recombination sites comprise both a FRT and a lox site, both the FLP and Cre recombinase will be required in the plant cell.

The FLP recombinase is a protein which catalyzes a site-specific reaction that is involved in amplifying the copy number of the two micron plasmid of *S. cerevisiae* during DNA replication. FLP protein has been cloned and expressed. See, for example, Cox (1993) *Proc. Natl. Acad. Sci. U.S.A.* 80:4223-4227. The FLP recombinase for use in the invention may be that derived from the genus *Saccharomyces*. The recombinase may be synthesized using plant preferred codons for optimum expression in a plant of interest. See, for example, U.S. application Ser. No. 08/972,258 filed Nov. 18, 1997, entitled "Novel Nucleic Acid Sequence Encoding FLP Recombinase", herein incorporated by reference. The bacteriophage recombinase Cre catalyzes site-specific recombination between two lox sites. The Cre recombinase is known in the art. See, for example, Guo et al. (1997) *Nature* 389:40-46; Abremski et al. (1984) *J. Biol. Chem.* 259:1509-1514; Chen et al. (1996) *Somat. Cell Mol. Genet.* 22:477-488; and Shaikh et al. (1977) *J. Biol. Chem.* 272:5695-5702. All of which are herein incorporated by reference. Such Cre sequence may also be synthesized using plant preferred codons.

Where appropriate, the nucleotide sequences to be inserted in the plant genome may be optimized for increased expression in the transformed plant. Where mammalian, yeast, or bacterial genes are used in the invention, they can be synthesized using plant preferred codons for improved expression. It is recognized that for expression in monocots, dicot genes can also be synthesized using monocot preferred codons. Methods are available in the art for synthesizing plant preferred genes. See, for example, U.S. Pat. Nos. 5,380,831, 5,436,391, and Murray et al. (1989) *Nucleic Acids Res.* 17:477-498, herein incorporated by reference.

The plant preferred codons may be determined from the codons utilized more frequently in the proteins expressed in the plant of interest. It is recognized that monocot or dicot preferred sequences may be constructed as well as plant preferred sequences for particular plant species. See, for example, EPA 0359472; EPA 0385962; WO 91/16432; Perlak et al. (1991) *Proc. Natl. Acad. Sci. USA*, 88:3324-3328; and Murray et al. (1989) *Nucleic Acids Research*, 17: 477-498. U.S. Pat. No. 5,380,831; U.S. Pat. No. 5,436,391; and the like, herein incorporated by reference. It is further recognized that all or any part of the gene sequence may be optimized or synthetic. That is, fully optimized or partially optimized sequences may also be used. Additional sequence modifications are known to enhance gene expression in a cellular host and can be used in the invention. These include elimination of sequences encoding spurious polyadenylation signals, exon-intron splice site signals, transposon-like repeats, and other such well-characterized sequences, which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The present invention also encompasses novel FLP recombination target sites (FRT). The FRT has been identified as a minimal sequence comprising two 11 base pair inverted repeats, separated by an 8 base spacer, as follows (SEQ ID NO:50; PCT Publication No. WO2007011733):

5'-AGTTCCTATTCTCTAGAAAGTATAGGAACT-3'

The domains of the minimal FRT recombination site comprise a pair of 11 base pair symmetry elements which are the FLP binding sites (nucleotides 1-11 and 20-30 of SEQ ID NO:50); the 8 base pair core, or spacer, region (nucleotides 12-19 of SEQ ID NO:50); and the polypyrimidine tracts (nucleotides 3-14 and nucleotides 16-29 of SEQ ID NO:50). A modified or mutant FRT recombination site can comprise 1, 2, 3, 4, 5, 6, 7, 8, 9, 10 or more alterations which include substitutions, additions, and/or deletions in one or more of these domains.

The eight base pair spacer is involved in DNA-DNA pairing during strand exchange. The asymmetry of the region determines the direction of site alignment in the recombination event, which will subsequently lead to either inversion or excision. Most of the spacer can be mutated without a loss of function. See, for example, Schlake and Bode (1994) Biochemistry 33:12746-12751, herein incorporated by reference.

Mutant FRT sites are provided for use in the practice of the methods of the present invention and have been described in PCT Publication No. WO2007011733, the contents of which are herein incorporated by reference. Such mutant sites may be constructed by PCR-based mutagenesis. While mutant FRT sites are provided herein, it is recognized that other mutant FRT sites may be used in the practice of the invention. The present invention is not the use of a particular FRT or recombination site, but rather that non-identical recombination sites or FRT sites can be utilized for targeted insertion and expression of nucleotide sequences in a plant genome. Thus, other mutant FRT sites can be constructed and utilized based upon the present disclosure.

As discussed above, bringing genomic DNA containing a target site with non-identical recombination sites together with a vector containing a transfer cassette with corresponding non-identical recombination sites, in the presence of the recombinase, results in recombination. The nucleotide sequence of the transfer cassette located between the flanking recombination sites is exchanged with the nucleotide sequence of the target site located between the flanking recombination sites. In this manner, nucleotide sequences of interest may be precisely incorporated into the genome of the host.

It is recognized that many variations of the invention can be practiced. For example, target sites can be constructed having multiple non-identical recombination sites. Thus, multiple genes or nucleotide sequences can be stacked or ordered at precise locations in the plant genome. Likewise, once a target site has been established within the genome, additional recombination sites may be introduced by incorporating such sites within the nucleotide sequence of the transfer cassette and the transfer of the sites to the target sequence. Thus, once a target site has been established, it is possible to subsequently add sites, or alter sites through recombination.

Another variation includes providing a promoter or transcription initiation region operably linked with the target site in an organism. For example, the promoter will be 5' to the first recombination site. By transforming the organism with a transfer cassette comprising a coding region, expression of the coding region will occur upon integration of the transfer cassette into the target site. This embodiment provides for a method to select transformed cells, particularly plant cells, by providing a selectable marker sequence as the coding sequence.

Other advantages of the present system include the ability to reduce the complexity of integration of transgenes or transferred DNA in an organism by utilizing transfer cassettes as discussed above and selecting organisms with simple integration patterns. In the same manner, preferred sites within the genome can be identified by comparing several transformation events. A preferred site within the genome includes one that does not disrupt expression of essential sequences and provides for adequate expression of the transgene sequence.

The methods of the invention also provide for means to combine multiple cassettes at one location within the genome. Recombination sites may be added or deleted at target sites within the genome.

Any means known in the art for bringing the three components of the system together may be used in the invention. For example, a plant can be stably transformed to harbor the target site in its genome. Using the recombinase, either transiently or stably integrated into the genome of the plant, the transfer cassette flanked by corresponding non-identical recombination sites is inserted into the transformed plant's genome.

Alternatively, the components of the system may be brought together by sexually crossing transformed plants. In this embodiment, a transformed plant, parent one, containing a target site integrated in its genome can be sexually crossed with a second plant, parent two, that has been genetically transformed with a transfer cassette containing flanking non-identical recombination sites, which correspond to those in plant one. Either plant one or plant two contains within its genome a nucleotide sequence expressing recombinase. The recombinase may be under the control of a constitutive or inducible promoter.

Inducible promoters include heat-inducible promoters, estradiol-responsive promoters, chemical inducible promoters, and the like. Pathogen inducible promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *The Plant Cell* 4:645-656; and Van Loon (1985) *Plant Mol. Virol.* 4:111-116. In this manner, expression of recombinase and subsequent activity at the recombination sites can be controlled.

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

Promoters which are seed or embryo-specific and may be useful in the invention include soybean Kunitz trypsin inhibitor (Kti3) (Jofuku and Goldberg, (1989) Plant Cell 1:1079-1093), patatin (potato tubers) (Rocha-Sosa, M., et al. (1989) EMBO J. 8:23-29), convicilin, vicilin, and legumin (pea cotyledons) (Rerie, W. G., et al. (1991) Mol. Gen. Genet. 259: 149-157; Newbigin, E. J., et al. (1990) Planta 180:461-470; Higgins, T. J. V., et al. (1988) Plant. Mol. Biol. 11:683-695), zein (maize endosperm) (Schernthaner, J. P., et al. (1988) EMBO J. 7:1249-1255), phaseolin (bean cotyledon) (Segupta-Gopalan, C., et al. (1985) Proc. Natl. Acad. Sci. U.S.A. 82:3320-3324), phytohemagglutinin (bean cotyledon) (Voelker, T. et al. (1987) EMBO J. 6:3571-3577), B-conglycinin and glycinin (soybean cotyledon) (Chen, Z-L, et al. (1988) EMBO J. 7:297-302), glutelin (rice endosperm), hordein (barley endosperm) (Marris, C., et al. (1988) Plant Mol. Biol. 10:359-366), glutenin and gliadin (wheat endosperm) (Colot, V., et al. (1987) EMBO J. 6:3559-3564), and sporamin (sweet potato tuberous root) (Hattori, T., et al. (1990) Plant Mol. Biol. 14:595-604). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al. (1989) Bio/Technology 7:L929-932), bean lectin and bean beta-phaseolin promoters to express luciferase (Riggs et al. (1989) Plant Sci. 63:47-57), and wheat glutenin promoters to express chloramphenicol acetyl transferase (Colot et al. (1987) EMBO J. 6:3559-3564).

The compositions and methods of the invention are useful in targeting the integration of transferred nucleotide sequences to a specific chromosomal site. The nucleotide sequence may encode any nucleotide sequence of interest. Particular genes of interest include those which provide a readily analyzable functional feature to the host cell and/or organism, such as marker genes, as well as other genes that alter the phenotype of the recipient cells, and the like. Thus, genes effecting plant growth, height, susceptibility to disease or insects, nutritional value, and the like may be utilized in the invention. The nucleotide sequence also may encode an antisense sequence to turn off or modify gene expression.

It is recognized that the nucleotide sequences will be utilized in a functional expression unit or cassette. By functional expression unit or cassette is intended, the nucleotide sequence of interest with a functional promoter, and in most instances a termination region. There are various ways to achieve the functional expression unit within the practice of the invention. In one embodiment of the invention, the nucleic acid of interest is transferred or inserted into the genome as a functional expression unit. Alternatively, the nucleotide sequence may be inserted into a site within the genome which is 3' to a promoter region. In this latter instance, the insertion of the coding sequence 3' to the promoter region is such that a functional expression unit is achieved upon integration.

For convenience, for expression in plants, the nucleic acid encoding target sites and the transfer cassettes, including the nucleotide sequences of interest, can be contained within expression cassettes. An "expression cassette" will comprise a transcriptional initiation region, or promoter, operably linked to the nucleic acid fragment encoding the RNA of interest. Such an expression cassette may be provided with a plurality of restriction sites for insertion of the gene or genes of interest to be under the transcriptional regulation of the regulatory regions.

The transcriptional initiation region, the promoter, may be native or homologous or foreign or heterologous to the host, or could be the natural sequence or a synthetic sequence. By foreign is intended that the transcriptional initiation region is not found in the wild-type host into which the transcriptional initiation region is introduced.

For protein expression, the expression cassette will include in the 5-prime to 3-prime direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the potato proteinase inhibitor (PinII) gene or from Ti-plasmid of *A. tumefaciens*, such as the octopine synthase and nopaline synthase termination regions. See also, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; Joshi et al. (1987) *Nucleic Acid Res.* 15:9627-9639.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein, O., Fuerst, T. R., and Moss, B. (1989) *PNAS USA,* 86:6126-6130); potyvirus leaders, for example, TEV leader (Tobacco Etch Virus) (Allison et al. (1986); MDMV leader (Maize Dwarf Mosaic Virus); *Virology,* 154: 9-20), and human immunoglobulin heavy-chain binding protein (BiP), (Macejak, D. G., and P. Sarnow (1991) *Nature,* 353:90-94; untranslated leader from the coat protein mRNA of alfalfa mosaic virus (AMV RNA 4), (Jobling, S. A., and Gehrke, L., (1987) *Nature,* 325:622-625; tobacco mosaic virus leader (TMV), (Gallie et al. (1989) *Molecular Biology of RNA*, pages 237-256, Gallie et al. (1987) *Nucl. Acids Res.* 15:3257-3273; and maize chlorotic mottle virus leader (MCMV) (Lommel, S. A. et al. (1991) *Virology,* 81:382-385). See also, Della-Cioppa et al. (1987) *Plant Physiology,* 84:965-968. Other methods known to enhance translation can also be utilized, for example, introns, and the like.

The expression cassettes may contain one or more than one gene or nucleic acid sequence to be transferred and expressed in the transformed plant. Thus, each nucleic acid sequence will be operably linked to 5' and 3' regulatory sequences. Alternatively, multiple expression cassettes may be provided.

Generally, the expression cassette will comprise a selectable marker gene for the selection of transformed cells. Selectable marker genes are utilized for the selection of transformed cells or tissues.

See generally, G. T. Yarranton (1992) *Curr. Opin. Biotech.,* 3:506-511; Christopherson et al. (1992) *Proc. Natl. Acad. Sci. USA,* 89:6314-6318; Yao et al. (1992) Cell, 71:63-72; W. S. Reznikoff (1992) *Mol. Microbiol.,* 6:2419-2422; Barkley et al. (1980) *The Operon*, pp. 177-220; Hu et al. (1987) *Cell,* 48:555-566; Brown et al. (1987) *Cell,* 49:603-612; Figge et al. (1988) *Cell,* 52:713-722; Deuschle et al. (1989) *Proc. Natl. Acad. Aci. USA,* 86:5400-5404; Fuerst et al. (1989) *Proc. Natl. Acad. Sci. USA,* 86:2549-2553; Deuschle et al. (1990) Science, 248:480-483; M. Gossen (1993) PhD Thesis, University of Heidelberg; Reines et al. (1993) *Proc. Natl. Acad. Sci. USA,* 90:1917-1921; Labow et al. (1990) *Mol. Cell. Bio.,* 10:3343-3356; Zambretti et al. (1992) *Proc. Natl. Acad. Sci. USA,* 89:3952-3956; Baim et al. (1991) *Proc. Natl. Acad. Sci.*

USA, 88:5072-5076; Wyborski et al. (1991) *Nuc. Acids Res.*, 19:4647-4653; A. Hillenand-Wissman (1989) *Topics in Mol. and Struc. Biol.*, 10:143-162; Degenkolb et al. (1991) *Antimicrob. Agents Chemother.*, 35:1591-1595; Kleinschnidt et al. (1988) *Biochemistry*, 27:1094-1104; Gatz et al. (1992) *Plant J.*, 2:397-404; A. L. Bonin (1993) PhD Thesis, University of Heidelberg; Gossen et al. (1992) *Proc. Natl. Acad. Sci. USA*, 89:5547-5551; Oliva et al. (1992) *Antimicrob. Agents Chemother.*, 36:913-919; Hlavka et al. (1985) *Handbook of Exp. Pharmacology*, 78; Gill et al. (1988) Nature 334:721-724. Such disclosures are herein incorporated by reference.

The methods of the invention can also be utilized to find optimal integration sites within a plant genome. In this manner, a plant is transformed with an expression cassette comprising a selectable marker gene. The expression cassette is a target site as the marker gene is flanked by non-identical recombination sites. Transformed protoplast, tissues, or whole plants can be tested to determine the levels of activity of the inserted gene. By comparison of cellular activities of the gene in different insertion sites, preferred integration sites may be found wherein the gene is expressed at high or acceptable levels. These plants can then be utilized with subsequent retargeting techniques to replace the marker gene with other genes or nucleotide sequences of interest. In the same manner, multiple genes may be inserted at the optimal site for expression.

Alternatively, the process of creating a target line can be combined with the development of a trait-containing transgenic product line. In this scheme, a target site will be obtained as a by-product once the transgenic product line is selected and well characterized. Since a trait gene or a group of genes responsible for the trait is already placed at a particular locus, that site is convenient for stacking of additional new traits through RMCE. A common selectable marker gene cassette is usually used for plant transformation to facilitate the selection of transformed events, such as the 35S:hpt and sams:als cassettes used in soybean transformation (US patent publication WO 00/37662) and the 35S:BAR and UBIQ:GAT cassettes used in maize transformation. Consequently, two incompatible recombinase recognition sites can be incorporated in the selectable marker gene cassette which can then be linked to any trait gene of interest for transformation. Once integrated in a plant genome the incorporated incompatible recombinase sites can be used for RMCE.

Methods for transformation of plants are known in the art. Suitable methods of transforming plant cells include microinjection (Crossway et al. (1986) *Biotechniques* 4:320-334), electroporation (Riggs et al. (1986) *Proc. Natl. Acad. Sci. USA*, 83:5602-5606), *Agrobacterium* mediated transformation (Hinchee et al. (1988) *Biotechnology*, 6:915-921), direct gene transfer (Paszkowski et al. (1984) *EMBO J.*, 3:2717-2722), and ballistic particle acceleration (see, for example, Sanford et al., U.S. Pat. No. 4,945,050; WO91/10725 and McCabe et al. (1988) Biotechnology, 6:923-926). Also see, Weissinger et al. (1988) *Annual Rev. Genet.*, 22:421-477; Sanford et al. (1987) *Particulate Science and Technology*, 5:27-37 (onion); Christou et al. (1988) *Plant Physiol.* 87:671-674 (soybean); McCabe et al. (1988) *Bio/Technology*, 6:923-926 (soybean); Datta et al. (1990) *Biotechnology*, 8:736-740 (rice); Klein et al. (1988) *Proc. Natl. Acad. Sci. USA*, 85:4305-4309 (maize); Klein et al. (1988) *Biotechnology*, 6:559-563 (maize); WO91/10725 (maize); Klein et al. (1988) *Plant Physiol.*, 91:440-444 (maize); Fromm et al. (1990) *Biotechnology*, 8:833-839; and Gordon-Kamm et al. (1990) *Plant Cell*, 2:603-618 (maize); Hooydaas-Van Slogteren & Hooykaas (1984) *Nature* (London), 311:763-764; Bytebier et al. (1987) *Proc. Natl. Acad. Sci. USA*, 84:5345-5349 (Liliaceae); De Wet et al. (1985) In *The Experimental Manipulation of Ovule Tissues*, ed. G. P. Chapman et al., pp. 197-209. Longman, N.Y. (pollen); Kaeppler et al. (1990) *Plant Cell Reports*, 9:415-418; and Kaeppler et al. (1992) *Theor. Appl. Genet.*, 84:560-566 (whisker-mediated transformation); D'Halluin et al. (1992) *Plant Cell*, 4:1495-1505 (electroporation); Li et al. (1993)*Plant Cell Reports*, 12:250-255 and Christou and Ford (1995) *Annals of Botany*, 75:407-413 (rice); Osjoda et al. (1996) *Nature Biotechnology*, 14:745-750 (maize via *Agrobacterium tumefaciens*); all of which are herein incorporated by reference.

The cells which have been transformed may be grown into plants in accordance with conventional approaches. See, for example, McCormick et al. (1986) *Plant Cell Reports*, 5:81-84. These regenerated plants may then be pollinated with either the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

Embodiments of the invention include the following:

In one embodiment, a soybean cell, plant or seed having stably incorporated in its genome an isolated nucleic acid fragment comprising at least one first expression cassette of interest adjacent to a target site, wherein said target site comprises a selectable marker protein-coding sequence, wherein the selectable marker protein-coding sequence is bounded by a first recombination site and a second non-identical recombination site. The target site may be genetically linked to a chromosomal region comprising a sequence selected from the group consisting of SEQ ID NO:55, SEQ ID NO:56, SEQ ID NO:57, SEQ ID NO:58, SEQ ID NO:59, SEQ ID NO:60, SEQ ID NO:61 and SEQ ID NO:62.

In another embodiment, a soybean cell, plant or seed having stably incorporated in its genome an isolated nucleic acid fragment comprising a target site, wherein said target site comprises a promoter operably linked to a selectable marker protein-coding sequence, wherein the selectable marker protein-coding sequence is bounded by a first recombination site and a second non-identical recombination site, further wherein the first recombination site is between the promoter and the selectable marker protein-coding sequence. The target site may further comprise at least one additional non-identical recombination site, wherein the at least one additional non-identical recombination site is bounded by the selectable marker protein-coding sequence and the second non-identical recombination site. The target site may be genetically linked to a chromosomal region comprising a sequence selected from the group consisting of SEQ ID NO:55, SEQ ID NO:56, SEQ ID NO:57, SEQ ID NO:58, SEQ ID NO:59, SEQ ID NO:60, SEQ ID NO:61 and SEQ ID NO:62.

In another embodiment, a soybean cell, plant or seed having stably incorporated in its genome a transfer cassette comprising at least three non-identical recombination sites, where the transfer cassette comprises a polynucleotide encoding a selectable marker protein-coding sequence bounded by a first recombination site and a second non-identical recombination site, wherein the transfer cassette further comprises a third non-identical recombination site bounded by the selectable marker protein-coding sequence and the second non-identical recombination site, wherein the transfer cassette further comprises at least one expression cassette of interest, wherein the at least one expression cassette of interest is bounded by the third non-identical recombination site and the second non-identical recombination site. The transfer cassette may be genetically linked to a chromosomal region comprising a sequence selected from the group consisting of SEQ ID NO:55, SEQ ID NO:56, SEQ ID NO:57, SEQ ID NO:58, SEQ ID NO:59, SEQ ID NO:60, SEQ ID NO:61 and SEQ ID NO:62.

In another embodiment, a method for stacking of multiple expression cassettes of interest into a specific chromosomal site in a soybean genome, said method comprising: (a) transforming a first soybean cell with an isolated nucleic acid fragment comprising at least a first expression cassette of interest adjacent to a target site, wherein said target site comprises a first selectable marker protein-coding sequence, wherein the first selectable marker protein-coding sequence is bounded by a first recombination site and a second non-identical recombination site; (b) regenerating a transgenic plant from the transformed soybean cell of step (a); (c) introducing into a second soybean cell from the transgenic plant of step (b) a transfer cassette, wherein said transfer cassette comprises a second selectable marker protein-coding sequence, wherein the second selectable marker protein-coding sequence is bounded by the first recombination site and the second non-identical recombination sites of the target site; and (d) providing a recombinase that recognizes and implements recombination at the non-identical recombination sites. Optionally, the method may further comprise, between steps (b) and (c), identifying a transgenic plant of step (b), wherein the transgenic plant has desirable levels of gene expression for the at least one first expression cassette of interest.

In another embodiment, a second method for stacking of multiple expression cassettes of interest into a specific chromosomal site in a soybean genome, said method comprising: (a) obtaining a transgenic soybean cell comprising a target site, wherein said target site comprises a first recombination site and a second non-identical recombination site; (b) introducing into the transgenic soybean cell of step (a) a transfer cassette, wherein said transfer cassette comprises a selectable marker protein-coding sequence, wherein the selectable marker protein-coding sequence is bounded by the first recombination site and the second non-identical recombination site; and (c) providing a recombinase that recognizes and implements recombination at the non-identical recombination sites.

In another embodiment, a method for creating a transgenic soybean cell comprising a target site suitable for stacking of multiple expression cassettes of interest into a specific chromosomal site in a soybean genome, said method comprising transforming a soybean cell with an isolated nucleic acid fragment comprising at least a first expression cassette of interest adjacent to a target site, wherein said target site comprises a selectable marker protein-coding sequence, wherein the selectable marker protein-coding sequence is bounded by a first recombination site and a second non-identical recombination site.

In one or more of the embodiments, the transfer cassette may further comprise a third non-identical recombination site bounded by the second selectable marker protein-coding sequence and the second non-identical recombination site.

In one or more of the embodiments, the transfer cassette may further comprise at least one second expression cassette of interest, wherein the at least one second expression cassette of interest is bounded by the third non-identical recombination site and the second non-identical recombination site.

In one or more of the embodiments, the non-identical recombination sites may be selected from the group consisting of FRT1 (SEQ ID NO:50), FRT5 (SEQ ID NO:51), FRT6 (SEQ ID NO:52), FRT12 (SEQ ID NO:53) and FRT87 (SEQ ID NO:54).

In one or more of the embodiments, the soybean cell may be transformed with the isolated nucleic acid fragment by gene bombardment.

In one or more of the embodiments, the transfer cassette may be introduced into the soybean cell by gene bombardment.

In one or more of the embodiments, providing the recombinase comprises transiently expressing within the soybean cell an expression cassette comprising a polynucleotide encoding the recombinase. In another embodiment, the recombinase is FLP. In another embodiment, the FLP has been synthesized using maize preferred codons.

In one or more or the embodiments, the first selectable marker protein-coding sequence encodes a protein selected from the group consisting of a hygromycin phosphotransferase and a sulfonylurea-tolerant acetolactate synthase. For example, the sulfonylurea-tolerant acetolactate synthase may have an amino acid sequence comprising SEQ ID NO:63 or SEQ ID NO:64.

In one or more of the embodiments, the target site comprises a promoter operably linked to the first selectable marker protein-coding sequence, wherein the first recombination site is between the promoter and the first selectable marker protein-coding sequence.

A recombinant DNA construct of the present invention may comprise at least one regulatory sequence.

A regulatory sequence may be a promoter.

A number of promoters can be used in recombinant DNA constructs of the present invention. The promoters can be selected based on the desired outcome, and may include constitutive, tissue-specific, inducible, or other promoters for expression in the host organism.

A composition of the present invention is a plant comprising in its genome any of the recombinant DNA constructs of the present invention. Compositions also may include any progeny of the plant, and any seed obtained from the plant or its progeny, wherein the progeny or seed comprises within its genome the recombinant DNA construct (or suppression DNA construct). Progeny includes subsequent generations obtained by self-pollination or out-crossing of a plant.

A method of producing seed (for example, seed that can be sold as a trait-containing product offering) comprising any of the preceding methods, and further comprising obtaining seeds from said progeny plant, wherein said seeds comprise in their genome said recombinant DNA construct.

The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

The following examples are offered by way of illustration and not by way of limitation.

EXAMPLES

Aspects of the present invention are exemplified in the following Examples. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

In the discussion below, parts and percentages are by weight and degrees are Celsius, unless otherwise stated. Sequences of promoters, cDNA, adaptors, and primers listed herein are in the 5' to 3' orientation unless described otherwise. Routine techniques in molecular biology are described in Ausubel et al. *Current Protocols in Molecular Biology*; John Wiley & Sons: New York, 1990 and Sambrook et al. *Molecular Cloning: A Laboratory Manual*; Cold Spring Harbor Laboratory Press: Cold Spring Harbor, 1989.

Example 1

FLP/FRT Mediated RMCE Experimental Design and DNA Construction

Figure 1D:
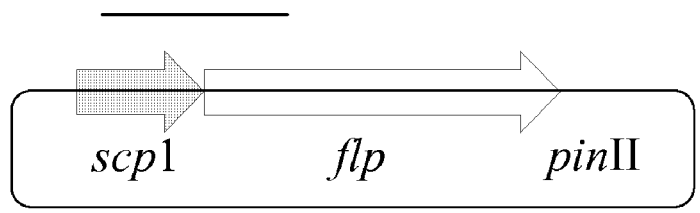
Figure 2A:
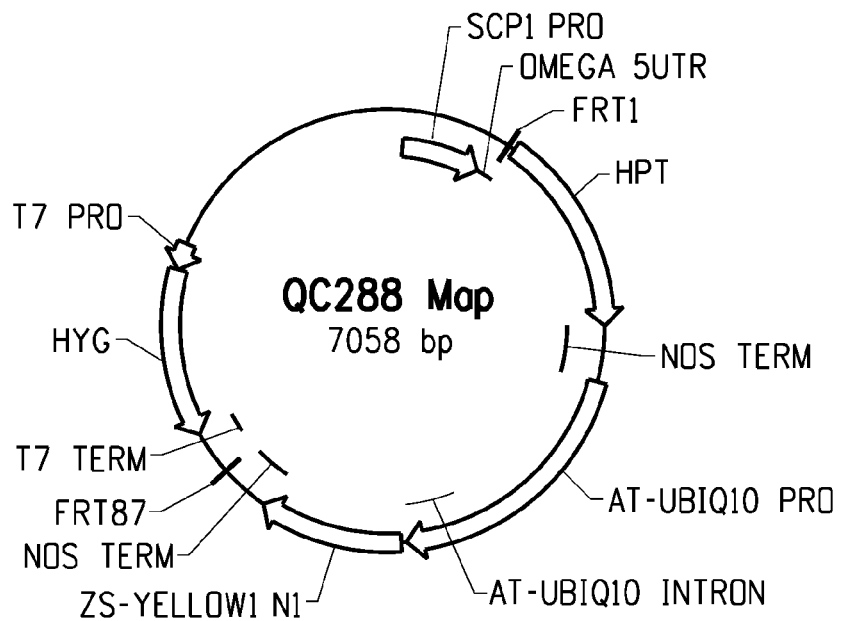
FIG. 2A-2C show the maps of the target DNA construct QC288, the donor DNA construct QC329 and the FLP expression construct QC292.
Figure 2B:
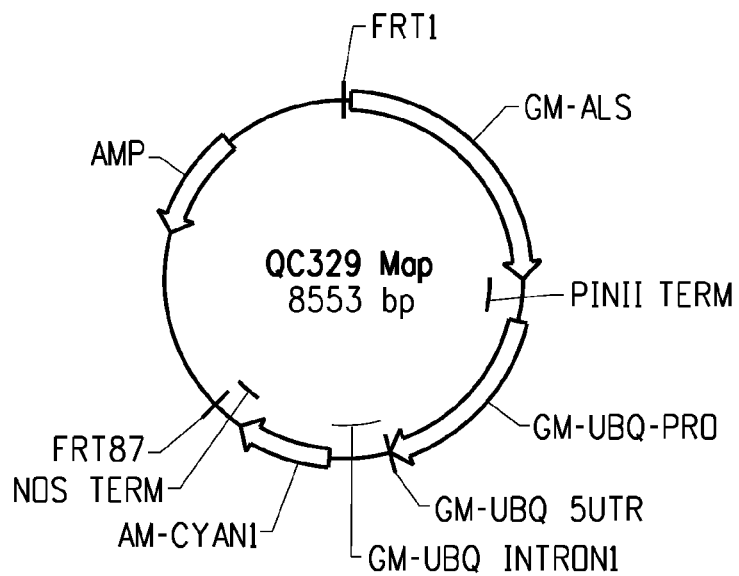
Figure 3C:
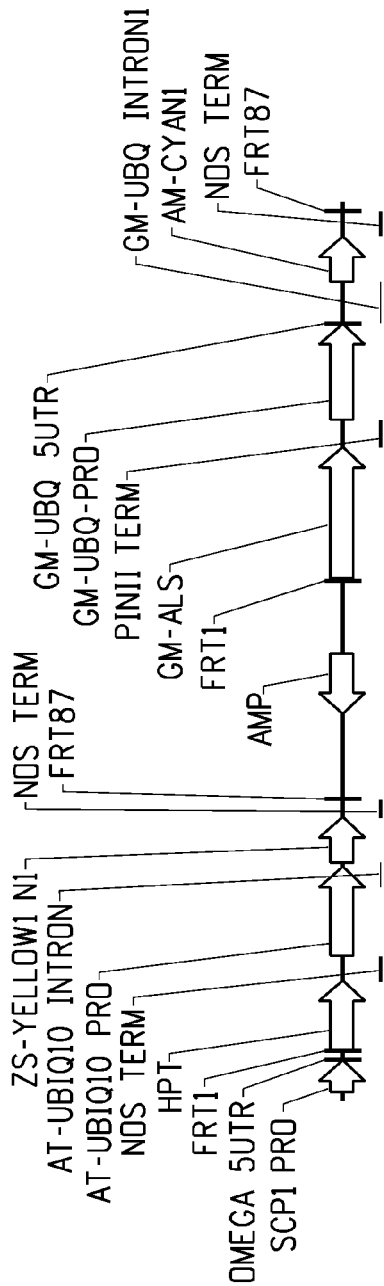

The target QC288A and donor QC329 constructs were designed each containing a FRT1 site (solid triangle) and a FRT87 site (open triangle) in the same orientation (FIG. 1A, FIG. 2A, FIG. 1B, FIG. 2B). FRT1 is the wild-type recombination site for FLP recombinase and FRT87 is a modified recombination site (PCT Publication No. WO2007011733 published on Jan. 25, 2007). The circular QC329 DNA could integrate into the linear QC288A DNA previously placed in soybean genome by FLP recombinase mediated DNA recombination at either the FRT1 site or the FRT87 site to form collinear intermediates that contained two FRT1 sites and two FRT87 sites. FLP recombinase mediated excision could occur to excise the intervening fragment either between the two FRT1 sites or between the FRT87 sites. The net result of the integration via recombination between one identical pair of FRT sites and subsequent excision via recombination between the other pair of FRT sites would be the replacement of the target DNA with the recombined RMCE DNA QC288A329 (FIG. 1C, FIG. 3A). If the gene excision step failed to occur, the intermediates would remain as SSI events containing all the components of both the target and donor constructs (FIG. 3B, FIG. 3C).

The target construct QC288A contained a selectable marker gene hpt driven by a constitutive promoter scp1 and transgenic events were selected with hygromycin. The donor construct QC329 contained a promoter-less selectable marker gene als that would not be expressed unless a promoter was placed in front of it. During retransformation the promoter-less als gene of QC329 could be brought downstream of the scp1 promoter by RMCE and the resulted QC288A329 DNA would enable retransformation events to be selected with chlorsulfuron due to the als gene activation. SSI events with QC329 integrated at the FRT1 site would also be similarly selected. However, random integration events of QC329 would not be able to survive chlorsulfuron selection unless the promoter-less als gene happened to insert downstream of a native promoter. A yellow fluorescent reporter gene cassette ubiq10:yfp was included in QC288A and a cyan fluorescent reporter gene cassette ubq:cfp was included in QC329 to facilitate transgenic events characterization (FIG. 1A, FIG. 1B, FIG. 2A, FIG. 2B).

The target DNA construct QC288 was made through multiple cloning steps using components from existing DNA constructs (Li et al, (2007) Plant Mol. Biol. 65:329-341). Restriction enzymes and DNA modifying enzymes such as DNA polymerase Klenow fragment and DNA ligase were used according to manufacturers' recommendations (New England Biolabs, Beverly, Mass., USA; Promega, Madison, Wis., USA; or Invitrogen, Carlsbad, Calif., USA). The FRT87 recombination site DNA fragment was released from construct PHP20234 with BamHI/SmaI digestion and cloned into BamHI/PvuII sites of pZSL141 to make QC278 consisted of als-FRT87. The FRT1 recombination site was made by annealing two 92 bp complementary oligos SEQ ID NO:6 and 7 engineered with multiple cloning sites (Sigma-Genosys, The Woodlands, Tex., USA). The BamHI/HpaI FRT1 DNA fragment was cloned into the BamHI/SmaI sites of construct pZSL90 to make QC280 consisted of scp1-FRT1:yfp:nos. The DNA fragment containing hpt coding sequence and nos terminator was release from pZSL93 with SpeI/XmaI digestion and cloned into the SpeI/XmaI sites of QC280 to make QC282 consisted of scp1-FRT1:hpt:nos+yfp:nos. The scp1-FRT1:hpt:nos+yfp:nos fragment was released from QC282 with Hind III/EcoRV digestion and cloned into the HindIII/BamHI sites of QC278 (the BamHI site was completely filled in with Klenow DNA polymerase) to make QC284 consisted of scp1-FRT1:hpt:nos+yfp:nos-FRT87. The ubiq10 promoter fragment was released from construct QC257i with BamHI/XmaI digestion and cloned into the BamHI/XmaI sites of QC282 to make QC286 consisted of scp1-FRT1:hpt:nos+ubiq10:yfp:nos. The final target construct QC288 consisted of scp1-FRT1:hpt:nos+ubiq10:yfp:nos-FRT87 was made by cloning BamHI/SphI fragment from QC286 into the BamHI/SphI sites of QC284 (FIG. 2A).

The donor construct QC329 was made by first cloning the BamHI/HindIII FRT1 DNA fragment into the BamHI/HindIII sites of construct pSMamCyan to make QC281 consisted of FRT1:cfp:nos. The FRT87 site was added by cloning the AflII/SpeI fragment of the above QC284 (the SpeI site was completely filled with Klenow DNA polymerase) into the AflII/EcoRI sites of QC281 (the EcoRI site was completely filled in with Klenow DNA polymerase) to make QC283 consisted of FRT1:cfp:nos-FRT87. The ubiq10 promoter fragment was released from QC257i with BamHI/XmaI digestion and cloned into the BamHI/XmaI sites of QC283 to make QC285 consisted of FRT1-ubiq10:cfp:nos-FRT87. Separately, the als:pinII fragment was released from QC257i with BglII/KpnI digestion (the BglII site was completely filled in with Klenow DNA polymerase) and cloned into the EcoCRI/KpnI sites of pZSL81 to make QC279 consisted of als:pinII. The SpeI/XmaI fragment of QC279 was then cloned into the SpeI/XmaI sites of QC285 to make QC287 consisted of FRT1-als:pinII+ubiq10:cfp:nos-FRT87. The ubiq10 promoter was later replaced with a soybean ubiquitin promoter ubq by cloning the XmaI/NcoI ubq promoter fragment from QC319 into the XmaI/NcoI sites of QC287 to make the final donor vector QC329 consisted of FRT1-als:pinII+ubq:cfp:nos-FRT87 (FIG. 2B).

Figure 2C:
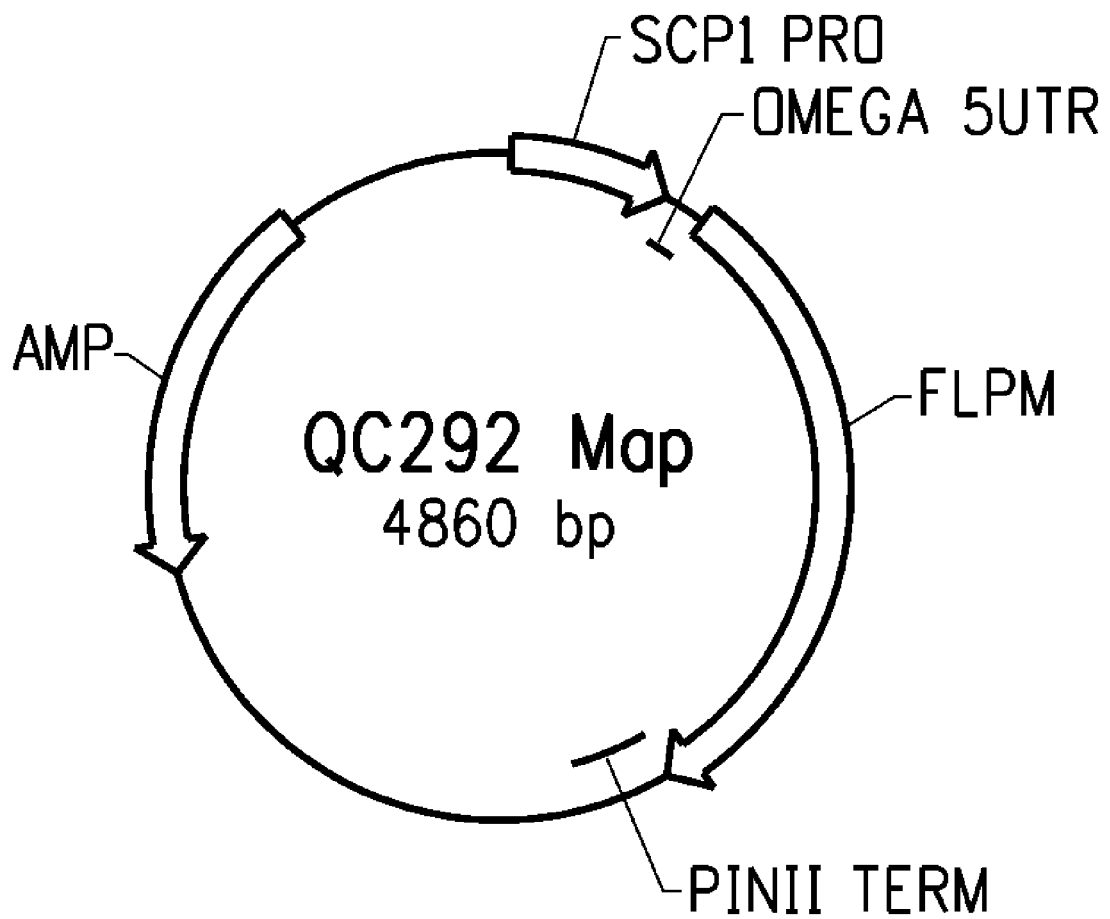

The FLP expression construct QC292 containing scp1:flp:pinII was made by simply cloning the BamHI/HindIII scp1 promoter fragment from pZSL90 into the BamHI/HindIII sites of construct PHP5096 (FIG. 2C).

Example 2

Target Event Creation and Characterization

The scp1-FRT1:hpt:nos+ubiq10:yfp:nos-FRT87 cassette of QC288 was released as a 4544 bp DNA fragment QC288A with AscI digestion, resolved by agarose gel electrophoresis, and purified using a Qiagen gel extraction kit (Qiagen, Valencia, Calif., USA). Soybean embryogenic suspension cultures were transformed with QC288A DNA following the biolistic bombardment transformation protocol using 30 μg/ml hygromycin for transgenic events selection (Li et al, (2007) Plant Mol. Biol. 65:329-341; Klein et al. (1987) Nature 327:70-73; U.S. Pat. No. 4,945,050)).

Soybean somatic embryos from the Jack cultivar were induced as follows. Cotyledons (smaller than 3 mm in length) were dissected from surface-sterilized, immature seeds and were cultured for 6-10 weeks under fluorescent light at 26° C. on a Murashige and Skoog media ("MS media") containing 0.7% agar and supplemented with 10 mg/ml 2,4-dichlorophenoxyacetic acid (2,4-D). Globular stage somatic embryos, which produced secondary embryos, were then excised and placed into flasks containing liquid MS medium supplemented with 2,4-D (10 mg/ml) and cultured in the light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont™ Biolistic™ PDS1000/HE instrument (helium retrofit) (Bio-Rad Laboratories, Hercules, Calif.). To 50 μl of a 60 mg/ml 1.0 mm gold particle suspension were added (in order): 30 μl of 10 ng/μl QC288A DNA fragment, 20 μl of 0.1 M spermidine, and 25 μl of 5 M $CaCl_2$. The particle preparation was then agitated for 3 minutes, spun in a centrifuge for 10 seconds and the supernatant removed. The DNA-coated particles were then washed once in 400 μl 100% ethanol and resuspended in 45 μl of 100% ethanol. The DNA/particle suspension was sonicated three times for one second each. 5 μl of the DNA-coated gold particles was then loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 30 μg/ml hygromycin as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 30 μg/ml hygromycin selection agent to increase mass. The embryogenic suspension cultures were then transferred to solid agar MS media plates without 2,4-D supplement to allow somatic embryos to develop. A sample of each event was collected at this stage for PCR and quantitative PCR analysis.

Cotyledon stage somatic embryos were dried-down (by transferring them into an empty small Petri dish that was seated on top of a 10 cm Petri dish to allow slow dry down) to mimic the last stages of soybean seed development. Dried-down embryos were placed on germination solid media, and transgenic soybean plantlets were regenerated. The transgenic plants were then transferred to soil and maintained in growth chambers for seed production.

Eighty two putative transgenic events were produced from transformation experiments with the target DNA fragment QC288A. Somatic embryo samples of the events were analyzed by quantitative PCR (qPCR), regular PCR, and Southern to identify events with a single complete copy of the transgene. Since DNA could be fragmented during biolistic bombardment, three major components, scp1, hpt, and yfp of QC288A were checked by qPCR. Endogenous controls were used to normalize different samples and a calibrator containing single copy of the transgene component was included for calculating the relative transgene copy numbers of the samples by comparing their relative quantifications to that of the calibrator. Since the relative quantification values contained fractions, copy numbers were considered to be 0, 1, or 2 for values of <0.3, 0.4-1.4, or 1.5-2.4, respectively. Approximately 50% of the 82 events contained one copy of the QC288A transgene based on the qPCR analysis.

Genomic DNA samples of transgenic events were analyzed by qPCR using Taqman technology and the universal Taqman DNA polymerase reaction mixture in a 7500 real time PCR system (Applied Biosystems, Foster City, Calif.). Relative quantification methodology was applied in single tube duplex PCR reactions, one for the target gene and the other for an endogenous control gene to normalize the reactions across samples. After 2 minutes incubation at 50° C. to activate the Taq DNA polymerase and 10 minutes incubation at 95° C. to denature the DNA templates, 40 cycles of 15 seconds at 95° C. and 1 minute at 60° C. were performed. A soybean heat shock protein (hsp) gene was used as the endogenous control. A transgenic DNA sample known containing single copy of the transgene component was included as the calibrator. Three components including scp1 promoter, hpt, yfp of the target QC288A were analyzed. Primers used were SEQ ID NO:8, SEQ ID NO:9, and VIC labeled MGB probe SEQ ID NO:10 (Applied Biosystems) for the hsp control, SEQ ID NO:11, SEQ ID NO:12, and FAM labeled BHQ1 probe SEQ ID NO:13 (Sigma Genosis) for scp1, SEQ ID NO:14, SEQ ID NO:15, and FAM labeled BHQ1 probe SEQ ID NO:16 for hpt, SEQ ID NO:17, SEQ ID NO:18, and FAM labeled BHQ1 probe SEQ ID NO:19 for yfp.

The intactness of QC288A transgene ends was checked by regular PCR. Soybean genomic DNA was prepared from leaf discs or somatic embryos using an extraction buffer containing 7 M urea, 1.5 M NaCl, 50 mM Tris, pH 8.0, 20 mM EDTA, and 1% N-lauroyl-sarcosine followed by phenol/chloroform extractions and isopropanol precipitations. A typical 25 μl PCR reaction consisted of 10 ng genomic DNA, 200 nM of each primer, 200 μM dNTPs, 1×PCR buffer, and 2.5 units of High Fidelity Taq DNA polymerase (Invitrogen). A typical PCR was done at 94° C. for 3 min followed by 40 cycles at 94° C. for 0.5 min denaturizing, 60° C. for 1 min annealing, 68° C. for 1~3 min extension (depending on the size of PCR amplicon), and then a final 5 min extension at 68° C. using a GeneAmp 9700 PCR system (Applied Biosystems). The 5' end intactness of the QC288A transgene in target plants was analyzed with primers SEQ ID NO:23 and SEQ ID NO:24 to amplify a 657 bp band. The 3' end intactness of the QC288 transgene was analyzed with primers SEQ ID NO:25 and SEQ ID NO:26 to amplify a 441 bp band. Only events positive for both the PCR analyses were selected.

Selected events were further analyzed by Southern with two probes hpt and yfp. Soybean genomic DNA was digested with EcoRV, resolved in 0.7% agarose gel, and blotted to a nylon membrane using a TurboBlotter (Schleicher & Schuell Bioscience, Germany) with 20×SSC (Invitrogen) and crosslinked by UV light. Digoxigenin labeled DNA probes were made by PCR from plasmid DNA templates using the PCR DIG probe synthesis kit (Roche Applied Science, Indianapolis, Ind., USA). The 794 bp hpt probe was made with primers SEQ ID NO:28 and SEQ ID NO:29. The 693 bp yfp probe was made with primers SEQ ID NO:30 and SEQ ID NO:31. Southern blots were hybridized in DIG EasyHyb solution and detected with CDP-Star according to the manufacturer (Roche Applied Science). Hybridization signals were captured on BioMax light films (Eastman Kodak, New Haven, Conn., USA).

The restriction enzyme EcoRV cuts QC288A twice in the middle at positions 2078 and 3246. To each copy of the transgene, the hpt probe would hybridize to a 2078 or larger band, and the yfp probe would hybridize to a 1299 bp or larger band. The Southern analysis confirmed the copy numbers determined by qPCR for most events. Four events, each determined to contain a single intact copy of QC288A by qPCR, PCR, and Southern analyses, were selected for RMCE retransformation (Table 1).

Table 1 presents a summary of the analysis of single copy transgenic events selected at somatic embryo stage for RMCE retransformation. From a total of 82 events, four were selected as being single intact copy events as determined by the qPCR, Southern, and transgene end-specific PCR. Fraction values were produced by qPCR for transgene copy numbers. A value less than 0.3 was considered as zero copy and a value between 0.4 and 1.4 was considered as one copy. Due to the variations, different components of the same transgenic DNA were checked in order to make a copy number call. The intactness of FRT1 site was checked by PCR with primers Scp1-S/Hygro-A (SEQ ID NO:23/SEQ ID NO:24). The intactness of FRT87 site was checked with primers Yfp-3/Frt87-A (SEQ ID NO:25/SEQ ID NO:26).

TABLE 1

Analysis of Target Events

| Target | Quantitative PCR | | | PCR | | Southern-EcoRV | |
| --- | --- | --- | --- | --- | --- | --- | --- |
| Event | scp1 | hpt | yfp | FRT1 | FRT87 | yfp | hpt |
| M | 1.0 | 0.6 | 1.0 | + | + | 1 | 1 |
| A | 1.1 | 0.6 | 1.1 | + | + | 1 | 1 |
| B | 0.9 | 0.6 | 1.0 | + | + | 1 | 1 |
| N | 1.0 | 0.8 | 1.0 | + | + | 1 | 1 |

Example 3

Retransformation Event Creation and Characterization by PCR

Four transgenic events containing a single complete copy of the target QC288A DNA were maintained as suspension cultures and retransformed with the donor construct QC329 and the FLP construct QC292 at 10:1 ratio following the same biolistic bombardment transformation protocol described in EXAMPLE 2 except that retransformation events were selected using 90 ng/ml chlorsulfuron (DuPont, Wilmington, Del., USA). RMCE would only occur in cells containing all three DNA QC288A, QC329, and QC292 and would bring the promoter-less als coding region of QC329 downstream of the scp1 promoter of QC288A previously placed in soybean genome for expression and thus chlorsulfuron resistance.

Figure 1E:
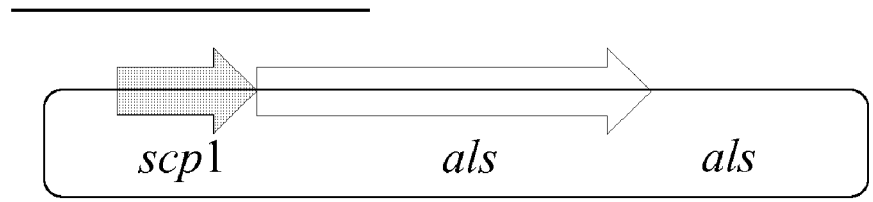

The somatic embryo samples of putative retransformation events were screened by PCR as described in EXAMPLE 2 using construct-specific primers as depicted in FIGS. 1A-1E. Plasmid DNA of constructs QC288, QC329, QC292 were included as positive controls. An unrelated construct QC165 was used as a positive control for RMCE DNA QC288A329 since they both contain the same scp1:als cassette (FIG. 1C, FIG. 1E). Wild-type DNA and no DNA template negative controls were also included (FIG. 4).

QC288A-specific PCR was done using primers SEQ ID NO:11 and SEQ ID NO:24 to give a 416 bp band (FIG. 1A). Five events M-1, A-1, B-1, B-2, and N-1 were positive and two events M-2 and M-3 were negative (FIG. 4A). The results suggested that the two negative events no longer contained the hpt component of QC288A. Event B-1 produced a much weaker QC288A-specific PCR band suggesting that it contained less QC288A DNA than other positive events. QC288A329-specific PCR was done using primers SEQ ID NO:11 and SEQ ID NO:27 to give a 497 bp band. The same primers would give a 426 bp band to the RMCE positive control construct QC165 (FIG. 1E). The same two events M-2 and M-3, while negative for QC288A, were positive for QC288A329 suggesting that they were complete RMCE events. The weak QC288A positive event B-1 was also positive for QC288A329, suggesting that this event was a chimeric RMCE event that still contained some original target cells. The other four QC288A positive events M-1, A-1, B-2, and N-1 were negative for QC288A329, suggesting that they were the original target events that had escaped the chlorsulfuron selection as false retransformation events. As expected, a slightly smaller band was detected in the positive control QC165 (FIG. 4B). QC329-specific PCR was done with primers SEQ ID NO:36 and SEQ ID NO:27 to give a 1027 bp band. The same primers would give a 982 bp band to the RMCE positive control construct QC165 (FIG. 1B, FIG. 1E). A weak QC329-specific PCR band was detected in event M-1, suggesting that this event was likely a chimeric random integration event with a portion of cells harboring the QC329 DNA (FIG. 4C). QC292-specific PCR was done with primers SEQ ID NO:11 and SEQ ID NO:37 to give a 368 bp band (FIG. 1D). A weak band was detected in event M-3, suggesting that this RMCE event might contain cells harboring the QC292 DNA (FIG. 4D). Overall, three putative RMCE events M-2, M-3, and B-1 were identified.

The three putative RMCE events M-2, M-3, and B-1 as well as their target parents M and B were analyzed by another PCR using primers SEQ ID NO:23 and SEQ ID NO:26 which would amplify a 5982 bp band from QC288A329 and a smaller 4393 bp band from QC288A (FIG. 1A, FIG. 1C). As expected, an approximately 5982 bp band was detected in the three putative RMCE events M-2, M-3, and B-1; and an approximately 4393 bp band was detected in their target parents M and B (FIG. 4E). More analyses as described below later confirmed that only M-2 and B-1 were true RMCE events while M-3 was indeed a SSI event with the donor DNA QC329 simply integrated at the FRT1 site of the target DNA QC288A.

Example 4

Retransformed T0 Plant Characterization by PCR and qPCR

T0 plants were regenerated from events M-1, M-2, M-3, B-1, and B-2 and analyzed by PCR and qPCR as described in EXAMPLE 2. DNA recombination at the FRT1 site was checked by regular PCR with two sets of primers SEQ ID NO:11/SEQ ID NO:24 and SEQ ID NO:11/SEQ ID NO:27. The original QC288A would be positive for SEQ ID NO:11/SEQ ID NO:24 and negative for SEQ ID NO:11/SEQ ID NO:27 while the recombination DNA QC288A329 would be negative for SEQ ID NO:11/SEQ ID NO:24 and positive for SEQ ID NO:11/SEQ ID NO:27 (FIG. 1A, FIG. 1C).

DNA recombination was further evaluated by the presence or absence of QC288A and QC329 components checked by qPCR. Since the scp1 promoter is outside of the FRT1 and FRT87 and thus not directly affected by DNA recombination, all events should be positive for scp1 qPCR. If an event only contained QC288A, the event would be positive for the QC288A-specific hpt, yfp qPCR. If an event contained both QC288A and QC329 in the cases of random integration and SSI, the event would be positive for all the hpt, yfp, and cfp qPCR. A RMCE event, in which the segment between the FRT1 and FRT87 sites of QC288A was replaced by the corresponding segment of QC329, would be negative for the QC288A-specific hpt, yfp qPCR and positive for the QC329-specific cfp qPCR (FIG. 1A, FIG. 1B, FIG. 1C). Genomic DNA samples of the retransformation events were analyzed by qPCR for hpt, yfp as described in EXAMPLE 2. The qPCR for cfp was done similarly using primers SEQ ID NO:20, SEQ ID NO:21, and FAM labeled MGB probe SEQ ID NO:22.

Table 2 presents the results of both the regular PCR and qPCR analyses described above for T0 plants from the five retransformed lines M-1, M-2, M-3, B-1, and B-2 and for their target parent plants M and B as controls. The QC288A-specific PCR was done with primers 35S-277F (SEQ ID NO:11) and Hygro-A (SEQ ID NO:24) as a target DNA control. The QC28A329-specific PCR was done with primers 35S-277F (SEQ ID NO:11) and Als-3 (SEQ ID NO:27) to check for DNA recombination at the FRT1 site. The event identities were determined by comparing all the results to predictions based on the construct maps presented in FIGS. 1A-1E. A target parent event would be positive for 355-277F/Hygro-A (SEQ ID NO:11/SEQ ID NO:24) and negative for 355-277F/Als-3 (SEQ ID NO:11/SEQ ID NO:27) PCR, positive for scp1, hpt, yfp and negative for cfp qPCR. A false retransformation event would be identical to its target parent since it was the original target that had escaped retransformation selection. A random integration event would be positive for 355-277F/Hygro-A (SEQ ID NO:11/SEQ ID NO:24) and negative for 355-277F/Als-3 (SEQ ID NO:11/SEQ ID NO:27) PCR, and positive for all scp1, hpt, yfp, and cfp qPCR. An RMCE event would be negative for 35S-277F/Hygro-A (SEQ ID NO:11/SEQ ID NO:24) and positive for 355-277F/Als-3 (SEQ ID NO:11/SEQ ID NO:27) PCR, and negative for hpt and yfp qPCR, and positive for scp1, and cfp qPCR. A SSI event would be negative for 35S-277F/Hygro-A and positive for 35S-277F/Als-3 PCR, and positive for all scp1, hpt, yfp, and cfp qPCR.

TABLE 2

Analysis of T0 Plants from Retransformed Events

| Transgenic Event | PCR (SEQ ID NOs) | | Quantitative PCR | | | | Event Identity |
|---|---|---|---|---|---|---|---|
| | SEQ: 11/24 | SEQ: 11/27 | scp1 | hpt | yfp | cfp | |
| M | + | − | 0.6 | 1.0 | 0.7 | 0.0 | Target |
| M-1 | + | − | 0.6 | 0.9 | 0.7 | 1.1 | Random |
| M-2 | − | + | 0.5 | 0.0 | 0.0 | 1.0 | RMCE |
| M-3 | − | + | 0.5 | 0.7 | 0.7 | 0.5 | SSI |
| B | + | − | 1.1 | 1.6 | 1.1 | 0.0 | Target |
| B-1 | − | + | 0.6 | 0.1 | 0.3 | 0.6 | RMCE |
| B-2 | + | − | 0.6 | 1.2 | 0.9 | 0.0 | False |

In summary: M-2 and B-1 are two RMCE events derived from two independent target lines; M-1 is a random integration event; M-3 is a SSI event integrated at the FRT1 site; and B-2 is a false retransformation event.

Example 5

Southern Analysis of Retransformed T0 Plants

T0 plants from retransformed lines M-1, M-2, M-3, B-1, B-2 were analyzed by Southern side-by-side with their corresponding target parents M and B T1 plants with probes yfp and cfp. Soybean genomic DNA was digested with NdeI, resolved in 0.7% agarose gel, and blotted to a nylon membrane using a TurboBlotter™ (Schleicher & Schuell Bioscience, Germany) with 20×SSC (Invitrogen) and crosslinked by UV light. Digoxigenin-labeled DNA probes were made by PCR from plasmid DNA templates using the PCR DIG probe synthesis kit (Roche Applied Science, Indianapolis, Ind., USA). The 693 bp yfp probe was made with primers SEQ ID NO:30 and SEQ ID NO:31. The 546 bp cfp probe was made with primers SEQ ID NO:32 and SEQ ID NO:33. Southern blots were hybridized in DIG EasyHyb™ solution and detected with CDP-Star® according to the manufacturer (Roche Applied Science). Hybridization signals were captured on Kodak™ BioMax® light films (Eastman Kodak, New Haven, Conn., USA).

The restriction enzyme NdeI cuts the 4544 bp QC288A DNA once at position 1119 into a 1188 bp 5' half and a 3356 bp 3' half, and also cuts the 8533 bp QC288A329 DNA once at position 4395 into a 4394 bp 5' half and a 1739 bp 3' half (FIG. 1A, FIG. 1C). In addition to the transgene-specific NdeI site, the enzyme has to cut another nearby NdeI site in soybean genomic DNA in order to produce a Southern band of certain size to be hybridized by a transgene probe.

The yfp and cfp probes were used to analyze the 3' half of the transgene locus. A target event would be positive for yfp and negative for cfp, a RMCE event would be negative for yfp and positive for cfp, and a random integration event or a SSI event would be positive for both yfp and cfp. More accurately, the cfp band in a RMCE sample would be 1617 bp smaller than the corresponding yfp band in its target parent sample because the 1739 bp 3' half of QC288A329 is 1617 bp shorter than the 3356 bp 3' half of QC288A. As expected, the yfp probe detected single band in the target events M, B, the random integration event M-1, the SSI event M-3, and the false event B-2 but not in the two RMCE events M-2 and B-1 (FIG. 5A). The cfp probe detected single band in the random integration event M-1, the SSI event M-3, and the RMCE events B-1, but three bands in another RMCE event M-2 (FIG. 5B). As expected, the middle cfp band in M-2 is approximately 1617 bp smaller than the yfp band in M while the cfp band in B-1 is approximately 1617 bp smaller than the yfp band in B. The two extra cfp bands in M-2 are of random sizes and are likely randomly integrated partial copies of the cfp gene that could not be detected by the qPCR (Table 2) that, with a 69 bp PCR amplicon, would detect only a small part of what the 546 bp cfp probe could detect in Southern.

Example 6

Confirmation of DNA Recombination by Sequencing

To check if DNA recombination at FRT1 and FRT87 sites was accurate, the transgenic gene QC288A329 was cloned by PCR amplification from M-2, M-3, and B-1. The 5' half was amplified as a 2730 bp PCR fragment using primers SEQ ID NO:23 and SEQ ID NO:34 while the 3' half was amplified as a 3351 bp PCR fragment using primers SEQ ID NO:35 and SEQ ID NO:26 (FIG. 1C). A 99 bp segment between the SEQ ID NO:35 and SEQ ID NO:34 primers overlaps the two fragments so that the entire transgene can be sequenced. The PCR fragments were cloned into pCR2.1-TOPO vector with TA cloning kit according to the manufacturer (Invitrogen). Plasmid DNA was prepared with Qiaprep plasmid DNA kit (Qiagen) and sequenced using Applied Biosystems 3700 capillary DNA analyzer and dye terminator cycle DNA sequencing kit. Sequence assembly and alignment were done using Vector NTI suite programs (Invitrogen). Sequence searches were done remotely using the NCBI advanced BLAST algorithm.

Since QC288A and QC288A329 sequences diverge downstream of the FRT1 site, with hpt in QC288A and als in QC288A329, and upstream of the nos terminator, with yfp in QC288A and cfp in QC288A329 (FIGS. 1A, C), alignment of the transgene sequences with the predicted QC288A and QC288A329 map sequences would confirm RMCE recombination at the sequence level. However, since the same 3351 bp SEQ ID NO:35/SEQ ID NO:26 PCR band could be obtained entirely from the donor construct QC329, the PCR using SEQ ID NO:35 and SEQ ID NO:26 primers would not distinguish the FRT1 site SSI event M-3 from the RMCE events M-2 and B-1.

Both the predicted 5' half 2730 bp band and 3' half 3551 bp band were successfully amplified from the three events M-2, M-3, and B-1, and subsequently cloned and sequenced. Their sequences were identical to the predicted QC288A329 map sequence and thus confirmed that DNA recombination occurred at the FRT1 site was accurate for the two RMCE events M-2 and B-1 and also for the SSI event M-3.

Example 7

Analysis of T0 and T1 Plants from Selected Target Lines

Transgenic target events were produced from transformation experiments with the target DNA fragment QC288A as described in EXAMPLE 2. Four target events selected at tissue culture stage were retransformed and RMCE retransformation events were obtained as described in EXAMPLES 3-6. Simultaneously, seventy-nine T0 transgenic target plants were produced from thirty-three target events by regenerating 1-3 plants per event. Leaf samples of all the T0 plants were analyzed by the same qPCR, PCR, and Southern analyses described above for copy number and gene intactness confirmation. Twenty single copy events (or lines) were selected based on the analyses and seed sets. Sixteen seeds from one T0 plant from each of ten lines selected from the twenty were planted to get T1 plants. Leaf samples of all the T1 plants were analyzed by three qPCR analyses specific to the scp1 promoter, ubq10 promoter, and yfp gene to check for segregation of the QC288A transgene. Homozygous T1 plants were obtained from eight lines. Three homozygous target lines A, B, and C were selected for RMCE retransformation experiments.

Table 3 presents the results of qPCR, PCR, and Southern analyses on T0 plants from three transgenic target lines. Fraction values were produced by qPCR for transgene copy numbers. A value less than 0.3 was considered as zero copy, a value between 0.4 and 1.3 was considered as one copy, and a value between 1.4 and 2.3 was considered as two copies. Multiple components of the target DNA (FIG. 1A) were checked in order to make a valid copy number call. The intactness of FRT1 site was checked by PCR with primers Scp1-S/Hygro-A (SEQ ID NO:23/SEQ ID NO:24) to give a 657 bp band. The intactness of FRT87 site was checked with primers Yfp-3/Frt87-A (SEQ ID NO:25/SEQ ID NO:26) to give a 1441 bp band. The full length transgene was checked with primers Scp1-S/Frt87-A (SEQ ID NO:23/SEQ ID NO:26) to give a 4393 bp band (FIG. 1A). All three lines carry a complete single copy of the transgenic target DNA.

TABLE 3

Analysis of T0 Plants from Target Lines

| Target Line | Quantitative PCT | | | PCR | | | Southern | |
|---|---|---|---|---|---|---|---|---|
| | scp1 | hpt | yfp | FRT1 | FRT87 | Full | hpt | yfp |
| A | 1.1 | 0.6 | 1.1 | + | + | + | 1 | 1 |
| B | 0.9 | 0.6 | 1.0 | + | + | + | 1 | 1 |
| C | 1.0 | 1.1 | 0.8 | + | + | + | 1 | 1 |

Table 4 presents the results of qPCR analyses on homozygous T1 plants from the three transgenic target lines. As above, a value less than 0.3 was considered as zero copy, a value between 0.4 and 1.3 was considered as one copy representing hemizygous plants, and a value between 1.4 and 2.3 was considered as two copies representing homozygous plants.

TABLE 4

Analysis of Homozygous T1 Plants from Target Lines

| Target Line | Quantitative PCT | | |
|---|---|---|---|
| | scp1 | ubq10 | yfp |
| A | 1.6 | 1.8 | 1.5 |
| B | 1.6 | 2.0 | 1.6 |
| C | 1.8 | 2.0 | 1.5 |

Example 8

Target Line Border Sequencing

Genomic DNA fragments bordering the QC288A transgene on both the 5' end and 3' end of six target lines were obtained by PCR amplification and cloned for sequencing.

The GenomeWalker kit (ClonTech, Mountain View, Calif., USA) was used to acquire the genomic DNA sequences bordering the transgenic genes. DNA samples of each target line were digested separately with blunt end restriction enzymes EcoRV, DraI, HpaI, and StuI before adding the GenomeWalker™ DNA adaptors. The first round of PCR was done with the adaptor-specific primer AP1 (SEQ ID NO:65) provided in the kit and QC288A-specific primers, Scp1-A (SEQ ID NO:66) for the 5' end border and Vec-S1 (SEQ ID NO:67) for the 3' border, respectively. The second round of PCR was done with the adaptor-specific primer AP2 (SEQ ID NO:68) provided in the kit and QC288A-specific primers, Scp1-A4 (SEQ ID NO:69) for the 5' end border and Vec-S2 (SEQ ID NO:70) for the 3' border, respectively. Specific DNA fragments amplified by the second round PCR were cloned into pCR2.1-TOPO® vector with TA cloning kit according to the manufacturer (Invitrogen). Plasmid DNA was prepared with Qiaprep® plasmid DNA kit (Qiagen) and sequenced using Applied Biosystems 3700 capillary DNA analyzer and dye terminator cycle DNA sequencing kit. Sequence assembly and alignment were done using VECTOR NTI® suite programs (Invitrogen). Sequence searches were done remotely using the NCBI advanced BLAST algorithm.

The bordering genomic DNA sequences and truncations of the transgene ends were revealed by aligning the PCR clone sequences to QC288A map sequence. Various lengths of bordering genomic DNA sequences were obtained and the truncations of transgene ends were revealed to be minor for all the six target lines. Target lines A, B, C, and N lost 5, 17, 22, and 2 bp of the 5' end of the transgene, and 0, 49, 11, and 0 bp of the 3' end of the transgene, respectively. Genomic DNA sequences of 601 bp (SEQ ID NO:55), 984 bp (SEQ ID NO:57), 496 bp (SEQ ID NO:61), and 452 bp (SEQ ID NO:59) bordering the 5' end of the transgene, and 2588 bp (SEQ ID NO:56), 1305 bp (SEQ ID NO:58), 543 bp (SEQ ID NO:62), and 377 bp (SEQ ID NO:60) bordering the 3' end of the transgene were obtained for the three target lines A, B, C and N, respectively. The bordering genomic DNA sequences were used to search NCBI nucleotide collection (nr/nt) database by BLASTN to determine if any endogenous gene of importance was interrupted by the transgene insertion. No significant homology to any known gene was found for any of the three target lines. The bordering genomic DNA sequences were also used to design primers for border-specific PCR analysis of the target lines and RMCE events derived from the target lines in subsequent retransformation.

Example 9

RMCE Event Creation Using Suspension Cultures Derived from Homozygous T1 Target Plants Suspension cultures were initiated from developing embryos from homozygous T1 plants of the three target lines A, B, and C and retransformed by co-bombardments with the donor construct QC329 and FLP expression construct QC292 plasmid DNA.

The homozygous transgenic target line cultures were retransformed with the donor construct QC329 and the Flp construct QC292 at a 10:1 ratio following the biolistic bombardment transformation protocol except using 90 ng/ml chlorsulfuron (DuPont, Wilmington, Del., USA) as the selection agent. RMCE could only occur in cells containing all three DNAs, QC288A, QC329, and QC292, and would bring the promoter-less als coding region of QC329 downstream of the scp1 promoter of QC288A previously placed in soybean genome through DNA recombination for expression and thus chlorsulfuron resistance.

Putative retransformation events were selected by chlorsulfuron resistance and checked for reporter gene cfp expression under a fluorescent microscope. CFP positive events were sampled at somatic embryo stage and screened by a common PCR with primers 35S-277F (SEQ ID NO:11) and Als-3 (SEQ ID NO:27) to amplify a RMCE-specific 497 bp band to check for DNA recombination around the FRT1 site. Then the events were analyzed by construct-specific qPCR to confirm DNA recombination at FRT1 site and to check for the presence of target, donor, and Flp DNA. RMCE, target, and donor-specific qPCR assays were designed around the FRT1 recombination site in each DNA construct. RMCE-specific qPCR employed 288A-1F (SEQ ID NO:71), Als-163R (SEQ ID NO:72) primers and FAM-labeled BHQ1 probe Als-110T (SEQ ID NO:73). Target-specific qPCR employed 288A-1F (SEQ ID NO:71), Hygro-116R (SEQ ID NO:74) primers and FAM-labeled BHQ1 probe Hygro-79T (SEQ ID NO:75). Donor-specific qPCR employed 329-1F (SEQ ID NO:76), Als-163R (SEQ ID NO:72) primers and FAM-labeled BHQ1 probe Als-110T (SEQ ID NO:73). Another qPCR assay specific to the Flp construct QC292 employed Ucp3-57F (SEQ ID NO:77), Flp-A (SEQ ID NO:78) primers and FAM-labeled BHQ1 probe OMEGA5UTR-87T (SEQ ID NO:79).

Border-specific PCR analyses specific to each target line 5' end and 3' end borders were done on corresponding events to check DNA recombination at FRT1 site, at FRT87 site, and also between FRT1 and FRT87 sites. The RMCE 5' border-specific PCR employed the common antisense primer Als3 (SEQ ID NO:27) and a target line 5' border sequence-specific sense primer, 53-151 (SEQ ID NO:80) for target line A, 70-1S (SEQ ID NO:81) for target line B, and 8H-ScaS1 (SEQ ID NO:82) for target line C. The RMCE 3' border-specific PCR employed the common sense primer Cyan-1 (SEQ ID NO:83) and a target line 3' border sequence-specific antisense primer, 53-1A (SEQ ID NO:84) for target line A, 70-1A (SEQ ID NO:85) for target line B, and 8H-VecA (SEQ ID NO:86) for target line C. The target 5' border-specific PCR employed the same target line 5' border sequence-specific sense primers but a target cassette-specific common antisense primer Hygro-A (SEQ ID NO:24). The target 3' border-specific PCR employed the same target line 3' border sequence-specific antisense primers but a target cassette-specific common sense primer Yfp-3 (SEQ ID NO:25). The full length PCR employed the same target line 5' border sequence-specific sense primer and the same target line 3' border sequence-specific antisense primer for each of the three target lines to simultaneously amplify a small excision band, the full target transgene band, and the full RMCE transgene band. Expected sizes of the RMCE 5' end-specific, RMCE 3' end-specific, Target 5' end-specific, Target 3' end-specific, full length Excision, full length Target, and full length RMCE PCR are 1117, 1351, 1036, 732, 1307, 5063, and 6652 bp for target line A events; 967, 1180, 886, 561, 986, 4742, and 6331 bp for target line B events; and 1018, 1294, 937, 675, 1151, 4907, and 6496 bp for target line C events.

Figure 3D:
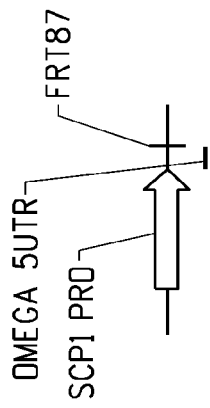

FIG. 6 presents the results of analyses of three retransformation events derived from target line A, including a CFP negative event A3 as a negative control, four retransformation events from target line B, and three retransformation events from target line C. For example, event A1 was positive for CFP expression and positive for DNA recombination at FRT1 site as determined by the common PCR. For construct-specific qPCR analyses, event A1 was positive for RMCE, contained one copy of donor DNA, and was free of either target or Flp DNA. For border-specific PCR analyses, event A1 was positive for both the 5' end and 3' end assays specific to RMCE, and negative for both the 5' end and 3' end assays specific to the target. Full length PCR from the 5' end border to the 3' end border amplified a small band specific to excision and failed to amplify any band specific to the target or RMCE. The excision was the outcome of DNA recombination between the FRT1 and FRT87 sites of either the target DNA QC288A, RMCE DNA QC288A329, or the intermediates SSI DNA QC288A329FRT1 and QC288A329FRT87 with all components flanked by the border FRT1 and FRT87 sites excised (FIG. 3D). The restored FRT site could be either FRT1 or FRT87 depending on the DNA strands crossing over position. Based on the above analyses, event A1 was a RMCE/Excision event contaminated with one randomly integrated copy of the donor DNA. Target DNA on two homologous chromosomes of the homozygous target line was replaced by RMCE on one chromosome and by excision on the other since target DNA was no longer detectable by either target-specific qPCR or target 5' border, 3' border, and full length border-specific PCR analyses.

Following similar analyses described above for event A1, the following conclusions were made for the other nine events listed in FIG. 6. Event A2 was a RMCE/Excision containing a randomly integrated copy of donor and a randomly integrated copy of Flp DNA. Event A3 was a homozygous Target escape carrying about five randomly integrated copies of the donor DNA. Events B1, B2, and B4 were all RMCE/Excision events with no randomly integrated copies of donor or Flp DNA. Event B3 was a RMCE/Excision containing randomly integrated donor DNA. Event C1 was an incomplete RMCE/Excision still containing the target DNA as detected by the 5' end and 3' end border-specific PCR analyses. The target-specific qPCR detected only 0.01 copy of target DNA for event C1. Events C2 and C3 were RMCE/RMCE (homozygous RMCE) with both the targets on homologous chromosomes being converted to RMCE since the RMCE-specific qPCR detected two copies while the target-specific qPCR as well as three border-specific PCR analyses failed to detect either any target-specific or excision-specific band. Both C2 and C3 events also contained randomly integrated donor DNA.

As examples, border-specific PCR analyses on events A1, A2, and A3 are shown in FIGS. 7A-7E. Genomic DNA samples extracted from somatic embryos of the three events were analyzed by RMCE-specific PCR specific to the 5' end border (FIG. 7A), and specific to the 3' end border (FIG. 7B). Events A1 and A2 were positive for the 1117 bp RMCE 5' end border-specific band and also positive for the 1351 bp RMCE 3' end border-specific band. Event A3 was negative for either the 5' end border or 3' end border band (FIG. 7A, FIG. 7B). When the same DNA samples were analyzed by Target-specific PCR specific to the 5' end border (FIG. 7C), and specific to the 3' end border (FIG. 7D), events A1 and A2 failed to produce any band. In contrast, event A3 was positive for the 1036 bp Target 5' end border-specific band and also positive for the 732 bp Target 3' end border-specific band (FIG. 7C, FIG. 7D). The full length 5' end border to 3' end border PCR amplified only the 1307 bp Excision-specific band for events A1 and A2 but not for event A3 (FIG. 7E). The expected 6652 bp RMCE-specific band that should exist in events A1 and A2 failed to be amplified due to the dominant competition advantage of the small Excision-specific products in the same PCR reactions. The same full length border-specific PCR amplified the 5063 bp Target-specific band from event A3 (FIG. 7E). Wild type DNA and water templates were included as negative controls in all the analyses.

Example 10

Characterization of T0 Plants from RMCE Events

T0 plants were regenerated from the RMCE events and their leaf samples were subjected to the same construct-specific qPCR and border-specific PCR analyses described in EXAMPLE 9. The analysis results of T0 plants of three independent events are listed in FIG. 8. Three plants A2-1, A2-2, and A2-3 of event A2, four plants C2-1, C2-2, C2-3, and C2-4 of event C2, and two plants C3-1, and C3-2 of event C3 all retained the same molecular signatures of their respective events A2, C2, and C3 that were revealed at the somatic embryo stage (FIG. 6). The differences of qPCR copy number values between the somatic embryo samples and the T0 plant samples were in the normal range of experimental variations.

Border-specific PCR analyses on plants listed in FIG. 8 are shown in FIGS. 9A-9E. Results of the RMCE-specific PCR specific to the 5' end border (FIG. 3A), specific to the 3' end border (FIG. 9B), the Target-specific PCR specific to the 5' end border (FIG. 9C), specific to the 3' end border (FIG. 9D), and the full length 5' end border to 3' end border PCR (FIG. 9E) for the T0 plant samples A2-1, A2-2, A2-3, A2-4, C2-1, C2-2, C2-3, C3-1, and C3-2 all matched the somatic embryo DNA A2, and C2 RMCE positive controls as well as the previous border-specific PCR analyses results (FIG. 6). Since A2 and its T0 plants A2-1, A2-2, A2-3, and A2-4 are all heterozygous RMCE/Excision, the full length PCR only amplified the small Excision-specific band but not the expected 6652 bp large RMCE band, since PCR amplification favored the small band. In contrast, the full length PCR amplified the 6496 bp RMCE band from homozygous RMCE events C2, C3 (not shown in FIGS. 9A-9E) and their T0 plants C2-1, C2-2, C2-3, C3-1, and C3-2 in the absence of the otherwise expected 1151 bp Excision-band. The Target parent DNA samples A and C were included as positive controls for Target and negative controls for RMCE. Wild-type DNA (wt) and no DNA template ($H_2O$) were included as negative controls.

Since the Target QC288A and the RMCE QC288A329 sequences diverge downstream of the FRT1 site, with hpt in QC288A and als in QC288A329, and upstream of the nos terminator, with yfp in QC288A and cfp in QC288A329, alignment of the transgene sequences with the predicted QC288A and QC288A329 map sequences should confirm RMCE recombination at the sequence level. The predicted sequences surrounding the FRT1 site were aligned to show the differences among Target, RMCE, and Excision downstream of the FRT1 site (FIG. 10A). Depending on the crossing-over position, Excision resulted from the recombination between FRT1 and FRT87 sites could restore either the FRT87 site or the FRT1 site (Groth, A. G. and Calos, M. P., *J. Mol. Biol.* 335:667-678 (2003)). The predicted sequences surrounding the FRT87 site were aligned to show the differences between Target and RMCE upstream of the nos terminator on the 5' end of the FRT87 site (FIG. 10B). The sequences of the genomic DNA part upstream of the scp1 promoter on the 5' end or downstream of the QC288A 3' end, though not shown, were different between Target line A and line C and were included in the alignment analyses described below.

The 21 DNA fragments amplified from seven representative samples Target parents A, C, RMCE events A2, C2 somatic embryos, and RMCE T0 plants A2-1, C2-1, and C3-1 bp the five border-specific PCR analyses were cloned and up to 4 clones derived from each fragment were sequenced to rule out sequence mutations caused by PCR (FIGS. 9A-9E). The transgenic gene sequences were aligned with predicted sequences of Target, RMCE, and Excision to confirm accurate DNA recombination around the FRT1 and FRT87 sites. Sequences obtained from the border-specific PCR DNA fragments were identical to their predicted corresponding sequences. The 5' end border-specific PCR fragments sequences of RMCE samples A2-1, A2, C2-1, C3-1, and C2 (FIG. 9A) matched the RMCE sequences surrounding the FRT1 site (FIG. 10A). The 3' end border-specific PCR fragments sequences of RMCE samples A2-1, A2, C2-1, C3-1, and C2 (FIG. 9B) matched the RMCE sequences surrounding the FRT87 site (FIG. 10B). The 5' end border-specific PCR fragments sequences of target samples A and C (FIG. 9C) matched the target sequences surrounding the FRT1 site (FIG. 10A). The 3' end border-specific PCR fragments sequences of target samples A and C (FIG. 9D) matched the target sequences surrounding the FRT87 site (FIG. 10B). The excision-specific PCR fragments sequences of A2-1, and A2 (FIG. 9E) matched one of the predicted excision-specific sequences containing the FRT1 site (FIG. 10A). Both the 5' and 3' ends of the full length Target fragment sequences of A and C or the full length RMCE sequences of C2-1, C3-1, and C2 (FIG. 9E) matched the ends of the original QC288A sequence or the predicted QC288A329 sequence, respectively (FIGS. 10A-10B).

Example 11

Characterization of T1 Plants from RMCE Events

T1 seeds harvested from T0 plants A2-1, A2-2, A2-3, A2-4, C3-1, and C3-2 were germinated and the T1 plants were analyzed by the same construct-specific qPCR analyses done previously on their parents. Since the four T0 plants of event A2 were identical and the two T0 plants of event C3 were identical based on previous analyses (FIG. 8 and FIGS. 9A-9E), a total of 42 T1 plants derived from the four A2 T0 plants and a total of 48 T1 plants derived from the two C3 T0 plants were treated as two populations for segregation analysis. Since all four A2 T0 plants were confirmed to be heterozygous for RMCE/Excision and contaminated with Donor and Flp DNA (FIG. 8), the Excision should segregate away from RMCE, and the Donor and Flp should also segregate if they were in a different site that was not linked to the RMCE/Excision target site. The RMCE-specific qPCR would detect two copies, one copy, or null of RMCE for plants that are RMCE/RMCE, RMCE/Excision, and Excision/Excision, respectively. Similarly, Target-specific qPCR, Donor-specific qPCR, and Flp-specific qPCR would detect two copies, one copy, or null of Target, Donor, or Flp for homozygous (homo), hemizygous (hemi), or null of the Target, Donor, or Flp gene, respectively.

Of the forty-two A2 T1 plants, the RMCE/Excision site segregated as twelve RMCE/RMCE, eighteen RMCE/Excision, and twelve Excision/Excision. The Donor and Flp were apparently linked and segregated independently from the RMCE as fifteen homozygous, sixteen hemizygous, and eleven null. Seven plants were RMCE/Excision and free of any Donor or Flp. One plant was clean homozygous RMCE/RMCE and free of any Donor or Flp DNA. Consistent with previous analyses at T0 generation, all A2 T1 plants were free of the Target gene. All forty-eight C3 T1 plants were homozygous RMCE/RMCE and free of any Target or Flp consistent with the conclusion that the C3 T0 parent plants were homozygous RMCE/RMCE free of any Target or Flp (FIG. 8). The Donor was not linked to the RMCE site and segregated as twelve homozygous, twenty-four hemizygous, and twelve null. So twelve C3 T1 plants were clean homozygous RMCE/RMCE and free of any Donor or Flp DNA.

In summary, clean homozygous RMCE plants free of Donor, Target, or Flp DNA were obtained at the T1 generation from the retransformation of multiple Target lines by FLP/FRT recombinase mediated cassette exchange.

Example 12

Transgene Stacking Through Multiple Rounds of RMCE

With the success of RMCE confirmed, one can design strategies involving repeated RMCE to place multiple transgenes at the same genomic site where the target DNA QC288A has inserted. Two groups of transgenes can be stacked through two rounds of RMCE as illustrated in FIG. 11A and FIG. 11B. Three incompatible FLP recognition sites FRT1, FRT12, and FRT87 as exemplified by QC422 in FIG. 11A are incorporated in a first donor construct designed for retransformation of selected target QC288A transgenic lines with chlorsulfuron selection. The group 1 of transgenic genes can be cloned between the FRT12, and FRT87 sites. RMCE will happen between the target QC288A in the genome and the first donor QC422 or its derivative through the FRT1 and FRT87 sites. The first round RMCE retransformation events will contain, in addition to group 1 transgenes, three FLP recognition sites FRT1, FRT12, and FRT87 (FIG. 12A). Selected first round RMCE retransformation events will be retransformed with a second donor construct containing two FLP recognition sites FRT1 and FRT12 as exemplified by QC429 in FIG. 11B with hygromycin selection. The group 2 transgenic genes can be cloned upstream of the FRT12 site. The second round of RMCE will happen between the first RMCE DNA in the genome and the second donor QC429 or its derivative through the FRT1 and FRT12 sites. The second RMCE DNA will contain both group1 and group2 transgenic genes and the three FLP recognition sites FRT1, FRT12, and FRT87 at the same genomic site (FIG. 12B). Since the three FLP recognition sites are not compatible to each other, the transgenes are stable.

A third group of transgenic genes can be similarly stacked at the same genomic site. The first round of RMCE and the first donor construct will be the same as described above. The second donor construct for the second RMCE will also contain three FLP recognition sites as exemplified by QC459 in FIG. 13A with one of the three FRT sites FRT1, FRT6 and FRT12 never being used before i.e. FRT6. The group 2 of transgenic genes can be cloned between the FRT6 and FRT12 sites. Selected first round RMCE retransformation events will be retransformed with the second donor DNA with hygromycin selection. The second RMCE will happen between the first RMCE DNA in the genome and the second donor DNA though the FRT1 and FRT12 sites. The second round RMCE DNA will contain both group1 and group2 transgenic genes and four FLP recognition sites FRT1, FRT6, FRT12, and FRT87 at the same genomic site (FIG. 14A). Since the four FLP recognition sites are not compatible to each other, the transgenes are stable.

A third RMCE retransformation will be required to stack the third group of transgenic genes. Selected second round RMCE retransformation events will be retransformed with a third donor construct as exemplified by QC428 in FIG. 13B with two FLP recognition sites FRT1 and FRT6 with chlorsulfuron selection. The group 3 of transgenic genes can be cloned upstream of the FRT6 site. The third round RMCE DNA will contain all group 1, group 2, and group 3 transgenic genes and four FLP recognition sites FRT1, FRT6, FRT12, and FRT87 at the same genomic site (FIG. 14B). Since the four FLP recognition sites are not compatible to each other, the transgenes are stable.

Following the same strategy described above, more groups of transgenes can be stacked at the same genomic site using more incompatible FRT sites by additional rounds of RMCE retransformation.

Example 13

Construction of Vectors for Multiple Rounds of RMCE

The FRT12 recombination site was constructed by annealing two 106 bp complementary oligos (SEQ ID NO:38 and SEQ ID NO:39) engineered with multiple cloning sites (MWG-Biotech AG, Bridgeport, Calif., USA). The XmaI/FseI FRT12 DNA fragment was cloned into the XmaI/FseI sites of construct QC408 to make QC422 (SEQ ID NO:42; FIG. 11A) containing FRT1:als:pinII:FRT12-FRT87. QC429 (SEQ ID NO:43; FIG. 11B) and its intermediates and derivatives were made via multiple steps using routine cloning techniques as described in EXAMPLE 1.

The FRT6 recombination site was made by annealing two 106 bp complementary oligos (SEQ ID NO:40 and SEQ ID NO:41) engineered with multiple cloning sites (MWG-Biotech AG). The AscI/XmaI FRT6 DNA fragment was cloned into the AscI/XmaI sites of construct QC408 to make QC430 containing FRT1:als:pinII:FRT6-FRT87. QC459 (SEQ ID NO:44; FIG. 13A), QC428 (SEQ ID NO:45; FIG. 13B) and their intermediates and derivatives were made via multiple steps using routine cloning techniques as described in EXAMPLE 1.

Example 14

Creation of Target Sites During Development of Transgenic Product Lines

Since target lines for RMCE are created using traditional transformation method, which will place the target DNA in the genome randomly, significant effort is required to produce and characterize multiple target events to identify a target line that meets desired criteria. The process may take several years and require as much effort as developing a trait-containing transgenic product line. If the process of creating a target line can be combined with the development of a trait-containing transgenic product line, a target site will be obtained as a by-product once the transgenic product line is selected and well characterized. Furthermore, a trait gene or a group of genes responsible for the trait is already placed at the site making it convenient to stack new traits through RMCE. A common selectable marker gene cassette is usually used for plant transformation to facilitate the selection of transformed events, such as the 35S:hpt and sams:als cassettes used in soybean transformation (US patent publication WO 00/37662) and the 35S:bar and ubiq:gat cassettes used in maize transformation. Consequently, two incompatible recombinase recognition sites such as FRT1 and FRT87 can be incorporated in the selectable marker gene cassette which can then be linked to any trait gene of interest for transformation. Once integrated in a plant genome the incorporated FRT1 and FRT87 sites can be used for RMCE.

Using the promoter trap design, the soybean transformation selectable marker gene cassette sams:als can be modified to include a FRT1 site between the sams promoter and the als coding region and a FRT87 site downstream of the als terminator exemplified by construct QC448 (FIG. 15A). Multiple restriction sites can be engineered upstream of the sams promoter and also downstream of the als terminator for the cloning of trait genes of interest. Once placed in soybean genome the sams-FRT1:als-FRT87 cassette can be used as a target site for RMCE with any donor construct containing a promoterless marker gene such as FRT1-hpt-FRT87. DNA construct QC448 (FIG. 15A) was made from constructs containing components such as FRT1, FRT87, sams promoter, als coding sequence etc. described in EXAMPLES 1 and 7 via multiple steps using routine molecular cloning techniques described in EXAMPLE 1. First, QC446 was made by cloning the 1283 bp SphI/FseI fragment containing the als term from pZSL141 into the SphI/FseI sites of QC408. Then the 2790 bp HpaI/NotI FRT1:als:als term-FRT87 fragment of QC446, the HpaI digestion was partial, was cloned into the NcoI/NotI sites of QC431 to make QC447 containing sams-FRT1:als:als term-FRT87, the NcoI site was filled in by Klenow polymerase. The sams-FRT1:als:als term-FRT87 cassette was released with XmaI/NotI from QC447 and moved to the XmaI/NotI sites pZSL141 to make the final plasmid QC448 from which the cassette could be conveniently released with AscI digestion for DNA fragment preparation.

The Gateway® cloning technology, which is based on the lambda phage site-specific recombination system (Invitrogen), can be utilized to link the sams-FRT1:als-FRT87 marker gene to trait genes. The construct QC448 (FIG. 15A) was cut at the 5' end of the sams promoter with SmaI digestion. A Gateway® conversion DNA fragment containing the attR1 and attR2 recombination sites (Invitrogen) was inserted to the SmaI site of QC448 bp blunt end ligation with T4 DNA ligase to make construct QC449 and QC449i, with the Gateway® DNA fragment inverted, as the destination vectors (FIG. 15B, FIG. 15C). Trait genes will need to be first cloned between two corresponding recombinase recognition sites attL1 and attL2 as an entry vector. In vitro recombination catalyzed by LR clonase between the attL sites on an entry vector and the attR sites on the destination vector will result in the linkage of the trait genes to the marker gene in tandem or diverse orientation depending on the relative orientations of the attL and attR sites.

Figure 16A:
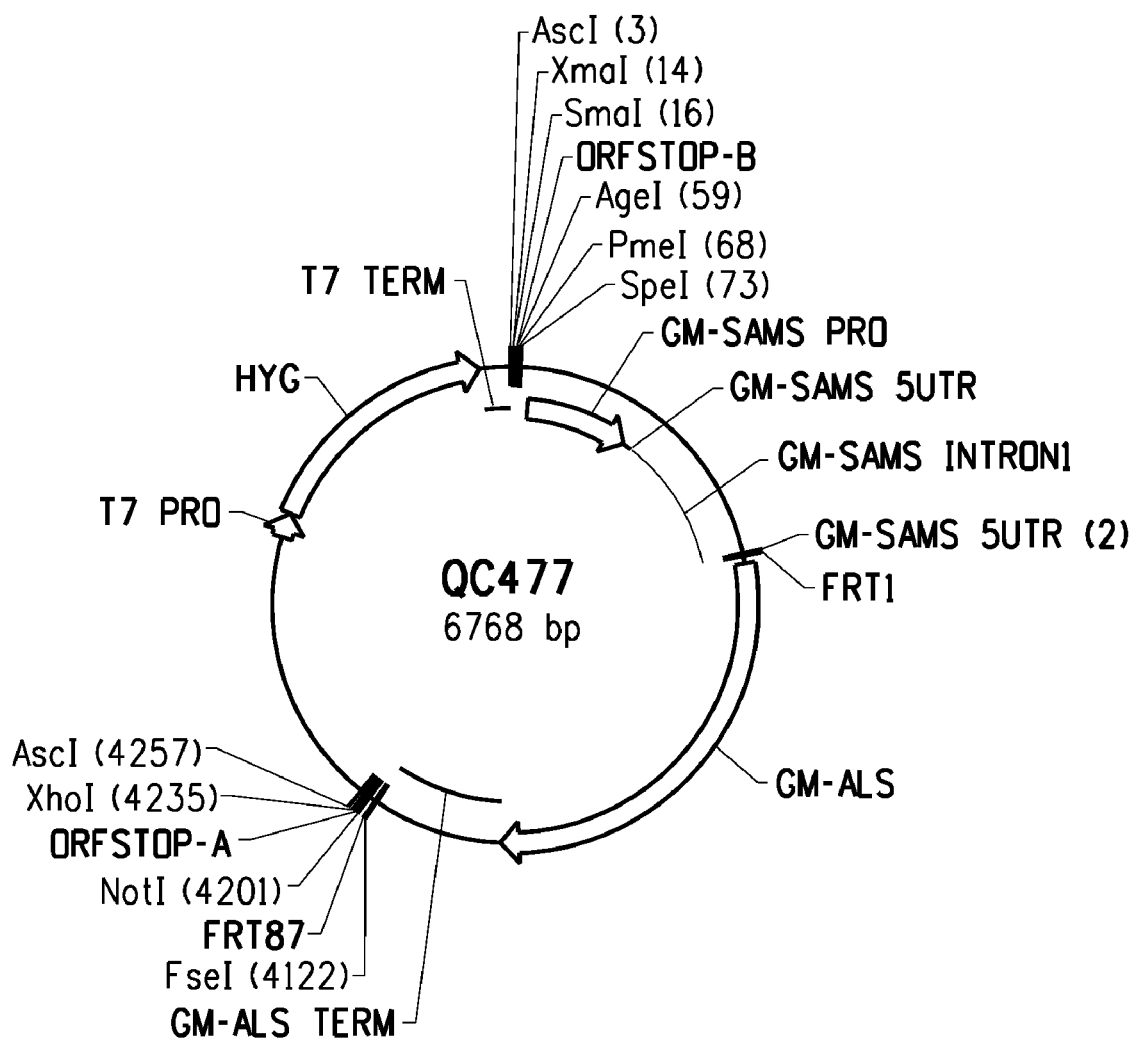

An improved version of QC448 was made by adding stop codons in all open reading frames on each end of the sams:als cassette to form QC477 containing ORFSTOP-B-sams-FRT1:als:als term:FRT87-ORFSTOP-A (FIG. 16A). To remove a few extra base pairs between the FRT1 and the als gene, the 888 bp KpnI/EcoRI fragment of pZSL91 was moved to the SpeI/EcoRI sites of QC446 to form QC474. Both the SpeI and KpnI sites were first treated with mung bean nuclease to become blunt. The sams-FRT1:als:als term:FRT87 fragment of QC474 was released with NotI complete digestion and HpaI partial digestion and cloned into the NcoI and NotI sites of QC431 to form QC475, the NcoI site was first blunted with mung bean nuclease. ORFSOPTA-B (SEQ ID NO:88), with stop codons in all open reading frames, was synthesized as an oligo duplex with appropriate cloning sites incorporated on the ends and in the middle (MWG-Biotech AG). The duplex was digested with XhoI/SpeI and cloned into the XhoI/XbaI sites of pZSL141 to form QC476. Finally, the 4128 bp NotI/SpeI sams-FRT1:als:als term:FRT87 fragment of QC475 was moved to the NotI/SpeI sites of QC476 to form QC477 (FIG. 16A).

Figure 16B:
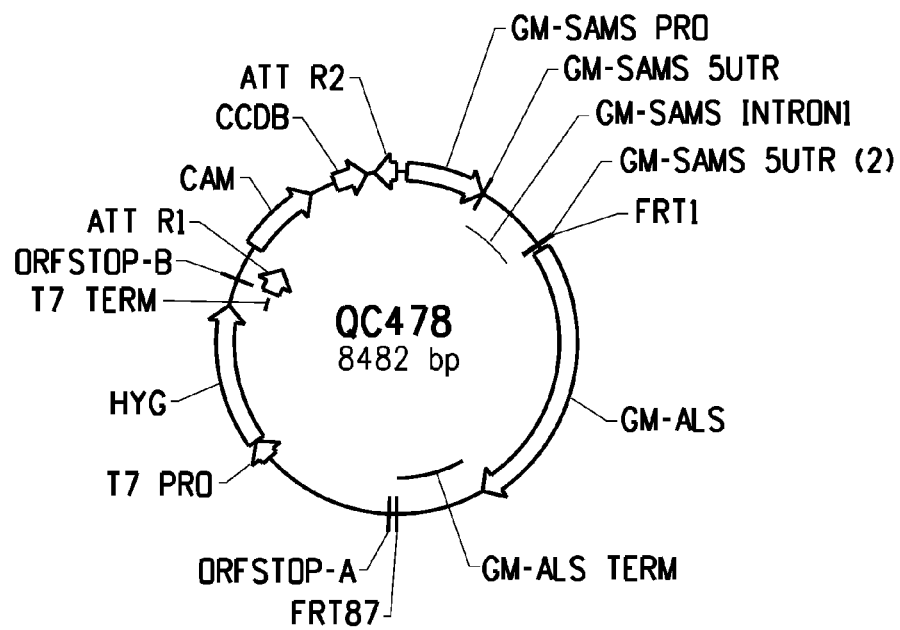
Figure 16C:
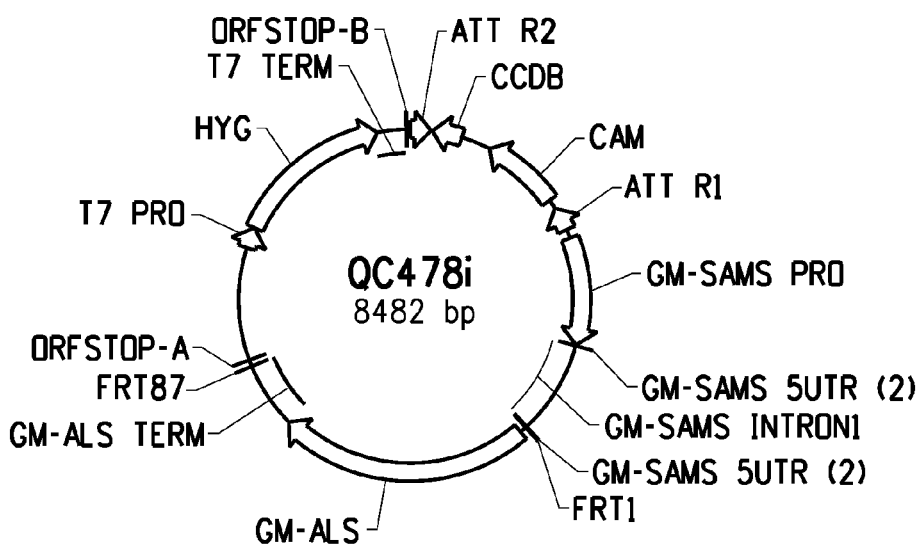
Figure 16D:
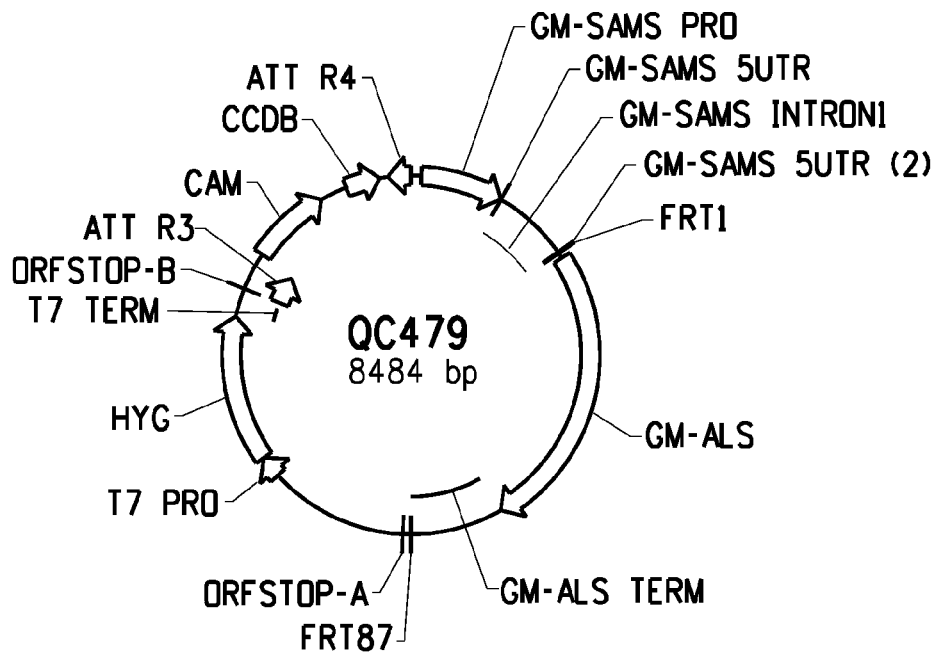
Figure 16E:
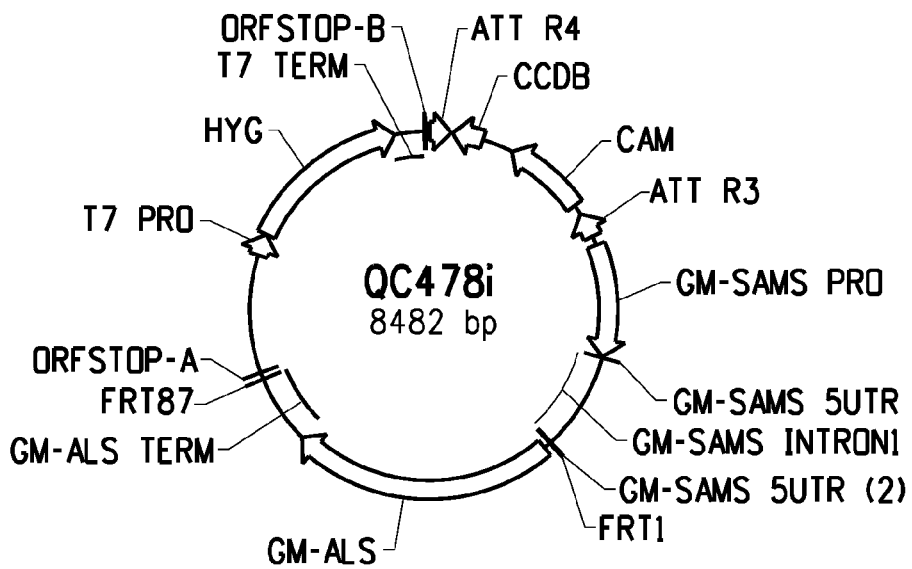

A Gateway® conversion DNA fragment containing the attR1 and attR2 recombination sites (Invitrogen) was inserted to the PmeI sites of QC477 bp blunt end ligation with T4 DNA ligase to make construct QC478 and QC478i, with the Gateway® DNA fragment inverted, as the destination vectors (FIG. 16B, FIG. 16C). Another Gateway® conversion DNA fragment containing the attR3 and attR4 recombination sites (Invitrogen) was inserted into the PmeI sites of QC477 bp

Example 15

Stacking of Fatty Acid Modifying Genes and Amino Acid Modifying Genes at the Target B Site by Two Rounds of SSI A retransformation event designated "B-5", produced from the retransformation of the target B culture with the donor DNA QC329 (EXAMPLE 3), was confirmed by multiple PCR and qPCR analyses to be a RMCE event. The B-5 event containing the QC288A329 (FIG. 1C) transgenes was regenerated into fertile T0 plants. Homozygous T1 plants of B-5 were identified by qPCR and their developing embryos were used to initiate new embryogenic cultures for gene stacking experiments using donor DNA QC436 for the first round of SSI. The QC436 construct contains a promoter-less selectable marker gene HPT between the FRT1 and FRT12 sites, and between the FRT12 and FRT87 sites inverted repeats of the soybean delta 9 desaturase gene fragment (GM-FAD2-1 (TR1)) and thioesterase gene fragment (GM-THIOESTERASE 2 (TR4)) controlled by a common promoter KTI3 (FIG. 17A). Since the target DNA QC288A329 does not contain a FRT12 site, RMCE between the target QC288A329 and the donor QC436 DNA can only happen between the two FRT1 sites and the two FRT87 sites. Consequently, all the components between the FRT1 and FRT87 sites of QC288A329 can be replaced by the components between the FRT1 and FRT87 sites of QC436. The third recombination site FRT12 of QC436 is simultaneously introduced into the target B locus. Multiple retransformation events were produced and confirmed to be RMCE events by PCR and qPCR analyses (similar to EXAMPLES 3 and 4). Fatty acid profiling on somatic embryos of the QC288A436 (FIG. 17C) retransformation events revealed significantly elevated oleic acid (18:1) content, which is the phenotype expected for suppression of the endogenous delta9 desaturase and thioesterase 2 genes. One QC288A436 RMCE event culture, designated "B-5-3", was selected as the new target for next round SSI using the second donor DNA QC438.

The B-5-3 culture was directly retransformed with the donor DNA QC438 as similarly described in EXAMPLE 3. QC438 contains only two recombination sites, FRT1 and FRT12. The promoter-less selectable gene ALS and four other complete transgenes are flanked by the same FRT1 and FRT12 sites (FIG. 17B). The expression of the *Yarrowia* diacylglycerol acyltransferase gene (YL-DGAT1) is useful for the conversion of fatty acids to triacylglycerol to increase overall oil content. The expression of the other three genes, barley high lysine (BHL8), *Corynebacterium glutamicum* dihydrodipicolinate synthetase gene (CORYNE DAP A), and soybean cysteine synthase gene (GM-CGS (TR1)), are useful to increase the content of essential amino acids such as lysine and methionine. Retransformation events were selected by their resistance to chlorsulfuron and analyzed by multiple PCR and qPCR analyses (similar to EXAMPLES 3 and 4, with more gene-specific primers). One event, designated "B-5-3-2", was confirmed to be a RMCE stacking event containing the ALS selectable marker gene and the four traits genes YL-DGAT1, BHL8, CORYNE DAP A, and GM-CGS (TR1) of the donor QC438. The FAD2-1 and thioesterase 2 cosuppression cassette delivered by donor QC436 during the previous SSI remained intact. Fatty acid profiling of somatic embryo samples of B-5-3-2 detected the expected phenotypes of high oleic acid and high oil contents. Western analysis of somatic embryo or T0 plant leaf samples indicated the expression of all three genes, BHL8, CORYNE DAP A, and GM-CGS (TR1), which are designed to improve lysine and methionine contents.

---

What is claimed is:

1. A soybean cell, plant or seed having stably incorporated in its genome a transfer cassette genetically linked to a chromosomal region comprising a sequence selected from the group consisting of SEQ ID NO:55, SEQ ID NO:56, SEQ ID NO:57, SEQ ID NO:58, SEQ ID NO:59, SEQ ID NO:60, SEQ ID NO:61 and SEQ ID NO:62, wherein the transfer cassette comprises at least two non-identical recombination sites, wherein the transfer cassette further comprises a polynucleotide encoding a selectable marker protein-coding sequence bounded by a first recombination site and a second non-identical recombination site.

2. A method for stacking of multiple expression cassettes of interest into a specific chromosomal site in a soybean genome, said method comprising:
   a. obtaining a transgenic soybean cell comprising a target site genetically linked to a chromosomal region comprising a sequence selected from the group consisting of SEQ ID NO:55, SEQ ID NO:56, SEQ ID NO:57, SEQ ID NO:58, SEQ ID NO:59, SEQ ID NO:60, SEQ ID NO:61 and SEQ ID NO:62, wherein said target site comprises a first selectable marker protein-coding sequence, wherein the first selectable marker protein-coding sequence is bounded by a first recombination site and a second non-identical recombination site;
   b. introducing into the transgenic soybean cell of step (a) a transfer cassette, wherein said transfer cassette comprises a second selectable marker protein-coding sequence, wherein the second selectable marker protein-coding sequence is bounded by the first recombination site and the second non-identical recombination site, and further wherein the transfer cassette further comprises at least one expression cassette of interest, wherein the at least one expression cassette of interest is bounded by the second selectable marker protein-coding sequence and the second non-identical recombination site; and
   c. providing a recombinase that recognizes and implements recombination at the non-identical recombination sites.

3. The soybean cell, plant or seed of claim 1, wherein the transfer cassette further comprises a third non-identical recombination site bounded by the selectable marker protein-coding sequence and the second non-identical recombination site.

4. The soybean cell, plant or seed of claim 3, wherein the transfer cassette further comprises at least one expression cassette of interest, wherein the at least one expression cassette of interest is bounded by the third non-identical recombination site and the second non-identical recombination site.

5. The soybean cell, plant or seed of claim 1, wherein at least one of said non-identical recombination sites is selected from the group consisting of FRT1 (SEQ ID NO:50), FRT5 (SEQ ID NO:51), FRT6 (SEQ ID NO:52), FRT12 (SEQ ID NO:53) and FRT87 (SEQ ID NO:54).

6. The soybean cell, plant or seed of claim 1, wherein said selectable marker protein-coding sequence encodes a protein selected from the group consisting of a hygromycin phosphotransferase, a sulfonylurea-tolerant acetolactate synthase, and a sulfonylurea-tolerant acetolactate synthase that has an amino acid sequence comprising SEQ ID NO:63 or SEQ ID NO:64.

7. The soybean cell, plant or seed of claim 1, wherein the transfer cassette is bordered by any one chromosomal region comprising:
   a) SEQ ID NO:55;
   b) SEQ ID NO:56;
   c) SEQ ID NO:57;
   d) SEQ ID NO:58;
   e) SEQ ID NO:59;
   f) SEQ ID NO:60;
   g) SEQ ID NO:61; or
   h) SEQ ID NO:62.

8. The soybean cell, plant or seed of claim 1, wherein the transfer cassette is genetically linked to any one combination of chromosomal regions comprising:
   a) SEQ ID NO:55 and SEQ ID NO:56;
   b) SEQ ID NO:57 and SEQ ID NO:58;
   c) SEQ ID NO:59 and SEQ ID NO:60; or
   d) SEQ ID NO:61 and SEQ ID NO:62.

9. The soybean cell, plant or seed of claim 1, wherein the transfer cassette is bordered by any one combination of chromosomal regions comprising:
   a) SEQ ID NO:55 and SEQ ID NO:56;
   b) SEQ ID NO:57 and SEQ ID NO:58;
   c) SEQ ID NO:59 and SEQ ID NO:60; or
   d) SEQ ID NO:61 and SEQ ID NO:62.

10. The method of claim 2, wherein the transfer cassette further comprises a third non-identical recombination site bounded by the second selectable marker gene and the at least one expression cassette of interest.

11. The method of claim 2, step (c), wherein providing said recombinase comprises transiently expressing within said soybean cell an expression cassette comprising a polynucleotide encoding said recombinase.

12. The method of claim 11, wherein said recombinase is flippase (FLP).

13. The method of claim 12, wherein said FLP has been synthesized using maize preferred codons.

14. The method of claim 2, wherein said first selectable marker protein-coding sequence encodes a protein selected from the group consisting of a hygromycin phosphotransferase, a sulfonylurea-tolerant acetolactate synthase, and a sulfonylurea-tolerant acetolactate synthase that has an amino acid sequence comprising SEQ ID NO:63 or SEQ ID NO:64.

15. The method of claim 2, wherein the target site comprises a promoter operably linked to the first selectable marker protein-coding sequence, further wherein the first recombination site is between the promoter and the first selectable marker protein-coding sequence.

16. The method of claim 2, wherein the target site is bordered by any one chromosomal region comprising:
   a) SEQ ID NO:55;
   b) SEQ ID NO:56;
   c) SEQ ID NO:57;
   d) SEQ ID NO:58;
   e) SEQ ID NO:59;
   f) SEQ ID NO:60;
   g) SEQ ID NO:61; or
   h) SEQ ID NO:62.

17. The method of claim 2, wherein the target site is genetically linked to any one combination of chromosomal regions comprising:
   a) SEQ ID NO:55 and SEQ ID NO:56;
   b) SEQ ID NO:57 and SEQ ID NO:58;
   c) SEQ ID NO:59 and SEQ ID NO:60; or
   d) SEQ ID NO:61 and SEQ ID NO:62.

18. The method of claim 2, wherein the target site is bordered by any one combination of chromosomal regions comprising:
   a) SEQ ID NO:55 and SEQ ID NO:56;
   b) SEQ ID NO:57 and SEQ ID NO:58;
   c) SEQ ID NO:59 and SEQ ID NO:60; or
   d) SEQ ID NO:61 and SEQ ID NO:62.

19. The method of claim 2, wherein at least one of said non-identical recombination sites is selected from the group consisting of FRT1 (SEQ ID NO:50), FRT5 (SEQ ID NO:51), FRT6 (SEQ ID NO:52), FRT12 (SEQ ID NO:53) and FRT87 (SEQ ID NO:54).

* * * * *